US012378546B2

(12) United States Patent
Scharenberg et al.

(10) Patent No.: US 12,378,546 B2
(45) **Date of Patent: *Aug. 5, 2025**

(54) COUPLING ENDONUCLEASES WITH END-PROCESSING ENZYMES DRIVES HIGH EFFICIENCY GENE DISRUPTION

(71) Applicant: SEATTLE CHILDREN'S HOSPITAL, Seattle, WA (US)

(72) Inventors: Andrew M. Scharenberg, Seattle, WA (US); Michael T. Certo, Seattle, WA (US); Kamila Sabina Gwiazda, Seattle, WA (US)

(73) Assignee: SEATTLE CHILDREN'S RESEARCH INSTITUTE, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,930

(22) Filed: Dec. 1, 2023

(65) Prior Publication Data

US 2024/0102001 A1 Mar. 28, 2024

Related U.S. Application Data

(60) Continuation of application No. 17/244,190, filed on Apr. 29, 2021, now Pat. No. 11,873,479, which is a continuation of application No. 15/215,405, filed on Jul. 20, 2016, now Pat. No. 11,008,565, which is a continuation of application No. 14/949,744, filed on Nov. 23, 2015, now Pat. No. 10,995,332, which is a division of application No. 14/173,705, filed on Feb. 5, 2014, now abandoned, which is a division of application No. 13/405,183, filed on Feb. 24, 2012, now Pat. No. 8,673,557.

(60) Provisional application No. 61/447,672, filed on Feb. 28, 2011.

(51) Int. Cl.

| | |
|---|---|
| ***C12N 9/22*** | (2006.01) |
| ***A61K 9/00*** | (2006.01) |
| ***A61K 35/28*** | (2015.01) |
| ***A61K 38/45*** | (2006.01) |
| ***A61K 38/46*** | (2006.01) |
| ***A61K 38/52*** | (2006.01) |
| ***C12N 9/12*** | (2006.01) |
| ***C12N 9/14*** | (2006.01) |
| ***C12N 9/90*** | (2006.01) |
| ***C12N 15/10*** | (2006.01) |
| ***C12N 15/62*** | (2006.01) |
| ***C12Q 1/00*** | (2006.01) |
| ***C12Q 1/34*** | (2006.01) |
| *A61K 35/12* | (2015.01) |

(52) U.S. Cl.

CPC .......... *C12N 15/102* (2013.01); *A61K 9/0019* (2013.01); *A61K 35/28* (2013.01); *A61K 38/45* (2013.01); *A61K 38/465* (2013.01); *A61K 38/52* (2013.01); *C12N 9/1252* (2013.01); *C12N 9/22* (2013.01); *C12N 9/90* (2013.01); *C12N 15/62* (2013.01); *A61K 2035/124* (2013.01); *C07K 2319/60* (2013.01); *C12N 2800/80* (2013.01); *C12N 2840/203* (2013.01)

(58) Field of Classification Search

CPC .... C12N 15/102; C12N 2800/80; C12N 9/22; C12N 9/1252; C12N 9/14; C12Q 1/005; C12Q 1/34; A61K 38/52

See application file for complete search history.

(56) References Cited

U.S. PATENT DOCUMENTS

| | | | |
|---|---|---|---|
| 8,673,557 | B2 | 3/2014 | Scharenberg |
| 2004/0180352 | A1 | 9/2004 | Padgett et al. |
| 2006/0206949 | A1 | 9/2006 | Arnould et al. |
| 2008/0271166 | A1 | 10/2008 | Epinat et al. |
| 2012/0244131 | A1 | 9/2012 | Delacote et al. |

FOREIGN PATENT DOCUMENTS

| | | | |
|---|---|---|---|
| CA | 2815512 | A1 | 5/2012 |
| EP | 2 412 806 | A1 | 2/2012 |
| WO | 2012058458 | A2 | 5/2012 |
| WO | 2013009525 | A1 | 1/2013 |

OTHER PUBLICATIONS

Keijzers et al., Int. J. Mol. Sci., 2019, 20, 74, pp. 1-15.*

Zhang, Jinjin et al., "Crystal structures of λ exonuclease in complex with DNA suggest an electrostatic ratchet mechanism for processivity" PNAS, Jul. 19, 2011, pp. 11872-11877, vol. 108, No. 29.

Mazur, D. J. et al., "Identification and expression of the TREX1 and TREX2 cDNA sequences encoding mammalian 3'→5' exonucleases," The Journal of Biological Chemistry, vol. 274, No. 28, 1999, pp. 19655-19660.

Communication pursuant to Rule 69 EPC issued for European patent application No. 19183306.0 mailed Feb. 10, 2020, 9 pages.

Perrino, F. W., et al., "The Human TREX2 3'-5'-Exonuclease Structure Suggests a Mechanism for Efficient Nonprocessive DNA Catalysis," The Journal of Biological Chemistry, 280(15), 2005, pp. 15212-15218.

Stoddard, B. L., "Homing Endonucleases: From Microbial Genetic Invaders to Reagents for Targeted DNA Modification," Structure (19), 2011, pp. 7-15.

(Continued)

*Primary Examiner* — Maryam Monshipouri

(74) *Attorney, Agent, or Firm* — Rothwell, Figg, Ernst & Manbeck, P.C.

(57) ABSTRACT

The present disclosure relates to the co-expression of an endonuclease with an end-processing enzyme for the purpose of enhanced processing of the polynucleotide ends generated by endonuclease cleavage.

17 Claims, 39 Drawing Sheets

Specification includes a Sequence Listing.

(56) References Cited

OTHER PUBLICATIONS

Decision on Motions 37 CFR 41.125(a), *Seattle Childrem's Research Institute* v. *Cellectis*, Interference No. 106,052, filed Apr. 27, 2017, 55 pages.
Decision on Priority 37 CFR 41.125(a), *Cellectis* v. *Seattle Childrem's Research Institute*, Interference No. 106,052, filed Aug. 30, 2018, 44 pages.
Smith et al., A combinatorial approach to create artificial homing endonucleases cleaving chosen sequences, Nov. 27, 2006, Nucleic Acid Research vol. 34, No. 22 e149, 1-12.
United States Patent and Trademark Office Patent Trial and Appeal Board, Judgment, in Patent Interference No. 106,052, Aug. 30, 2018, pp. 1-4, available at acts.uspto.gov.
United States Patent and Trademark Office Patent Trial and Appeal Board, Decision on Motions, in Patent Interference No. 106,052, Apr. 27, 2017, pp. 1-55, available at acts.uspto.gov.
Office Action in corresponding Canadian application No. 2828303, mailed Dec. 14, 2017.
Communication issued Apr. 10, 2017 in the European Patent Application No. 12751744.9 filed Sep. 26, 2013.
Ahn, Byungchan et al., "Regulation of WRN Helicase Activity in Human Base Excision Repair" The Journal of Biological Chemistry, Dec. 17, 2004, pp. 53465-53474, vol. 279, No. 51.
Ashworth, Justin et al., "Computational redesign of endonuclease DNA binding and cleavage specificity" Nature, Jun. 1, 2006, pp. 656-659, vol. 441.
Balasubramanian, Nandakumar et al., "Physical Interaction between the Herpes Simplex Virus Type 1 Exonuclease, UL12, and the DNA Double-Strand Break-Sensing MRN Complex" Journal of Virology, Dec. 2010, pp. 12504-12514, vol. 84, No. 24.
Bennardo, N., and J.M. Stark, "ATM Limits Incorrect End Utilization During Non-Homologous End Joining of Multiple Chromosome Breaks," PLOS Genetics 6(11):1-11, Nov. 2010.
Bennardo, N., et al., "Limiting the Persistence of a Chromosome Break Diminishes Its Mutagenic Potential," PLoS Genetics 5(10):1-14, Oct. 2009.
Boch, Jens et al., "Breaking the Code of DNA Binding Specificity of TAL-Type III Effectors" Science, Dec. 11, 2009, pp. 1509-1512, vol. 326.
Chevalier, Brett S. et al., "Design, Activity, and Structure of a Highly Specific Artificial Endonuclease" Molecular Cell, Oct. 2002, pp. 895-905, vol. 10.
Coates, Brad S., et al., "A Helitron-Like Transposon Superfamily from Lepidoptera Disrupts (GAAA)n Microsatellites and is Responsible for Flanking Sequence Similarity within a Microsatellite Family," J. Mol. Evol. 70:275-288, 2010.
Dahlroth, Sue-Li et al., "Crystal structure of the shutoff and exonuclease protein from the oncogenic Kaposi's sarcoma-associated herpesvirus" FEBS Journal, 2009, pp. 6636-6645, vol. 276.
EP communication received in application No. 12751744.9, dated Mar. 18, 2015.
Epinat, Jean-Charles et al., "A novel engineered meganuclease induces homologous recombination in yeast and mammalian cells" Nucleic Acids Research, 2003, pp. 2952-2962, vol. 31, No. 11.
Farjardo-Sanchez, E., "Computer Design of Obligate Heterodimer Meganucleases Allows Efficient Cutting of Custom DNA Sequences," Nucleic Acids Res. 36(7):2164-2173, 2008.
Gammon, Don B. et al., "The 3'-to-5' Exonuclease Activity of Vaccinia Virus DNA Polymerase is Essential and Plays a Role in Promoting Virus Genetic Recombination" Journal of Virology, May 2009, pp. 4236-4250, vol. 83, No. 9.
Garcia, Valerie et al., "Bidirectional resection of DNA double-strand breaks by Mre11 and Exo1" Nature, Nov. 10, 2011, pp. 241-244, vol. 479.
Glaunsinger, Britt et al., "The Exonuclease and Host Shutoff Functions of the SOX Protein of Kaposi's Sarcoma-Associated Herpesvirus are Genetically Separable" Journal of Virology, Jun. 2005, pp. 7396-7401, vol. 79, No. 12.
Gunn, A., et al., Correct End Use During End Joining of Multiple Chromosomal Double Strand Breaks is Influenced by Repair Protein RAD50, DNA-Dependent Protein Kinase DNA-PKcs, and Transcription Context J. Biol. Chem. 286 (49):42470-42482 Dec. 9, 2011.
International Search Report and Written Opinion dated Jun. 7, 2012, received in connection with PCT/US12/26653.
Ishchenko, Alexander A., et al., "The 3'→5' Exonuclease of Apn1 Provides an Alternative Pathway to Repair 7,8-Dihydro-8-Oxodeoxyguanosine in *Saccharomyces cerevisiae*," Molecular and Cellular Biology, pp. 6380-6390, Aug. 2005.
Jagannathan, Indu et al., "Activity of FEN1 Endonuclease on Nucleosome Substrates is Dependent upon DNA Sequence but Not Flap Orientation" The Journal of Biological Chemistry, May 20, 2011, pp. 17521-17529, vol. 286, No. 20.
Kratz, Katja, et al., "Deficiency of FANCD2-Associated Nuclease KIAA1018/FAN1 Sensitizes Cells to Interstrand Crosslinking Agents," Cell 142, 77-99, Jul. 9, 2010.
Kurosawa, Ava et al., "Functions and Regulation of Artemis: A Goddess in the Maintenance of Genome Integrity" J. Radiat. Res., 2010, pp. 503-509, vol. 51.
Lee, Byung-In et al., "The RAD2 Domain of Human Exonuclease 1 Exhibits 5' to 3' Exonuclease and Flap Structure-specific Endonuclease Activities" The Journal of Biological Chemistry, Dec. 31, 1999, pp. 37763-37769, vol. 274, No. 53.
Lenain, Christelle et al., "The Apollo 5' Exonuclease Functions Together with TRF2 to Protect Telomeres from DNA Repair" Current Biology, Jul. 11, 2006, pp. 1303-1310, vol. 16.
Mahajan, Kiran N. et al., "Association of terminal deoxynucleotidyl transferase with Ku" PNAS, Nov. 23, 1999, pp. 13926-13931, vol. 96, No. 24.
Marcaida, Maria J. et al. (2010) Homing endonucleases: from basics to therapeutic applications, Cell. Mol. Life Sci., 67:727-748.
Mashimo, Tomoji et al., "Efficient gene targeting by TAL effector nucleases coinjected with exonucleases in zygotes" Scientific Reports, Feb. 13, 2013 vol. 3, Article No. 1253.
Mazur, Dan J. et al., "Excision of 3' Termini by the Trex1 and TREX2 3'→5' Exonucleases—Characterization of the Recombinant Proteins" The Journal of Biological Chemistry, May 18, 2001, pp. 17022-17029, vol. 276, No. 20.
Monteilhet, Claude et al. (1990) Purification and characterization of the in vitro activity of I-Sce I, a novel and highly specific endonuclease encoded by a group I intron, Nucleic Acids Research, 18(6):1407-1413.
Moscou, Matthew J. et al., "A Simple Cipher Governs DNA Recognition by TAL Effectors" Science, Dec. 11, 2009, p. 1501, vol. 326.
Nicoletie, M.L., et al., "Mre11-Rad50-Xrs2 and Sae2 Promote 5' Strand Resection of DNA Double-Strand Breaks," Nat. Struct. Mot. Biol. 17(12):1478-1485, Dec. 2010.
Nimonkar, Amitabh V. et al., "BLM-DNA2-RPA-MRN and EX01-BLM-RPA-MRN constitute two DNA end resection machineries for human DNA break repair" Genes & Development, 2011, pp. 350-362, vol. 25.
Orans, Jillian et al., "Structures of Human Exonuclease 1 DNA Complexes Suggest a Unified Mechanism for Nuclease Family" Cell, Apr. 15, 2011, pp. 212-223, vol. 145.
Paques, Frédéric et al., "Meganucleases and DNA Double-Strand Break-Induced Recombination: Perspectives for Gene Therapy" Current Gene Therapy, 2007, pp. 49-66, vol. 7.
Porteus, M.H. and Baltimore D., "Chimeric Nucleases stimulate Gene Targeting in Human Cells," Science 300(5620):763, May 2003.
Reuven, Nina Bacher et al., "The Herpes Simplex Virus Type 1 Alkaline Nuclease and Single-Stranded DNA Binding Protein Mediate Strand Exchange in Vitro" Journal of Virology, Jul. 2003, pp. 7245-7433 vol. 77 No. 13.
Smith, J., et al., "A Combinatorial Approach to Create Artificial Homing Endonucleases Cleaving Chosen Sequences," Nucleic Acids Res. 34(22):1-12, 2006.
Tsutakawa, Susan E. et al., "Human Flap Endonuclease Structures, DNA Double-Base Flipping, and a Unified Understanding of the FEN1 Superfamily" Cell, Apr. 15, 2011, pp. 198-211, vol. 145.

(56) References Cited

OTHER PUBLICATIONS

Vallur, et al., Complementary Roles for Exonuclease 1 and Flap Endonuclease 1 in Maintenance of Triplet Repeats, The Journal of Biological Chemistry 285(37):28514-28519, Sep. 10, 2010.
Yoon, Jung-Hoon et al., "Characterization of the 3'→5' Exonuclease Activity Found in Human Nucleoside Diphosphate Kinase 1 (NDK1) and Several of Its Homologues" Biochemistry, 2005, pp. 15774-15786 vol. 44.
Zhang, Jinjin et al., "Crystal Structure of *E. coli* RecE Protein Reveals a Toroidal Tetramer for Processing Double-Stranded DNA Breaks" Structure, May 13, 2009, pp. 690-702, vol. 17.

* cited by examiner

Sce

| SEQ ID NO | |
|---|---|
| 10 | TAGGTCAGGGTTCACACTAGTTAGGGATAACAGGGTAATACCTGCAGGTTGCCGGTGGTGCA |
| 11 | TAGGTCAGGGTTCACACTAGTTAGG---------GTAATACCTGCAGGTTGCCGGTGGTGCA |
| 12 | TAGGTCAGGGTTCACACTAGTTAGGGATAACAGGGTAATACCTGCAGGTTGCCGGTGGTGCA |
| 13 | TAGGTCAGGGTTCACACTAGTTAGGGATAACAGGGTAATACCTGCAGGTTGCCGGTGGTGCA |
| 14 | TAGGTCAGGGTTCACACTAGTTAGGGATAACAGGGTAATACCTGCAGGTTGCCGGTGGTGCA |
| 15 | TAGGTCAGGGTTCACACTAGTTAGGGATAACAGGGTAATACCTGCAGGTTGCCGGTGGTGCA |
| 16 | TAGGTCAGGGTTCACACTAGTTAGGGATAACAGGGTAATACCTGCAGGTTGCCGGTGGTGCA |
| 17 | TAGGTCAGGGTTCACACTAG------ATAACAGGGTAATACCTGCAGGTTGCCGGTGGTGCA |
| 18 | TAGGTCAGGGTTCACACTAGTTAGGGATA-CAGGGTAATACCTGCAGGTTGCCGGTGGTGCA |
| 19 | TAGGTCAGGGTTCACACTAGTTAGGGATAACAGGGTAATACCTGCAGGTTGCCGGTGGTGCA |
| 20 | TAGGTCAGGGTTCACACTAGTTAGG---------GTAATACCTGCAAGTTGCCGGTGGTGCA |
| 21 | TAGGTCAGGGTTCACACTAGTTAGGGA---------------TGCAGGTTGCCGGTGGTGCA |
| 22 | TAGGTCAGGGTTCACACTAGTTAGGGATAACAGGGTAATACCTGCAGGTTGCCGGTGGTGCA |
| 23 | TAGGTCAGGGTTCACACTA-------------------TACCTGCAGGTTGCCGGTGGTGCA |
| 24 | TAGGTCAGGGTTCACACTAGTTAGGGATAACAGGGTAATACCTGCAGGTTGCCGGTGGTGCA |
| 25 | TAGGTCAGGGTTCACACTAGTTAGGGATAACAGGGTAATACCTGCAGGTTGCCGGTGGTGCA |
| 26 | TAGGTCAGGGTTCACACTAGTTAGGGATAACAGGGTAATACCTGCAGGTTGCCGGTGGTGCA |
| 27 | TAGGTCAGGGTTCACACTAGGTAGGTA-----GGGCAA--CCTGCAGGTTGCCGGTGGTGCA |
| 28 | TAGGTCAGGGTTCACACTAGTTAGGGATAACAGGGTAATACCTGCAGGTTGCCGGTGGTGCA |
| 29 | TAGGTCAGGGTTCACACTAGTTAGGGATAACAGGGTAATACCTGCAGGTTGCCGGTGGTGCA |
| 30 | TAGGTCAGGGTTCACACTAGTTAGGGATAACAGGGTAATACCTGCAGGTTGCCGGTGGTGCA |
| 31 | TAGGTCAGGGTTCACACTAGTTAGGGATAACAGGGTAATACCTGCAGGTTGCCGGTGGTGCA |
| 32 | TAGGTCAGGGTTCACACTAGTTAGGGATAACAGGGTAATACCTGCAGGTTGCCGGTGGTGCA |
| 33 | TAGGTCAGGGTTCACACTAGTTAGG---------GTAATACCTGCAGGTTGCCGGTGGTGCA |
| 34 | TAGGTCAGGGTTCACACTAGTTAGGGATAACAGGGTAATACCTGCAGGTTGCCGGTGGTGCA |
| 35 | TAGGTCAGGGTTCACACTAGTTAGGGATAACAGGGTAATACCTGCAGGTTGCCGGTGGTGCA |
| 36 | TAGGTCAGGGTTCACACTAGTTAGGGATAACAGGGTAATACCTGCAGGTTGCCGGTGGTGCA |
| 37 | TAGGTCAGGGTTCACACTAGTTAGGGATAACAGGGTAATACCTGCAGGTTGCCGGTGGTGCA |
| 38 | TAGGTCAGGGTTCACACTAGTTAGGGATAAC-------TACCTGCAGGTTGCCGGTGGTGCA |
| 39 | TAGGTCAGGGTTCACACTAGTTAGGGATAACAGGGTAATACCTGCAGGTTGCCGGTGGTGCA |
| 40 | TAGGTCAGGGTTCACACTA-------ATAACAGGGTAATACCTGCAGGTTGCCGGTGGTGCA |
| 41 | TAGGTCAGGGTTCACACTAGTTAGGGATAACAGGGTAATACCTGCTGGTTGCCGGTGGTGCA |
| 42 | TAGGTCAGGGTTCACACTAGTTAGGGATAACAGGGTAATACCTGCAGGTTGCCGGTGGTGCA |
| 43 | TAGGTCAGGGTTCACACTAGTTAGGGATAACAGGGTAATACCTGCAGGTTGCCGGTGGTGCA |
| 44 | TAGGTCAGGGTTCACACTAGTTAGG---------GTAATACCTGCAAGTTGCCGGTGGTGCC |
| 45 | TAGGTCAGGGTTCACACTAGTTAGGGATAACAGGGTAATACCTGCAGGTTGCCGGTGGTGCA |
| 46 | TAGGTCAGGGTTCACACTAGTTAGG-ATAACAGGGTAATACCTGCAGGTTGCCGGTGGTGCA |
| 47 | TAGGTCAGGGTTCACACTAGTTAGG-ATAACAGGGTAATACCTGCAGGTTGCCGGTGGTGCA |
| 48 | TAGGTCAGGGTTCACACTAGTTAGGGATAACAGGGTAATACCTGCAGGTTGCCGGTGGTGCA |
| 49 | TAGGTCAGGGTTCACACTAGTTAGGGATAACAGGGTAATACCTGCAGGTTGCCGGTGGTGCA |
| 50 | TAGGTCAGGGTTCACACTAGTTAGGGATAACAGGGTAATACCTGCAGGTTGCCGGTGGTGCA |
| 51 | TAGGTCAGGGTTCACACTAGTTAGG-ATAACAGGGTAATACCTGCAGGTTGCCGGTGGTGCA |
| 52 | TAGGTCAGGGTTCACACTAG------ATAACAGGGTAATACCTGCAGGTTGCCGGTGGTGCA |
| 53 | TAGGTCAGGGTTCACACTAGTTAGGGATAACAGGGTAATACCTGCAGGTTACCGGTGGTGCA |
| 54 | TAGGTCAGGGTTCACACTAGTTAGGGATAACAGGGTAATACCTGCAGGTTGCCGGTGGTGCA |
| 55 | TAGGTCAGGGTTCACACTAGTTAGGGATAACAGGGTAATACATGCAGGTTGCCGGTGGTGCA |
| 56 | TAGGTCAGGGTTCACACTAGTTAGGGATAACAGGGTAATACCTGCAGGTTGCCGGTGGTGCA |
| 57 | TAGGTCAGGGTTCACACTAGTTAGGGATAACAGGGTAATACCTGCAGGTTGCCGGTGGTGCA |

FIG. 6A

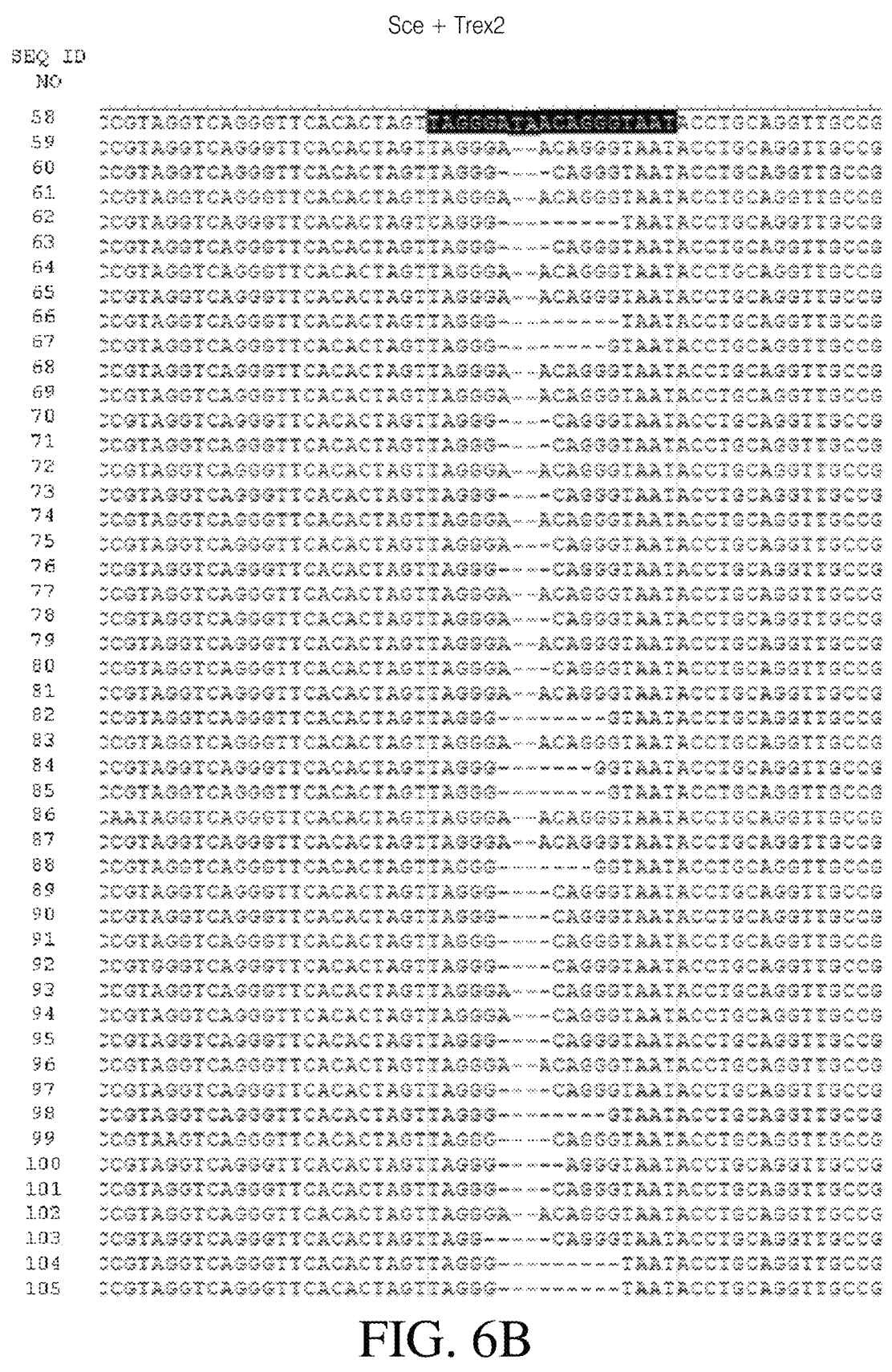

Sce + Trex2

| SEQ ID NO | |
|---|---|
| 58 | CCGTAGGTCAGGGTTCACACTAGTTAGGGATAACAGGGTAATACCTGCAGGTTGCCG |
| 59 | CCGTAGGTCAGGGTTCACACTAGTTAGGGA--ACAGGGTAATACCTGCAGGTTGCCG |
| 60 | CCGTAGGTCAGGGTTCACACTAGTTAGGG----CAGGGTAATACCTGCAGGTTGCCG |
| 61 | CCGTAGGTCAGGGTTCACACTAGTTAGGGA--ACAGGGTAATACCTGCAGGTTGCCG |
| 62 | CCGTAGGTCAGGGTTCACACTAGTCAGGG---------TAATACCTGCAGGTTGCCG |
| 63 | CCGTAGGTCAGGGTTCACACTAGTTAGGG----CAGGGTAATACCTGCAGGTTGCCG |
| 64 | CCGTAGGTCAGGGTTCACACTAGTTAGGGA--ACAGGGTAATACCTGCAGGTTGCCG |
| 65 | CCGTAGGTCAGGGTTCACACTAGTTAGGGA--ACAGGGTAATACCTGCAGGTTGCCG |
| 66 | CCGTAGGTCAGGGTTCACACTAGTTAGGG---------TAATACCTGCAGGTTGCCG |
| 67 | CCGTAGGTCAGGGTTCACACTAGTTAGGG--------GTAATACCTGCAGGTTGCCG |
| 68 | CCGTAGGTCAGGGTTCACACTAGTTAGGGA--ACAGGGTAATACCTGCAGGTTGCCG |
| 69 | CCGTAGGTCAGGGTTCACACTAGTTAGGGA--ACAGGGTAATACCTGCAGGTTGCCG |
| 70 | CCGTAGGTCAGGGTTCACACTAGTTAGGG----CAGGGTAATACCTGCAGGTTGCCG |
| 71 | CCGTAGGTCAGGGTTCACACTAGTTAGGG----CAGGGTAATACCTGCAGGTTGCCG |
| 72 | CCGTAGGTCAGGGTTCACACTAGTTAGGGA--ACAGGGTAATACCTGCAGGTTGCCG |
| 73 | CCGTAGGTCAGGGTTCACACTAGTTAGGG----CAGGGTAATACCTGCAGGTTGCCG |
| 74 | CCGTAGGTCAGGGTTCACACTAGTTAGGGA--ACAGGGTAATACCTGCAGGTTGCCG |
| 75 | CCGTAGGTCAGGGTTCACACTAGTTAGGGA---CAGGGTAATACCTGCAGGTTGCCG |
| 76 | CCGTAGGTCAGGGTTCACACTAGTTAGGG----CAGGGTAATACCTGCAGGTTGCCG |
| 77 | CCGTAGGTCAGGGTTCACACTAGTTAGGGA--ACAGGGTAATACCTGCAGGTTGCCG |
| 78 | CCGTAGGTCAGGGTTCACACTAGTTAGGGA---CAGGGTAATACCTGCAGGTTGCCG |
| 79 | CCGTAGGTCAGGGTTCACACTAGTTAGGGA--ACAGGGTAATACCTGCAGGTTGCCG |
| 80 | CCGTAGGTCAGGGTTCACACTAGTTAGGGA---CAGGGTAATACCTGCAGGTTGCCG |
| 81 | CCGTAGGTCAGGGTTCACACTAGTTAGGGA--ACAGGGTAATACCTGCAGGTTGCCG |
| 82 | CCGTAGGTCAGGGTTCACACTAGTTAGGG--------GTAATACCTGCAGGTTGCCG |
| 83 | CCGTAGGTCAGGGTTCACACTAGTTAGGGA--ACAGGGTAATACCTGCAGGTTGCCG |
| 84 | CCGTAGGTCAGGGTTCACACTAGTTAGGG-------GGTAATACCTGCAGGTTGCCG |
| 85 | CCGTAGGTCAGGGTTCACACTAGTTAGGG--------GTAATACCTGCAGGTTGCCG |
| 86 | CAATAGGTCAGGGTTCACACTAGTTAGGGA--ACAGGGTAATACCTGCAGGTTGCCG |
| 87 | CCGTAGGTCAGGGTTCACACTAGTTAGGGA--ACAGGGTAATACCTGCAGGTTGCCG |
| 88 | CCGTAGGTCAGGGTTCACACTAGTTAGGG-------GGTAATACCTGCAGGTTGCCG |
| 89 | CCGTAGGTCAGGGTTCACACTAGTTAGGG----CAGGGTAATACCTGCAGGTTGCCG |
| 90 | CCGTAGGTCAGGGTTCACACTAGTTAGGG----CAGGGTAATACCTGCAGGTTGCCG |
| 91 | CCGTAGGTCAGGGTTCACACTAGTTAGGG----CAGGGTAATACCTGCAGGTTGCCG |
| 92 | CCGTGGGTCAGGGTTCACACTAGTTAGGG----CAGGGTAATACCTGCAGGTTGCCG |
| 93 | CCGTAGGTCAGGGTTCACACTAGTTAGGGA---CAGGGTAATACCTGCAGGTTGCCG |
| 94 | CCGTAGGTCAGGGTTCACACTAGTTAGGGA---CAGGGTAATACCTGCAGGTTGCCG |
| 95 | CCGTAGGTCAGGGTTCACACTAGTTAGGG----CAGGGTAATACCTGCAGGTTGCCG |
| 96 | CCGTAGGTCAGGGTTCACACTAGTTAGGGA--ACAGGGTAATACCTGCAGGTTGCCG |
| 97 | CCGTAGGTCAGGGTTCACACTAGTTAGGG----CAGGGTAATACCTGCAGGTTGCCG |
| 98 | CCGTAGGTCAGGGTTCACACTAGTTAGGG--------GTAATACCTGCAGGTTGCCG |
| 99 | CCGTAAGTCAGGGTTCACACTAGTTAGGG----CAGGGTAATACCTGCAGGTTGCCG |
| 100 | CCGTAGGTCAGGGTTCACACTAGTTAGGG-----AGGGTAATACCTGCAGGTTGCCG |
| 101 | CCGTAGGTCAGGGTTCACACTAGTTAGGG----CAGGGTAATACCTGCAGGTTGCCG |
| 102 | CCGTAGGTCAGGGTTCACACTAGTTAGGGA--ACAGGGTAATACCTGCAGGTTGCCG |
| 103 | CCGTAGGTCAGGGTTCACACTAGTTAGG-----CAGGGTAATACCTGCAGGTTGCCG |
| 104 | CCGTAGGTCAGGGTTCACACTAGTTAGGG---------TAATACCTGCAGGTTGCCG |
| 105 | CCGTAGGTCAGGGTTCACACTAGTTAGGG---------TAATACCTGCAGGTTGCCG |

FIG. 6B

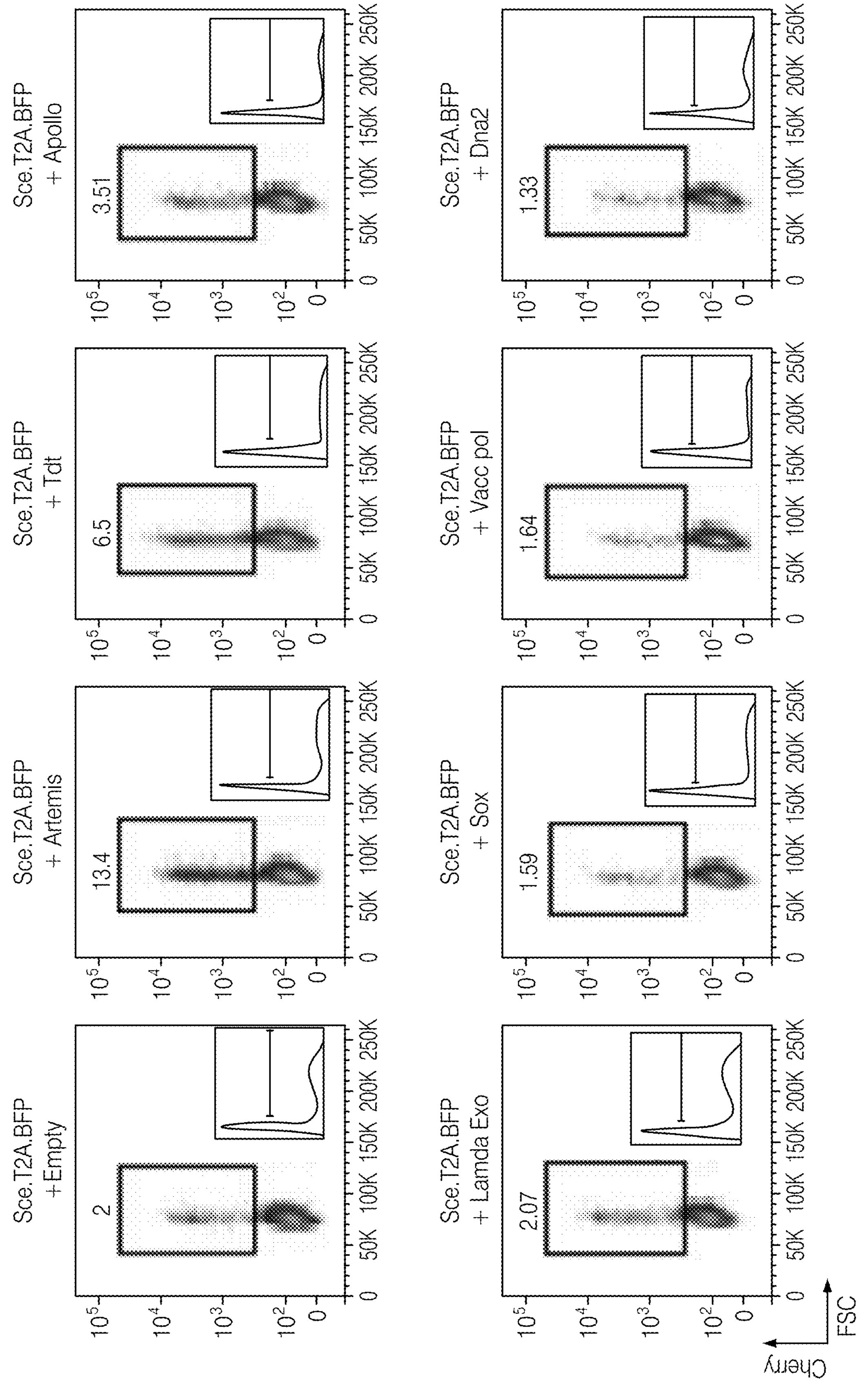
FIG. 17A$_1$

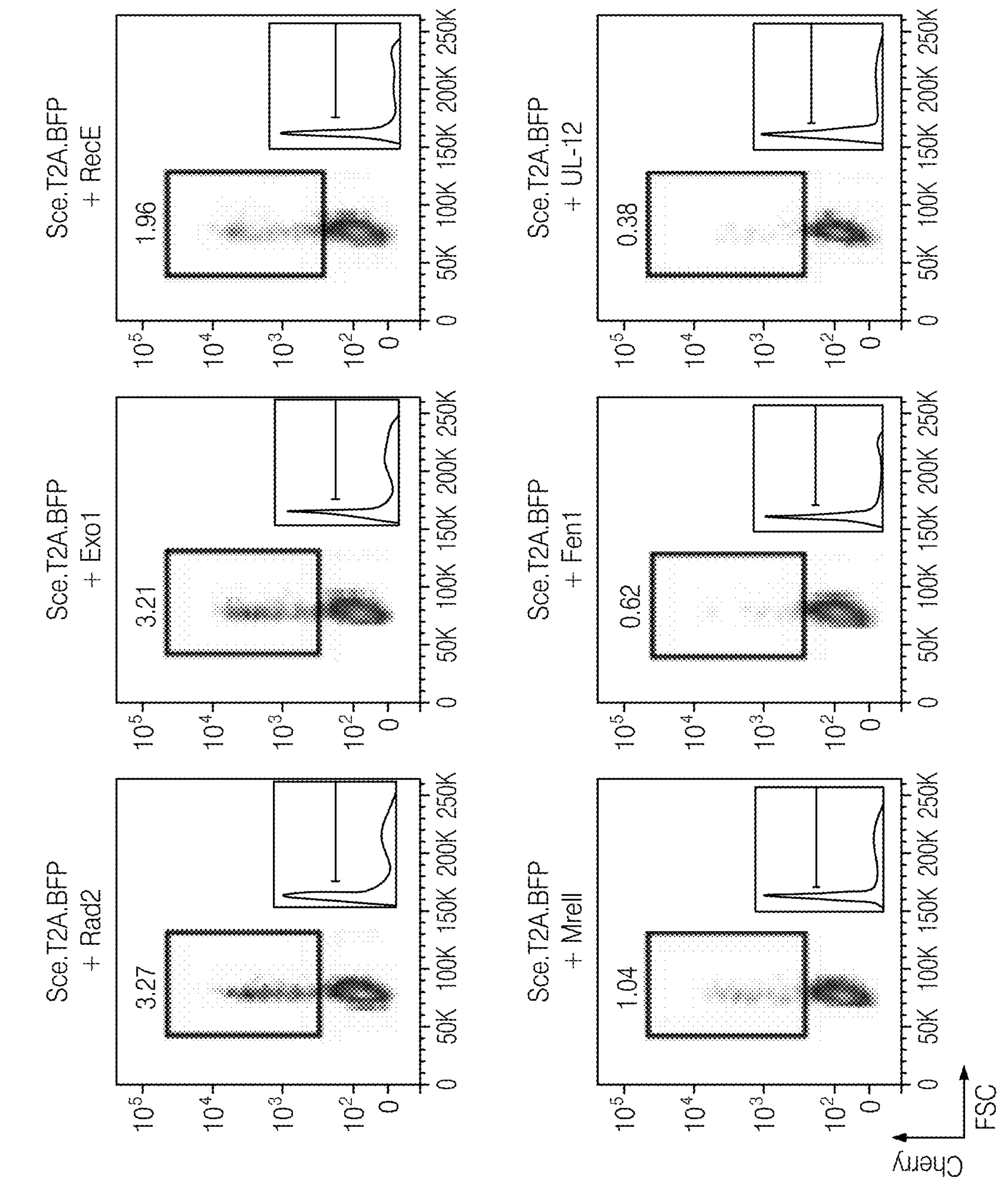
FIG. 17A$_2$

SEQUENCE LISTING

```
Sequence total quantity: 147
SEQ ID NO: 1            moltype = DNA  length = 18
FEATURE                 Location/Qualifiers
misc_feature            1..18
                        note = Sequence of the I-SceI target site
source                  1..18
                        mol_type = other DNA
                        organism = synthetic construct
SEQUENCE: 1
tagggataac agggtaat                                                18

SEQ ID NO: 2            moltype = DNA  length = 22
FEATURE                 Location/Qualifiers
misc_feature            1..22
                        note = Sequence of the I-LtrI target site
source                  1..22
                        mol_type = other DNA
                        organism = synthetic construct
SEQUENCE: 2
aatgctccta tacgacgttt ag                                           22

SEQ ID NO: 3            moltype = DNA  length = 22
FEATURE                 Location/Qualifiers
misc_feature            1..22
                        note = Sequence of the I-GpiI target site
source                  1..22
                        mol_type = other DNA
                        organism = synthetic construct
SEQUENCE: 3
ttttcctgta tatgacttaa at                                           22

SEQ ID NO: 4            moltype = DNA  length = 22
FEATURE                 Location/Qualifiers
misc_feature            1..22
                        note = Sequence of the I-GzeI target site
source                  1..22
                        mol_type = other DNA
                        organism = synthetic construct
SEQUENCE: 4
gcccctcata acccgtatca ag                                           22

SEQ ID NO: 5            moltype = DNA  length = 21
FEATURE                 Location/Qualifiers
misc_feature            1..21
                        note = Sequence of the I-xMpeMI target site
source                  1..21
                        mol_type = other DNA
                        organism = synthetic construct
SEQUENCE: 5
tagataacca taagtgctaa t                                            21

SEQ ID NO: 6            moltype = DNA  length = 22
FEATURE                 Location/Qualifiers
misc_feature            1..22
                        note = Sequence of the I-PanMI target site
source                  1..22
```

-continued

```
                       mol_type = other DNA
                       organism = synthetic construct
SEQUENCE: 6
gctcctcata atccttatca ag                                            22

SEQ ID NO: 7           moltype = DNA  length = 24
FEATURE                Location/Qualifiers
misc_feature           1..24
                       note = Sequence of the I-CreI target site
source                 1..24
                       mol_type = other DNA
                       organism = synthetic construct
SEQUENCE: 7
tcaaaacgtc gtgagacagt ttgg                                          24

SEQ ID NO: 8           moltype = DNA  length = 22
FEATURE                Location/Qualifiers
misc_feature           1..22
                       note = Sequence of the I-OnuI target site
source                 1..22
                       mol_type = other DNA
                       organism = synthetic construct
SEQUENCE: 8
tttccactta ttcaaccttt ta                                            22

SEQ ID NO: 9           moltype = DNA  length = 22
FEATURE                Location/Qualifiers
misc_feature           1..22
                       note = Sequence of the I-HjeMI target site
source                 1..22
                       mol_type = other DNA
                       organism = synthetic construct
SEQUENCE: 9
ttgaggaggt ttctctgtta at                                            22

SEQ ID NO: 10          moltype = DNA  length = 20
FEATURE                Location/Qualifiers
misc_feature           1..20
                       note = Sequence of the I-AniI target site
source                 1..20
                       mol_type = other DNA
                       organism = synthetic construct
SEQUENCE: 10
tgaggaggtt tctctgtaaa                                               20

SEQ ID NO: 11          moltype = DNA  length = 53
FEATURE                Location/Qualifiers
misc_feature           1..53
                       note = Sequence of amplicon surrounding the I-SceI target
                        site treated with I-SceI.
source                 1..53
                       mol_type = other DNA
                       organism = synthetic construct
SEQUENCE: 11
taggtcaggg ttcacactag ttagggtaat acctgcaggt tgccggtggt gca          53

SEQ ID NO: 12          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 12
taggtcaggg ttcacactag ttagggataa cagggtaata cctgcaggtt gccggtggtg  60
ca                                                                  62

SEQ ID NO: 13          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 13
taggtcaggg ttcacactag ttagggataa cagggtaata cctgcaggtt gccggtggtg  60
ca                                                                  62
```

-continued

```
SEQ ID NO: 14          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 14
taggtcaggg ttcacactag ttagggataa cagggtaata cctgcaggtt gccggtggtg  60
ca                                                                 62

SEQ ID NO: 15          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 15
taggtcaggg ttcacactag ttagggataa cagggtaata cctgcaggtt gccggtggtg  60
ca                                                                 62

SEQ ID NO: 16          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 16
taggtcaggg ttcacactag ttagggataa cagggtaata cctgcaggtt gccggtggtg  60
ca                                                                 62

SEQ ID NO: 17          moltype = DNA  length = 56
FEATURE                Location/Qualifiers
misc_feature           1..56
                       note = Sequence of amplicon surrounding the I-SceI target
                        site treated with I-SceI.
source                 1..56
                       mol_type = other DNA
                       organism = synthetic construct
SEQUENCE: 17
taggtcaggg ttcacactag ataacagggt aatacctgca ggttgccggt ggtgca      56

SEQ ID NO: 18          moltype = DNA  length = 61
FEATURE                Location/Qualifiers
misc_feature           1..61
                       note = Sequence of amplicon surrounding the I-SceI target
                        site treated with I-SceI.
source                 1..61
                       mol_type = other DNA
                       organism = synthetic construct
SEQUENCE: 18
taggtcaggg ttcacactag ttagggatac agggtaatac ctgcaggttg ccggtggtgc  60
a                                                                  61

SEQ ID NO: 19          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 19
taggtcaggg ttcacactag ttagggataa cagggtaata cctgcaggtt gccggtggtg  60
ca                                                                 62

SEQ ID NO: 20          moltype = DNA  length = 53
FEATURE                Location/Qualifiers
misc_feature           1..53
                       note = Sequence of amplicon surrounding the I-SceI target
                        site treated with I-SceI.
source                 1..53
                       mol_type = other DNA
```

-continued

```
                      organism = synthetic construct
SEQUENCE: 20
taggtcaggg ttcacactag ttagggtaat acctgcaggt tgccggtggt gca          53

SEQ ID NO: 21          moltype = DNA  length = 47
FEATURE                Location/Qualifiers
misc_feature           1..47
                       note = Sequence of amplicon surrounding the I-SceI target
                        site treated with I-SceI.
source                 1..47
                       mol_type = other DNA
                       organism = synthetic construct
SEQUENCE: 21
taggtcaggg ttcacactag ttagggatgc aggttgccgg tggtgca                 47

SEQ ID NO: 22          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 22
taggtcaggg ttcacactag ttagggataa cagggtaata cctgcaggtt gccggtggtg  60
ca                                                                  62

SEQ ID NO: 23          moltype = DNA  length = 43
FEATURE                Location/Qualifiers
misc_feature           1..43
                       note = Sequence of amplicon surrounding the I-SceI target
                        site treated with I-SceI.
source                 1..43
                       mol_type = other DNA
                       organism = synthetic construct
SEQUENCE: 23
taggtcaggg ttcacactat acctgcaggt tgccggtggt gca                     43

SEQ ID NO: 24          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 24
taggtcaggg ttcacactag ttagggataa cagggtaata cctgcaggtt gccggtggtg  60
ca                                                                  62

SEQ ID NO: 25          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 25
taggtcaggg ttcacactag ttagggataa cagggtaata cctgcaggtt gccggtggtg  60
ca                                                                  62

SEQ ID NO: 26          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 26
taggtcaggg ttcacactag ttagggataa cagggtaata cctgcaggtt gccggtggtg  60
ca                                                                  62

SEQ ID NO: 27          moltype = DNA  length = 55
FEATURE                Location/Qualifiers
misc_feature           1..55
                       note = Sequence of amplicon surrounding the I-SceI target
                        site treated with I-SceI.
```

-continued

```
source                1..55
                      mol_type = other DNA
                      organism = synthetic construct
SEQUENCE: 27
taggtcaggg ttcacactag ttaggtaggg caacctgcag gttgccggtg gtgca       55

SEQ ID NO: 28         moltype = DNA  length = 62
FEATURE               Location/Qualifiers
misc_feature          1..62
                      note = Sequence of amplicon surrounding the I-SceI target
                       site treated with I-SceI.
source                1..62
                      mol_type = other DNA
                      organism = synthetic construct
SEQUENCE: 28
taggtcaggg ttcacactag ttagggataa cagggtaata cctgcaggtt gccggtggtg  60
ca                                                                 62

SEQ ID NO: 29         moltype = DNA  length = 62
FEATURE               Location/Qualifiers
misc_feature          1..62
                      note = Sequence of amplicon surrounding the I-SceI target
                       site treated with I-SceI.
source                1..62
                      mol_type = other DNA
                      organism = synthetic construct
SEQUENCE: 29
taggtcaggg ttcacactag ttagggataa cagggtaata cctgcaggtt gccggtggtg  60
ca                                                                 62

SEQ ID NO: 30         moltype = DNA  length = 62
FEATURE               Location/Qualifiers
misc_feature          1..62
                      note = Sequence of amplicon surrounding the I-SceI target
                       site treated with I-SceI.
source                1..62
                      mol_type = other DNA
                      organism = synthetic construct
SEQUENCE: 30
taggtcaggg ttcacactag ttagggataa cagggtaata cctgcaggtt gccggtggtg  60
ca                                                                 62

SEQ ID NO: 31         moltype = DNA  length = 62
FEATURE               Location/Qualifiers
misc_feature          1..62
                      note = Sequence of amplicon surrounding the I-SceI target
                       site treated with I-SceI.
source                1..62
                      mol_type = other DNA
                      organism = synthetic construct
SEQUENCE: 31
taggtcaggg ttcacactag ttagggataa cagggtaata cctgcaggtt gccggtggtg  60
ca                                                                 62

SEQ ID NO: 32         moltype = DNA  length = 62
FEATURE               Location/Qualifiers
misc_feature          1..62
                      note = Sequence of amplicon surrounding the I-SceI target
                       site treated with I-SceI.
source                1..62
                      mol_type = other DNA
                      organism = synthetic construct
SEQUENCE: 32
taggtcaggg ttcacactag ttagggataa cagggtaata cctgcaggtt gccggtggtg  60
ca                                                                 62

SEQ ID NO: 33         moltype = DNA  length = 53
FEATURE               Location/Qualifiers
misc_feature          1..53
                      note = Sequence of amplicon surrounding the I-SceI target
                       site treated with I-SceI.
source                1..53
                      mol_type = other DNA
                      organism = synthetic construct
SEQUENCE: 33
taggtcaggg ttcacactag ttagggtaat acctgcaggt tgccggtggt gca         53

SEQ ID NO: 34         moltype = DNA  length = 62
FEATURE               Location/Qualifiers
```

```
misc_feature           1..62
                       note = Sequence of amplicon surrounding the I-SceI target
                        site treated with I-SceI.
source                 1..62
                       mol_type = other DNA
                       organism = synthetic construct
SEQUENCE: 34
taggtcaggg ttcacactag ttagggataa cagggtaata cctgcaggtt gccggtggtg  60
ca                                                                 62

SEQ ID NO: 35          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 35
taggtcaggg ttcacactag ttagggataa cagggtaata cctgcaggtt gccggtggtg  60
ca                                                                 62

SEQ ID NO: 36          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 36
taggtcaggg ttcacactag ttagggataa cagggtaata cctgcaggtt gccggtggtg  60
ca                                                                 62

SEQ ID NO: 37          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 37
taggtcaggg ttcacactag ttagggataa cagggtaata cctgcaggtt gccggtggtg  60
ca                                                                 62

SEQ ID NO: 38          moltype = DNA  length = 55
FEATURE                Location/Qualifiers
misc_feature           1..55
                       note = Sequence of amplicon surrounding the I-SceI target
                        site treated with I-SceI.
source                 1..55
                       mol_type = other DNA
                       organism = synthetic construct
SEQUENCE: 38
taggtcaggg ttcacactag ttagggataa ctacctgcag gttgccggtg gtgca       55

SEQ ID NO: 39          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 39
taggtcaggg ttcacactag ttagggataa cagggtaata cctgcaggtt gccggtggtg  60
ca                                                                 62

SEQ ID NO: 40          moltype = DNA  length = 55
FEATURE                Location/Qualifiers
misc_feature           1..55
                       note = Sequence of amplicon surrounding the I-SceI target
                        site treated with I-SceI.
source                 1..55
                       mol_type = other DNA
                       organism = synthetic construct
SEQUENCE: 40
taggtcaggg ttcacactaa taacagggta atacctgcag gttgccggtg gtgca       55
```

-continued

```
SEQ ID NO: 41          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 41
taggtcaggg ttcacactag ttagggataa cagggtaata cctgctggtt gccggtggtg  60
ca                                                                  62

SEQ ID NO: 42          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 42
taggtcaggg ttcacactag ttagggataa cagggtaata cctgcaggtt gccggtggtg  60
ca                                                                  62

SEQ ID NO: 43          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 43
taggtcaggg ttcacactag ttagggataa cagggtaata cctgcaggtt gccggtggtg  60
ca                                                                  62

SEQ ID NO: 44          moltype = DNA  length = 53
FEATURE                Location/Qualifiers
misc_feature           1..53
                       note = Sequence of amplicon surrounding the I-SceI target
                        site treated with I-SceI.
source                 1..53
                       mol_type = other DNA
                       organism = synthetic construct
SEQUENCE: 44
taggtcaggg ttcacactag ttagggtaat acctgcaagt tgccggtggt gcc          53

SEQ ID NO: 45          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 45
taggtcaggg ttcacactag ttagggataa cagggtaata cctgcaggtt gccggtggtg  60
ca                                                                  62

SEQ ID NO: 46          moltype = DNA  length = 61
FEATURE                Location/Qualifiers
misc_feature           1..61
                       note = Sequence of amplicon surrounding the I-SceI target
                        site treated with I-SceI.
source                 1..61
                       mol_type = other DNA
                       organism = synthetic construct
SEQUENCE: 46
taggtcaggg ttcacactag ttaggataac agggtaatac ctgcaggttg ccggtggtgc  60
a                                                                   61

SEQ ID NO: 47          moltype = DNA  length = 61
FEATURE                Location/Qualifiers
misc_feature           1..61
                       note = Sequence of amplicon surrounding the I-SceI target
                        site treated with I-SceI.
source                 1..61
                       mol_type = other DNA
```

```
                       organism = synthetic construct
SEQUENCE: 47
taggtcaggg ttcacactag ttaggataac agggtaatac ctgcaggttg ccggtggtgc  60
a                                                                  61

SEQ ID NO: 48          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 48
taggtcaggg ttcacactag ttagggataa cagggtaata cctgcaggtt gccggtggtg  60
ca                                                                 62

SEQ ID NO: 49          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 49
taggtcaggg ttcacactag ttagggataa cagggtaata cctgcaggtt gccggtggtg  60
ca                                                                 62

SEQ ID NO: 50          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 50
taggtcaggg ttcacactag ttagggataa cagggtaata cctgcaggtt gccggtggtg  60
ca                                                                 62

SEQ ID NO: 51          moltype = DNA  length = 61
FEATURE                Location/Qualifiers
misc_feature           1..61
                       note = Sequence of amplicon surrounding the I-SceI target
                        site treated with I-SceI.
source                 1..61
                       mol_type = other DNA
                       organism = synthetic construct
SEQUENCE: 51
taggtcaggg ttcacactag ttaggataac agggtaatac ctgcaggttg ccggtggtgc  60
a                                                                  61

SEQ ID NO: 52          moltype = DNA  length = 56
FEATURE                Location/Qualifiers
misc_feature           1..56
                       note = Sequence of amplicon surrounding the I-SceI target
                        site treated with I-SceI.
source                 1..56
                       mol_type = other DNA
                       organism = synthetic construct
SEQUENCE: 52
taggtcaggg ttcacactag ataacagggt aatacctgca ggttgccggt ggtgca      56

SEQ ID NO: 53          moltype = DNA  length = 62
FEATURE                Location/Qualifiers
misc_feature           1..62
                       note = Sequence of amplicon surrounding the I-SceI target
                        site treated with I-SceI.
source                 1..62
                       mol_type = other DNA
                       organism = synthetic construct
SEQUENCE: 53
taggtcaggg ttcacactag ttagggataa cagggtaata cctgcaggtt accggtggtg  60
ca                                                                 62

SEQ ID NO: 54          moltype = DNA  length = 62
FEATURE                Location/Qualifiers
misc_feature           1..62
```

-continued

```
                        note = Sequence of amplicon surrounding the I-SceI target
                         site treated with I-SceI.
source                  1..62
                        mol_type = other DNA
                        organism = synthetic construct
SEQUENCE: 54
taggtcaggg ttcacactag ttagggataa cagggtaata cctgcaggtt gccggtggtg  60
ca                                                                 62

SEQ ID NO: 55           moltype = DNA  length = 62
FEATURE                 Location/Qualifiers
misc_feature            1..62
                        note = Sequence of amplicon surrounding the I-SceI target
                         site treated with I-SceI.
source                  1..62
                        mol_type = other DNA
                        organism = synthetic construct
SEQUENCE: 55
taggtcaggg ttcacactag ttagggataa cagggtaata catgcaggtt gccggtggtg  60
ca                                                                 62

SEQ ID NO: 56           moltype = DNA  length = 62
FEATURE                 Location/Qualifiers
misc_feature            1..62
                        note = Sequence of amplicon surrounding the I-SceI target
                         site treated with I-SceI.
source                  1..62
                        mol_type = other DNA
                        organism = synthetic construct
SEQUENCE: 56
taggtcaggg ttcacactag ttagggataa cagggtaata cctgcaggtt gccggtggtg  60
ca                                                                 62

SEQ ID NO: 57           moltype = DNA  length = 62
FEATURE                 Location/Qualifiers
misc_feature            1..62
                        note = Sequence of amplicon surrounding the I-SceI target
                         site treated with I-SceI.
source                  1..62
                        mol_type = other DNA
                        organism = synthetic construct
SEQUENCE: 57
taggtcaggg ttcacactag ttagggataa cagggtaata cctgcaggtt gccggtggtg  60
ca                                                                 62

SEQ ID NO: 58           moltype = DNA  length = 62
FEATURE                 Location/Qualifiers
misc_feature            1..62
                        note = Sequence of amplicon surrounding the I-SceI target
                         site treated with I-SceI and Trex2.
source                  1..62
                        mol_type = other DNA
                        organism = synthetic construct
SEQUENCE: 58
ccgtaggtca gggttcacac tagttaggga taacagggta atacctgcag gttgccggtg  60
gt                                                                 62

SEQ ID NO: 59           moltype = DNA  length = 60
FEATURE                 Location/Qualifiers
misc_feature            1..60
                        note = Sequence of amplicon surrounding the I-SceI target
                         site treated with I-SceI and Trex2.
source                  1..60
                        mol_type = other DNA
                        organism = synthetic construct
SEQUENCE: 59
ccgtaggtca gggttcacac tagttaggga acagggtaat acctgcaggt tgccggtggt  60

SEQ ID NO: 60           moltype = DNA  length = 58
FEATURE                 Location/Qualifiers
misc_feature            1..58
                        note = Sequence of amplicon surrounding the I-SceI target
                         site treated with I-SceI and Trex2.
source                  1..58
                        mol_type = other DNA
                        organism = synthetic construct
SEQUENCE: 60
ccgtaggtca gggttcacac tagttagggc agggtaatac ctgcaggttg ccggtggt    58
```

-continued

```
SEQ ID NO: 61          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 61
ccgtaggtca gggttcacac tagttaggga acagggtaat acctgcaggt tgccggtggt  60

SEQ ID NO: 62          moltype = DNA  length = 53
FEATURE                Location/Qualifiers
misc_feature           1..53
                       note = Sequence of amplicon surrounding the I-SceI target
                        site treated with I-SceI and Trex2.
source                 1..53
                       mol_type = other DNA
                       organism = synthetic construct
SEQUENCE: 62
ccgtaggtca gggttcacac tagtcagggt aatacctgca ggttgccggt ggt         53

SEQ ID NO: 63          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 63
ccgtaggtca gggttcacac tagttagggc agggtaatac ctgcaggttg ccggtggt    58

SEQ ID NO: 64          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 64
ccgtaggtca gggttcacac tagttaggga acagggtaat acctgcaggt tgccggtggt  60

SEQ ID NO: 65          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 65
ccgtaggtca gggttcacac tagttaggga acagggtaat acctgcaggt tgccggtggt  60

SEQ ID NO: 66          moltype = DNA  length = 53
FEATURE                Location/Qualifiers
misc_feature           1..53
                       note = Sequence of amplicon surrounding the I-SceI target
                        site treated with I-SceI and Trex2.
source                 1..53
                       mol_type = other DNA
                       organism = synthetic construct
SEQUENCE: 66
ccgtaggtca gggttcacac tagttagggt aatacctgca ggttgccggt ggt         53

SEQ ID NO: 67          moltype = DNA  length = 54
FEATURE                Location/Qualifiers
misc_feature           1..54
                       note = Sequence of amplicon surrounding the I-SceI target
                        site treated with I-SceI and Trex2.
source                 1..54
                       mol_type = other DNA
                       organism = synthetic construct
SEQUENCE: 67
ccgtaggtca gggttcacac tagttagggg taatacctgc aggttgccgg tggt        54

SEQ ID NO: 68          moltype = DNA  length = 60
FEATURE                Location/Qualifiers
```

-continued

```
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 68
ccgtaggtca gggttcacac tagttaggga acagggtaat acctgcaggt tgccggtggt  60

SEQ ID NO: 69          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 69
ccgtaggtca gggttcacac tagttaggga acagggtaat acctgcaggt tgccggtggt  60

SEQ ID NO: 70          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 70
ccgtaggtca gggttcacac tagttagggc agggtaatac ctgcaggttg ccggtggt    58

SEQ ID NO: 71          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 71
ccgtaggtca gggttcacac tagttagggc agggtaatac ctgcaggttg ccggtggt    58

SEQ ID NO: 72          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 72
ccgtaggtca gggttcacac tagttaggga acagggtaat acctgcaggt tgccggtggt  60

SEQ ID NO: 73          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 73
ccgtaggtca gggttcacac tagttagggc agggtaatac ctgcaggttg ccggtggt    58

SEQ ID NO: 74          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 74
ccgtaggtca gggttcacac tagttaggga acagggtaat acctgcaggt tgccggtggt  60

SEQ ID NO: 75          moltype = DNA  length = 59
FEATURE                Location/Qualifiers
misc_feature           1..59
                       note = Sequence of amplicon surrounding the I-SceI target
```

-continued

```
                       site treated with I-SceI and Trex2.
source                 1..59
                       mol_type = other DNA
                       organism = synthetic construct
SEQUENCE: 75
ccgtaggtca gggttcacac tagttaggga cagggtaata cctgcaggtt gccggtggt   59

SEQ ID NO: 76          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 76
ccgtaggtca gggttcacac tagttagggc aggtaatacc tgcaggtttg ccggtggt    58

SEQ ID NO: 77          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 77
ccgtaggtca gggttcacac tagttaggga acagggtaat acctgcaggt tgccggtggt  60

SEQ ID NO: 78          moltype = DNA  length = 59
FEATURE                Location/Qualifiers
misc_feature           1..59
                       note = Sequence of amplicon surrounding the I-SceI target
                        site treated with I-SceI and Trex2.
source                 1..59
                       mol_type = other DNA
                       organism = synthetic construct
SEQUENCE: 78
ccgtaggtca gggttcacac tagttaggga cagggtaata cctgcaggtt gccggtggt   59

SEQ ID NO: 79          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 79
ccgtaggtca gggttcacac tagttaggga acagggtaat acctgcaggt tgccggtggt  60

SEQ ID NO: 80          moltype = DNA  length = 59
FEATURE                Location/Qualifiers
misc_feature           1..59
                       note = Sequence of amplicon surrounding the I-SceI target
                        site treated with I-SceI and Trex2.
source                 1..59
                       mol_type = other DNA
                       organism = synthetic construct
SEQUENCE: 80
ccgtaggtca gggttcacac tagttaggga cagggtaata cctgcaggtt gccggtggt   59

SEQ ID NO: 81          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 81
ccgtaggtca gggttcacac tagttaggga acagggtaat acctgcaggt tgccggtggt  60

SEQ ID NO: 82          moltype = DNA  length = 54
FEATURE                Location/Qualifiers
misc_feature           1..54
                       note = Sequence of amplicon surrounding the I-SceI target
                        site treated with I-SceI and Trex2.
source                 1..54
```

```
                        mol_type = other DNA
                        organism = synthetic construct
SEQUENCE: 82
ccgtaggtca gggttcacac tagttagggg taatacctgc aggttgccgg tggt        54

SEQ ID NO: 83           moltype = DNA  length = 60
FEATURE                 Location/Qualifiers
misc_feature            1..60
                        note = Sequence of amplicon surrounding the I-SceI target
                         site treated with I-SceI and Trex2.
source                  1..60
                        mol_type = other DNA
                        organism = synthetic construct
SEQUENCE: 83
ccgtaggtca gggttcacac tagttaggga acagggtaat acctgcaggt tgccggtggt  60

SEQ ID NO: 84           moltype = DNA  length = 55
FEATURE                 Location/Qualifiers
misc_feature            1..55
                        note = Sequence of amplicon surrounding the I-SceI target
                         site treated with I-SceI and Trex2.
source                  1..55
                        mol_type = other DNA
                        organism = synthetic construct
SEQUENCE: 84
ccgtaggtca gggttcacac tagttagggg gtaatacctg caggttgccg gtggt       55

SEQ ID NO: 85           moltype = DNA  length = 54
FEATURE                 Location/Qualifiers
misc_feature            1..54
                        note = Sequence of amplicon surrounding the I-SceI target
                         site treated with I-SceI and Trex2.
source                  1..54
                        mol_type = other DNA
                        organism = synthetic construct
SEQUENCE: 85
ccgtaggtca gggttcacac tagttagggg taatacctgc aggttgccgg tggt        54

SEQ ID NO: 86           moltype = DNA  length = 60
FEATURE                 Location/Qualifiers
misc_feature            1..60
                        note = Sequence of amplicon surrounding the I-SceI target
                         site treated with I-SceI and Trex2.
source                  1..60
                        mol_type = other DNA
                        organism = synthetic construct
SEQUENCE: 86
caataggtca gggttcacac tagttaggga acagggtaat acctgcaggt tgccggtggt  60

SEQ ID NO: 87           moltype = DNA  length = 60
FEATURE                 Location/Qualifiers
misc_feature            1..60
                        note = Sequence of amplicon surrounding the I-SceI target
                         site treated with I-SceI and Trex2.
source                  1..60
                        mol_type = other DNA
                        organism = synthetic construct
SEQUENCE: 87
ccgtaggtca gggttcacac tagttaggga acagggtaat acctgcaggt tgccggtggt  60

SEQ ID NO: 88           moltype = DNA  length = 55
FEATURE                 Location/Qualifiers
misc_feature            1..55
                        note = Sequence of amplicon surrounding the I-SceI target
                         site treated with I-SceI and Trex2.
source                  1..55
                        mol_type = other DNA
                        organism = synthetic construct
SEQUENCE: 88
ccgtaggtca gggttcacac tagttagggg gtaatacctg caggttgccg gtggt       55

SEQ ID NO: 89           moltype = DNA  length = 58
FEATURE                 Location/Qualifiers
misc_feature            1..58
                        note = Sequence of amplicon surrounding the I-SceI target
                         site treated with I-SceI and Trex2.
source                  1..58
                        mol_type = other DNA
                        organism = synthetic construct
```

```
SEQUENCE: 89
ccgtaggtca gggttcacac tagttagggc agggtaatac ctgcaggttg ccggtggt    58

SEQ ID NO: 90          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 90
ccgtaggtca gggttcacac tagttagggc agggtaatac ctgcaggttg ccggtggt    58

SEQ ID NO: 91          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 91
ccgtaggtca gggttcacac tagttagggc agggtaatac ctgcaggttg ccggtggt    58

SEQ ID NO: 92          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 92
ccgtgggtca gggttcacac tagttagggc agggtaatac ctgcaggttg ccggtggt    58

SEQ ID NO: 93          moltype = DNA  length = 59
FEATURE                Location/Qualifiers
misc_feature           1..59
                       note = Sequence of amplicon surrounding the I-SceI target
                        site treated with I-SceI and Trex2.
source                 1..59
                       mol_type = other DNA
                       organism = synthetic construct
SEQUENCE: 93
ccgtaggtca gggttcacac tagttaggga cagggtaata cctgcaggtt gccggtggt   59

SEQ ID NO: 94          moltype = DNA  length = 59
FEATURE                Location/Qualifiers
misc_feature           1..59
                       note = Sequence of amplicon surrounding the I-SceI target
                        site treated with I-SceI and Trex2.
source                 1..59
                       mol_type = other DNA
                       organism = synthetic construct
SEQUENCE: 94
ccgtaggtca gggttcacac tagttaggga cagggtaata cctgcaggtt gccggtggt   59

SEQ ID NO: 95          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 95
ccgtaggtca gggttcacac tagttagggc agggtaatac ctgcaggttg ccggtggt    58

SEQ ID NO: 96          moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 96
ccgtaggtca gggttcacac tagttaggga acagggtaat acctgcaggt tgccggtggt  60
```

-continued

```
SEQ ID NO: 97          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 97
cagggtaata cctgcaggtt gccggtggtc agggtaatac ctgcaggttg ccggtggt    58

SEQ ID NO: 98          moltype = DNA  length = 54
FEATURE                Location/Qualifiers
misc_feature           1..54
                       note = Sequence of amplicon surrounding the I-SceI target
                        site treated with I-SceI and Trex2.
source                 1..54
                       mol_type = other DNA
                       organism = synthetic construct
SEQUENCE: 98
cagggtaata cctgcaggtt gccggtggtg taatacctgc aggttgccgg tggt        54

SEQ ID NO: 99          moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 99
cagggtaata cctgcaggtt gccggtggtc agggtaatac ctgcaggttg ccggtggt    58

SEQ ID NO: 100         moltype = DNA  length = 57
FEATURE                Location/Qualifiers
misc_feature           1..57
                       note = Sequence of amplicon surrounding the I-SceI target
                        site treated with I-SceI and Trex2.
source                 1..57
                       mol_type = other DNA
                       organism = synthetic construct
SEQUENCE: 100
ccgtaggtca gggttcacac tagttaggga gggtaatacc tgcaggttgc cggtggt     57

SEQ ID NO: 101         moltype = DNA  length = 58
FEATURE                Location/Qualifiers
misc_feature           1..58
                       note = Sequence of amplicon surrounding the I-SceI target
                        site treated with I-SceI and Trex2.
source                 1..58
                       mol_type = other DNA
                       organism = synthetic construct
SEQUENCE: 101
ccgtaggtca gggttcacac tagttagggc agggtaatac ctgcaggttg ccggtggt    58

SEQ ID NO: 102         moltype = DNA  length = 60
FEATURE                Location/Qualifiers
misc_feature           1..60
                       note = Sequence of amplicon surrounding the I-SceI target
                        site treated with I-SceI and Trex2.
source                 1..60
                       mol_type = other DNA
                       organism = synthetic construct
SEQUENCE: 102
ccgtaggtca gggttcacac tagttaggga acagggtaat acctgcaggt tgccggtggt  60

SEQ ID NO: 103         moltype = DNA  length = 57
FEATURE                Location/Qualifiers
misc_feature           1..57
                       note = Sequence of amplicon surrounding the I-SceI target
                        site treated with I-SceI and Trex2.
source                 1..57
                       mol_type = other DNA
                       organism = synthetic construct
SEQUENCE: 103
ccgtaggtca gggttcacac tagttaggca gggtaatacc tgcaggttgc cggtggt     57

SEQ ID NO: 104         moltype = DNA  length = 53
```

```
FEATURE                Location/Qualifiers
misc_feature           1..53
                       note = Sequence of amplicon surrounding the I-SceI target
                        site treated with I-SceI and Trex2.
source                 1..53
                       mol_type = other DNA
                       organism = synthetic construct
SEQUENCE: 104
ccgtaggtca gggttcacac tagttagggt aatacctgca ggttgccggt ggt         53

SEQ ID NO: 105         moltype = DNA  length = 53
FEATURE                Location/Qualifiers
misc_feature           1..53
                       note = Sequence of amplicon surrounding the I-SceI target
                        site treated with I-SceI and Trex2.
source                 1..53
                       mol_type = other DNA
                       organism = synthetic construct
SEQUENCE: 105
ccgtaggtca gggttcacac tagttagggt aatacctgca ggttgccggt ggt         53

SEQ ID NO: 106         moltype = DNA  length = 18
FEATURE                Location/Qualifiers
misc_feature           1..18
                       note = I-SceI target site 5'-3'
source                 1..18
                       mol_type = other DNA
                       organism = synthetic construct
SEQUENCE: 106
tagggataac agggtaat                                                18

SEQ ID NO: 107         moltype = DNA  length = 18
FEATURE                Location/Qualifiers
misc_feature           1..18
                       note = I-SceI target site 3'-5'
source                 1..18
                       mol_type = other DNA
                       organism = synthetic construct
SEQUENCE: 107
attaccctgt tatcccta                                                18

SEQ ID NO: 108         moltype = DNA  length = 24
FEATURE                Location/Qualifiers
misc_feature           1..24
                       note = VF2468 target site 5'-3'
source                 1..24
                       mol_type = other DNA
                       organism = synthetic construct
SEQUENCE: 108
gagcagcgtc ttcgagagtg agga                                         24

SEQ ID NO: 109         moltype = DNA  length = 24
FEATURE                Location/Qualifiers
misc_feature           1..24
                       note = VF2468 target site 3'-5'
source                 1..24
                       mol_type = other DNA
                       organism = synthetic construct
SEQUENCE: 109
tcctcactct cgaagacgct gctc                                         24

SEQ ID NO: 110         moltype = DNA  length = 7611
FEATURE                Location/Qualifiers
misc_feature           1..7611
                       note = Plasmid pCVL.SFFV.HA.NLS.SceOpt.IRES.mTagBFP
source                 1..7611
                       mol_type = other DNA
                       organism = synthetic construct
SEQUENCE: 110
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
```

-continued gggagaatta gatcgcgatg ggaaaaaatt cggttaaggc caggggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800
cggttaactt ttaaaagaaa aggggggatt ggggggtaca gtgcagggga aagaatagta 1860
gacataatag caacagacat acaaactaaa gaattacaaa aacaaattac aaaaattcaa 1920
aattttatcg attacgcgtc acgtgctagc tgcagtaacg ccattttgca aggcatggaa 1980
aaataccaaa ccaagaatag agaagttcag atcaagggcg ggtacatgaa aatagctaac 2040
gttgggccaa acaggatatc tgcggtgagc agtttcggcc ccggcccggg gccaagaaca 2100
gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt cccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcaag aacatcaaga agaaccaggt 2460
catgaacctg ggccccaaca gcaagctgct gaaggagtac aagagccagc tgatcgagct 2520
gaacatcgag cagttcgagg ccggcatcgg cctgatcctg ggcgacgcct acatcaggag 2580
cagggacgag ggcaagacct actgcatgca gttcgagtgg aagaacaagg cctacatgga 2640
ccacgtgtgc ctgctgtacg accagtgggt gctgagcccc ccccacaaga aggagagggt 2700
gaaccacctg ggcaacctgg tcatcacctg gggcgcccag accttcaagc accaggcctt 2760
caacaagctg gccaacctgt tcatcgtgaa caacaagaag accatcccca acaacctggt 2820
ggagaactac ctgaccccca tgagcctggc ctactggttc atggacgacg gcggcaagtg 2880
ggactacaac aagaacagca ccaacaagag catcgtgctg aacacccaga gcttcacctt 2940
cgaggaggtg gagtacctgg tgaagggcct gaggaacaag ttccagctga actgctacgt 3000
gaagatcaac aagaacaagc ccatcatcta catcgacagc atgagctacc tgatcttcta 3060
caacctgatc aagccctacc tgatccccca gatgatgtac aagctgccca acaccatcag 3120
cagcgagacc ttcctgaagt gacctgcagg tcgagcatgc atctagggcg gccaattccg 3180
cccctctccc tcccccccc ctaacgttac tggccgaagc cgcttggaat aaggccggtg 3240
tgcgtttgtc tatatgtgat tttccaccat attgccgtct tttggcaatg tgagggcccg 3300
gaaacctggc cctgtcttct tgacgagcat tcctaggggt ctttcccctc tcgccaaagg 3360
aatgcaaggt ctgttgaatg tcgtgaagga agcagttcct ctggaagctt cttgaagaca 3420
aacaacgtct gtagcgaccc tttgcaggca gcggaacccc ccacctggcg acaggtgcct 3480
ctgcggccaa aagccacgtg tataagatac acctgcaaag gcggcacaac cccagtgcca 3540
cgttgtgagt tggatagttg tggaaagagt caaatggctc tcctcaagcg tattcaacaa 3600
ggggctgaag gatgcccaga aggtacccca ttgtatggga tctgatctgg ggcctcggtg 3660
cacatgcttt acatgtgttt agtcgaggtt aaaaaaacgt ctaggccccc cgaaccacgg 3720
ggacgtggtt ttcctttgaa aaacacgatg ataagcttgc cacaaccctt accggtcgcc 3780
accatgagcg agctgattaa ggagaacatg cacatgaagc tgtacatgga gggcaccgtg 3840
gacaaccatc acttcaagtg cacatccgag ggcgaaggca agccctacga gggcacccag 3900
accatgagaa tcaaggtggt cgagggcggc cctctcccct tcgccttcga catcctggct 3960
actagcttcc tctacggcag caagaccttc atcaaccaca cccagggcat ccccgacttc 4020
ttcaagcagt ccttccctga gggcttcaca tgggagagag tcaccacata cgaagacggg 4080
ggcgtgctga ccgctaccca ggacaccagc ctccaggacg gctgcctcat ctacaacgtc 4140
aagatcagag gggtgaactt cacatccaac ggccctgtga tgcagaagaa aacactcggc 4200
tgggaggcct tcaccgagac gctgtacccc gctgacggcg gcctggaagg cagaaacgac 4260
atggccctga agctcgtggg cgggagccat ctgatcgcaa acatcaagac cacatataga 4320
tccaagaaac ccgctaagaa cctcaagatg cctggcgtct actatgtgga ctacagactg 4380
gaaagaatca aggaggccaa caacgagacc tacgtcgagc agcacgaggt ggcagtggcc 4440
agatactgcg acctccctag caaactgggg cacaagctta attgattcta gagtcgaccg 4500
agcatcttac cgccatttat acccatattt gttctgtttt tcttgatttg ggtatacatt 4560
taaatgttaa tagaacaaaa tggtggggca atcatttaca tttttaggga tatgtaatta 4620
ctagttcagg tgtattgcca caagacaaac atgttaagaa actttcccgt tatttacgct 4680
ctgttcctgt taatcaacct ctggattaca aaatttgtga aagattgact gatattctta 4740
actatgttgc tccttttacg ctgtgtggat atgctgcttt atagcctctg tatctagcta 4800
ttgcttcccg tacggctttc gttttctcct ccttgtataa atcctggttg ctgtctcttt 4860
tagaggagtt gtggcccgtt gtccgtcaac gtggcgtggt gtgctctgtg tttgctgacg 4920
caacccccac tggctggggc attgccacca cctgtcaact cctttctggg actttcgctt 4980
tccccctccc gatcgccacg gcagaactca tcgccgcctg ccttgcccgc tgctggacag 5040
gggctaggtt gctgggcact gataattccg tggtgttgtc atcggtacct ttttaaaaga 5100
aaaggggggga ctggaagggc taattcactc ccaacgaaga caagatatca taacttcgta 5160
tagcatacat tatacgaagt tataatttat ttgtgaaatt tgtgatgcta ttgctttatt 5220
tgtaaccata tgtttatttg tgaaatttgt gatgctattg ctttatttgt aaccattgct 5280
ttttgcttgt actgggtctc tctggttaga ccagatctga gcctgggagc tctctggcta 5340

-continued

```
actagggaac ccactgctta agcctcaata aagcttgcct cgaccagcct cgactgtgcc  5400
ttctagttgc cagccatctg ttgtttgccc ctcccccgtg ccttccttga ccctggaagg  5460
tgccactccc actgtccttt cctaataaaa tgaggaaatt gcatcgcatt gtctgagtag  5520
gtgtcattct attctggggg gtggggtggg gcaggacagc aagggggagg attgggaaga  5580
caatagcagg catgctgggg atgcggtggg ctctatggcc tgcagctgca ttaatgaatc  5640
ggccaacgcg cggggagagg cggtttgcgt attgggcgct cttccgcttc ctcgctcact  5700
gactcgctgc gctcggtcgt tcggctgcgg cgagcggtat cagctcactc aaaggcggta  5760
atacggttat ccacagaatc aggggataac gcaggaaaga acatgtgagc aaaaggccag  5820
caaaaggcca ggaaccgtaa aaaggccgcg ttgctggcgt ttttccatag gctccgcccc  5880
cctgacgagc atcacaaaaa tcgacgctca agtcagaggt ggcgaaaccc gacaggacta  5940
taaagatacc aggcgtttcc ccctggaagc tccctcgtgc gctctcctgt tccgaccctg  6000
ccgcttaccg gatacctgtc cgcctttctc ccttcgggaa gcgtggcgct ttctcatagc  6060
tcacgctgta ggtatctcag ttcggtgtag gtcgttcgct ccaagctggg ctgtgtgcac  6120
gaaccccccg ttcagcccga ccgctgcgcc ttatccggta actatcgtct tgagtccaac  6180
ccggtaagac acgacttatc gccactggca gcagccactg gtaacaggat tagcagagcg  6240
aggtatgtag gcggtgctac agagttcttg aagtggtggc ctaactacgg ctacactaga  6300
aggacagtat ttggtatctg cgctctgctg aagccagtta ccttcggaaa aagagttggt  6360
agctcttgat ccggcaaaca aaccaccgct ggtagcggtg gtttttttgt ttgcaagcag  6420
cagattacgc gcagaaaaaa aggatctcaa gaagatcctt tgatcttttc tacggggtct  6480
gacgctcagt ggaacgaaaa ctcacgttaa gggattttgg tcatgagatt atcaaaaagg  6540
atcttcacct agatcctttt aaattaaaaa tgaagtttta aatcaatcta aagtatatat  6600
gagtaaactt ggtctgacag ttaccaatgc ttaatcagtg aggcacctat ctcagcgatc  6660
tgtctatttc gttcatccat agttgcctga ctccccgtcg tgtagataac tacgatacgg  6720
gagggcttac catctggccc cagtgctgca atgataccgc gagacccacg ctcaccggct  6780
ccagatttat cagcaataaa ccagccagcc ggaagggccg agcgcagaag tggtcctgca  6840
actttatccg cctccatcca gtctattaat tgttgccggg aagctagagt aagtagttcg  6900
ccagttaata gtttgcgcaa cgttgttgcc attgctacag gcatcgtggt gtcacgctcg  6960
tcgtttggta tggcttcatt cagctccggt tcccaacgat caaggcgagt tacatgatcc  7020
cccatgttgt gcaaaaaagc ggttagctcc ttcggtcctc cgatcgttgt cagaagtaag  7080
ttggccgcag tgttatcact catggttatg gcagcactgc ataattctct tactgtcatg  7140
ccatccgtaa gatgcttttc tgtgactggt gagtactcaa ccaagtcatt ctgagaatag  7200
tgtatgcggc gaccgagttg ctcttgcccg gcgtcaatac gggataatac cgcgccacat  7260
agcagaactt taaaagtgct catcattgga aaacgttctt cggggcgaaa actctcaagg  7320
atcttaccgc tgttgagatc cagttcgatg taacccactc gtgcacccaa ctgatcttca  7380
gcatctttta ctttcaccag cgtttctggg tgagcaaaaa caggaaggca aaatgccgca  7440
aaaaagggaa taagggcgac acggaaatgt tgaatactca tactcttcct ttttcaatat  7500
tattgaagca tttatcaggg ttattgtctc atgagcggat acatatttga atgtatttag  7560
aaaaataaac aaataggggt tccgcgcaca tttccccgaa aagtgccacc t           7611

SEQ ID NO: 111          moltype = DNA  length = 7611
FEATURE                 Location/Qualifiers
misc_feature            1..7611
                        note = Plasmid pCVL.SFFV.HA.NLS.SceOptD44A.IRES.mTagBFP
source                  1..7611
                        mol_type = other DNA
                        organism = synthetic construct
SEQUENCE: 111
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
```

-continued

```
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcaag aacatcaaga agaaccaggt  2460
catgaacctg ggccccaaca gcaagctgct gaaggagtac aagagccagc tgatcgagct  2520
gaacatcgag cagttcgagg ccggcatcgg cctgatcctg ggcgctgcct acatcaggag  2580
cagggacgag ggcaagacct actgcatgca gttcgagtgg aagaacaagg cctacatgga  2640
ccacgtgtgc ctgctgtacg accagtgggt gctgagcccc ccccacaaga aggagagggt  2700
gaaccacctg ggcaacctgg tcatcacctg gggcgcccag accttcaagc accaggcctt  2760
caacaagctg gccaacctgt tcatcgtgaa caacaagaag accatcccca acaacctggt  2820
ggagaactac ctgaccccca tgagcctggc ctactggttc atggacgacg gcggcaagtg  2880
ggactacaac aagaacagca ccaacaagag catcgtgctg aacacccaga gcttcacctt  2940
cgaggaggtg gagtacctgg tgaagggcct gaggaacaag ttccagctga actgctacgt  3000
gaagatcaac aagaacaagc ccatcatcta catcgacagc atgagctacc tgatcttcta  3060
caacctgatc aagccctacc tgatccccca gatgatgtac aagctgccca acaccatcag  3120
cagcgagacc ttcctgaagt gacctgcagg tcgagcatgc atctagggcg gccaattccg  3180
cccctctccc tccccccccc ctaacgttac tggccgaagc cgcttggaat aaggccggtg  3240
tgcgtttgtc tatatgtgat tttccaccat attgccgtct tttggcaatg tgagggcccg  3300
gaaacctggc cctgtcttct tgacgagcat tcctaggggt ctttcccctc tcgccaaagg  3360
aatgcaaggt ctgttgaatg tcgtgaagga agcagttcct ctggaagctt cttgaagaca  3420
aacaacgtct gtagcgaccc tttgcaggca gcggaacccc ccacctggcg acaggtgcct  3480
ctgcggccaa aagccacgtg tataagatac acctgcaaag gcggcacaac cccagtgcca  3540
cgttgtgagt tggatagttg tggaaagagt caaatggctc tcctcaagcg tattcaacaa  3600
ggggctgaag gatgcccaga aggtacccca ttgtatggga tctgatctgg ggcctcggtg  3660
cacatgcttt acatgtgttt agtcgaggtt aaaaaaacgt ctaggccccc cgaaccacgg  3720
ggacgtggtt ttcctttgaa aaacacgatg ataagcttgc cacaaccctt accggtcgcc  3780
accatgagcg agctgattaa ggagaacatg cacatgaagc tgtacatgga gggcaccgtg  3840
gacaaccatc acttcaagtg cacatccgag ggcgaaggca agccctacga gggcacccag  3900
accatgagaa tcaaggtggt cgagggcggc cctctcccct tcgccttcga catcctggct  3960
actagcttcc tctacggcag caagaccttc atcaaccaca cccagggcat ccccgacttc  4020
ttcaagcagt ccttccctga gggcttcaca tgggagagag tcaccacata cgaagacggg  4080
ggcgtgctga ccgctaccca ggacaccagc ctccaggacg gctgcctcat ctacaacgtc  4140
aagatcagag gggtgaactt cacatccaac ggccctgtga tgcagaagaa aacactcggc  4200
tgggaggcct tcaccgagac gctgtacccc gctgacggcg gcctggaagg cagaaacgac  4260
atggccctga agctcgtggg cgggagccat ctgatcgcaa acatcaagac cacatataga  4320
tccaagaaac ccgctaagaa cctcaagatg cctggcgtct actatgtgga ctacagactg  4380
gaaagaatca aggaggccaa caacgagacc tacgtcgagc agcacgaggt ggcagtggcc  4440
agatactgcg acctccctag caaactgggg cacaagctta attgattcta gagtcgaccg  4500
agcatcttac cgccatttat acccatattt gttctgtttt tcttgatttg ggtatacatt  4560
taaatgttaa tagaacaaaa tggtggggca atcatttaca tttttaggga tatgtaatta  4620
ctagttcagg tgtattgcca caagacaaac atgttaagaa actttcccgt tatttacgct  4680
ctgttcctgt taatcaacct ctggattaca aaatttgtga aagattgact gatattctta  4740
actatgttgc tccttttacg ctgtgtggat atgctgcttt atagcctctg tatctagcta  4800
ttgcttcccg tacggctttc gttttctcct ccttgtataa atcctggttg ctgtctcttt  4860
tagaggagtt gtggcccgtt gtccgtcaac gtggcgtggt gtgctctgtg tttgctgacg  4920
caacccccac tggctggggc attgccacca cctgtcaact cctttctggg actttcgctt  4980
tccccctccc gatcgccacg gcagaactca tcgccgcctg ccttgcccgc tgctggacag  5040
gggctaggtt gctgggcact gataattccg tggtgttgtc atcggtacct ttttaaaaga  5100
aaagggggga ctggaagggc taattcactc ccaacgaaga caagatatca taacttcgta  5160
tagcatacat tatacgaagt tataatttat ttgtgaaatt tgtgatgcta ttgctttatt  5220
tgtaaccata tgtttatttg tgaaatttgt gatgctattg ctttatttgt aaccattgct  5280
ttttgcttgt actgggtctc tctggttaga ccagatctga gcctgggagc tctctggcta  5340
actagggaac ccactgctta agcctcaata aagcttgcct cgaccagcct cgactgtgcc  5400
ttctagttgc cagccatctg ttgtttgccc ctcccccgtg ccttccttga ccctggaagg  5460
tgccactccc actgtccttt cctaataaaa tgaggaaatt gcatcgcatt gtctgagtag  5520
gtgtcattct attctggggg gtggggtggg gcaggacagc aagggggagg attgggaaga  5580
caatagcagg catgctgggg atgcggtggg ctctatggcc tgcagctgca ttaatgaatc  5640
ggccaacgcg cggggagagg cggtttgcgt attgggcgct cttccgcttc ctcgctcact  5700
gactcgctgc gctcggtcgt tcggctgcgg cgagcggtat cagctcactc aaaggcggta  5760
atacggttat ccacagaatc aggggataac gcaggaaaga acatgtgagc aaaaggccag  5820
caaaaggcca ggaaccgtaa aaaggccgcg ttgctggcgt ttttccatag gctccgcccc  5880
cctgacgagc atcacaaaaa tcgacgctca agtcagaggt ggcgaaaccc gacaggacta  5940
taaagatacc aggcgtttcc ccctggaagc tccctcgtgc gctctcctgt tccgaccctg  6000
ccgcttaccg gatacctgtc cgcctttctc ccttcgggaa gcgtggcgct ttctcatagc  6060
tcacgctgta ggtatctcag ttcggtgtag gtcgttcgct ccaagctggg ctgtgtgcac  6120
gaaccccccg ttcagcccga ccgctgcgcc ttatccggta actatcgtct tgagtccaac  6180
ccggtaagac acgacttatc gccactggca gcagccactg gtaacaggat tagcagagcg  6240
aggtatgtag gcggtgctac agagttcttg aagtggtggc ctaactacgg ctacactaga  6300
aggacagtat ttggtatctg cgctctgctg aagccagtta ccttcggaaa aagagttggt  6360
agctcttgat ccggcaaaca aaccaccgct ggtagcggtg gtttttttgt ttgcaagcag  6420
cagattacgc gcagaaaaaa aggatctcaa gaagatcctt tgatcttttc tacggggtct  6480
gacgctcagt ggaacgaaaa ctcacgttaa gggattttgg tcatgagatt atcaaaaagg  6540
atcttcacct agatcctttt aaattaaaaa tgaagtttta aatcaatcta aagtatatat  6600
gagtaaactt ggtctgacag ttaccaatgc ttaatcagtg aggcacctat ctcagcgatc  6660
```

-continued

```
tgtctatttc gttcatccat agttgcctga ctccccgtcg tgtagataac tacgatacgg  6720
gagggcttac catctggccc cagtgctgca atgataccgc gagacccacg ctcaccggct  6780
ccagatttat cagcaataaa ccagccagcc ggaagggccg agcgcagaag tggtcctgca  6840
actttatccg cctccatcca gtctattaat tgttgccggg aagctagagt aagtagttcg  6900
ccagttaata gtttgcgcaa cgttgttgcc attgctacag gcatcgtggt gtcacgctcg  6960
tcgtttggta tggcttcatt cagctccggt tcccaacgat caaggcgagt tacatgatcc  7020
cccatgttgt gcaaaaaagc ggttagctcc ttcggtcctc cgatcgttgt cagaagtaag  7080
ttggccgcag tgttatcact catggttatg gcagcactgc ataattctct tactgtcatg  7140
ccatccgtaa gatgcttttc tgtgactggt gagtactcaa ccaagtcatt ctgagaatag  7200
tgtatgcggc gaccgagttg ctcttgcccg gcgtcaatac gggataatac cgcgccacat  7260
agcagaactt taaaagtgct catcattgga aaacgttctt cggggcgaaa actctcaagg  7320
atcttaccgc tgttgagatc cagttcgatg taacccactc gtgcacccaa ctgatcttca  7380
gcatctttta ctttcaccag cgtttctggg tgagcaaaaa caggaaggca aaatgccgca  7440
aaaaagggaa taagggcgac acggaaatgt tgaatactca tactcttcct ttttcaatat  7500
tattgaagca tttatcaggg ttattgtctc atgagcggat acatatttga atgtatttag  7560
aaaaataaac aaataggggt tccgcgcaca tttccccgaa aagtgccacc t           7611

SEQ ID NO: 112         moltype = DNA  length = 8394
FEATURE                Location/Qualifiers
misc_feature           1..8394
                       note = Plasmid
                        pCVL.SFFV.HA.NLS.Sce(Opt).T2A.Trex2.IRES.mTagBFP
source                 1..8394
                       mol_type = other DNA
                       organism = synthetic construct
SEQUENCE: 112
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gagggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcaag aacatcaaga agaaccaggt  2460
catgaacctg ggccccaaca gcaagctgct gaaggagtac aagagccagc tgatcgagct  2520
gaacatcgag cagttcgagg ccggcatcgg cctgatcctg ggcgacgcct acatcaggag  2580
cagggacgag ggcaagacct actgcatgca gttcgagtgg aagaacaagg cctacatgga  2640
ccacgtgtgc ctgctgtacg accagtgggt gctgagcccc ccccacaaga aggagagggt  2700
gaaccacctg ggcaacctgg tcatcacctg gggcgcccag accttcaagc accaggcctt  2760
caacaagctg gccaacctgt tcatcgtgaa caacaagaag accatcccca acaacctggt  2820
ggagaactac ctgaccccca tgagcctggc ctactggttc atggacgacg gcggcaagtg  2880
ggactacaac aagaacagca ccaacaagag catcgtgctg aacacccaga gcttcacctt  2940
cgaggaggtg gagtacctgg tgaagggcct gaggaacaag ttccagctga actgctacgt  3000
gaagatcaac aagaacaagc ccatcatcta catcgacagc atgagctacc tgatcttcta  3060
caacctgatc aagccctacc tgatccccca gatgatgtac aagctgccca acaccatcag  3120
cagcgagacc ttcctgaagg gcggcggcgg atccggtgag ggcagaggaa gtcttctaac  3180
```

-continued

```
atgcggtgac gtggaggaga atccgggccc ctccggatct gagccacctc gggctgagac  3240
ctttgtattc ctggacctag aagccactgg gctcccaaac atggaccctg agattgcaga  3300
gatatccctt tttgctgttc accgctcttc cctggagaac ccagaacggg atgattctgg  3360
ttccttggtg ctgccccgtg ttctggacaa gctcacactg tgcatgtgcc cggagcgccc  3420
ctttactgcc aaggccagtg agattactgg tttgagcagc gaaagcctga tgcactgcgg  3480
gaaggctggt ttcaatggcg ctgtggtaag gacactgcag ggcttcctaa gccgccagga  3540
gggccccatc tgccttgtgg cccacaatgg cttcgattat gacttcccac tgctgtgcac  3600
ggagctacaa cgtctgggtg cccatctgcc ccaagacact gtctgcctgg acacactgcc  3660
tgcattgcgg ggcctggacc gtgctcacag ccacggcacc agggctcaag gccgcaaaag  3720
ctacagcctg gccagtctct tccaccgcta cttccaggct gaacccagtg ctgcccattc  3780
agcagaaggt gatgtgcaca ccctgcttct gatcttcctg catcgtgctc ctgagctgct  3840
cgcctgggca gatgagcagg cccgcagctg ggctcatatt gagcccatgt acgtgccacc  3900
tgatggtcca agcctcgaag cctgacctgc aggtcgagca tgcatctagg gcggccaatt  3960
ccgcccctct ccctcccccc cccctaacgt tactggccga agccgcttgg aataaggccg  4020
gtgtgcgttt gtctatatgt gattttccac catattgccg tcttttggca atgtgagggc  4080
ccggaaacct ggccctgtct tcttgacgag cattcctagg ggtctttccc ctctcgccaa  4140
aggaatgcaa ggtctgttga atgtcgtgaa ggaagcagtt cctctggaag cttcttgaag  4200
acaaacaacg tctgtagcga ccctttgcag gcagcggaac cccccacctg gcgacaggtg  4260
cctctgcggc caaaagccac gtgtataaga tacacctgca aaggcggcac aaccccagtg  4320
ccacgttgtg agttggatag ttgtggaaag agtcaaatgg ctctcctcaa gcgtattcaa  4380
caaggggctg aaggatgccc agaaggtacc ccattgtatg ggatctgatc tggggcctcg  4440
gtgcacatgc tttacatgtg tttagtcgag gttaaaaaaa cgtctaggcc ccccgaacca  4500
cggggacgtg gttttccttt gaaaaacacg atgataagct tgccacaacc cttaccggtc  4560
gccaccatga gcgagctgat taaggagaac atgcacatga agctgtacat ggagggcacc  4620
gtggacaacc atcacttcaa gtgcacatcc gagggcgaag gcaagcccta cgagggcacc  4680
cagaccatga gaatcaaggt ggtcgagggc ggccctctcc ccttcgcctt cgacatcctg  4740
gctactagct tcctctacgg cagcaagacc ttcatcaacc acacccaggg catccccgac  4800
ttcttcaagc agtccttccc tgagggcttc acatgggaga gagtcaccac atacgaagac  4860
gggggcgtgc tgaccgctac ccaggacacc agcctccagg acggctgcct catctacaac  4920
gtcaagatca gaggggtgaa cttcacatcc aacggccctg tgatgcagaa gaaaacactc  4980
ggctgggagg ccttcaccga gacgctgtac cccgctgacg gcggcctgga aggcagaaac  5040
gacatggccc tgaagctcgt gggcgggagc catctgatcg caaacatcaa gaccacatat  5100
agatccaaga aacccgctaa gaacctcaag atgcctggcg tctactatgt ggactacaga  5160
ctggaaagaa tcaaggaggc caacaacgag acctacgtcg agcagcacga ggtggcagtg  5220
gccagatact gcgacctccc tagcaaactg gggcacaagc ttaattgatt ctagagtcga  5280
ccgagcatct taccgccatt tatacccata tttgttctgt ttttcttgat ttgggtatac  5340
atttaaatgt taatagaaca aaatggtggg gcaatcattt acatttttag ggatatgtaa  5400
ttactagttc aggtgtattg ccacaagaca aacatgttaa gaaactttcc cgttatttac  5460
gctctgttcc tgttaatcaa cctctggatt acaaaatttg tgaaagattg actgatattc  5520
ttaactatgt tgctcctttt acgctgtgtg gatatgctgc tttatagcct ctgtatctag  5580
ctattgcttc ccgtacggct ttcgttttct cctccttgta taaatcctgg ttgctgtctc  5640
ttttagagga gttgtggccc gttgtccgtc aacgtggcgt ggtgtgctct gtgtttgctg  5700
acgcaacccc cactggctgg ggcattgcca ccacctgtca actcctttct gggactttcg  5760
ctttcccct cccgatcgcc acggcagaac tcatcgccgc ctgccttgcc cgctgctgga  5820
caggggctag gttgctgggc actgataatt ccgtggtgtt gtcatcggta ccttttaaa  5880
agaaaagggg ggactggaag ggctaattca ctcccaacga agacaagata tcataacttc  5940
gtatagcata cattatacga agttataatt tatttgtgaa atttgtgatg ctattgcttt  6000
atttgtaacc atatgtttat ttgtgaaatt tgtgatgcta ttgctttatt tgtaaccatt  6060
gctttttgct tgtactgggt ctctctggtt agaccagatc tgagcctggg agctctctgg  6120
ctaactaggg aacccactgc ttaagcctca ataaagcttg cctcgaccag cctcgactgt  6180
gccttctagt tgccagccat ctgttgtttg cccctccccc gtgccttcct tgaccctgga  6240
aggtgccact cccactgtcc tttcctaata aaatgaggaa attgcatcgc attgtctgag  6300
taggtgtcat tctattctgg ggggtggggt ggggcaggac agcaaggggg aggattggga  6360
agacaatagc aggcatgctg gggatgcggt gggctctatg gcctgcagct gcattaatga  6420
atcggccaac gcgcggggag aggcggtttg cgtattgggc gctcttccgc ttcctcgctc  6480
actgactcgc tgcgctcggt cgttcggctg cggcgagcgg tatcagctca ctcaaaggcg  6540
gtaatacggt tatccacaga atcaggggat aacgcaggaa agaacatgtg agcaaaaggc  6600
cagcaaaagg ccaggaaccg taaaaaggcc gcgttgctgg cgtttttcca taggctccgc  6660
ccccctgacg agcatcacaa aaatcgacgc tcaagtcaga ggtggcgaaa cccgacagga  6720
ctataaagat accaggcgtt tccccctgga agctccctcg tgcgctctcc tgttccgacc  6780
ctgccgctta ccggatacct gtccgccttt ctcccttcgg gaagcgtggc gctttctcat  6840
agctcacgct gtaggtatct cagttcggtg taggtcgttc gctccaagct gggctgtgtg  6900
cacgaacccc ccgttcagcc cgaccgctgc gccttatccg gtaactatcg tcttgagtcc  6960
aacccggtaa gacacgactt atcgccactg gcagcagcca ctggtaacag gattagcaga  7020
gcgaggtatg taggcggtgc tacagagttc ttgaagtggt ggcctaacta cggctacact  7080
agaaggacag tatttggtat ctgcgctctg ctgaagccag ttaccttcgg aaaaagagtt  7140
ggtagctctt gatccggcaa acaaaccacc gctggtagcg gtggtttttt tgtttgcaag  7200
cagcagatta cgcgcagaaa aaaaggatct caagaagatc ctttgatctt ttctacgggg  7260
tctgacgctc agtggaacga aaactcacgt taagggattt tggtcatgag attatcaaaa  7320
aggatcttca cctagatcct tttaaattaa aaatgaagtt ttaaatcaat ctaaagtata  7380
tatgagtaaa cttggtctga cagttaccaa tgcttaatca gtgaggcacc tatctcagcg  7440
atctgtctat ttcgttcatc catagttgcc tgactccccg tcgtgtagat aactacgata  7500
cgggagggct taccatctgg ccccagtgct gcaatgatac cgcgagaccc acgctcaccg  7560
gctccagatt tatcagcaat aaaccagcca gccggaaggg ccgagcgcag aagtggtcct  7620
gcaactttat ccgcctccat ccagtctatt aattgttgcc gggaagctag agtaagtagt  7680
tcgccagtta atagtttgcg caacgttgtt gccattgcta caggcatcgt ggtgtcacgc  7740
tcgtcgtttg gtatggcttc attcagctcc ggttcccaac gatcaaggcg agttacatga  7800
tcccccatgt tgtgcaaaaa agcggttagc tccttcggtc ctccgatcgt tgtcagaagt  7860
aagttggccg cagtgttatc actcatggtt atggcagcac tgcataattc tcttactgtc  7920
```

```
atgccatccg taagatgctt ttctgtgact ggtgagtact caaccaagtc attctgagaa  7980
tagtgtatgc ggcgaccgag ttgctcttgc ccggcgtcaa tacgggataa taccgcgcca  8040
catagcagaa ctttaaaagt gctcatcatt ggaaaacgtt cttcggggcg aaaactctca  8100
aggatcttac cgctgttgag atccagttcg atgtaaccca ctcgtgcacc caactgatct  8160
tcagcatctt ttactttcac cagcgtttct gggtgagcaa aaacaggaag gcaaaatgcc  8220
gcaaaaaagg gaataagggc gacacggaaa tgttgaatac tcatactctt cctttttcaa  8280
tattattgaa gcatttatca gggttattgt ctcatgagcg gatacatatt tgaatgtatt  8340
tagaaaaata aacaaatagg ggttccgcgc acatttcccc gaaaagtgcc acct        8394

SEQ ID NO: 113         moltype = DNA  length = 8394
FEATURE                Location/Qualifiers
misc_feature           1..8394
                       note = Plasmid
                        pCVL.SFFV.HA.NLS.SceOptD44A.T2A.Trex2.IRES.mTagBFP
source                 1..8394
                       mol_type = other DNA
                       organism = synthetic construct
SEQUENCE: 113
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcaag aacatcaaga agaaccaggt  2460
catgaacctg ggccccaaca gcaagctgct gaaggagtac aagagccagc tgatcgagct  2520
gaacatcgag cagttcgagg ccggcatcgg cctgatcctg ggcgctgcct acatcaggag  2580
cagggacgag ggcaagacct actgcatgca gttcgagtgg aagaacaagg cctacatgga  2640
ccacgtgtgc ctgctgtacg accagtgggt gctgagcccc ccccacaaga aggagagggt  2700
gaaccacctg ggcaacctgg tcatcacctg gggcgcccag accttcaagc accaggcctt  2760
caacaagctg gccaacctgt tcatcgtgaa caacaagaag accatcccca acaacctggt  2820
ggagaactac ctgaccccca tgagcctggc ctactggttc atggacgacg gcggcaagtg  2880
ggactacaac aagaacagca ccaacaagag catcgtgctg aacacccaga gcttcacctt  2940
cgaggaggtg gagtacctgg tgaagggcct gaggaacaag ttccagctga actgctacgt  3000
gaagatcaac aagaacaagc ccatcatcta catcgacagc atgagctacc tgatcttcta  3060
caacctgatc aagccctacc tgatccccca gatgatgtac aagctgccca acaccatcag  3120
cagcgagacc ttcctgaagg gcggcggcgg atccggtgag ggcagaggaa gtcttctaac  3180
atgcggtgac gtggaggaga atccgggccc ctccggatct gagccacctc gggctgagac  3240
ctttgtattc ctggacctag aagccactgg gctcccaaac atggaccctg agattgcaga  3300
gatatccctt tttgctgttc accgctcttc cctggagaac ccagaacggg atgattctgg  3360
ttccttggtg ctgccccgtg ttctggacaa gctcacactg tgcatgtgcc cggagcgccc  3420
ctttactgcc aaggccagtg agattactgg tttgagcagc gaaagcctga tgcactgcgg  3480
gaaggctggt ttcaatggcg ctgtggtaag gacactgcag ggcttcctaa gccgccagga  3540
gggcccccatc tgccttgtgg cccacaatgg cttcgattat gacttcccac tgctgtgcac  3600
ggagctacaa cgtctgggtg cccatctgcc ccaagacact gtctgcctgg acacactgcc  3660
```

-continued

```
tgcattgcgg ggcctggacc gtgctcacag ccacggcacc agggctcaag gccgcaaaag  3720
ctacagcctg gccagtctct tccaccgcta cttccaggct gaacccagtg ctgcccattc  3780
agcagaaggt gatgtgcaca ccctgcttct gatcttcctg catcgtgctc ctgagctgct  3840
cgcctgggca gatgagcagg cccgcagctg ggctcatatt gagcccatgt acgtgccacc  3900
tgatggtcca agcctcgaag cctgacctgc aggtcgagca tgcatctagg gcggccaatt  3960
ccgcccctct ccctcccccc cccctaacgt tactggccga agccgcttgg aataaggccg  4020
gtgtgcgttt gtctatatgt gattttccac catattgccg tcttttggca atgtgagggc  4080
ccggaaacct ggccctgtct tcttgacgag cattcctagg ggtctttccc ctctcgccaa  4140
aggaatgcaa ggtctgttga atgtcgtgaa ggaagcagtt cctctggaag cttcttgaag  4200
acaaacaacg tctgtagcga ccctttgcag gcagcggaac cccccacctg gcgacaggtg  4260
cctctgcggc caaaagccac gtgtataaga tacacctgca aaggcggcac aaccccagtg  4320
ccacgttgtg agttggatag ttgtggaaag agtcaaatgg ctctcctcaa gcgtattcaa  4380
caaggggctg aaggatgccc agaaggtacc ccattgtatg ggatctgatc tggggcctcg  4440
gtgcacatgc tttacatgtg tttagtcgag gttaaaaaaa cgtctaggcc ccccgaacca  4500
cggggacgtg gttttccttt gaaaaacacg atgataagct tgccacaacc cttaccggtc  4560
gccaccatga gcgagctgat taaggagaac atgcacatga agctgtacat ggagggcacc  4620
gtggacaacc atcacttcaa gtgcacatcc gagggcgaag gcaagcccta cgagggcacc  4680
cagaccatga gaatcaaggt ggtcgagggc ggccctctcc ccttcgcctt cgacatcctg  4740
gctactagct tcctctacgg cagcaagacc ttcatcaacc acacccaggg catccccgac  4800
ttcttcaagc agtccttccc tgagggcttc acatgggaga gagtcaccac atacgaagac  4860
gggggcgtgc tgaccgctac ccaggacacc agcctccagg acggctgcct catctacaac  4920
gtcaagatca gaggggtgaa cttcacatcc aacggccctg tgatgcagaa gaaaacactc  4980
ggctgggagg ccttcaccga gacgctgtac cccgctgacg gcggcctgga aggcagaaac  5040
gacatggccc tgaagctcgt gggcgggagc catctgatcg caaacatcaa gaccacatat  5100
agatccaaga aacccgctaa gaacctcaag atgcctggcg tctactatgt ggactacaga  5160
ctggaaagaa tcaaggaggc caacaacgag acctacgtcg agcagcacga ggtggcagtg  5220
gccagatact gcgacctccc tagcaaactg gggcacaagc ttaattgatt ctagagtcga  5280
ccgagcatct taccgccatt tatacccata tttgttctgt ttttcttgat ttgggtatac  5340
atttaaatgt taatagaaca aaatggtggg gcaatcattt acatttttag ggatatgtaa  5400
ttactagttc aggtgtattg ccacaagaca aacatgttaa gaaactttcc cgttatttac  5460
gctctgttcc tgttaatcaa cctctggatt acaaaatttg tgaaagattg actgatattc  5520
ttaactatgt tgctcctttt acgctgtgtg gatatgctgc tttatagcct ctgtatctag  5580
ctattgcttc ccgtacggct ttcgttttct cctccttgta taaatcctgg ttgctgtctc  5640
ttttagagga gttgtggccc gttgtccgtc aacgtggcgt ggtgtgctct gtgtttgctg  5700
acgcaacccc cactggctgg ggcattgcca ccacctgtca actcctttct gggactttcg  5760
ctttcccccct cccgatcgcc acggcagaac tcatcgccgc ctgccttgcc cgctgctgga  5820
caggggctag gttgctgggc actgataatt ccgtggtgtt gtcatcggta ccttttttaaa  5880
agaaaagggg ggactggaag ggctaattca ctcccaacga agacaagata tcataacttc  5940
gtatagcata cattatacga agttataatt tatttgtgaa atttgtgatg ctattgcttt  6000
atttgtaacc atatgtttat ttgtgaaatt tgtgatgcta ttgctttatt tgtaaccatt  6060
gctttttgct tgtactgggt ctctctggtt agaccagatc tgagcctggg agctctctgg  6120
ctaactaggg aacccactgc ttaagcctca ataaagcttg cctcgaccag cctcgactgt  6180
gccttctagt tgccagccat ctgttgtttg cccctccccc gtgccttcct tgaccctgga  6240
aggtgccact cccactgtcc tttcctaata aaatgaggaa attgcatcgc attgtctgag  6300
taggtgtcat tctattctgg ggggtggggt ggggcaggac agcaaggggg aggattggga  6360
agacaatagc aggcatgctg gggatgcggt gggctctatg gcctgcagct gcattaatga  6420
atcggccaac gcgcggggag aggcggtttg cgtattgggc gctcttccgc ttcctcgctc  6480
actgactcgc tgcgctcggt cgttcggctg cggcgagcgg tatcagctca ctcaaaggcg  6540
gtaatacggt tatccacaga atcaggggat aacgcaggaa agaacatgtg agcaaaaggc  6600
cagcaaaagg ccaggaaccg taaaaaggcc gcgttgctgg cgtttttcca taggctccgc  6660
ccccctgacg agcatcacaa aaatcgacgc tcaagtcaga ggtggcgaaa cccgacagga  6720
ctataaagat accaggcgtt tccccctgga agctccctcg tgcgctctcc tgttccgacc  6780
ctgccgctta ccggatacct gtccgccttt ctcccttcgg gaagcgtggc gctttctcat  6840
agctcacgct gtaggtatct cagttcggtg taggtcgttc gctccaagct gggctgtgtg  6900
cacgaacccc ccgttcagcc cgaccgctgc gccttatccg gtaactatcg tcttgagtcc  6960
aacccggtaa gacacgactt atcgccactg gcagcagcca ctggtaacag gattagcaga  7020
gcgaggtatg taggcggtgc tacagagttc ttgaagtggt ggcctaacta cggctacact  7080
agaaggacag tatttggtat ctgcgctctg ctgaagccag ttaccttcgg aaaaagagtt  7140
ggtagctctt gatccggcaa acaaaccacc gctggtagcg gtggtttttt tgtttgcaag  7200
cagcagatta cgcgcagaaa aaaaggatct caagaagatc ctttgatctt ttctacgggg  7260
tctgacgctc agtggaacga aaactcacgt taagggattt tggtcatgag attatcaaaa  7320
aggatcttca cctagatcct tttaaattaa aaatgaagtt ttaaatcaat ctaaagtata  7380
tatgagtaaa cttggtctga cagttaccaa tgcttaatca gtgaggcacc tatctcagcg  7440
atctgtctat ttcgttcatc catagttgcc tgactccccg tcgtgtagat aactacgata  7500
cgggagggct taccatctgg ccccagtgct gcaatgatac cgcgagaccc acgctcaccg  7560
gctccagatt tatcagcaat aaaccagcca gccggaaggg ccgagcgcag aagtggtcct  7620
gcaactttat ccgcctccat ccagtctatt aattgttgcc gggaagctag agtaagtagt  7680
tcgccagtta atagtttgcg caacgttgtt gccattgcta caggcatcgt ggtgtcacgc  7740
tcgtcgtttg gtatggcttc attcagctcc ggttcccaac gatcaaggcg agttacatga  7800
tcccccatgt tgtgcaaaaa agcggttagc tccttcggtc ctccgatcgt tgtcagaagt  7860
aagttggccg cagtgttatc actcatggtt atggcagcac tgcataattc tcttactgtc  7920
atgccatccg taagatgctt ttctgtgact ggtgagtact caaccaagtc attctgagaa  7980
tagtgtatgc ggcgaccgag ttgctcttgc ccggcgtcaa tacgggataa taccgcgcca  8040
catagcagaa ctttaaaagt gctcatcatt ggaaaacgtt cttcggggcg aaaactctca  8100
aggatcttac cgctgttgag atccagttcg atgtaaccca ctcgtgcacc caactgatct  8160
tcagcatctt ttactttcac cagcgtttct gggtgagcaa aaacaggaag gcaaaatgcc  8220
gcaaaaaagg gaataagggc gacacggaaa tgttgaatac tcatactctt cctttttcaa  8280
tattattgaa gcatttatca gggttattgt ctcatgagcg gatacatatt tgaatgtatt  8340
tagaaaaata aacaaatagg ggttccgcgc acatttcccc gaaaagtgcc acct        8394
```

```
SEQ ID NO: 114          moltype = DNA  length = 7671
FEATURE                 Location/Qualifiers
misc_feature            1..7671
                        note = Plasmid pCVL.SFFV.HA.NLS.I-Ani I.IRES.mTagBFP
source                  1..7671
                        mol_type = other DNA
                        organism = synthetic construct
SEQUENCE: 114
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcggc agcgatctga cctacgccta  2460
tctggtgggc ctgttcgagg gcgacggata tttttccatc actaaaaagg gcaagtacct  2520
gacctatgag ctgggaattg aactgtctat caaggatgtg cagctgatct acaagatcaa  2580
gaagatcctg gggatcggca ttgtgagctt caggaagaga aacgagattg aaatggtggc  2640
cctgaggatc agggataaga atcacctgaa atctaagatt ctgcccatct tcgagaagta  2700
tcctatgttt agtaacaaac agtacgacta tctgaggttt agaaatgctc tgctgagcgg  2760
catcatctcc ctggaggatc tgccagacta tacccggtcc gacgagcccc tgaacagcat  2820
cgaatccatc attaatacat cttacttcag tgcctggctg gtgggcttca tcgaggctga  2880
agggtgcttc tctgtgtaca aactgaacaa ggacgatgac tatctgattg ccagttttga  2940
tatcgctcag agggatggag acatcctgat tagcgccatc agaaagtacc tgtccttcac  3000
cacaaaggtg tatctggaca aaacaaattg tagcaaactg aaggtcacta gcgtgcgctc  3060
cgtggagaac atcattaagt tcctgcagaa tgctcctgtg aaactgctgg gcaacaaaaa  3120
gctgcagtac aaactgtggc tgaagcagct gcggaaaatc tctcgctaca gtgaaaaaat  3180
caagattcca tccaattatt aacctgcagg tcgagcatgc atctagggcg gccaattccg  3240
cccctctccc tcccccccc ctaacgttac tggccgaagc cgcttggaat aaggccggtg  3300
tgcgtttgtc tatatgtgat tttccaccat attgccgtct tttggcaatg tgagggcccg  3360
gaaacctggc cctgtcttct tgacgagcat tcctaggggt ctttcccctc tcgccaaagg  3420
aatgcaaggt ctgttgaatg tcgtgaagga agcagttcct ctggaagctt cttgaagaca  3480
aacaacgtct gtagcgaccc tttgcaggca gcggaacccc ccacctggcg acaggtgcct  3540
ctgcggccaa aagccacgtg tataagatac acctgcaaag gcggcacaac cccagtgcca  3600
cgttgtgagt tggatagttg tggaaagagt caaatggctc tcctcaagcg tattcaacaa  3660
ggggctgaag gatgcccaga aggtacccca ttgtatggga tctgatctgg ggcctcggtg  3720
cacatgcttt acatgtgttt agtcgaggtt aaaaaaacgt ctaggccccc cgaaccacgg  3780
ggacgtggtt ttcctttgaa aaacacgatg ataagcttgc cacaaccctt accggtcgcc  3840
accatgagcg agctgattaa ggagaacatg cacatgaagc tgtacatgga gggcaccgtg  3900
gacaaccatc acttcaagtg cacatccgag ggcgaaggca agccctacga gggcacccag  3960
accatgagaa tcaaggtggt cgagggcggc cctctcccct tcgccttcga catcctggct  4020
actagcttcc tctacggcag caagaccttc atcaaccaca cccagggcat ccccgacttc  4080
ttcaagcagt ccttccctga gggcttcaca tgggagagag tcaccacata cgaagacggg  4140
ggcgtgctga ccgctaccca ggacaccagc ctccaggacg gctgcctcat ctacaacgtc  4200
```

```
aagatcagag gggtgaactt cacatccaac ggccctgtga tgcagaagaa aacactcggc  4260
tgggaggcct tcaccgagac gctgtacccc gctgacggcg gcctggaagg cagaaacgac  4320
atggccctga agctcgtggg cgggagccat ctgatcgcaa acatcaagac cacatataga  4380
tccaagaaac ccgctaagaa cctcaagatg cctggcgtct actatgtgga ctacagactg  4440
gaaagaatca aggaggccaa caacgagacc tacgtcgagc agcacgaggt ggcagtggcc  4500
agatactgcg acctccctag caaactgggg cacaagctta attgattcta gagtcgaccg  4560
agcatcttac cgccatttat acccatattt gttctgtttt tcttgatttg ggtatacatt  4620
taaatgttaa tagaacaaaa tggtggggca atcatttaca tttttaggga tatgtaatta  4680
ctagttcagg tgtattgcca caagacaaac atgttaagaa actttcccgt tatttacgct  4740
ctgttcctgt taatcaacct ctggattaca aaatttgtga aagattgact gatattctta  4800
actatgttgc tccttttacg ctgtgtggat atgctgcttt atagcctctg tatctagcta  4860
ttgcttcccg tacggctttc gttttctcct ccttgtataa atcctggttg ctgtctcttt  4920
tagaggagtt gtggcccgtt gtccgtcaac gtggcgtggt gtgctctgtg tttgctgacg  4980
caacccccac tggctggggc attgccacca cctgtcaact cctttctggg actttcgctt  5040
tccccctccc gatcgccacg gcagaactca tcgccgcctg ccttgcccgc tgctggacag  5100
gggctaggtt gctgggcact gataattccg tggtgttgtc atcggtacct ttttaaaaga  5160
aaagggggga ctggaagggc taattcactc ccaacgaaga caagatatca taacttcgta  5220
tagcatacat tatacgaagt tataatttat ttgtgaaatt tgtgatgcta ttgctttatt  5280
tgtaaccata tgtttatttg tgaaatttgt gatgctattg ctttatttgt aaccattgct  5340
ttttgcttgt actgggtctc tctggttaga ccagatctga gcctgggagc tctctggcta  5400
actagggaac ccactgctta agcctcaata aagcttgcct cgaccagcct cgactgtgcc  5460
ttctagttgc cagccatctg ttgtttgccc ctcccccgtg ccttccttga ccctggaagg  5520
tgccactccc actgtccttt cctaataaaa tgaggaaatt gcatcgcatt gtctgagtag  5580
gtgtcattct attctggggg gtggggtggg gcaggacagc aagggggagg attgggaaga  5640
caatagcagg catgctgggg atgcggtggg ctctatggcc tgcagctgca ttaatgaatc  5700
ggccaacgcg cggggagagg cggtttgcgt attgggcgct cttccgcttc ctcgctcact  5760
gactcgctgc gctcggtcgt tcggctgcgg cgagcggtat cagctcactc aaaggcggta  5820
atacggttat ccacagaatc aggggataac gcaggaaaga acatgtgagc aaaaggccag  5880
caaaaggcca ggaaccgtaa aaaggccgcg ttgctggcgt ttttccatag gctccgcccc  5940
cctgacgagc atcacaaaaa tcgacgctca agtcagaggt ggcgaaaccc gacaggacta  6000
taaagatacc aggcgtttcc ccctggaagc tccctcgtgc gctctcctgt tccgaccctg  6060
ccgcttaccg gatacctgtc cgcctttctc ccttcgggaa gcgtggcgct ttctcatagc  6120
tcacgctgta ggtatctcag ttcggtgtag gtcgttcgct ccaagctggg ctgtgtgcac  6180
gaaccccccg ttcagcccga ccgctgcgcc ttatccggta actatcgtct tgagtccaac  6240
ccggtaagac acgacttatc gccactggca gcagccactg gtaacaggat tagcagagcg  6300
aggtatgtag gcggtgctac agagttcttg aagtggtggc ctaactacgg ctacactaga  6360
aggacagtat ttggtatctg cgctctgctg aagccagtta ccttcggaaa aagagttggt  6420
agctcttgat ccggcaaaca aaccaccgct ggtagcggtg gtttttttgt ttgcaagcag  6480
cagattacgc gcagaaaaaa aggatctcaa gaagatcctt tgatcttttc tacggggtct  6540
gacgctcagt ggaacgaaaa ctcacgttaa gggattttgg tcatgagatt atcaaaaagg  6600
atcttcacct agatcctttt aaattaaaaa tgaagtttta aatcaatcta aagtatatat  6660
gagtaaactt ggtctgacag ttaccaatgc ttaatcagtg aggcacctat ctcagcgatc  6720
tgtctatttc gttcatccat agttgcctga ctccccgtcg tgtagataac tacgatacgg  6780
gagggcttac catctggccc cagtgctgca atgataccgc gagacccacg ctcaccggct  6840
ccagatttat cagcaataaa ccagccagcc ggaagggccg agcgcagaag tggtcctgca  6900
actttatccg cctccatcca gtctattaat tgttgccggg aagctagagt aagtagttcg  6960
ccagttaata gtttgcgcaa cgttgttgcc attgctacag gcatcgtggt gtcacgctcg  7020
tcgtttggta tggcttcatt cagctccggt tcccaacgat caaggcgagt tacatgatcc  7080
cccatgttgt gcaaaaaagc ggttagctcc ttcggtcctc cgatcgttgt cagaagtaag  7140
ttggccgcag tgttatcact catggttatg gcagcactgc ataattctct tactgtcatg  7200
ccatccgtaa gatgcttttc tgtgactggt gagtactcaa ccaagtcatt ctgagaatag  7260
tgtatgcggc gaccgagttg ctcttgcccg gcgtcaatac gggataatac cgcgccacat  7320
agcagaactt taaaagtgct catcattgga aaacgttctt cggggcgaaa actctcaagg  7380
atcttaccgc tgttgagatc cagttcgatg taacccactc gtgcacccaa ctgatcttca  7440
gcatctttta ctttcaccag cgtttctggg tgagcaaaaa caggaaggca aaatgccgca  7500
aaaaagggaa taagggcgac acggaaatgt tgaatactca tactcttcct ttttcaatat  7560
tattgaagca tttatcaggg ttattgtctc atgagcggat acatatttga atgtatttag  7620
aaaaataaac aaataggggt tccgcgcaca tttccccgaa aagtgccacc t           7671
```

```
SEQ ID NO: 115          moltype = DNA  length = 8445
FEATURE                 Location/Qualifiers
misc_feature            1..8445
                        note = Plasmid
                         pCVL.SFFV.HA.NLS.IAni-I.T2A.Trex2.IRES.mTagBFP
source                  1..8445
                        mol_type = other DNA
                        organism = synthetic construct
SEQUENCE: 115
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
atttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
```

-continued

```
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcggc agcgatctga cctacgccta  2460
tctggtgggc ctgttcgagg gcgacggata tttttccatc actaaaaagg gcaagtacct  2520
gacctatgag ctgggaattg aactgtctat caaggatgtg cagctgatct acaagatcaa  2580
gaagatcctg ggatcggca ttgtgagctt caggaagaga aacgagattg aaatggtggc  2640
cctgaggatc agggataaga atcacctgaa atctaagatt ctgcccatct tcgagaagta  2700
tcctatgttt agtaacaaac agtacgacta tctgaggttt agaaatgctc tgctgagcgg  2760
catcatctcc ctggaggatc tgccagacta tacccggtcc gacgagcccc tgaacagcat  2820
cgaatccatc attaatacat cttacttcag tgcctggctg gtgggcttca tcgaggctga  2880
agggtgcttc tctgtgtaca aactgaacaa ggacgatgac tatctgattg ccagttttga  2940
tatcgctcag agggatggag acatcctgat tagcgccatc agaaagtacc tgtccttcac  3000
cacaaaggtg tatctggaca aaacaaattg tagcaaactg aaggtcacta gcgtgcgctc  3060
cgtggagaac atcattaagt tcctgcagaa tgctcctgtg aaactgctgg gcaacaaaaa  3120
gctgcagtac aaactgtggc tgaagcagct gcggaaaatc tctcgctaca gtgaaaaaat  3180
caagattcca tccaattatg gatccggtga gggcagagga agtcttctaa catgcggtga  3240
cgtggaggag aatccgggcc cctccggatc tgagccacct cgggctgaga cctttgtatt  3300
cctggaccta gaagccactg ggctcccaaa catggaccct gagattgcag agatatccct  3360
ttttgctgtt caccgctctt ccctggagaa cccagaacgg gatgattctg gttccttggt  3420
gctgccccgt gttctggaca agctcacact gtgcatgtgc ccggagcgcc cctttactgc  3480
caaggccagt gagattactg gtttgagcag cgaaagcctg atgcactgcg ggaaggctgg  3540
tttcaatggc gctgtggtaa ggacactgca gggcttccta agccgccagg agggccccat  3600
ctgccttgtg gcccacaatg gcttcgatta tgacttccca ctgctgtgca cggagctaca  3660
acgtctgggt gcccatctgc cccaagacac tgtctgcctg gacacactgc ctgcattgcg  3720
gggcctggac cgtgctcaca gccacggcac cagggctcaa ggccgcaaaa gctacagcct  3780
ggccagtctc ttccaccgct acttccaggc tgaacccagt gctgcccatt cagcagaagg  3840
tgatgtgcac accctgcttc tgatcttcct gcatcgtgct cctgagctgc tcgcctgggc  3900
agatgagcag gcccgcagct gggctcatat tgagcccatg tacgtgccac ctgatggtcc  3960
aagcctcgaa gcctgacctg caggtcgagc atgcatctag ggcggccaat tccgcccctc  4020
tccctccccc ccccctaacg ttactggccg aagccgcttg gaataaggcc ggtgtgcgtt  4080
tgtctatatg tgattttcca ccatattgcc gtcttttggc aatgtgaggg cccggaaacc  4140
tggccctgtc ttcttgacga gcattcctag gggtctttcc cctctcgcca aaggaatgca  4200
aggtctgttg aatgtcgtga aggaagcagt tcctctggaa gcttcttgaa gacaaacaac  4260
gtctgtagcg accctttgca ggcagcggaa ccccccacct ggcgacaggt gcctctgcgg  4320
ccaaaagcca cgtgtataag atacacctgc aaaggcggca caaccccagt gccacgttgt  4380
gagttggata gttgtggaaa gagtcaaatg gctctcctca agcgtattca acaaggggct  4440
gaaggatgcc cagaaggtac cccattgtat gggatctgat ctggggcctc ggtgcacatg  4500
ctttacatgt gtttagtcga ggttaaaaaa acgtctaggc cccccgaacc acggggacgt  4560
ggttttcctt tgaaaaacac gatgataagc ttgccacaac ccttaccggt cgccaccatg  4620
agcgagctga ttaaggagaa catgcacatg aagctgtaca tggagggcac cgtggacaac  4680
catcacttca agtgcacatc cgagggcgaa ggcaagccct acgagggcac ccagaccatg  4740
agaatcaagg tggtcgaggg cggccctctc cccttcgcct tcgacatcct ggctactagc  4800
ttcctctacg gcagcaagac cttcatcaac cacacccagg gcatccccga cttcttcaag  4860
cagtccttcc ctgagggctt cacatgggag agagtcacca catacgaaga cgggggcgtg  4920
ctgaccgcta cccaggacac cagcctccag gacggctgcc tcatctacaa cgtcaagatc  4980
agaggggtga acttcacatc caacggccct gtgatgcaga agaaaacact cggctgggag  5040
gccttcaccg agacgctgta ccccgctgac ggcggcctgg aaggcagaaa cgacatggcc  5100
ctgaagctcg tgggcgggag ccatctgatc gcaaacatca agaccacata tagatccaag  5160
aaacccgcta agaacctcaa gatgcctggc gtctactatg tggactacag actggaaaga  5220
atcaaggagg ccaacaacga gacctacgtc gagcagcacg aggtggcagt ggccagatac  5280
tgcgacctcc ctagcaaact ggggcacaag cttaattgat tctagagtcg accgagcatc  5340
ttaccgccat ttatacccat atttgttctg tttttcttga tttgggtata catttaaatg  5400
```

-continued

```
ttaatagaac aaaatggtgg ggcaatcatt tacattttta gggatatgta attactagtt  5460
caggtgtatt gccacaagac aaacatgtta agaaactttc ccgttattta cgctctgttc  5520
ctgttaatca acctctggat tacaaaattt gtgaaagatt gactgatatt cttaactatg  5580
ttgctccttt tacgctgtgt ggatatgctg ctttatagcc tctgtatcta gctattgctt  5640
cccgtacggc tttcgttttc tcctccttgt ataaatcctg gttgctgtct cttttagagg  5700
agttgtggcc cgttgtccgt caacgtggcg tggtgtgctc tgtgtttgct gacgcaaccc  5760
ccactggctg gggcattgcc accacctgtc aactcctttc tgggactttc gctttccccc  5820
tcccgatcgc cacggcagaa ctcatcgccg cctgccttgc ccgctgctgg acaggggcta  5880
ggttgctggg cactgataat tccgtggtgt tgtcatcggt acctttttaa aagaaaaggg  5940
gggactggaa gggctaattc actcccaacg aagacaagat atcataactt cgtatagcat  6000
acattatacg aagttataat ttatttgtga aatttgtgat gctattgctt tatttgtaac  6060
catatgttta tttgtgaaat ttgtgatgct attgctttat ttgtaaccat tgctttttgc  6120
ttgtactggg tctctctggt tagaccagat ctgagcctgg gagctctctg gctaactagg  6180
gaacccactg cttaagcctc aataaagctt gcctcgacca gcctcgactg tgccttctag  6240
ttgccagcca tctgttgttt gcccctcccc cgtgccttcc ttgaccctgg aaggtgccac  6300
tcccactgtc ctttcctaat aaaatgagga aattgcatcg cattgtctga gtaggtgtca  6360
ttctattctg gggggtgggg tggggcagga cagcaagggg gaggattggg aagacaatag  6420
caggcatgct ggggatgcgg tgggctctat ggcctgcagc tgcattaatg aatcggccaa  6480
cgcgcgggga gaggcggttt gcgtattggg cgctcttccg cttcctcgct cactgactcg  6540
ctgcgctcgg tcgttcggct gcggcgagcg gtatcagctc actcaaaggc ggtaatacgg  6600
ttatccacag aatcagggga taacgcagga aagaacatgt gagcaaaagg ccagcaaaag  6660
gccaggaacc gtaaaaaggc cgcgttgctg gcgtttttcc ataggctccg cccccctgac  6720
gagcatcaca aaaatcgacg ctcaagtcag aggtggcgaa acccgacagg actataaaga  6780
taccaggcgt ttccccctgg aagctccctc gtgcgctctc ctgttccgac cctgccgctt  6840
accggatacc tgtccgcctt tctcccttcg ggaagcgtgg cgctttctca tagctcacgc  6900
tgtaggtatc tcagttcggt gtaggtcgtt cgctccaagc tgggctgtgt gcacgaaccc  6960
cccgttcagc ccgaccgctg cgccttatcc ggtaactatc gtcttgagtc caacccggta  7020
agacacgact tatcgccact ggcagcagcc actggtaaca ggattagcag agcgaggtat  7080
gtaggcggtg ctacagagtt cttgaagtgg tggcctaact acggctacac tagaaggaca  7140
gtatttggta tctgcgctct gctgaagcca gttaccttcg gaaaaagagt tggtagctct  7200
tgatccggca aacaaaccac cgctggtagc ggtggttttt ttgtttgcaa gcagcagatt  7260
acgcgcagaa aaaaaggatc tcaagaagat cctttgatct tttctacggg gtctgacgct  7320
cagtggaacg aaaactcacg ttaagggatt ttggtcatga gattatcaaa aaggatcttc  7380
acctagatcc ttttaaatta aaaatgaagt tttaaatcaa tctaaagtat atatgagtaa  7440
acttggtctg acagttacca atgcttaatc agtgaggcac ctatctcagc gatctgtcta  7500
tttcgttcat ccatagttgc ctgactcccc gtcgtgtaga taactacgat acgggagggc  7560
ttaccatctg gccccagtgc tgcaatgata ccgcgagacc cacgctcacc ggctccagat  7620
ttatcagcaa taaaccagcc agccggaagg gccgagcgca gaagtggtcc tgcaacttta  7680
tccgcctcca tccagtctat taattgttgc cgggaagcta gagtaagtag ttcgccagtt  7740
aatagtttgc gcaacgttgt tgccattgct acaggcatcg tggtgtcacg ctcgtcgttt  7800
ggtatggctt cattcagctc cggttcccaa cgatcaaggc gagttacatg atcccccatg  7860
ttgtgcaaaa aagcggttag ctccttcggt cctccgatcg ttgtcagaag taagttggcc  7920
gcagtgttat cactcatggt tatggcagca ctgcataatt ctcttactgt catgccatcc  7980
gtaagatgct tttctgtgac tggtgagtac tcaaccaagt cattctgaga atagtgtatg  8040
cggcgaccga gttgctcttg cccggcgtca atacgggata ataccgcgcc acatagcaga  8100
actttaaaag tgctcatcat tggaaaacgt tcttcggggc gaaaactctc aaggatctta  8160
ccgctgttga gatccagttc gatgtaaccc actcgtgcac ccaactgatc ttcagcatct  8220
tttactttca ccagcgtttc tgggtgagca aaaacaggaa ggcaaaatgc cgcaaaaaag  8280
ggaataaggg cgacacggaa atgttgaata ctcatactct tcctttttca atattattga  8340
agcatttatc agggttattg tctcatgagc ggatacatat ttgaatgtat ttagaaaaat  8400
aaacaaatag gggttccgcg cacatttccc cgaaaagtgc cacct                 8445

SEQ ID NO: 116          moltype = DNA  length = 7011
FEATURE                 Location/Qualifiers
misc_feature            1..7011
                        note = pCVL.MND.SceOPT.2A.TagBFP
source                  1..7011
                        mol_type = other DNA
                        organism = synthetic construct
SEQUENCE: 116
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
```

-continued

```
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgta ggaacagaga aacaggagaa tatgggccaa acaggatatc  1980
tgtggtaagc agttcctgcc ccggctcagg gccaagaaca gttggaacag cagaatatgg  2040
gccaaacagg atatctgtgg taagcagttc ctgccccggc tcagggccaa gaacagatgg  2100
tccccagatg cggtcccgcc ctcagcagtt tctagagaac catcagatgt ttccagggtg  2160
ccccaaggac ctgaaatgac cctgtgcctt atttgaacta accaatcagt tcgcttctcg  2220
cttctgttcg cgcgcttctg ctccccgagc tctatataag cagagctcgt ttagtgaacc  2280
gtcagatcgc ctggagacgc catccacgct gttttgactt ccatagaagg atctcgagcc  2340
accatgggcg tataccccta cgacgtgccc gactacgccc ccgggccccc taagaaaaag  2400
aggaaggtga agaacatcaa gaagaaccag gtcatgaacc tgggccccaa cagcaagctg  2460
ctgaaggagt acaagagcca gctgatcgag ctgaacatcg agcagttcga ggccggcatc  2520
ggcctgatcc tgggcgacgc ctacatcagg agcagggacg agggcaagac ctactgcatg  2580
cagttcgagt ggaagaacaa ggcctacatg gaccacgtgt gcctgctgta cgaccagtgg  2640
gtgctgagcc cccccacaa gaaggagagg gtgaaccacc tgggcaacct ggtcatcacc  2700
tggggcgccc agaccttcaa gcaccaggcc ttcaacaagc tggccaacct gttcatcgtg  2760
aacaacaaga agaccatccc caacaacctg gtggagaact acctgacccc catgagcctg  2820
gcctactggt tcatggacga cggcggcaag tgggactaca acaagaacag caccaacaag  2880
agcatcgtgc tgaacaccca gagcttcacc ttcgaggagg tggagtacct ggtgaagggc  2940
ctgaggaaca agttccagct gaactgctac gtgaagatca acaagaacaa gcccatcatc  3000
tacatcgaca gcatgagcta cctgatcttc tacaacctga tcaagcccta cctgatcccc  3060
cagatgatgt acaagctgcc caacaccatc agcagcgaga ccttcctgaa gggcggcggc  3120
ggatccggtg agggcagagg aagtcttcta acatgcggtg acgtggagga gaatccgggc  3180
cccatgagcg agctgattaa ggagaacatg cacatgaagc tgtacatgga gggcaccgtg  3240
gacaaccatc acttcaagtg cacatccgag ggcgaaggca agccctacga gggcacccag  3300
accatgagaa tcaaggtggt cgagggcggc cctctcccct tcgccttcga catcctggct  3360
actagcttcc tctacggcag caagaccttc atcaaccaca cccagggcat ccccgacttc  3420
ttcaagcagt ccttccctga gggcttcaca tgggagagag tcaccacata cgaagacggg  3480
ggcgtgctga ccgctaccca ggacaccagc ctccaggacg gctgcctcat ctacaacgtc  3540
aagatcagag gggtgaactt cacatccaac ggccctgtga tgcagaagaa aacactcggc  3600
tgggaggcct tcaccgagac gctgtacccc gctgacggcg gcctggaagg cagaaacgac  3660
atggccctga agctcgtggg cgggagccat ctgatcgcaa acatcaagac cacatataga  3720
tccaagaaac ccgctaagaa cctcaagatg cctggcgtct actatgtgga ctacagactg  3780
gaaagaatca aggaggccaa caacgagacc tacgtcgagc agcacgaggt ggcagtggcc  3840
agatactgcg acctccctag caaactgggg cacaagctta attgattcta gagtcgaccg  3900
agcatcttac cgccatttat acccatattt gttctgtttt tcttgatttg ggtatacatt  3960
taaatgttaa tagaacaaaa tggtggggca atcatttaca tttttaggga tatgtaatta  4020
ctagttcagg tgtattgcca caagacaaac atgttaagaa actttcccgt tatttacgct  4080
ctgttcctgt taatcaacct ctggattaca aaatttgtga aagattgact gatattctta  4140
actatgttgc tccttttacg ctgtgtggat atgctgcttt atagcctctg tatctagcta  4200
ttgcttcccg tacggctttc gttttctcct ccttgtataa atcctggttg ctgtctcttt  4260
tagaggagtt gtggcccgtt gtccgtcaac gtggcgtggt gtgctctgtg tttgctgacg  4320
caacccccac tggctggggc attgccacca cctgtcaact cctttctggg actttcgctt  4380
tccccctccc gatcgccacg gcagaactca tcgccgcctg ccttgcccgc tgctggacag  4440
gggctaggtt gctgggcact gataattccg tggtgttgtc atcggtacct ttttaaaaga  4500
aaagggggga ctggaagggc taattcactc ccaacgaaga caagatatca taacttcgta  4560
tagcatacat tatacgaagt tataatttat ttgtgaaatt tgtgatgcta ttgctttatt  4620
tgtaaccata tgtttatttg tgaaatttgt gatgctattg ctttatttgt aaccattgct  4680
ttttgcttgt actgggtctc tctggttaga ccagatctga gcctgggagc tctctggcta  4740
actagggaac ccactgctta agcctcaata aagcttgcct cgaccagcct cgactgtgcc  4800
ttctagttgc cagccatctg ttgtttgccc ctcccccgtg ccttccttga ccctggaagg  4860
tgccactccc actgtccttt cctaataaaa tgaggaaatt gcatcgcatt gtctgagtag  4920
gtgtcattct attctggggg gtggggtggg gcaggacagc aagggggagg attgggaaga  4980
caatagcagg catgctgggg atgcggtggg ctctatggcc tgcagctgca ttaatgaatc  5040
ggccaacgcg cggggagagg cggtttgcgt attgggcgct cttccgcttc ctcgctcact  5100
gactcgctgc gctcggtcgt tcggctgcgg cgagcggtat cagctcactc aaaggcggta  5160
atacggttat ccacagaatc aggggataac gcaggaaaga acatgtgagc aaaaggccag  5220
caaaaggcca ggaaccgtaa aaaggccgcg ttgctggcgt ttttccatag gctccgcccc  5280
cctgacgagc atcacaaaaa tcgacgctca agtcagaggt ggcgaaaccc gacaggacta  5340
taaagatacc aggcgtttcc ccctggaagc tccctcgtgc gctctcctgt tccgaccctg  5400
ccgcttaccg gatacctgtc cgcctttctc ccttcgggaa gcgtggcgct ttctcatagc  5460
tcacgctgta ggtatctcag ttcggtgtag gtcgttcgct ccaagctggg ctgtgtgcac  5520
gaaccccccg ttcagcccga ccgctgcgcc ttatccggta actatcgtct tgagtccaac  5580
ccggtaagac acgacttatc gccactggca gcagccactg gtaacaggat tagcagagcg  5640
aggtatgtag gcggtgctac agagttcttg aagtggtggc ctaactacgg ctacactaga  5700
aggacagtat ttggtatctg cgctctgctg aagccagtta ccttcggaaa aagagttggt  5760
agctcttgat ccggcaaaca aaccaccgct ggtagcggtg gtttttttgt ttgcaagcag  5820
cagattacgc gcagaaaaaa aggatctcaa gaagatcctt tgatcttttc tacggggtct  5880
```

```
gacgctcagt ggaacgaaaa ctcacgttaa gggattttgg tcatgagatt atcaaaaagg  5940
atcttcacct agatcctttt aaattaaaaa tgaagtttta aatcaatcta aagtatatat  6000
gagtaaactt ggtctgacag ttaccaatgc ttaatcagtg aggcacctat ctcagcgatc  6060
tgtctatttc gttcatccat agttgcctga ctccccgtcg tgtagataac tacgatacgg  6120
gagggcttac catctggccc cagtgctgca atgataccgc gagacccacg ctcaccggct  6180
ccagatttat cagcaataaa ccagccagcc ggaagggccg agcgcagaag tggtcctgca  6240
actttatccg cctccatcca gtctattaat tgttgccggg aagctagagt aagtagttcg  6300
ccagttaata gtttgcgcaa cgttgttgcc attgctacag gcatcgtggt gtcacgctcg  6360
tcgtttggta tggcttcatt cagctccggt tcccaacgat caaggcgagt tacatgatcc  6420
cccatgttgt gcaaaaaagc ggttagctcc ttcggtcctc cgatcgttgt cagaagtaag  6480
ttggccgcag tgttatcact catggttatg gcagcactgc ataattctct tactgtcatg  6540
ccatccgtaa gatgcttttc tgtgactggt gagtactcaa ccaagtcatt ctgagaatag  6600
tgtatgcggc gaccgagttg ctcttgcccg gcgtcaatac gggataatac cgcgccacat  6660
agcagaactt taaaagtgct catcattgga aaacgttctt cggggcgaaa actctcaagg  6720
atcttaccgc tgttgagatc cagttcgatg taacccactc gtgcacccaa ctgatcttca  6780
gcatctttta ctttcaccag cgtttctggg tgagcaaaaa caggaaggca aaatgccgca  6840
aaaaagggaa taagggcgac acggaaatgt tgaatactca tactcttcct ttttcaatat  6900
tattgaagca tttatcaggg ttattgtctc atgagcggat acatatttga atgtatttag  6960
aaaaataaac aaataggggt tccgcgcaca tttccccgaa aagtgccacc t           7011

SEQ ID NO: 117          moltype = DNA  length = 7968
FEATURE                 Location/Qualifiers
misc_feature            1..7968
                        note = Plasmid pCVL.SFFV.HA.NLS.CLS4617..IRES.mTagBFP
source                  1..7968
                        mol_type = other DNA
                        organism = synthetic construct
SEQUENCE: 117
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgcc aataccaaat ataacgaaga  2460
gttcctgctg tacctggccg gctttgtgga cggtgacggt agcatcatcg ctcagattaa  2520
accacgtcag acctataagt ttaaacatca gctacgtttg acctttaaag tgggtcaaaa  2580
gacccagcgc cgttggtttc tggacaaact agtggatgaa attggcgttg gttacgtagc  2640
tgattctggt agcatgtccg aatacaactt aagcgaaatc aagccgctgc acaacttcct  2700
gactcaactg cagccgtttc tggaactgaa acagaaacag gcaaacctgg ttctgaaaat  2760
tatcgaacag ctgccgtctg caaaagaatc cccggacaaa ttcctggaag tttgtacctg  2820
ggtggatcag gttgcagctc tgaacgattc taagacgcgt aaaaccactt ctgaaaccgt  2880
tcgtgctgtg ctggacagcc tgagcgagaa gaagaaatcc tccccggcgg ccggtggatc  2940
tgataagtat aatcaggctc tgtctaaata caaccaagca ctgtccaagt acaatcaggc  3000
cctgtctggt ggaggcggtt ccaacaaaaa attcctgctg tatcttgctg gatttgtgga  3060
```

-continued

```
ttctgatggc tccatcattg ctcagataaa accaggtcaa cgttacaagt tcaaacacca  3120
gctccgtttg accttttacg tcactcagaa gacacaaaga aggtggttct tggacaaatt  3180
ggttgatcgt attggtgtgg gctatgtcta cgactctggc tctgcttcaa actaccagct  3240
gtctgaaatt aagcctcttc ataacctgct cacccaactg caacccttct tgaagctcaa  3300
acagaagcaa gcaaatctgg ttttgaaaat catcgagcaa ctgccatctg ccaaggagtc  3360
ccctgacaag tttcttgaag tgtgtacttg ggtggatcag gttgctgcct tgaatgactc  3420
caagaccaga aaaaccacct ctgagactgt gagggcagtt ctggatagcc agtctgagaa  3480
gaaaaagtac tctccttagc ctgcaggtcg agcatgcatc tagggcggcc aattccgccc  3540
ctctccctcc cccccccta acgttactgg ccgaagccgc ttggaataag gccggtgtgc  3600
gtttgtctat atgtgatttt ccaccatatt gccgtctttt ggcaatgtga gggcccggaa  3660
acctggccct gtcttcttga cgagcattcc taggggtctt tcccctctcg ccaaaggaat  3720
gcaaggtctg ttgaatgtcg tgaaggaagc agttcctctg gaagcttctt gaagacaaac  3780
aacgtctgta gcgacccttt gcaggcagcg gaacccccca cctggcgaca ggtgcctctg  3840
cggccaaaag ccacgtgtat aagatacacc tgcaaaggcg gcacaacccc agtgccacgt  3900
tgtgagttgg atagttgtgg aaagagtcaa atggctctcc tcaagcgtat tcaacaaggg  3960
gctgaaggat gcccagaagg taccccattg tatgggatct gatctggggc ctcggtgcac  4020
atgctttaca tgtgtttagt cgaggttaaa aaaacgtcta ggccccccga accacgggga  4080
cgtggttttc ctttgaaaaa cacgatgata agcttgccac aacccttacc ggtcgccacc  4140
atgagcgagc tgattaagga gaacatgcac atgaagctgt acatggaggg caccgtggac  4200
aaccatcact tcaagtgcac atccgagggc gaaggcaagc cctacgaggg cacccagacc  4260
atgagaatca aggtggtcga gggcggccct ctccccttcg ccttcgacat cctggctact  4320
agcttcctct acggcagcaa gaccttcatc aaccacaccc agggcatccc cgacttcttc  4380
aagcagtcct tccctgaggg cttcacatgg gagagagtca ccacatacga agacgggggc  4440
gtgctgaccg ctacccagga caccagcctc caggacggct gcctcatcta caacgtcaag  4500
atcagagggg tgaacttcac atccaacggc cctgtgatgc agaagaaaac actcggctgg  4560
gaggccttca ccgagacgct gtaccccgct gacggcggcc tggaaggcag aaacgacatg  4620
gccctgaagc tcgtgggcgg gagccatctg atcgcaaaca tcaagaccac atatagatcc  4680
aagaaacccg ctaagaacct caagatgcct ggcgtctact atgtggacta cagactggaa  4740
agaatcaagg aggccaacaa cgagacctac gtcgagcagc acgaggtggc agtggccaga  4800
tactgcgacc tccctagcaa actggggcac aagcttaatt gattctagag tcgaccgagc  4860
atcttaccgc catttatacc catatttgtt ctgtttttct tgatttgggt atacatttaa  4920
atgttaatag aacaaaatgg tggggcaatc atttacattt ttagggatat gtaattacta  4980
gttcaggtgt attgccacaa gacaaacatg ttaagaaact ttcccgttat ttacgctctg  5040
ttcctgttaa tcaacctctg gattacaaaa tttgtgaaag attgactgat attcttaact  5100
atgttgctcc ttttacgctg tgtggatatg ctgctttaata gcctctgtat ctagctattg  5160
cttcccgtac ggctttcgtt ttctcctcct tgtataaatc ctggttgctg tctcttttag  5220
aggagttgtg gcccgttgtc cgtcaacgtg gcgtggtgtg ctctgtgttt gctgacgcaa  5280
cccccactgg ctggggcatt gccaccacct gtcaactcct ttctgggact ttcgctttcc  5340
ccctccccgat cgccacggca gaactcatcg ccgcctgcct tgcccgctgc tggacagggg  5400
ctaggttgct gggcactgat aattccgtgg tgttgtcatc ggtacctttt taaaagaaaa  5460
ggggggactg gaagggctaa ttcactccca acgaagacaa gatatcataa cttcgtatag  5520
catacattat acgaagttat aatttatttg tgaaatttgt gatgctattg ctttatttgt  5580
aaccatatgt ttatttgtga aatttgtgat gctattgctt tatttgtaac cattgctttt  5640
tgcttgtact gggtctctct ggttagacca gatctgagcc tgggagctct ctggctaact  5700
agggaaccca ctgcttaagc ctcaataaag cttgcctcga ccagcctcga ctgtgccttc  5760
tagttgccag ccatctgttg tttgcccctc ccccgtgcct tccttgaccc tggaaggtgc  5820
cactcccact gtcctttcct aataaaatga ggaaattgca tcgcattgtc tgagtaggtg  5880
tcattctatt ctggggggtg gggtggggca ggacagcaag ggggaggatt gggaagacaa  5940
tagcaggcat gctggggatg cggtgggctc tatggcctgc agctgcatta atgaatcggc  6000
caacgcgcgg ggagaggcgg tttgcgtatt gggcgctctt ccgcttcctc gctcactgac  6060
tcgctgcgct cggtcgttcg gctgcggcga gcggtatcag ctcactcaaa ggcggtaata  6120
cggttatcca cagaatcagg ggataacgca ggaaagaaca tgtgagcaaa aggccagcaa  6180
aaggccagga accgtaaaaa ggccgcgttg ctggcgtttt tccataggct ccgcccccct  6240
gacgagcatc acaaaaatcg acgctcaagt cagaggtggc gaaacccgac aggactataa  6300
agataccagg cgtttccccc tggaagctcc ctcgtgcgct ctcctgttcc gaccctgccg  6360
cttaccggat acctgtccgc ctttctccct tcgggaagcg tggcgctttc tcatagctca  6420
cgctgtaggt atctcagttc ggtgtaggtc gttcgctcca agctgggctg tgtgcacgaa  6480
ccccccgttc agcccgaccg ctgcgcctta tccggtaact atcgtcttga gtccaacccg  6540
gtaagacacg acttatcgcc actggcagca gccactggta acaggattag cagagcgagg  6600
tatgtaggcg gtgctacaga gttcttgaag tggtggccta actacggcta cactagaagg  6660
acagtatttg gtatctgcgc tctgctgaag ccagttacct tcggaaaaag agttggtagc  6720
tcttgatccg gcaaacaaac caccgctggt agcggtggtt tttttgtttg caagcagcag  6780
attacgcgca gaaaaaaagg atctcaagaa gatcctttga tcttttctac ggggtctgac  6840
gctcagtgga acgaaaactc acgttaaggg attttggtca tgagattatc aaaaaggatc  6900
ttcacctaga tccttttaaa ttaaaaatga agttttaaat caatctaaag tatatatgag  6960
taaacttggt ctgacagtta ccaatgctta atcagtgagg cacctatctc agcgatctgt  7020
ctatttcgtt catccatagt tgcctgactc cccgtcgtgt agataactac gatacgggag  7080
ggcttaccat ctggccccag tgctgcaatg ataccgcgag acccacgctc accggctcca  7140
gatttatcag caataaacca gccagccgga agggccgagc gcagaagtgg tcctgcaact  7200
ttatccgcct ccatccagtc tattaattgt tgccgggaag ctagagtaag tagttcgcca  7260
gttaatagtt tgcgcaacgt tgttgccatt gctacaggca tcgtggtgtc acgctcgtcg  7320
tttggtatgg cttcattcag ctccggttcc caacgatcaa ggcgagttac atgatccccc  7380
atgttgtgca aaaaagcggt tagctccttc ggtcctccga tcgttgtcag aagtaagttg  7440
gccgcagtgt tatcactcat ggttatggca gcactgcata attctcttac tgtcatgcca  7500
tccgtaagat gcttttctgt gactggtgag tactcaacca agtcattctg agaatagtgt  7560
atgcggcgac cgagttgctc ttgcccggcg tcaatacggg ataataccgc gccacatagc  7620
agaactttaa aagtgctcat cattggaaaa cgttcttcgg ggcgaaaact ctcaaggatc  7680
ttaccgctgt tgagatccag ttcgatgtaa cccactcgtg cacccaactg atcttcagca  7740
tcttttactt tcaccagcgt ttctgggtga gcaaaaacag gaaggcaaaa tgccgcaaaa  7800
```

-continued

```
aagggaataa gggcgacacg gaaatgttga atactcatac tcttcctttt tcaatattat  7860
tgaagcattt atcagggtta ttgtctcatg agcggataca tatttgaatg tatttagaaa  7920
aataaacaaa taggggttcc gcgcacattt ccccgaaaag tgccacct              7968

SEQ ID NO: 118          moltype = DNA  length = 8742
FEATURE                 Location/Qualifiers
misc_feature            1..8742
                        note = Plasmid
                         pCVL.SFFV.HA.NLS.CLS4617.T2A.Trex2.IRES.mTagBFP
source                  1..8742
                        mol_type = other DNA
                        organism = synthetic construct
SEQUENCE: 118
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgcc aataccaaat ataacgaaga  2460
gttcctgctg tacctggccg gctttgtgga cggtgacggt agcatcatcg ctcagattaa  2520
accacgtcag acctataagt ttaaacatca gctacgtttg acctttaaag tgggtcaaaa  2580
gacccagcgc cgttggtttc tggacaaact agtggatgaa attggcgttg gttacgtagc  2640
tgattctggt agcatgtccg aatacaactt aagcgaaatc aagccgctgc acaacttcct  2700
gactcaactg cagccgtttc tggaactgaa acagaaacag gcaaacctgg ttctgaaaat  2760
tatcgaacag ctgccgtctg caaaagaatc cccggacaaa ttcctggaag tttgtacctg  2820
ggtggatcag gttgcagctc tgaacgattc taagacgcgt aaaaccactt ctgaaaccgt  2880
tcgtgctgtg ctggacagcc tgagcgagaa gaagaaatcc tccccggcgg ccggtggatc  2940
tgataagtat aatcaggctc tgtctaaata caaccaagca ctgtccaagt acaatcaggc  3000
cctgtctggt ggaggcggtt ccaacaaaaa attcctgctg tatcttgctg gatttgtgga  3060
ttctgatggc tccatcattg ctcagataaa accaggtcaa cgttacaagt tcaaacacca  3120
gctccgtttg accttttacg tcactcagaa gacacaaaga aggtggttct tggacaaatt  3180
ggttgatcgt attggtgtgg gctatgtcta cgactctggc tctgcttcaa actaccagct  3240
gtctgaaatt aagcctcttc ataacctgct cacccaactg caacccttct tgaagctcaa  3300
acagaagcaa gcaaatctgg ttttgaaaat catcgagcaa ctgccatctg ccaaggagtc  3360
ccctgacaag tttcttgaag tgtgtacttg ggtggatcag gttgctgcct tgaatgactc  3420
caagaccaga aaaaccacct ctgagactgt gagggcagtt ctggatagcc agtctgagaa  3480
gaaaaagtac tctcctggat ccggtgaggg cagaggaagt cttctaacat gcggtgacgt  3540
ggaggagaat ccgggcccct ccggatctga gccacctcgg gctgagacct ttgtattcct  3600
ggacctagaa gccactgggc tcccaaacat ggaccctgag attgcagaga tatccctttt  3660
tgctgttcac cgctcttccc tggagaaccc agaacgggat gattctggtt ccttggtgct  3720
gccccgtgtt ctggacaagc tcacactgtg catgtgcccg gagcgcccct ttactgccaa  3780
ggccagtgag attactggtt tgagcagcga aagcctgatg cactgcggga aggctggttt  3840
caatggcgct gtggtaagga cactgcaggg cttcctaagc cgccaggagg gccccatctg  3900
ccttgtggcc cacaatggct tcgattatga cttcccactg ctgtgcacgg agctacaacg  3960
```

-continued

```
tctgggtgcc catctgcccc aagacactgt ctgcctggac acactgcctg cattgcgggg  4020
cctggaccgt gctcacagcc acggcaccag ggctcaaggc cgcaaaagct acagcctggc  4080
cagtctcttc caccgctact tccaggctga acccagtgct gcccattcag cagaaggtga  4140
tgtgcacacc ctgcttctga tcttcctgca tcgtgctcct gagctgctcg cctgggcaga  4200
tgagcaggcc cgcagctggg ctcatattga gcccatgtac gtgccacctg atggtccaag  4260
cctcgaagcc tgacctgcag gtcgagcatg catctagggc ggccaattcc gcccctctcc  4320
ctcccccccc cctaacgtta ctggccgaag ccgcttggaa taaggccggt gtgcgtttgt  4380
ctatatgtga ttttccacca tattgccgtc ttttggcaat gtgagggccc ggaaacctgg  4440
ccctgtcttc ttgacgagca ttcctagggg tctttcccct ctcgccaaag gaatgcaagg  4500
tctgttgaat gtcgtgaagg aagcagttcc tctggaagct tcttgaagac aaacaacgtc  4560
tgtagcgacc ctttgcaggc agcggaaccc cccacctggc gacaggtgcc tctgcggcca  4620
aaagccacgt gtataagata cacctgcaaa ggcggcacaa ccccagtgcc acgttgtgag  4680
ttggatagtt gtggaaagag tcaaatggct ctcctcaagc gtattcaaca aggggctgaa  4740
ggatgcccag aaggtacccc attgtatggg atctgatctg gggcctcggt gcacatgctt  4800
tacatgtgtt tagtcgaggt taaaaaaacg tctaggcccc ccgaaccacg gggacgtggt  4860
tttcctttga aaaacacgat gataagcttg ccacaaccct taccggtcgc caccatgagc  4920
gagctgatta aggagaacat gcacatgaag ctgtacatgg agggcaccgt ggacaaccat  4980
cacttcaagt gcacatccga gggcgaaggc aagccctacg agggcaccca gaccatgaga  5040
atcaaggtgg tcgagggcgg ccctctcccc ttcgccttcg acatcctggc tactagcttc  5100
ctctacggca gcaagacctt catcaaccac acccagggca tccccgactt cttcaagcag  5160
tccttccctg agggcttcac atgggagaga gtcaccacat acgaagacgg gggcgtgctg  5220
accgctaccc aggacaccag cctccaggac ggctgcctca tctacaacgt caagatcaga  5280
ggggtgaact tcacatccaa cggccctgtg atgcagaaga aaacactcgg ctgggaggcc  5340
ttcaccgaga cgctgtaccc cgctgacggc ggcctggaag gcagaaacga catggccctg  5400
aagctcgtgg gcgggagcca tctgatcgca aacatcaaga ccacatatag atccaagaaa  5460
cccgctaaga acctcaagat gcctggcgtc tactatgtgg actacagact ggaaagaatc  5520
aaggaggcca acaacgagac ctacgtcgag cagcacgagg tggcagtggc cagatactgc  5580
gacctcccta gcaaactggg gcacaagctt aattgattct agagtcgacc gagcatctta  5640
ccgccattta tacccatatt tgttctgttt ttcttgattt gggtatacat ttaaatgtta  5700
atagaacaaa atggtggggc aatcatttac atttttaggg atatgtaatt actagttcag  5760
gtgtattgcc acaagacaaa catgttaaga aactttcccg ttatttacgc tctgttcctg  5820
ttaatcaacc tctggattac aaaatttgtg aaagattgac tgatattctt aactatgttg  5880
ctccttttac gctgtgtgga tatgctgctt tatagcctct gtatctagct attgcttccc  5940
gtacggcttt cgttttctcc tccttgtata aatcctggtt gctgtctctt ttagaggagt  6000
tgtggcccgt tgtccgtcaa cgtggcgtgg tgtgctctgt gtttgctgac gcaaccccca  6060
ctggctgggg cattgccacc acctgtcaac tcctttctgg gactttcgct ttccccctcc  6120
cgatcgccac ggcagaactc atcgccgcct gccttgcccg ctgctggaca ggggctaggt  6180
tgctgggcac tgataattcc gtggtgttgt catcggtacc tttttaaaag aaaagggggg  6240
actggaaggg ctaattcact cccaacgaag acaagatatc ataacttcgt atagcataca  6300
ttatacgaag ttataattta tttgtgaaat ttgtgatgct attgctttat ttgtaaccat  6360
atgtttattt gtgaaatttg tgatgctatt gctttatttg taaccattgc tttttgcttg  6420
tactgggtct ctctggttag accagatctg agcctgggag ctctctggct aactagggaa  6480
cccactgctt aagcctcaat aaagcttgcc tcgaccagcc tcgactgtgc cttctagttg  6540
ccagccatct gttgtttgcc cctcccccgt gccttccttg accctggaag gtgccactcc  6600
cactgtcctt tcctaataaa atgaggaaat tgcatcgcat tgtctgagta ggtgtcattc  6660
tattctgggg ggtggggtgg ggcaggacag caagggggag gattgggaag acaatagcag  6720
gcatgctggg gatgcggtgg gctctatggc ctgcagctgc attaatgaat cggccaacgc  6780
gcggggagag gcggtttgcg tattgggcgc tcttccgctt cctcgctcac tgactcgctg  6840
cgctcggtcg ttcggctgcg gcgagcggta tcagctcact caaaggcggt aatacggtta  6900
tccacagaat caggggataa cgcaggaaag aacatgtgag caaaaggcca gcaaaaggcc  6960
aggaaccgta aaaaggccgc gttgctggcg tttttccata ggctccgccc ccctgacgag  7020
catcacaaaa atcgacgctc aagtcagagg tggcgaaacc cgacaggact ataaagatac  7080
caggcgtttc cccctggaag ctccctcgtg cgctctcctg ttccgaccct gccgcttacc  7140
ggatacctgt ccgcctttct cccttcggga agcgtggcgc tttctcatag ctcacgctgt  7200
aggtatctca gttcggtgta ggtcgttcgc tccaagctgg gctgtgtgca cgaacccccc  7260
gttcagcccg accgctgcgc cttatccggt aactatcgtc ttgagtccaa cccggtaaga  7320
cacgacttat cgccactggc agcagccact ggtaacagga ttagcagagc gaggtatgta  7380
ggcggtgcta cagagttctt gaagtggtgg cctaactacg gctacactag aaggacagta  7440
tttggtatct gcgctctgct gaagccagtt accttcggaa aaagagttgg tagctcttga  7500
tccggcaaac aaaccaccgc tggtagcggt ggtttttttg tttgcaagca gcagattacg  7560
cgcagaaaaa aaggatctca agaagatcct ttgatctttt ctacggggtc tgacgctcag  7620
tggaacgaaa actcacgtta agggattttg gtcatgagat tatcaaaaag gatcttcacc  7680
tagatccttt taaattaaaa atgaagtttt aaatcaatct aaagtatata tgagtaaact  7740
tggtctgaca gttaccaatg cttaatcagt gaggcaccta tctcagcgat ctgtctattt  7800
cgttcatcca tagttgcctg actccccgtc gtgtagataa ctacgatacg ggagggctta  7860
ccatctggcc ccagtgctgc aatgataccg cgagacccac gctcaccggc tccagattta  7920
tcagcaataa accagccagc cggaagggcc gagcgcagaa gtggtcctgc aactttatcc  7980
gcctccatcc agtctattaa ttgttgccgg gaagctagag taagtagttc gccagttaat  8040
agtttgcgca acgttgttgc cattgctaca ggcatcgtgg tgtcacgctc gtcgtttggt  8100
atggcttcat tcagctccgg ttcccaacga tcaaggcgag ttacatgatc ccccatgttg  8160
tgcaaaaaag cggttagctc cttcggtcct ccgatcgttg tcagaagtaa gttggccgca  8220
gtgttatcac tcatggttat ggcagcactg cataattctc ttactgtcat gccatccgta  8280
agatgctttt ctgtgactgg tgagtactca accaagtcat tctgagaata gtgtatgcgg  8340
cgaccgagtt gctcttgccc ggcgtcaata cgggataata ccgcgccaca tagcagaact  8400
ttaaaagtgc tcatcattgg aaaacgttct tcggggcgaa aactctcaag gatcttaccg  8460
ctgttgagat ccagttcgat gtaacccact cgtgcaccca actgatcttc agcatctttt  8520
actttcacca gcgtttctgg gtgagcaaaa acaggaaggc aaaatgccgc aaaaaaggga  8580
ataagggcga cacggaaatg ttgaatactc atactcttcc tttttcaata ttattgaagc  8640
atttatcagg gttattgtct catgagcgga tacatatttg aatgtattta gaaaaataaa  8700
```

```
caaatagggg ttccgcgcac atttccccga aaagtgccac ct                      8742

SEQ ID NO: 119         moltype = DNA  length = 8757
FEATURE                Location/Qualifiers
misc_feature           1..8757
                       note = Plasmid pCVL.SFFV.HA.NLS.mCre
                        I.T2A.Trex2.IRES.mTagBFP
source                 1..8757
                       mol_type = other DNA
                       organism = synthetic construct
SEQUENCE: 119
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgac accaagtata acaaggagtt  2460
cctgctgtat ctggctggtt tcgtcgatgg cgatggcagc attattgcac agattaagcc  2520
aaaccagtcc tataagttta agcaccagtt gtctctcact tttcaggtga cccaaaaaac  2580
ccaacgccgc tggttcctcg acaagctggt agacgagatc ggtgtgggct acgttcgcga  2640
tcgcggctcc gtttccgact acatcctcag cgagattaaa ccgctgcaca attttctgac  2700
ccaactgcag ccgtttctga agctcaaaca gaagcaagcg aacctggtgc tgaaaatcat  2760
cgaacagctc ccgtccgcga aggaatctcc ggataagttt ctggaagtgt gcacctgggt  2820
ggaccagatt gctgcactga atgattccaa aacccgcaag accacttctg agaccgttcg  2880
cgccgttctg gactctctct ctgaaaaaaa aaaatcttcc ccgaccggta gcggctcagg  2940
atctaaatcc caggctgtgg ctcacccgac agacggccag agggatttcg gggccaaagg  3000
atctgggtcg ggaagcggta ccatgaatac taaatacaat aaagaatttc ttctctacct  3060
cgcgggcttt gtggacggtg acggttccat catcgctcaa atcaaaccta atcaaagcta  3120
caaattcaaa catcagctgt ccctgacctt ccaagttacg cagaaaacgc agcgtcgttg  3180
gtttctggat aaattggttg atgaaattgg cgtaggttat gtacgtgacc gtggttctgt  3240
gtctgattat attctgtccg aaatcaagcc tctccataac ttcctcacgc agctgcaacc  3300
attcctgaaa ctgaagcaga aacaggctaa tctcgttctg aaaattattg aacagctgcc  3360
atctgctaaa gagtcccctg acaaattcct cgaggtttgt acttgggttg atcaaatcgc  3420
ggcccttaac gacagcaaga ctcgtaaaac taccagcgaa actgtccgtg cagtactcga  3480
ttccctgtcg gagaagaaga agagctctcc aggatccggt gagggcagag gaagtcttct  3540
aacatgcggt gacgtggagg agaatccggg cccctccgga tctgagccac ctcgggctga  3600
gacctttgta ttcctggacc tagaagccac tgggctccca aacatggacc ctgagattgc  3660
agagatatcc ctttttgctg ttcaccgctc ttccctggag aacccagaac gggatgattc  3720
tggttccttg gtgctgcccc gtgttctgga caagctcaca ctgtgcatgt gcccggagcg  3780
cccctttact gccaaggcca gtgagattac tggtttgagc agcgaaagcc tgatgcactg  3840
cgggaaggct ggtttcaatg gcgctgtggt aaggacactg cagggcttcc taagccgcca  3900
ggagggcccc atctgccttg tggcccacaa tggcttcgat tatgacttcc cactgctgtg  3960
cacggagcta caacgtctgg gtgcccatct gccccaagac actgtctgcc tggacacact  4020
gcctgcattg cggggcctgg accgtgctca cagccacggc accagggctc aaggccgcaa  4080
```

-continued

```
aagctacagc ctggccagtc tcttccaccg ctacttccag gctgaaccca gtgctgccca  4140
ttcagcagaa ggtgatgtgc acaccctgct tctgatcttc ctgcatcgtg ctcctgagct  4200
gctcgcctgg gcagatgagc aggcccgcag ctgggctcat attgagccca tgtacgtgcc  4260
acctgatggt ccaagcctcg aagcctgacc tgcaggtcga gcatgcatct agggcggcca  4320
attccgcccc tctccctccc ccccccctaa cgttactggc cgaagccgct tggaataagg  4380
ccggtgtgcg tttgtctata tgtgattttc caccatattg ccgtcttttg gcaatgtgag  4440
ggcccggaaa cctggccctg tcttcttgac gagcattcct aggggtcttt cccctctcgc  4500
caaaggaatg caaggtctgt tgaatgtcgt gaaggaagca gttcctctgg aagcttcttg  4560
aagacaaaca acgtctgtag cgaccctttg caggcagcgg aacccccac ctggcgacag  4620
gtgcctctgc ggccaaaagc cacgtgtata agatacacct gcaaaggcgg cacaacccca  4680
gtgccacgtt gtgagttgga tagttgtgga aagagtcaaa tggctctcct caagcgtatt  4740
caacaagggg ctgaaggatg cccagaaggt accccattgt atgggatctg atctggggcc  4800
tcggtgcaca tgctttacat gtgtttagtc gaggttaaaa aaacgtctag gcccccgaa  4860
ccacggggac gtggttttcc tttgaaaaac acgatgataa gcttgccaca acccttaccg  4920
gtcgccacca tgagcgagct gattaaggag aacatgcaca tgaagctgta catggagggc  4980
accgtggaca accatcactt caagtgcaca tccgagggcg aaggcaagcc ctacgagggc  5040
acccagacca tgagaatcaa ggtggtcgag ggcggccctc tccccttcgc cttcgacatc  5100
ctggctacta gcttcctcta cggcagcaag accttcatca accacaccca gggcatcccc  5160
gacttcttca agcagtcctt ccctgagggc ttcacatggg agagagtcac cacatacgaa  5220
gacgggggcg tgctgaccgc tacccaggac accagcctcc aggacggctg cctcatctac  5280
aacgtcaaga tcagaggggt gaacttcaca tccaacggcc ctgtgatgca gaagaaaaca  5340
ctcggctggg aggccttcac cgagacgctg taccccgctg acggcggcct ggaaggcaga  5400
aacgacatgg ccctgaagct cgtgggcggg agccatctga tcgcaaacat caagaccaca  5460
tatagatcca agaaacccgc taagaacctc aagatgcctg gcgtctacta tgtggactac  5520
agactggaaa gaatcaagga ggccaacaac gagacctacg tcgagcagca cgaggtggca  5580
gtggccagat actgcgacct ccctagcaaa ctggggcaca agcttaattg attctagagt  5640
cgaccgagca tcttaccgcc atttataccc atatttgttc tgtttttctt gatttgggta  5700
tacatttaaa tgttaataga acaaaatggt ggggcaatca tttacatttt tagggatatg  5760
taattactag ttcaggtgta ttgccacaag acaaacatgt taagaaactt tcccgttatt  5820
tacgctctgt tcctgttaat caacctctgg attacaaaat ttgtgaaaga ttgactgata  5880
ttcttaacta tgttgctcct tttacgctgt gtggatatgc tgctttatag cctctgtatc  5940
tagctattgc ttcccgtacg gctttcgttt tctcctcctt gtataaatcc tggttgctgt  6000
ctctttttaga ggagttgtgg cccgttgtcc gtcaacgtgg cgtggtgtgc tctgtgtttg  6060
ctgacgcaac ccccactggc tggggcattg ccaccacctg tcaactcctt tctgggactt  6120
tcgctttccc cctcccgatc gccacggcag aactcatcgc cgcctgcctt gcccgctgct  6180
ggacaggggc taggttgctg ggcactgata attccgtggt gttgtcatcg gtaccttttt  6240
aaaagaaaag gggggactgg aagggctaat tcactcccaa cgaagacaag atatcataac  6300
ttcgtatagc atacattata cgaagttata atttatttgt gaaatttgtg atgctattgc  6360
tttatttgta accatatgtt tatttgtgaa atttgtgatg ctattgcttt atttgtaacc  6420
attgcttttt gcttgtactg ggtctctctg gttagaccag atctgagcct gggagctctc  6480
tggctaacta gggaacccac tgcttaagcc tcaataaagc ttgcctcgac cagcctcgac  6540
tgtgccttct agttgccagc catctgttgt ttgcccctcc cccgtgcctt ccttgaccct  6600
ggaaggtgcc actcccactg tcctttccta ataaaatgag gaaattgcat cgcattgtct  6660
gagtaggtgt cattctattc tggggggtgg ggtggggcag gacagcaagg gggaggattg  6720
ggaagacaat agcaggcatg ctggggatgc ggtgggctct atggcctgca gctgcattaa  6780
tgaatcggcc aacgcgcggg gagaggcggt ttgcgtattg ggcgctcttc cgcttcctcg  6840
ctcactgact cgctgcgctc ggtcgttcgg ctgcggcgag cggtatcagc tcactcaaag  6900
gcggtaatac ggttatccac agaatcaggg gataacgcag gaaagaacat gtgagcaaaa  6960
ggccagcaaa aggccaggaa ccgtaaaaag gccgcgttgc tggcgttttt ccataggctc  7020
cgcccccctg acgagcatca caaaaatcga cgctcaagtc agaggtggcg aaacccgaca  7080
ggactataaa gataccaggc gtttccccct ggaagctccc tcgtgcgctc tcctgttccg  7140
accctgccgc ttaccggata cctgtccgcc tttctccctt cgggaagcgt ggcgctttct  7200
catagctcac gctgtaggta tctcagttcg gtgtaggtcg ttcgctccaa gctgggctgt  7260
gtgcacgaac cccccgttca gcccgaccgc tgcgccttat ccggtaacta tcgtcttgag  7320
tccaacccgg taagacacga cttatcgcca ctggcagcag ccactggtaa caggattagc  7380
agagcgaggt atgtaggcgg tgctacagag ttcttgaagt ggtggcctaa ctacggctac  7440
actagaagga cagtatttgg tatctgcgct ctgctgaagc cagttacctt cggaaaaaga  7500
gttggtagct cttgatccgg caaacaaacc accgctggta gcggtggttt ttttgtttgc  7560
aagcagcaga ttacgcgcag aaaaaaagga tctcaagaag atcctttgat cttttctacg  7620
gggtctgacg ctcagtggaa cgaaaactca cgttaaggga ttttggtcat gagattatca  7680
aaaaggatct tcacctagat ccttttaaat taaaaatgaa gttttaaatc aatctaaagt  7740
atatatgagt aaacttggtc tgacagttac caatgcttaa tcagtgaggc acctatctca  7800
gcgatctgtc tatttcgttc atccatagtt gcctgactcc ccgtcgtgta gataactacg  7860
atacgggagg gcttaccatc tggccccagt gctgcaatga taccgcgaga cccacgctca  7920
ccggctccag atttatcagc aataaaccag ccagccggaa gggccgagcg cagaagtggt  7980
cctgcaactt tatccgcctc catccagtct attaattgtt gccgggaagc tagagtaagt  8040
agttcgccag ttaatagttt gcgcaacgtt gttgccattg ctacaggcat cgtggtgtca  8100
cgctcgtcgt ttggtatggc ttcattcagc tccggttccc aacgatcaag gcgagttaca  8160
tgatccccca tgttgtgcaa aaaagcggtt agctccttcg gtcctccgat cgttgtcaga  8220
agtaagttgg ccgcagtgtt atcactcatg gttatggcag cactgcataa ttctcttact  8280
gtcatgccat ccgtaagatg cttttctgtg actggtgagt actcaaccaa gtcattctga  8340
gaatagtgta tgcggcgacc gagttgctct tgcccggcgt caatacggga taataccgcg  8400
ccacatagca gaactttaaa agtgctcatc attggaaaac gttcttcggg gcgaaaactc  8460
tcaaggatct taccgctgtt gagatccagt tcgatgtaac ccactcgtgc acccaactga  8520
tcttcagcat cttttacttt caccagcgtt tctgggtgag caaaaacagg aaggcaaaat  8580
gccgcaaaaa agggaataag ggcgacacgg aaatgttgaa tactcatact cttccttttt  8640
caatattatt gaagcattta tcagggttat tgtctcatga gcggatacat atttgaatgt  8700
atttagaaaa ataaacaaat aggggttccg cgcacatttc cccgaaaagt gccacct     8757
```

```
SEQ ID NO: 120          moltype = DNA  length = 7986
FEATURE                 Location/Qualifiers
misc_feature            1..7986
                        note = Plasmid pCVL.SFFV.HA.NLS.mCre.IRES.mTagBFP
source                  1..7986
                        mol_type = other DNA
                        organism = synthetic construct
SEQUENCE: 120
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgac accaagtata acaaggagtt  2460
cctgctgtat ctggctggtt tcgtcgatgg cgatggcagc attattgcac agattaagcc  2520
aaaccagtcc tataagttta agcaccagtt gtctctcact tttcaggtga cccaaaaaac  2580
ccaacgccgc tggttcctcg acaagctggt agacgagatc ggtgtgggct acgttcgcga  2640
tcgcggctcc gtttccgact acatcctcag cgagattaaa ccgctgcaca attttctgac  2700
ccaactgcag ccgtttctga agctcaaaca gaagcaagcg aacctggtgc tgaaaatcat  2760
cgaacagctc ccgtccgcga aggaatctcc ggataagttt ctggaagtgt gcacctgggt  2820
ggaccagatt gctgcactga atgattccaa aacccgcaag accacttctg agaccgttcg  2880
cgccgttctg gactctctct ctgaaaaaaa aaaatcttcc ccgaccggta gcggctcagg  2940
atctaaatcc caggctgtgg ctcacccgac agacggccag agggatttcg gggccaaagg  3000
atctgggtcg ggaagcggta ccatgaatac taaatacaat aaagaatttc ttctctacct  3060
cgcgggcttt gtggacggtg acggttccat catcgctcaa atcaaaccta atcaaagcta  3120
caaattcaaa catcagctgt ccctgacctt ccaagttacg cagaaaacgc agcgtcgttg  3180
gtttctggat aaattggttg atgaaattgg cgtaggttat gtacgtgacc gtggttctgt  3240
gtctgattat attctgtccg aaatcaagcc tctccataac ttcctcacgc agctgcaacc  3300
attcctgaaa ctgaagcaga aacaggctaa tctcgttctg aaaattattg aacagctgcc  3360
atctgctaaa gagtcccctg acaaattcct cgaggtttgt acttgggttg atcaaatcgc  3420
ggcccttaac gacagcaaga ctcgtaaaac taccagcgaa actgtccgtg cagtactcga  3480
ttccctgtcg gagaagaaga agagctctcc atagtaacct gcaggtcgag catgcatcta  3540
gggcggccaa ttccgcccct ctccctcccc ccccccctaac gttactggcc gaagccgctt  3600
ggaataaggc cggtgtgcgt ttgtctatat gtgattttcc accatattgc cgtcttttgg  3660
caatgtgagg gcccggaaac ctggccctgt cttcttgacg agcattccta ggggtctttc  3720
ccctctcgcc aaaggaatgc aaggtctgtt gaatgtcgtg aaggaagcag ttcctctgga  3780
agcttcttga agacaaacaa cgtctgtagc gaccctttgc aggcagcgga accccccacc  3840
tggcgacagg tgcctctgcg gccaaaagcc acgtgtataa gatacacctg caaaggcggc  3900
acaaccccag tgccacgttg tgagttggat agttgtggaa agagtcaaat ggctctcctc  3960
aagcgtattc aacaaggggc tgaaggatgc ccagaaggta ccccattgta tgggatctga  4020
tctggggcct cggtgcacat gctttacatg tgtttagtcg aggttaaaaa aacgtctagg  4080
ccccccgaac cacggggacg tggttttcct ttgaaaaaca cgatgataag cttgccacaa  4140
cccttaccgg tcgccaccat gagcgagctg attaaggaga acatgcacat gaagctgtac  4200
atggagggca ccgtggacaa ccatcacttc aagtgcacat ccgagggcga aggcaagccc  4260
```

-continued

```
tacgagggca cccagaccat gagaatcaag gtggtcgagg gcggccctct ccccttcgcc  4320
ttcgacatcc tggctactag cttcctctac ggcagcaaga ccttcatcaa ccacacccag  4380
ggcatccccg acttcttcaa gcagtccttc cctgagggct tcacatggga gagagtcacc  4440
acatacgaag acgggggcgt gctgaccgct acccaggaca ccagcctcca ggacggctgc  4500
ctcatctaca acgtcaagat cagaggggtg aacttcacat ccaacggccc tgtgatgcag  4560
aagaaaacac tcggctggga ggccttcacc gagacgctgt accccgctga cggcggcctg  4620
gaaggcagaa acgacatggc cctgaagctc gtgggcggga gccatctgat cgcaaacatc  4680
aagaccacat atagatccaa gaaacccgct aagaacctca agatgcctgg cgtctactat  4740
gtggactaca gactggaaag aatcaaggag gccaacaacg agacctacgt cgagcagcac  4800
gaggtggcag tggccagata ctgcgacctc cctagcaaac tggggcacaa gcttaattga  4860
ttctagagtc gaccgagcat cttaccgcca tttataccca tatttgttct gtttttcttg  4920
atttgggtat acatttaaat gttaatagaa caaaatggtg gggcaatcat ttacattttt  4980
agggatatgt aattactagt tcaggtgtat tgccacaaga caaacatgtt aagaaacttt  5040
cccgttattt acgctctgtt cctgttaatc aacctctgga ttacaaaatt tgtgaaagat  5100
tgactgatat tcttaactat gttgctcctt ttacgctgtg tggatatgct gctttatagc  5160
ctctgtatct agctattgct tcccgtacgg ctttcgtttt ctcctccttg tataaatcct  5220
ggttgctgtc tcttttagag gagttgtggc ccgttgtccg tcaacgtggc gtggtgtgct  5280
ctgtgtttgc tgacgcaacc cccactggct ggggcattgc caccacctgt caactccttt  5340
ctgggacttt cgctttcccc ctcccgatcg ccacggcaga actcatcgcc gcctgccttg  5400
cccgctgctg gacaggggct aggttgctgg gcactgataa ttccgtggtg ttgtcatcgg  5460
taccttttta aaagaaaagg ggggactgga agggctaatt cactcccaac gaagacaaga  5520
tatcataact tcgtatagca tacattatac gaagttataa tttatttgtg aaatttgtga  5580
tgctattgct ttatttgtaa ccatatgttt atttgtgaaa tttgtgatgc tattgcttta  5640
tttgtaacca ttgcttttttg cttgtactgg gtctctctgg ttagaccaga tctgagcctg  5700
ggagctctct ggctaactag ggaacccact gcttaagcct caataaagct tgcctcgacc  5760
agcctcgact gtgccttcta gttgccagcc atctgttgtt tgcccctccc ccgtgccttc  5820
cttgaccctg gaaggtgcca ctcccactgt cctttcctaa taaaatgagg aaattgcatc  5880
gcattgtctg agtaggtgtc attctattct ggggggtggg gtggggcagg acagcaaggg  5940
ggaggattgg gaagacaata gcaggcatgc tggggatgcg gtgggctcta tggcctgcag  6000
ctgcattaat gaatcggcca acgcgcgggg agaggcggtt tgcgtattgg gcgctcttcc  6060
gcttcctcgc tcactgactc gctgcgctcg gtcgttcggc tgcggcgagc ggtatcagct  6120
cactcaaagg cggtaatacg gttatccaca gaatcagggg ataacgcagg aaagaacatg  6180
tgagcaaaag gccagcaaaa ggccaggaac cgtaaaaagg ccgcgttgct ggcgtttttc  6240
cataggctcc gcccccctga cgagcatcac aaaaatcgac gctcaagtca gaggtggcga  6300
aacccgacag gactataaag ataccaggcg tttccccctg gaagctccct cgtgcgctct  6360
cctgttccga ccctgccgct taccggatac ctgtccgcct ttctcccttc gggaagcgtg  6420
gcgctttctc atagctcacg ctgtaggtat ctcagttcgg tgtaggtcgt tcgctccaag  6480
ctgggctgtg tgcacgaacc ccccgttcag cccgaccgct gcgccttatc cggtaactat  6540
cgtcttgagt ccaacccggt aagacacgac ttatcgccac tggcagcagc cactggtaac  6600
aggattagca gagcgaggta tgtaggcggt gctacagagt tcttgaagtg gtggcctaac  6660
tacggctaca ctagaaggac agtatttggt atctgcgctc tgctgaagcc agttaccttc  6720
ggaaaaagag ttggtagctc ttgatccggc aaacaaacca ccgctggtag cggtggtttt  6780
tttgtttgca agcagcagat tacgcgcaga aaaaaaggat ctcaagaaga tcctttgatc  6840
ttttctacgg ggtctgacgc tcagtggaac gaaaactcac gttaagggat tttggtcatg  6900
agattatcaa aaaggatctt cacctagatc cttttaaatt aaaaatgaag ttttaaatca  6960
atctaaagta tatatgagta aacttggtct gacagttacc aatgcttaat cagtgaggca  7020
cctatctcag cgatctgtct atttcgttca tccatagttg cctgactccc cgtcgtgtag  7080
ataactacga tacgggaggg cttaccatct ggccccagtg ctgcaatgat accgcgagac  7140
ccacgctcac cggctccaga tttatcagca ataaaccagc cagccggaag ggccgagcgc  7200
agaagtggtc ctgcaacttt atccgcctcc atccagtcta ttaattgttg ccgggaagct  7260
agagtaagta gttcgccagt taatagtttg cgcaacgttg ttgccattgc tacaggcatc  7320
gtggtgtcac gctcgtcgtt tggtatggct tcattcagct ccggttccca acgatcaagg  7380
cgagttacat gatcccccat gttgtgcaaa aaagcggtta gctccttcgg tcctccgatc  7440
gttgtcagaa gtaagttggc cgcagtgtta tcactcatgg ttatggcagc actgcataat  7500
tctcttactg tcatgccatc cgtaagatgc ttttctgtga ctggtgagta ctcaaccaag  7560
tcattctgag aatagtgtat gcggcgaccg agttgctctt gcccggcgtc aatacgggat  7620
aataccgcgc cacatagcag aactttaaaa gtgctcatca ttggaaaacg ttcttcgggg  7680
cgaaaactct caaggatctt accgctgttg agatccagtt cgatgtaacc cactcgtgca  7740
cccaactgat cttcagcatc ttttactttc accagcgttt ctgggtgagc aaaaacagga  7800
aggcaaaatg ccgcaaaaaa gggaataagg gcgacacgga aatgttgaat actcatactc  7860
ttcctttttc aatattattg aagcatttat cagggttatt gtctcatgag cggatacata  7920
tttgaatgta tttagaaaaa taaacaaata ggggttccgc gcacatttcc ccgaaaagtg  7980
ccacct                                                             7986
```

```
SEQ ID NO: 121          moltype = DNA  length = 7665
FEATURE                 Location/Qualifiers
misc_feature            1..7665
                        note = Plasmid pCVL.SFFV.HA.NLS.Hje.IRES.mTagBFP
source                  1..7665
                        mol_type = other DNA
                        organism = synthetic construct
SEQUENCE: 121
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
```

-continued cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc caggggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc ctgatcttca gacctggagg aggagatatg 960
agggacaatt ggagaagtga attatataaa tataaagtag taaaaattga accattagga 1020
gtagcaccca ccaaggcaaa gagaagagtg gtgcagagag aaaaaagagc agtgggaata 1080
ggagctttgt tccttgggtt cttgggagca gcaggaagca ctatgggcgc agcgtcaatg 1140
acgctgacgg tacaggccag acaattattg tctggtatag tgcagcagca gaacaatttg 1200
ctgagggcta ttgaggcgca acagcatctg ttgcaactca cagtctgggg catcaagcag 1260
ctccaggcaa gaatcctggc tgtggaaaga tacctaaagg atcaacagct cctggggatt 1320
tggggttgct ctggaaaact catttgcacc actgctgtgc cttggaatgc tagttggagt 1380
aatgaatctc tggaacagat ttggaatcac acgacctgga tggagtggga cagagaaatt 1440
aacaattaca caagcttaat acactcctta attgaagaat cgcaaaacca gcaagaaaag 1500
aatgaacaag aattattgga attagataaa tgggcaagtt tgtggaattg gtttaacata 1560
acaaattggc tgtggtatat aaaattattc ataatgatag taggaggctt ggtaggttta 1620
agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800
cggttaactt ttaaaagaaa aggggggatt ggggggtaca gtgcagggga aagaatagta 1860
gacataatag caacagacat acaaactaaa gaattacaaa aacaaattac aaaaattcaa 1920
aattttatcg attacgcgtc acgtgctagc tgcagtaacg ccattttgca aggcatggaa 1980
aaataccaaa ccaagaatag agaagttcag atcaagggcg ggtacatgaa aatagctaac 2040
gttgggccaa acaggatatc tgcggtgagc agtttcggcc ccggcccggg gccaagaaca 2100
gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt cccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcgat cttacgtacg cgtatttagt 2460
tggtctcttc gaaggggatg gatactttag tatcaccaag aaaggcaagt acttgactta 2520
tgaattaggt attgagctga gcatcaaaga cgtccaattg atttacaaga tcaaggacat 2580
cctaggtgtt ggcaaagtaa gcttcaggaa gagaaacgag attgaaatgg tttcattgag 2640
gatccgtgat aagaatcatc taaaaaactt catattgcct atatttgaca agtatccaat 2700
gttatccaac aaacagtacg actatttaag attcaaggat gcattgttat ctaacattat 2760
atactcagat gacttgcctg aatacgctag aagtaacgaa tcgattaatt ctgtagactc 2820
cattatcaac acatcatact tctccgcctg gctagttgga tttatagaag ctgagggctg 2880
tttcagtacg tacaagctga acaaagacga tgactacttg attgcttcat tcgacattgc 2940
ccaaaaagat ggtgatatct tgatttcagc aattcacaag tacttaagtt tcactactaa 3000
gatttaccta gacaagacta attgtagcag attgaaggtc accggtgtta gatccgtcaa 3060
gaacgtcgtt aagtttatcc agggtgctcc tgtcaaattg ttaggcaaca agaaactgca 3120
atacaagttg tggataaaac aactaaggaa gatttctagg tattccgaga agatccagct 3180
tccatcaaac tactagcctg caggtcgagc atgcatctag ggcggccaat tccgcccctc 3240
tccctccccc ccccctaacg ttactggccg aagccgcttg gaataaggcc ggtgtgcgtt 3300
tgtctatatg tgattttcca ccatattgcc gtcttttggc aatgtgaggg cccggaaacc 3360
tggccctgtc ttcttgacga gcattcctag gggtctttcc cctctcgcca aaggaatgca 3420
aggtctgttg aatgtcgtga aggaagcagt tcctctggaa gcttcttgaa gacaaacaac 3480
gtctgtagcg accctttgca ggcagcggaa ccccccacct ggcgacaggt gcctctgcgg 3540
ccaaaagcca cgtgtataag atacacctgc aaaggcggca caaccccagt gccacgttgt 3600
gagttggata gttgtggaaa gagtcaaatg gctctcctca agcgtattca acaaggggct 3660
gaaggatgcc cagaaggtac cccattgtat gggatctgat ctggggcctc ggtgcacatg 3720
ctttacatgt gtttagtcga ggttaaaaaa acgtctaggc cccccgaacc acggggacgt 3780
ggttttcctt tgaaaaacac gatgataagc ttgccacaac ccttaccggt cgccaccatg 3840
agcgagctga ttaaggagaa catgcacatg aagctgtaca tggagggcac cgtggacaac 3900
catcacttca agtgcacatc cgagggcgaa ggcaagccct acgagggcac ccagaccatg 3960
agaatcaagg tggtcgaggg cggccctctc cccttcgcct tcgacatcct ggctactagc 4020
ttcctctacg gcagcaagac cttcatcaac cacacccagg gcatccccga cttcttcaag 4080
cagtccttcc ctgagggctt cacatgggag agagtcacca catacgaaga cgggggcgtg 4140
ctgaccgcta cccaggacac cagcctccag gacggctgcc tcatctacaa cgtcaagatc 4200
agaggggtga acttcacatc caacggccct gtgatgcaga agaaaacact cggctgggag 4260
gccttcaccg agacgctgta ccccgctgac ggcggcctgg aaggcagaaa cgacatggcc 4320
ctgaagctcg tgggcgggag ccatctgatc gcaaacatca agaccacata tagatccaag 4380
aaacccgcta agaacctcaa gatgcctggc gtctactatg tggactacag actggaaaga 4440
atcaaggagg ccaacaacga gacctacgtc gagcagcacg aggtggcagt ggccagatac 4500
tgcgacctcc ctagcaaact ggggcacaag cttaattgat tctagagtcg accgagcatc 4560
ttaccgccat ttatacccat atttgttctg tttttcttga tttgggtata catttaaatg 4620
ttaatagaac aaaatggtgg ggcaatcatt tacatttttta gggatatgta attactagtt 4680
caggtgtatt gccacaagac aaacatgtta agaaactttc ccgttattta cgctctgttc 4740
ctgttaatca acctctggat tacaaaattt gtgaaagatt gactgatatt cttaactatg 4800
ttgctccttt tacgctgtgt ggatatgctg ctttatagcc tctgtatcta gctattgctt 4860
cccgtacggc tttcgttttc tcctccttgt ataaatcctg gttgctgtct cttttagagg 4920
agttgtggcc cgttgtccgt caacgtggcg tggtgtgctc tgtgtttgct gacgcaaccc 4980
ccactggctg gggcattgcc accacctgtc aactcctttc tgggactttc gctttccccc 5040
tcccgatcgc cacggcagaa ctcatcgccg cctgccttgc ccgctgctgg acaggggcta 5100
ggttgctggg cactgataat tccgtggtgt tgtcatcggt acctttttaa aagaaaaggg 5160

```
gggactggaa gggctaattc actcccaacg aagacaagat atcataactt cgtatagcat  5220
acattatacg aagttataat ttatttgtga aatttgtgat gctattgctt tatttgtaac  5280
catatgttta tttgtgaaat ttgtgatgct attgctttat ttgtaaccat tgctttttgc  5340
ttgtactggg tctctctggt tagaccagat ctgagcctgg gagctctctg gctaactagg  5400
gaacccactg cttaagcctc aataaagctt gcctcgacca gcctcgactg tgccttctag  5460
ttgccagcca tctgttgttt gcccctcccc cgtgccttcc ttgaccctgg aaggtgccac  5520
tcccactgtc ctttcctaat aaaatgagga aattgcatcg cattgtctga gtaggtgtca  5580
ttctattctg gggggtgggg tggggcagga cagcaagggg gaggattggg aagacaatag  5640
caggcatgct ggggatgcgg tgggctctat ggcctgcagc tgcattaatg aatcggccaa  5700
cgcgcgggga gaggcggttt gcgtattggg cgctcttccg cttcctcgct cactgactcg  5760
ctgcgctcgg tcgttcggct gcggcgagcg gtatcagctc actcaaaggc ggtaatacgg  5820
ttatccacag aatcagggga taacgcagga aagaacatgt gagcaaaagg ccagcaaaag  5880
gccaggaacc gtaaaaaggc cgcgttgctg gcgtttttcc ataggctccg cccccctgac  5940
gagcatcaca aaaatcgacg ctcaagtcag aggtggcgaa acccgacagg actataaaga  6000
taccaggcgt ttccccctgg aagctccctc gtgcgctctc ctgttccgac cctgccgctt  6060
accggatacc tgtccgcctt tctcccttcg ggaagcgtgg cgctttctca tagctcacgc  6120
tgtaggtatc tcagttcggt gtaggtcgtt cgctccaagc tgggctgtgt gcacgaaccc  6180
cccgttcagc ccgaccgctg cgccttatcc ggtaactatc gtcttgagtc caacccggta  6240
agacacgact tatcgccact ggcagcagcc actggtaaca ggattagcag agcgaggtat  6300
gtaggcggtg ctacagagtt cttgaagtgg tggcctaact acggctacac tagaaggaca  6360
gtatttggta tctgcgctct gctgaagcca gttaccttcg gaaaaagagt tggtagctct  6420
tgatccggca aacaaaccac cgctggtagc ggtggttttt ttgtttgcaa gcagcagatt  6480
acgcgcagaa aaaaaggatc tcaagaagat cctttgatct tttctacggg gtctgacgct  6540
cagtggaacg aaaactcacg ttaagggatt ttggtcatga gattatcaaa aaggatcttc  6600
acctagatcc ttttaaatta aaaatgaagt tttaaatcaa tctaaagtat atatgagtaa  6660
acttggtctg acagttacca atgcttaatc agtgaggcac ctatctcagc gatctgtcta  6720
tttcgttcat ccatagttgc ctgactcccc gtcgtgtaga taactacgat acgggagggc  6780
ttaccatctg gccccagtgc tgcaatgata ccgcgagacc cacgctcacc ggctccagat  6840
ttatcagcaa taaaccagcc agccggaagg gccgagcgca gaagtggtcc tgcaacttta  6900
tccgcctcca tccagtctat taattgttgc cgggaagcta gagtaagtag ttcgccagtt  6960
aatagtttgc gcaacgttgt tgccattgct acaggcatcg tggtgtcacg ctcgtcgttt  7020
ggtatggctt cattcagctc cggttcccaa cgatcaaggc gagttacatg atcccccatg  7080
ttgtgcaaaa aagcggttag ctccttcggt cctccgatcg ttgtcagaag taagttggcc  7140
gcagtgttat cactcatggt tatggcagca ctgcataatt ctcttactgt catgccatcc  7200
gtaagatgct tttctgtgac tggtgagtac tcaaccaagt cattctgaga atagtgtatg  7260
cggcgaccga gttgctcttg cccggcgtca atacgggata ataccgcgcc acatagcaga  7320
actttaaaag tgctcatcat tggaaaacgt tcttcggggc gaaaactctc aaggatctta  7380
ccgctgttga gatccagttc gatgtaaccc actcgtgcac ccaactgatc ttcagcatct  7440
tttactttca ccagcgtttc tgggtgagca aaaacaggaa ggcaaaatgc cgcaaaaaag  7500
ggaataaggg cgacacggaa atgttgaata ctcatactct tcctttttca atattattga  7560
agcatttatc agggttattg tctcatgagc ggatacatat ttgaatgtat ttagaaaaat  7620
aaacaaatag gggttccgcg cacatttccc cgaaaagtgc cacct                 7665

SEQ ID NO: 122          moltype = DNA  length = 8439
FEATURE                 Location/Qualifiers
misc_feature            1..8439
                        note = Plasmid
                         pCVL.SFFV.HA.NLS.ReoHje.T2A.Trex2.IRES.mTagBFP
source                  1..8439
                        mol_type = other DNA
                        organism = synthetic construct
SEQUENCE: 122
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gagggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
```

-continued agaatagttt ttgctgtact ttctatagtg aatagagtta ggcagggata ttcaccatta 1680
tcgtttcaga cccacctccc aaccccgagg ggacccgaca ggcccgaagg aatagaagaa 1740
gaaggtggag agagagacag agacagatcc attcgattag tgaacggatc tcgacggtat 1800
cggttaactt ttaaaagaaa aggggggatt ggggggtaca gtgcagggga aagaatagta 1860
gacataatag caacagacat acaaactaaa gaattacaaa aacaaattac aaaaattcaa 1920
aattttatcg attacgcgtc acgtgctagc tgcagtaacg ccattttgca aggcatggaa 1980
aaataccaaa ccaagaatag agaagttcag atcaagggcg ggtacatgaa aatagctaac 2040
gttgggccaa acaggatatc tgcggtgagc agtttcggcc ccggcccggg gccaagaaca 2100
gatggtcacc gcagtttcgg ccccggcccg aggccaagaa cagatggtcc ccagatatgg 2160
cccaaccctc agcagtttct taagacccat cagatgtttc caggctcccc caaggacctg 2220
aaatgaccct gcgccttatt tgaattaacc aatcagcctg cttctcgctt ctgttcgcgc 2280
gcttctgctt cccgagctct ataaaagagc tcacaacccc tcactcggcg cgccagtcct 2340
ccgacagact gagtcgcccg ctcgagccgc caccatggga tatccatacg atgtcccaga 2400
ttatgcgcca cctaagaaga aacgcaaagt cgaattcgat cttacgtacg cgtatttagt 2460
tggtctcttc gaaggggatg gatactttag tatcaccaag aaaggcaagt acttgactta 2520
tgaattaggt attgagctga gcatcaaaga cgtccaattg atttacaaga tcaaggacat 2580
cctaggtgtt ggcaaagtaa gcttcaggaa gagaaacgag attgaaatgg tttcattgag 2640
gatccgtgat aagaatcatc taaaaaactt catattgcct atatttgaca agtatccaat 2700
gttatccaac aaacagtacg actatttaag attcaaggat gcattgttat ctaacattat 2760
atactcagat gacttgcctg aatacgctag aagtaacgaa tcgattaatt ctgtagactc 2820
cattatcaac acatcatact tctccgcctg gctagttgga tttatagaag ctgagggctg 2880
tttcagtacg tacaagctga acaaagacga tgactacttg attgcttcat tcgacattgc 2940
ccaaaaagat ggtgatatct tgatttcagc aattcacaag tacttaagtt tcactactaa 3000
gatttaccta gacaagacta attgtagcag attgaaggtc accggtgtta gatccgtcaa 3060
gaacgtcgtt aagtttatcc agggtgctcc tgtcaaattg ttaggcaaca agaaactgca 3120
atacaagttg tggataaaac aactaaggaa gatttctagg tattccgaga agatccagct 3180
tccatcaaac tacagatccg gtgagggcag aggaagtctt ctaacatgcg gtgacgtgga 3240
ggagaatccg ggccccctccg gatctgagcc acctcgggct gagacctttg tattcctgga 3300
cctagaagcc actgggctcc caaacatgga ccctgagatt gcagagatat ccctttttgc 3360
tgttcaccgc tcttccctgg agaacccaga acgggatgat tctggttcct tggtgctgcc 3420
ccgtgttctg gacaagctca cactgtgcat gtgcccggag cgcccctta ctgccaaggc 3480
cagtgagatt actggtttga gcagcgaaag cctgatgcac tgcgggaagg ctggtttcaa 3540
tggcgctgtg gtaaggacac tgcagggctt cctaagccgc caggagggcc ccatctgcct 3600
tgtggcccac aatggcttcg attatgactt cccactgctg tgcacggagc tacaacgtct 3660
gggtgcccat ctgccccaag acactgtctg cctggacaca ctgcctgcat tgcggggcct 3720
ggaccgtgct cacagccacg gcaccagggc tcaaggccgc aaaagctaca gcctggccag 3780
tctcttccac cgctacttcc aggctgaacc cagtgctgcc cattcagcag aaggtgatgt 3840
gcacaccctg cttctgatct tcctgcatcg tgctcctgag ctgctcgcct gggcagatga 3900
gcaggcccgc agctgggctc atattgagcc catgtacgtg ccacctgatg gtccaagcct 3960
cgaagcctga cctgcaggtc gagcatgcat ctagggcggc caattccgcc cctctccctc 4020
cccccccct aacgttactg gccgaagccg cttggaataa ggccggtgtg cgtttgtcta 4080
tatgtgattt tccaccatat tgccgtcttt tggcaatgtg agggcccgga aacctggccc 4140
tgtcttcttg acgagcattc ctaggggtct ttcccctctc gccaaaggaa tgcaaggtct 4200
gttgaatgtc gtgaaggaag cagttcctct ggaagcttct tgaagacaaa caacgtctgt 4260
agcgaccctt tgcaggcagc ggaacccccc acctggcgac aggtgcctct gcggccaaaa 4320
gccacgtgta taagatacac ctgcaaaggc ggcacaaccc cagtgccacg ttgtgagttg 4380
gatagttgtg gaaagagtca aatggctctc ctcaagcgta ttcaacaagg ggctgaagga 4440
tgcccagaag gtaccccatt gtatgggatc tgatctgggg cctcggtgca catgctttac 4500
atgtgtttag tcgaggttaa aaaaacgtct aggccccccg aaccacgggg acgtggtttt 4560
cctttgaaaa acacgatgat aagcttgcca caacccttac cggtcgccac catgagcgag 4620
ctgattaagg agaacatgca catgaagctg tacatggagg gcaccgtgga caaccatcac 4680
ttcaagtgca catccgaggg cgaaggcaag ccctacgagg gcacccagac catgagaatc 4740
aaggtggtcg agggcggccc tctccccttc gccttcgaca tcctggctac tagcttcctc 4800
tacggcagca agaccttcat caaccacacc cagggcatcc ccgacttctt caagcagtcc 4860
ttccctgagg gcttcacatg ggagagagtc accacatacg aagacggggg cgtgctgacc 4920
gctacccagg acaccagcct ccaggacggc tgcctcatct acaacgtcaa gatcagaggg 4980
gtgaacttca catccaacgg ccctgtgatg cagaagaaaa cactcggctg ggaggccttc 5040
accgagacgc tgtaccccgc tgacggcggc ctggaaggca gaaacgacat ggccctgaag 5100
ctcgtgggcg ggagccatct gatcgcaaac atcaagacca catatagatc caagaaaccc 5160
gctaagaacc tcaagatgcc tggcgtctac tatgtggact acagactgga aagaatcaag 5220
gaggccaaca acgagaccta cgtcgagcag cacgaggtgg cagtggccag atactgcgac 5280
ctccctagca aactggggca caagcttaat tgattctaga gtcgaccgag catcttaccg 5340
ccatttatac ccatatttgt tctgtttttc ttgatttggg tatacattta aatgttaata 5400
gaacaaaatg gtggggcaat catttacatt tttagggata tgtaattact agttcaggtg 5460
tattgccaca agacaaacat gttaagaaac tttcccgtta tttacgctct gttcctgtta 5520
atcaacctct ggattacaaa atttgtgaaa gattgactga tattcttaac tatgttgctc 5580
cttttacgct gtgtggatat gctgctttat agcctctgta tctagctatt gcttcccgta 5640
cggctttcgt ttctcctcc ttgtataaat cctggttgct gtctctttta gaggagttgt 5700
ggcccgttgt ccgtcaacgt ggcgtggtgt gctctgtgtt tgctgacgca acccccactg 5760
gctggggcat tgccaccacc tgtcaactcc tttctgggac tttcgctttc cccctcccga 5820
tcgccacggc agaactcatc gccgcctgcc ttgcccgctg ctggacaggg gctaggttgc 5880
tgggcactga taattccgtg gtgttgtcat cggtaccttt ttaaaagaaa aggggggact 5940
ggaagggcta attcactccc aacgaagaca agatatcata acttcgtata gcatacatta 6000
tacgaagtta taatttattt gtgaaatttg tgatgctatt gctttatttg taaccatatg 6060
tttatttgtg aaatttgtga tgctattgct ttatttgtaa ccattgcttt ttgcttgtac 6120
tgggtctctc tggttagacc agatctgagc ctgggagctc tctggctaac tagggaaccc 6180
actgcttaag cctcaataaa gcttgcctcg accagcctcg actgtgcctt ctagttgcca 6240
gccatctgtt gtttgcccct cccccgtgcc ttccttgacc ctggaaggtg ccactcccac 6300
tgtcctttcc taataaaatg aggaaattgc atcgcattgt ctgagtaggt gtcattctat 6360

-continued

```
tctgggggt ggggtggggc aggacagcaa gggggaggat tgggaagaca atagcaggca  6420
tgctggggat gcggtgggct ctatggcctg cagctgcatt aatgaatcgg ccaacgcgcg  6480
gggagaggcg gtttgcgtat tgggcgctct tccgcttcct cgctcactga ctcgctgcgc  6540
tcggtcgttc ggctgcggcg agcggtatca gctcactcaa aggcggtaat acggttatcc  6600
acagaatcag gggataacgc aggaaagaac atgtgagcaa aaggccagca aaaggccagg  6660
aaccgtaaaa aggccgcgtt gctggcgttt ttccataggc tccgcccccc tgacgagcat  6720
cacaaaaatc gacgctcaag tcagaggtgg cgaaacccga caggactata aagataccag  6780
gcgtttcccc ctggaagctc cctcgtgcgc tctcctgttc cgaccctgcc gcttaccgga  6840
tacctgtccg cctttctccc ttcgggaagc gtggcgcttt ctcatagctc acgctgtagg  6900
tatctcagtt cggtgtaggt cgttcgctcc aagctgggct gtgtgcacga accccccgtt  6960
cagcccgacc gctgcgcctt atccggtaac tatcgtcttg agtccaaccc ggtaagacac  7020
gacttatcgc cactggcagc agccactggt aacaggatta gcagagcgag gtatgtaggc  7080
ggtgctacag agttcttgaa gtggtggcct aactacggct acactagaag gacagtattt  7140
ggtatctgcg ctctgctgaa gccagttacc ttcggaaaaa gagttggtag ctcttgatcc  7200
ggcaaacaaa ccaccgctgg tagcggtggt ttttttgttt gcaagcagca gattacgcgc  7260
agaaaaaaag gatctcaaga agatcctttg atcttttcta cggggtctga cgctcagtgg  7320
aacgaaaact cacgttaagg gattttggtc atgagattat caaaaaggat cttcacctag  7380
atccttttaa attaaaaatg aagttttaaa tcaatctaaa gtatatatga gtaaacttgg  7440
tctgacagtt accaatgctt aatcagtgag gcacctatct cagcgatctg tctatttcgt  7500
tcatccatag ttgcctgact ccccgtcgtg tagataacta cgatacggga gggcttacca  7560
tctggcccca gtgctgcaat gataccgcga gacccacgct caccggctcc agatttatca  7620
gcaataaacc agccagccgg aagggccgag cgcagaagtg gtcctgcaac tttatccgcc  7680
tccatccagt ctattaattg ttgccgggaa gctagagtaa gtagttcgcc agttaatagt  7740
ttgcgcaacg ttgttgccat tgctacaggc atcgtggtgt cacgctcgtc gtttggtatg  7800
gcttcattca gctccggttc ccaacgatca aggcgagtta catgatcccc catgttgtgc  7860
aaaaaagcgg ttagctcctt cggtcctccg atcgttgtca gaagtaagtt ggccgcagtg  7920
ttatcactca tggttatggc agcactgcat aattctctta ctgtcatgcc atccgtaaga  7980
tgcttttctg tgactggtga gtactcaacc aagtcattct gagaatagtg tatgcggcga  8040
ccgagttgct cttgcccggc gtcaatacgg gataataccg cgccacatag cagaacttta  8100
aaagtgctca tcattggaaa acgttcttcg gggcgaaaac tctcaaggat cttaccgctg  8160
ttgagatcca gttcgatgta acccactcgt gcacccaact gatcttcagc atcttttact  8220
ttcaccagcg tttctgggtg agcaaaaaca ggaaggcaaa atgccgcaaa aaagggaata  8280
agggcgacac ggaaatgttg aatactcata ctcttccttt ttcaatatta ttgaagcatt  8340
tatcagggtt attgtctcat gagcggatac atatttgaat gtatttagaa aaataaacaa  8400
ataggggttc cgcgcacatt tccccgaaaa gtgccacct                        8439

SEQ ID NO: 123          moltype = DNA  length = 7803
FEATURE                 Location/Qualifiers
misc_feature            1..7803
                        note = Plasmid pCVL.SFFV.HA.NLS.sPan2.IRES.mTagBFP
source                  1..7803
                        mol_type = other DNA
                        organism = synthetic construct
SEQUENCE: 123
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
```

-continued

```
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattctct actttggaat ctaagttgaa  2460
cccatcttac atctctggtt tcgtcgacgg tgaaggttct ttcatgttga ctatcatcaa  2520
ggacaacaag tacaagttgg gttggagagt tgtttgtaga ttcgttatct ctttgcacaa  2580
gaaggacttg tctttgttga acaagatcaa ggaatttttc gacgtcggta acgttttctt  2640
gatgactaag gactctgctc aatacagagt tgaatctttg aagggtttgg acttgatcat  2700
caaccacttc gacaagtacc cattgatcac taagaagcaa gctgactaca agttgttcaa  2760
gatggctcac aacttaatta agaacaagtc tcacttgact aaggaaggtt tgttggaatt  2820
ggttgctatc aaggctgtta tcaacaacgg tttgaacaac gacttgtcta tcgctttccc  2880
aggtatcaac actatcttga ggcctgacac ttctttgcca caaatcttga acccattctg  2940
gttgtctggt ttcgttgacg ctgaaggttg tttctctgtt gttgttttca agtctaagac  3000
ttctaagttg ggtgaagctg ttaagttgtc tttcatcttg actcaatcta acagagacga  3060
atacttgatc aagtctttga tcgaatacct aggttgtggt aacacttctt tggacccaag  3120
aggtactatc gacttcaagg ttactaactt ctcttctatc aaggacatca tcgttccatt  3180
cttcatcaag tacccattga aggtaacaa gaacttggac ttcactgact tctgtgaagt  3240
tgttagattg atggaaaaca agtctcactt gactaaggaa ggtttggacc aaatcaagaa  3300
gatcagaaac agaatgaaca ctaacagaaa gtagcctgca ggtcgagcat gcatctaggg  3360
cggccaattc cgcccctctc cctccccccc ccctaacgtt actggccgaa gccgcttgga  3420
ataaggccgg tgtgcgtttg tctatatgtg attttccacc atattgccgt cttttggcaa  3480
tgtgagggcc cggaaacctg gccctgtctt cttgacgagc attcctaggg gtctttcccc  3540
tctcgccaaa ggaatgcaag gtctgttgaa tgtcgtgaag gaagcagttc ctctggaagc  3600
ttcttgaaga caaacaacgt ctgtagcgac cctttgcagg cagcggaacc ccccacctgg  3660
cgacaggtgc ctctgcggcc aaaagccacg tgtataagat acacctgcaa aggcggcaca  3720
accccagtgc cacgttgtga gttggatagt tgtggaaaga gtcaaatggc tctcctcaag  3780
cgtattcaac aaggggctga aggatgccca gaaggtaccc cattgtatgg gatctgatct  3840
ggggcctcgg tgcacatgct ttacatgtgt ttagtcgagg ttaaaaaaac gtctaggccc  3900
cccgaaccac ggggacgtgg ttttcctttg aaaaacacga tgataagctt gccacaaccc  3960
ttaccggtcg ccaccatgag cgagctgatt aaggagaaca tgcacatgaa gctgtacatg  4020
gagggcaccg tggacaacca tcacttcaag tgcacatccg agggcgaagg caagccctac  4080
gagggcaccc agaccatgag aatcaaggtg gtcgagggcg gccctctccc cttcgccttc  4140
gacatcctgg ctactagctt cctctacggc agcaagacct tcatcaacca cacccagggc  4200
atccccgact tcttcaagca gtccttccct gagggcttca catgggagag agtcaccaca  4260
tacgaagacg gggggcgtgct gaccgctacc caggacacca gcctccagga cggctgcctc  4320
atctacaacg tcaagatcag aggggtgaac ttcacatcca acggccctgt gatgcagaag  4380
aaaacactcg gctgggaggc cttcaccgag acgctgtacc ccgctgacgg cggcctggaa  4440
ggcagaaacg acatggccct gaagctcgtg ggcgggagcc atctgatcgc aaacatcaag  4500
accacatata gatccaagaa acccgctaag aacctcaaga tgcctggcgt ctactatgtg  4560
gactacagac tggaaagaat caaggaggcc aacaacgaga cctacgtcga gcagcacgag  4620
gtggcagtgg ccagatactg cgacctccct agcaaactgg ggcacaagct taattgattc  4680
tagagtcgac cgagcatctt accgccattt atacccatat ttgttctgtt tttcttgatt  4740
tgggtataca tttaaatgtt aatagaacaa aatggtgggg caatcattta catttttagg  4800
gatatgtaat tactagttca ggtgtattgc cacaagacaa acatgttaag aaactttccc  4860
gttatttacg ctctgttcct gttaatcaac ctctggatta caaaatttgt gaaagattga  4920
ctgatattct taactatgtt gctcctttta cgctgtgtgg atatgctgct ttatagcctc  4980
tgtatctagc tattgcttcc cgtacggctt tcgttttctc ctccttgtat aaatcctggt  5040
tgctgtctct tttagaggag ttgtggcccg ttgtccgtca acgtggcgtg gtgtgctctg  5100
tgtttgctga cgcaaccccc actggctggg gcattgccac cacctgtcaa ctcctttctg  5160
ggactttcgc tttccccctc ccgatcgcca cggcagaact catcgccgcc tgccttgccc  5220
gctgctggac aggggctagg ttgctgggca ctgataattc cgtggtgttg tcatcggtac  5280
ctttttaaaa gaaaaggggg gactggaagg gctaattcac tcccaacgaa gacaagatat  5340
cataacttcg tatagcatac attatacgaa gttataattt atttgtgaaa tttgtgatgc  5400
tattgcttta tttgtaacca tatgtttatt tgtgaaattt gtgatgctat tgctttattt  5460
gtaaccattg ctttttgctt gtactgggtc tctctggtta gaccagatct gagcctggga  5520
gctctctggc taactaggga acccactgct taagcctcaa taaagcttgc ctcgaccagc  5580
ctcgactgtg ccttctagtt gccagccatc tgttgtttgc ccctcccccg tgccttcctt  5640
gaccctggaa ggtgccactc ccactgtcct ttcctaataa aatgaggaaa ttgcatcgca  5700
ttgtctgagt aggtgtcatt ctattctggg gggtggggtg gggcaggaca gcaaggggga  5760
ggattgggaa gacaatagca ggcatgctgg ggatgcggtg ggctctatgg cctgcagctg  5820
cattaatgaa tcggccaacg cgcggggaga ggcggtttgc gtattgggcg ctcttccgct  5880
tcctcgctca ctgactcgct gcgctcggtc gttcggctgc ggcgagcggt atcagctcac  5940
tcaaaggcgg taatacggtt atccacagaa tcaggggata acgcaggaaa gaacatgtga  6000
gcaaaaggcc agcaaaaggc caggaaccgt aaaaaggccg cgttgctggc gtttttccat  6060
aggctccgcc cccctgacga gcatcacaaa aatcgacgct caagtcagag gtggcgaaac  6120
ccgacaggac tataaagata ccaggcgttt ccccctggaa gctccctcgt gcgctctcct  6180
gttccgaccc tgccgcttac cggatacctg tccgcctttc tcccttcggg aagcgtggcg  6240
ctttctcata gctcacgctg taggtatctc agttcggtgt aggtcgttcg ctccaagctg  6300
ggctgtgtgc acgaaccccc cgttcagccc gaccgctgcg ccttatccgg taactatcgt  6360
cttgagtcca acccggtaag acacgactta tcgccactgg cagcagccac tggtaacagg  6420
attagcagag cgaggtatgt aggcggtgct acagagttct tgaagtggtg gcctaactac  6480
ggctacacta gaaggacagt atttggtatc tgcgctctgc tgaagccagt taccttcgga  6540
aaaagagttg gtagctcttg atccggcaaa caaaccaccg ctggtagcgg tggttttttt  6600
gtttgcaagc agcagattac gcgcagaaaa aaaggatctc aagaagatcc tttgatcttt  6660
tctacggggt ctgacgctca gtggaacgaa aactcacgtt aagggatttt ggtcatgaga  6720
ttatcaaaaa ggatcttcac ctagatcctt ttaaattaaa aatgaagttt taaatcaatc  6780
taaagtatat atgagtaaac ttggtctgac agttaccaat gcttaatcag tgaggcacct  6840
```

-continued

```
atctcagcga tctgtctatt tcgttcatcc atagttgcct gactccccgt cgtgtagata  6900
actacgatac gggagggctt accatctggc cccagtgctg caatgatacc gcgagaccca  6960
cgctcaccgg ctccagattt atcagcaata aaccagccag ccggaagggc cgagcgcaga  7020
agtggtcctg caactttatc cgcctccatc cagtctatta attgttgccg ggaagctaga  7080
gtaagtagtt cgccagttaa tagtttgcgc aacgttgttg ccattgctac aggcatcgtg  7140
gtgtcacgct cgtcgtttgg tatggcttca ttcagctccg gttcccaacg atcaaggcga  7200
gttacatgat cccccatgtt gtgcaaaaaa gcggttagct ccttcggtcc tccgatcgtt  7260
gtcagaagta agttggccgc agtgttatca ctcatggtta tggcagcact gcataattct  7320
cttactgtca tgccatccgt aagatgcttt tctgtgactg gtgagtactc aaccaagtca  7380
ttctgagaat agtgtatgcg gcgaccgagt tgctcttgcc cggcgtcaat acgggataat  7440
accgcgccac atagcagaac tttaaaagtg ctcatcattg gaaaacgttc ttcggggcga  7500
aaactctcaa ggatcttacc gctgttgaga tccagttcga tgtaacccac tcgtgcaccc  7560
aactgatctt cagcatcttt tactttcacc agcgtttctg ggtgagcaaa aacaggaagg  7620
caaaatgccg caaaaaaggg aataagggcg acacggaaat gttgaatact catactcttc  7680
ctttttcaat attattgaag catttatcag ggttattgtc tcatgagcgg atacatattt  7740
gaatgtattt agaaaaataa acaaataggg gttccgcgca catttccccg aaaagtgcca  7800
cct                                                                7803
```

```
SEQ ID NO: 124          moltype = DNA  length = 8577
FEATURE                 Location/Qualifiers
misc_feature            1..8577
                        note = Plasmid pCVL.SFFV.HA.NLS.sPan2.T2A.Trex2.IRES.mTagBFP
source                  1..8577
                        mol_type = other DNA
                        organism = synthetic construct
SEQUENCE: 124
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattctct actttggaat ctaagttgaa  2460
cccatcttac atctctggtt tcgtcgacgg tgaaggttct ttcatgttga ctatcatcaa  2520
ggacaacaag tacaagttgg gttggagagt tgtttgtaga ttcgttatct ctttgcacaa  2580
gaaggacttg tctttgttga acaagatcaa ggaatttttc gacgtcggta acgttttctt  2640
gatgactaag gactctgctc aatacagagt tgaatctttg aagggtttgg acttgatcat  2700
caaccacttc gacaagtacc cattgatcac taagaagcaa gctgactaca agttgttcaa  2760
gatggctcac aacttaatta agaacaagtc tcacttgact aaggaaggtt tgttggaatt  2820
ggttgctatc aaggctgtta tcaacaacgg tttgaacaac gacttgtcta tcgctttccc  2880
aggtatcaac actatcttga ggcctgacac ttctttgcca caaatcttga acccattctg  2940
gttgtctggt ttcgttgacg ctgaaggttg tttctctgtt gttgttttca agtctaagac  3000
ttctaagttg ggtgaagctg ttaagttgtc tttcatcttg actcaatcta acagagacga  3060
atacttgatc aagtctttga tcgaatacct aggttgtggt aacacttctt tggacccaag  3120
aggtactatc gacttcaagg ttactaactt ctcttctatc aaggacatca tcgttccatt  3180
```

-continued

```
cttcatcaag tacccattga agggtaacaa gaacttggac ttcactgact tctgtgaagt  3240
tgttagattg atggaaaaca agtctcactt gactaaggaa ggtttggacc aaatcaagaa  3300
gatcagaaac agaatgaaca ctaacagaaa gggatccggt gagggcagag gaagtcttct  3360
aacatgcggt gacgtggagg agaatccggg cccctccgga tctgagccac ctcgggctga  3420
gacctttgta ttcctggacc tagaagccac tgggctccca aacatggacc ctgagattgc  3480
agagatatcc ctttttgctg ttcaccgctc ttccctggag aacccagaac gggatgattc  3540
tggttccttg gtgctgcccc gtgttctgga caagctcaca ctgtgcatgt gcccggagcg  3600
cccctttact gccaaggcca gtgagattac tggtttgagc agcgaaagcc tgatgcactg  3660
cgggaaggct ggtttcaatg gcgctgtggt aaggacactg cagggcttcc taagccgcca  3720
ggagggcccc atctgccttg tggcccacaa tggcttcgat tatgacttcc cactgctgtg  3780
cacggagcta caacgtctgg gtgcccatct gccccaagac actgtctgcc tggacacact  3840
gcctgcattg cggggcctgg accgtgctca cagccacggc accagggctc aaggccgcaa  3900
aagctacagc ctggccagtc tcttccaccg ctacttccag gctgaaccca gtgctgccca  3960
ttcagcagaa ggtgatgtgc acaccctgct tctgatcttc ctgcatcgtg ctcctgagct  4020
gctcgcctgg gcagatgagc aggcccgcag ctgggctcat attgagccca tgtacgtgcc  4080
acctgatggt ccaagcctcg aagcctgacc tgcaggtcga gcatgcatct agggcggcca  4140
attccgcccc tctccctccc ccccccctaa cgttactggc cgaagccgct tggaataagg  4200
ccggtgtgcg tttgtctata tgtgattttc caccatattg ccgtcttttg gcaatgtgag  4260
ggcccggaaa cctggccctg tcttcttgac gagcattcct aggggtcttt cccctctcgc  4320
caaaggaatg caaggtctgt tgaatgtcgt gaaggaagca gttcctctgg aagcttcttg  4380
aagacaaaca acgtctgtag cgaccctttg caggcagcgg aaccccccac ctggcgacag  4440
gtgcctctgc ggccaaaagc cacgtgtata agatacacct gcaaaggcgg cacaacccca  4500
gtgccacgtt gtgagttgga tagttgtgga aagagtcaaa tggctctcct caagcgtatt  4560
caacaagggg ctgaaggatg cccagaaggt accccattgt atgggatctg atctggggcc  4620
tcggtgcaca tgctttacat gtgtttagtc gaggttaaaa aaacgtctag gccccccgaa  4680
ccacggggac gtggttttcc tttgaaaaac acgatgataa gcttgccaca acccttaccg  4740
gtcgccacca tgagcgagct gattaaggag aacatgcaca tgaagctgta catggagggc  4800
accgtggaca accatcactt caagtgcaca tccgagggcg aaggcaagcc ctacgagggc  4860
acccagacca tgagaatcaa ggtggtcgag ggcggccctc tcccgttcgc cttcgacatc  4920
ctggctacta gcttcctcta cggcagcaag accttcatca accacaccca gggcatcccc  4980
gacttcttca agcagtcctt ccctgagggc ttcacatggg agagagtcac cacatacgaa  5040
gacgggggcg tgctgaccgc tacccaggac accagcctcc aggacggctg cctcatctac  5100
aacgtcaaga tcagaggggt gaacttcaca tccaacggcc ctgtgatgca gaagaaaaca  5160
ctcggctggg aggccttcac cgagacgctg taccccgctg acggcggcct ggaaggcaga  5220
aacgacatgg ccctgaagct cgtgggcggg agccatctga tcgcaaacat caagaccaca  5280
tatagatcca agaaacccgc taagaacctc aagatgcctg gcgtctacta tgtggactac  5340
agactggaaa gaatcaagga ggccaacaac gagacctacg tcgagcagca cgaggtggca  5400
gtggccagat actgcgacct ccctagcaaa ctggggcaca agcttaattg attctagagt  5460
cgaccgagca tcttaccgcc atttataccc atatttgttc tgtttttctt gatttgggta  5520
tacatttaaa tgttaataga acaaaatggt ggggcaatca tttacatttt tagggatatg  5580
taattactag ttcaggtgta ttgccacaag acaaacatgt taagaaactt tcccgttatt  5640
tacgctctgt tcctgttaat caacctctgg attacaaaat ttgtgaaaga ttgactgata  5700
ttcttaacta tgttgctcct tttacgctgt gtggatatgc tgctttatag cctctgtatc  5760
tagctattgc ttcccgtacg gctttcgttt tctcctcctt gtataaatcc tggttgctgt  5820
ctcttttaga ggagttgtgg cccgttgtcc gtcaacgtgg cgtggtgtgc tctgtgtttg  5880
ctgacgcaac ccccactggc tggggcattg ccaccacctg tcaactcctt tctgggactt  5940
tcgctttccc cctcccgatc gccacggcag aactcatcgc cgcctgcctt gcccgctgct  6000
ggacaggggc taggttgctg ggcactgata attccgtggt gttgtcatcg gtaccttttt  6060
aaaagaaaag gggggactgg aagggctaat tcactcccaa cgaagacaag atatcataac  6120
ttcgtatagc atacattata cgaagttata atttatttgt gaaatttgtg atgctattgc  6180
tttatttgta accatatgtt tatttgtgaa atttgtgatg ctattgcttt atttgtaacc  6240
attgcttttt gcttgtactg ggtctctctg gttagaccag atctgagcct gggagctctc  6300
tggctaacta gggaacccac tgcttaagcc tcaataaagc ttgcctcgac cagcctcgac  6360
tgtgccttct agttgccagc catctgttgt ttgcccctcc cccgtgcctt ccttgaccct  6420
ggaaggtgcc actcccactg tcctttccta ataaaatgag gaaattgcat cgcattgtct  6480
gagtaggtgt cattctattc tggggggtgg ggtggggcag gacagcaagg gggaggattg  6540
ggaagacaat agcaggcatg ctggggatgc ggtgggctct atggcctgca gctgcattaa  6600
tgaatcggcc aacgcgcggg gagaggcggt ttgcgtattg ggcgctcttc cgcttcctcg  6660
ctcactgact cgctgcgctc ggtcgttcgg ctgcggcgag cggtatcagc tcactcaaag  6720
gcggtaatac ggttatccac agaatcaggg gataacgcag gaaagaacat gtgagcaaaa  6780
ggccagcaaa aggccaggaa ccgtaaaaag gccgcgttgc tggcgttttt ccataggctc  6840
cgcccccctg acgagcatca caaaaatcga cgctcaagtc agaggtggcg aaacccgaca  6900
ggactataaa gataccaggc gtttccccct ggaagctccc tcgtgcgctc tcctgttccg  6960
accctgccgc ttaccggata cctgtccgcc tttctccctt cgggaagcgt ggcgctttct  7020
catagctcac gctgtaggta tctcagttcg gtgtaggtcg ttcgctccaa gctgggctgt  7080
gtgcacgaac cccccgttca gcccgaccgc tgcgccttat ccggtaacta tcgtcttgag  7140
tccaacccgg taagacacga cttatcgcca ctggcagcag ccactggtaa caggattagc  7200
agagcgaggt atgtaggcgg tgctacagag ttcttgaagt ggtggcctaa ctacggctac  7260
actagaagga cagtatttgg tatctgcgct ctgctgaagc cagttacctt cggaaaaaga  7320
gttggtagct cttgatccgg caaacaaacc accgctggta gcggtggttt ttttgtttgc  7380
aagcagcaga ttacgcgcag aaaaaaagga tctcaagaag atcctttgat cttttctacg  7440
gggtctgacg ctcagtggaa cgaaaactca cgttaaggga ttttggtcat gagattatca  7500
aaaaggatct tcacctagat ccttttaaat taaaaatgaa gttttaaatc aatctaaagt  7560
atatatgagt aaacttggtc tgacagttac caatgcttaa tcagtgaggc acctatctca  7620
gcgatctgtc tatttcgttc atccatagtt gcctgactcc ccgtcgtgta gataactacg  7680
atacgggagg gcttaccatc tggccccagt gctgcaatga taccgcgaga cccacgctca  7740
ccggctccag atttatcagc aataaaccag ccagccggaa gggccgagcg cagaagtggt  7800
cctgcaactt tatccgcctc catccagtct attaattgtt gccgggaagc tagagtaagt  7860
agttcgccag ttaatagttt gcgcaacgtt gttgccattg ctacaggcat cgtggtgtca  7920
```

-continued

```
cgctcgtcgt ttggtatggc ttcattcagc tccggttccc aacgatcaag gcgagttaca  7980
tgatccccca tgttgtgcaa aaaagcggtt agctccttcg gtcctccgat cgttgtcaga  8040
agtaagttgg ccgcagtgtt atcactcatg gttatggcag cactgcataa ttctcttact  8100
gtcatgccat ccgtaagatg cttttctgtg actggtgagt actcaaccaa gtcattctga  8160
gaatagtgta tgcggcgacc gagttgctct tgcccggcgt caatacggga taataccgcg  8220
ccacatagca gaactttaaa agtgctcatc attggaaaac gttcttcggg gcgaaaactc  8280
tcaaggatct taccgctgtt gagatccagt tcgatgtaac ccactcgtgc acccaactga  8340
tcttcagcat cttttacttt caccagcgtt tctgggtgag caaaaacagg aaggcaaaat  8400
gccgcaaaaa agggaataag ggcgacacgg aaatgttgaa tactcatact cttccttttt  8460
caatattatt gaagcattta tcagggttat tgtctcatga gcggatacat atttgaatgt  8520
atttagaaaa ataaacaaat aggggttccg cgcacatttc cccgaaaagt gccacct     8577

SEQ ID NO: 125          moltype = DNA  length = 7806
FEATURE                 Location/Qualifiers
misc_feature            1..7806
                        note = Plasmid pCVL.SFFV.HA.NLS.I-OnuOpt.IRES.mTagBFP
source                  1..7806
                        mol_type = other DNA
                        organism = synthetic construct
SEQUENCE: 125
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcagc cgccgcgaga gcatcaaccc  2460
ctggattctg accggcttcg ccgacgccga gggcagcttc ctgctgcgca tccgcaacaa  2520
caacaagagc agcgtgggct acagcaccga gctgggcttc cagatcaccc tgcacaacaa  2580
ggacaagagc atcctggaga acatccagag catctggaag gtgggcgtga tcgccaacag  2640
cggcgacaac gccgtgagcc tgaaggtgac ccgcttcgag gacctgaagg tgatcatcga  2700
ccacttcgag aagtaccccc tgatcaccca gaagctgggc gactacatgc tgttcaagca  2760
ggccttctgc gtgatggaga acaaggagca cctgaagatc aacggcatca aggagctggt  2820
gcgcatcaag gccaagctga actggggcct gaccgacgag ctgaagaagg ccttccccga  2880
gatcatcagc aaggagcgca gcctgatcaa caagaacatc cccaacttca agtggctggc  2940
cggcttcacc agcggcgagg gctgcttctt cgtgaacctg atcaagagca agagcaagct  3000
gggcgtgcag gtgcagctgg tgttcagcat cacccagcac atcaaggaca agaacctgat  3060
gaacagcctg atcacctacc tgggctgcgg ctacatcaag gagaagaaca agagcgagtt  3120
cagctggctg gacttcgtgg tgaccaagtt cagcgacatc aacgacaaga tcatccccgt  3180
gttccaggag aacaccctga tcggcgtgaa gctggaggac ttcgaggact ggtgcaaggt  3240
ggccaagctg atcgaggaga agaagcacct gaccgagagc ggcctggacg agatcaagaa  3300
gatcaagctg aacatgaaca agggccgcgt gttctagcct gcaggtcgag catgcatcta  3360
gggcggccaa ttccgcccct ctccctcccc ccccctaac gttactggcc gaagccgctt  3420
ggaataaggc cggtgtgcgt ttgtctatat gtgattttcc accatattgc cgtcttttgg  3480
caatgtgagg gcccggaaac ctggccctgt cttcttgacg agcattccta ggggtctttc  3540
```

-continued

```
ccctctcgcc aaaggaatgc aaggtctgtt gaatgtcgtg aaggaagcag ttcctctgga  3600
agcttcttga agacaaacaa cgtctgtagc gaccctttgc aggcagcgga acccccacc  3660
tggcgacagg tgcctctgcg gccaaaagcc acgtgtataa gatacacctg caaaggcggc  3720
acaaccccag tgccacgttg tgagttggat agttgtggaa agagtcaaat ggctctcctc  3780
aagcgtattc aacaaggggc tgaaggatgc ccagaaggta ccccattgta tgggatctga  3840
tctggggcct cggtgcacat gctttacatg tgtttagtcg aggttaaaaa aacgtctagg  3900
ccccccgaac cacggggacg tggttttcct ttgaaaaaca cgatgataag cttgccacaa  3960
cccttaccgg tcgccaccat gagcgagctg attaaggaga acatgcacat gaagctgtac  4020
atggagggca ccgtggacaa ccatcacttc aagtgcacat ccgagggcga aggcaagccc  4080
tacgagggca cccagaccat gagaatcaag gtggtcgagg gcggccctct ccccttcgcc  4140
ttcgacatcc tggctactag cttcctctac ggcagcaaga ccttcatcaa ccacacccag  4200
ggcatccccg acttcttcaa gcagtccttc cctgagggct tcacatggga gagagtcacc  4260
acatacgaag acgggggcgt gctgaccgct acccaggaca ccagcctcca ggacggctgc  4320
ctcatctaca acgtcaagat cagaggggtg aacttcacat ccaacggccc tgtgatgcag  4380
aagaaaacac tcggctggga ggccttcacc gagacgctgt accccgctga cggcggcctg  4440
gaaggcagaa acgacatggc cctgaagctc gtgggcggga gccatctgat cgcaaacatc  4500
aagaccacat atagatccaa gaaacccgct aagaacctca agatgcctgg cgtctactat  4560
gtggactaca gactggaaag aatcaaggag gccaacaacg agacctacgt cgagcagcac  4620
gaggtggcag tggccagata ctgcgacctc cctagcaaac tggggcacaa gcttaattga  4680
ttctagagtc gaccgagcat cttaccgcca tttataccca tatttgttct gtttttcttg  4740
atttgggtat acatttaaat gttaatagaa caaaatggtg gggcaatcat ttacattttt  4800
agggatatgt aattactagt tcaggtgtat tgccacaaga caaacatgtt aagaaacttt  4860
cccgttattt acgctctgtt cctgttaatc aacctctgga ttacaaaatt tgtgaaagat  4920
tgactgatat tcttaactat gttgctcctt ttacgctgtg tggatatgct gctttatagc  4980
ctctgtatct agctattgct tcccgtacgg ctttcgtttt ctcctccttg tataaatcct  5040
ggttgctgtc tcttttagag gagttgtggc ccgttgtccg tcaacgtggc gtggtgtgct  5100
ctgtgtttgc tgacgcaacc cccactggct ggggcattgc caccacctgt caactccttt  5160
ctgggacttt cgctttcccc ctcccgatcg ccacggcaga actcatcgcc gcctgccttg  5220
cccgctgctg gacaggggct aggttgctgg gcactgataa ttccgtggtg ttgtcatcgg  5280
taccttttta aaagaaaagg ggggactgga agggctaatt cactcccaac gaagacaaga  5340
tatcataact tcgtatagca tacattatac gaagttataa tttatttgtg aaatttgtga  5400
tgctattgct ttatttgtaa ccatatgttt atttgtgaaa tttgtgatgc tattgcttta  5460
tttgtaacca ttgcttttg cttgtactgg gtctctctgg ttagaccaga tctgagcctg  5520
ggagctctct ggctaactag ggaacccact gcttaagcct caataaagct tgcctcgacc  5580
agcctcgact gtgccttcta gttgccagcc atctgttgtt tgcccctccc ccgtgccttc  5640
cttgaccctg gaaggtgcca ctcccactgt cctttcctaa taaaatgagg aaattgcatc  5700
gcattgtctg agtaggtgtc attctattct ggggggtggg gtggggcagg acagcaaggg  5760
ggaggattgg gaagacaata gcaggcatgc tggggatgcg gtgggctcta tggcctgcag  5820
ctgcattaat gaatcggcca acgcgcgggg agaggcggtt tgcgtattgg gcgctcttcc  5880
gcttcctcgc tcactgactc gctgcgctcg gtcgttcggc tgcggcgagc ggtatcagct  5940
cactcaaagg cggtaatacg gttatccaca gaatcagggg ataacgcagg aaagaacatg  6000
tgagcaaaag gccagcaaaa ggccaggaac cgtaaaaagg ccgcgttgct ggcgtttttc  6060
cataggctcc gcccccctga cgagcatcac aaaaatcgac gctcaagtca gaggtggcga  6120
aacccgacag gactataaag ataccaggcg tttccccctg gaagctccct cgtgcgctct  6180
cctgttccga ccctgccgct taccggatac ctgtccgcct ttctcccttc gggaagcgtg  6240
gcgctttctc atagctcacg ctgtaggtat ctcagttcgg tgtaggtcgt tcgctccaag  6300
ctgggctgtg tgcacgaacc ccccgttcag cccgaccgct gcgccttatc cggtaactat  6360
cgtcttgagt ccaacccggt aagacacgac ttatcgccac tggcagcagc cactggtaac  6420
aggattagca gagcgaggta tgtaggcggt gctacagagt tcttgaagtg gtggcctaac  6480
tacggctaca ctagaaggac agtatttggt atctgcgctc tgctgaagcc agttaccttc  6540
ggaaaaagag ttggtagctc ttgatccggc aaacaaacca ccgctggtag cggtggtttt  6600
tttgtttgca agcagcagat tacgcgcaga aaaaaaggat ctcaagaaga tcctttgatc  6660
ttttctacgg ggtctgacgc tcagtggaac gaaaactcac gttaagggat tttggtcatg  6720
agattatcaa aaaggatctt cacctagatc cttttaaatt aaaaatgaag ttttaaatca  6780
atctaaagta tatatgagta aacttggtct gacagttacc aatgcttaat cagtgaggca  6840
cctatctcag cgatctgtct atttcgttca tccatagttg cctgactccc cgtcgtgtag  6900
ataactacga tacgggaggg cttaccatct ggccccagtg ctgcaatgat accgcgagac  6960
ccacgctcac cggctccaga tttatcagca ataaaccagc cagccggaag ggccgagcgc  7020
agaagtggtc ctgcaacttt atccgcctcc atccagtcta ttaattgttg ccgggaagct  7080
agagtaagta gttcgccagt taatagtttg cgcaacgttg ttgccattgc tacaggcatc  7140
gtggtgtcac gctcgtcgtt tggtatggct tcattcagct ccggttccca acgatcaagg  7200
cgagttacat gatcccccat gttgtgcaaa aaagcggtta gctccttcgg tcctccgatc  7260
gttgtcagaa gtaagttggc cgcagtgtta tcactcatgg ttatggcagc actgcataat  7320
tctcttactg tcatgccatc cgtaagatgc ttttctgtga ctggtgagta ctcaaccaag  7380
tcattctgag aatagtgtat gcggcgaccg agttgctctt gcccggcgtc aatacgggat  7440
aataccgcgc cacatagcag aactttaaaa gtgctcatca ttggaaaacg ttcttcgggg  7500
cgaaaactct caaggatctt accgctgttg agatccagtt cgatgtaacc cactcgtgca  7560
cccaactgat cttcagcatc ttttactttc accagcgttt ctgggtgagc aaaaacagga  7620
aggcaaaatg ccgcaaaaaa gggaataagg gcgacacgga aatgttgaat actcatactc  7680
ttcctttttc aatattattg aagcatttat cagggttatt gtctcatgag cggatacata  7740
tttgaatgta tttagaaaaa taaacaaata ggggttccgc gcacatttcc ccgaaaagtg  7800
ccacct                                                             7806
```

```
SEQ ID NO: 126          moltype = DNA  length = 8580
FEATURE                 Location/Qualifiers
misc_feature            1..8580
                        note = Plasmid
                         pCVL.SFFV.HA.NLS.I-OnuOpt.T2A.Trex2.IRES.mTagBFP
source                  1..8580
```

```
                        mol_type = other DNA
                        organism = synthetic construct
SEQUENCE: 126
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcagc cgccgcgaga gcatcaaccc  2460
ctggattctg accggcttcg ccgacgccga gggcagcttc ctgctgcgca tccgcaacaa  2520
caacaagagc agcgtgggct acagcaccga gctgggcttc cagatcaccc tgcacaacaa  2580
ggacaagagc atcctggaga acatccagag catctggaag gtgggcgtga tcgccaacag  2640
cggcgacaac gccgtgagcc tgaaggtgac ccgcttcgag gacctgaagg tgatcatcga  2700
ccacttcgag aagtaccccc tgatcaccca gaagctgggc gactacatgc tgttcaagca  2760
ggccttctgc gtgatggaga acaaggagca cctgaagatc aacggcatca aggagctggt  2820
gcgcatcaag gccaagctga actggggcct gaccgacgag ctgaagaagg ccttccccga  2880
gatcatcagc aaggagcgca gcctgatcaa caagaacatc cccaacttca agtggctggc  2940
cggcttcacc agcggcgagg gctgcttctt cgtgaacctg atcaagagca agagcaagct  3000
gggcgtgcag gtgcagctgg tgttcagcat cacccagcac atcaaggaca agaacctgat  3060
gaacagcctg atcacctacc tgggctgcgg ctacatcaag gagaagaaca agagcgagtt  3120
cagctggctg gacttcgtgg tgaccaagtt cagcgacatc aacgacaaga tcatccccgt  3180
gttccaggag aacaccctga tcggcgtgaa gctggaggac ttcgaggact ggtgcaaggt  3240
ggccaagctg atcgaggaga agaagcacct gaccgagagc ggcctggacg agatcaagaa  3300
gatcaagctg aacatgaaca agggccgcgt gttcggatcc ggtgagggca gaggaagtct  3360
tctaacatgc ggtgacgtgg aggagaatcc gggcccctcc ggatctgagc cacctcgggc  3420
tgagaccttt gtattcctgg acctagaagc cactgggctc ccaaacatgg accctgagat  3480
tgcagagata tccctttttg ctgttcaccg ctcttccctg gagaacccag aacgggatga  3540
ttctggttcc ttggtgctgc cccgtgttct ggacaagctc acactgtgca tgtgcccgga  3600
gcgccccttt actgccaagg ccagtgagat tactggtttg agcagcgaaa gcctgatgca  3660
ctgcgggaag gctggtttca atggcgctgt ggtaaggaca ctgcagggct tcctaagccg  3720
ccaggagggc cccatctgcc ttgtggccca caatggcttc gattatgact tcccactgct  3780
gtgcacggag ctacaacgtc tgggtgccca tctgccccaa gacactgtct gcctggacac  3840
actgcctgca ttgcggggcc tggaccgtgc tcacagccac ggcaccaggg ctcaaggccg  3900
caaaagctac agcctggcca gtctcttcca ccgctacttc caggctgaac ccagtgctgc  3960
ccattcagca gaaggtgatg tgcacaccct gcttctgatc ttcctgcatc gtgctcctga  4020
gctgctcgcc tgggcagatg agcaggcccg cagctgggct catattgagc ccatgtacgt  4080
gccacctgat ggtccaagcc tcgaagcctg acctgcaggt cgagcatgca tctagggcgg  4140
ccaattccgc ccctctccct cccccccccc taacgttact ggccgaagcc gcttggaata  4200
aggccggtgt gcgtttgtct atatgtgatt ttccaccata ttgccgtctt ttggcaatgt  4260
gagggcccgg aaacctggcc ctgtcttctt gacgagcatt cctaggggtc tttcccctct  4320
cgccaaagga atgcaaggtc tgttgaatgt cgtgaaggaa gcagttcctc tggaagcttc  4380
ttgaagacaa acaacgtctg tagcgaccct ttgcaggcag cggaaccccc cacctggcga  4440
caggtgcctc tgcggccaaa agccacgtgt ataagataca cctgcaaagg cggcacaacc  4500
ccagtgccac gttgtgagtt ggatagttgt ggaaagagtc aaatggctct cctcaagcgt  4560
```

-continued

```
attcaacaag gggctgaagg atgcccagaa ggtaccccat tgtatgggat ctgatctggg  4620
gcctcggtgc acatgcttta catgtgttta gtcgaggtta aaaaaacgtc taggcccccc  4680
gaaccacggg gacgtggttt tcctttgaaa aacacgatga taagcttgcc acaaccctta  4740
ccggtcgcca ccatgagcga gctgattaag gagaacatgc acatgaagct gtacatggag  4800
ggcaccgtgg acaaccatca cttcaagtgc acatccgagg gcgaaggcaa gccctacgag  4860
ggcacccaga ccatgagaat caaggtggtc gagggcggcc ctctcccctt cgccttcgac  4920
atcctggcta ctagcttcct ctacggcagc aagaccttca tcaaccacac ccagggcatc  4980
cccgacttct tcaagcagtc cttccctgag ggcttcacat gggagagagt caccacatac  5040
gaagacgggg gcgtgctgac cgctacccag gacaccagcc tccaggacgg ctgcctcatc  5100
tacaacgtca agatcagagg ggtgaacttc acatccaacg gccctgtgat gcagaagaaa  5160
acactcggct gggaggcctt caccgagacg ctgtaccccg ctgacggcgg cctggaaggc  5220
agaaacgaca tggccctgaa gctcgtgggc gggagccatc tgatcgcaaa catcaagacc  5280
acatatagat ccaagaaacc cgctaagaac ctcaagatgc ctggcgtcta ctatgtggac  5340
tacagactgg aaagaatcaa ggaggccaac aacgagacct acgtcgagca gcacgaggtg  5400
gcagtggcca gatactgcga cctccctagc aaactggggc acaagcttaa ttgattctag  5460
agtcgaccga gcatcttacc gccatttata cccatatttg ttctgttttt cttgatttgg  5520
gtatacattt aaatgttaat agaacaaaat ggtggggcaa tcatttacat ttttagggat  5580
atgtaattac tagttcaggt gtattgccac aagacaaaca tgttaagaaa ctttcccgtt  5640
atttacgctc tgttcctgtt aatcaacctc tggattacaa aatttgtgaa agattgactg  5700
atattcttaa ctatgttgct ccttttacgc tgtgtggata tgctgcttta tagcctctgt  5760
atctagctat tgcttcccgt acggctttcg ttttctcctc cttgtataaa tcctggttgc  5820
tgtctctttt agaggagttg tggcccgttg tccgtcaacg tggcgtggtg tgctctgtgt  5880
ttgctgacgc aacccccact ggctggggca ttgccaccac ctgtcaactc ctttctggga  5940
ctttcgcttt ccccctcccg atcgccacgg cagaactcat cgccgcctgc cttgcccgct  6000
gctggacagg ggctaggttg ctgggcactg ataattccgt ggtgttgtca tcggtacctt  6060
tttaaaagaa aaggggggac tggaagggct aattcactcc caacgaagac aagatatcat  6120
aacttcgtat agcatacatt atacgaagtt ataatttatt tgtgaaattt gtgatgctat  6180
tgctttattt gtaaccatat gtttatttgt gaaatttgtg atgctattgc tttatttgta  6240
accattgctt tttgcttgta ctgggtctct ctggttagac cagatctgag cctgggagct  6300
ctctggctaa ctagggaacc cactgcttaa gcctcaataa agcttgcctc gaccagcctc  6360
gactgtgcct tctagttgcc agccatctgt tgtttgcccc tcccccgtgc cttccttgac  6420
cctggaaggt gccactccca ctgtcctttc ctaataaaat gaggaaattg catcgcattg  6480
tctgagtagg tgtcattcta ttctgggggg tggggtgggg caggacagca agggggagga  6540
ttgggaagac aatagcaggc atgctgggga tgcggtgggc tctatggcct gcagctgcat  6600
taatgaatcg gccaacgcgc ggggagaggc ggtttgcgta ttgggcgctc ttccgcttcc  6660
tcgctcactg actcgctgcg ctcggtcgtt cggctgcggc gagcggtatc agctcactca  6720
aaggcggtaa tacggttatc cacagaatca ggggataacg caggaaagaa catgtgagca  6780
aaaggccagc aaaaggccag gaaccgtaaa aaggccgcgt tgctggcgtt tttccatagg  6840
ctccgccccc ctgacgagca tcacaaaaat cgacgctcaa gtcagaggtg gcgaaacccg  6900
acaggactat aaagatacca ggcgtttccc cctggaagct ccctcgtgcg ctctcctgtt  6960
ccgaccctgc cgcttaccgg atacctgtcc gcctttctcc cttcgggaag cgtggcgctt  7020
tctcatagct cacgctgtag gtatctcagt tcggtgtagg tcgttcgctc caagctgggc  7080
tgtgtgcacg aaccccccgt tcagcccgac cgctgcgcct tatccggtaa ctatcgtctt  7140
gagtccaacc cggtaagaca cgacttatcg ccactggcag cagccactgg taacaggatt  7200
agcagagcga ggtatgtagg cggtgctaca gagttcttga agtggtggcc taactacggc  7260
tacactagaa ggacagtatt tggtatctgc gctctgctga agccagttac cttcggaaaa  7320
agagttggta gctcttgatc cggcaaacaa accaccgctg gtagcggtgg tttttttgtt  7380
tgcaagcagc agattacgcg cagaaaaaaa ggatctcaag aagatccttt gatcttttct  7440
acggggtctg acgctcagtg gaacgaaaac tcacgttaag ggattttggt catgagatta  7500
tcaaaaagga tcttcaccta gatcctttta aattaaaaat gaagttttaa atcaatctaa  7560
agtatatatg agtaaacttg gtctgacagt taccaatgct taatcagtga ggcacctatc  7620
tcagcgatct gtctatttcg ttcatccata gttgcctgac tccccgtcgt gtagataact  7680
acgatacggg agggcttacc atctggcccc agtgctgcaa tgataccgcg agacccacgc  7740
tcaccggctc cagatttatc agcaataaac cagccagccg gaagggccga gcgcagaagt  7800
ggtcctgcaa ctttatccgc ctccatccag tctattaatt gttgccggga agctagagta  7860
agtagttcgc cagttaatag tttgcgcaac gttgttgcca ttgctacagg catcgtggtg  7920
tcacgctcgt cgtttggtat ggcttcattc agctccggtt cccaacgatc aaggcgagtt  7980
acatgatccc ccatgttgtg caaaaaagcg gttagctcct tcggtcctcc gatcgttgtc  8040
agaagtaagt tggccgcagt gttatcactc atggttatgg cagcactgca taattctctt  8100
actgtcatgc catccgtaag atgcttttct gtgactggtg agtactcaac caagtcattc  8160
tgagaatagt gtatgcggcg accgagttgc tcttgcccgg cgtcaatacg ggataatacc  8220
gcgccacata gcagaacttt aaaagtgctc atcattggaa aacgttcttc ggggcgaaaa  8280
ctctcaagga tcttaccgct gttgagatcc agttcgatgt aacccactcg tgcacccaac  8340
tgatcttcag catcttttac tttcaccagc gtttctgggt gagcaaaaac aggaaggcaa  8400
aatgccgcaa aaaagggaat aagggcgaca cggaaatgtt gaatactcat actcttcctt  8460
tttcaatatt attgaagcat ttatcagggt tattgtctca tgagcggata catatttgaa  8520
tgtatttaga aaaataaaca aataggggtt ccgcgcacat ttccccgaaa agtgccacct  8580

SEQ ID NO: 127          moltype = DNA  length = 7833
FEATURE                 Location/Qualifiers
misc_feature            1..7833
                        note = Plasmid pCVL.SFFV.HA.NLS.I-LTR I.IRES.mTagBFP
source                  1..7833
                        mol_type = other DNA
                        organism = synthetic construct
SEQUENCE: 127
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
```

-continued

```
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcttc ccagttcaag ctagaaacga  2460
caacatctct ccatggacta tcactggttt cgctgacgct gaatcttctt tcatgttgac  2520
tgtttctaag gactctaaga gaaacactgg ttggtctgtt agaccaagat tcagaatcgg  2580
tttgcacaac aaggacgtga ctatcttgaa gtctatcaga gaatacttgg gcgccggtat  2640
catcacttct gacaaggacg ctagaatcag attcgaatct ttgaaggaat tggaagttgt  2700
tatcaaccac ttcgacaagt acccattgat cactcaaaag agagctgact acttgttgtt  2760
caagaaggct ttctacttaa ttaagaacaa ggaacacttg actgaagaag gtttgaacca  2820
aatcttgact ttgaaggctt ctttgaactt gggtttgtct gaagaattga aggaagcatt  2880
cccaaacact atcccagctg aaaagttact agttactggt caagaaatcc cagactctaa  2940
ctgggttgct ggtttcactg ctggtgaagg ttctttctac atcagaatcg ctaagaactc  3000
tactttgaag actggttacc aagttcaatc tgttttccaa atcactcaag acacgcgtga  3060
catcgaattg atgaagaact tgatctctta cttgaactgt ggtaacatca gaatcagaaa  3120
gtacaagggt tctgaaggta tccacgacac ttgtgttgac ttggttgtta ctaacttgaa  3180
cgacatcaag gaaaagatca tcccattctt caacaagaac cacatcatcg gtgttaagtt  3240
gcaagactac agagactggt gtaaggttgt tactttgatc gacaacaagg aacacttgac  3300
ttctgaaggt ttggaaaaga tccaaaagat caaggaaggt atgaacagag gtagatcttt  3360
gtagcctgca ggtcgagcat gcatctaggg cggccaattc cgcccctctc cctccccccc  3420
ccctaacgtt actggccgaa gccgcttgga ataaggccgg tgtgcgtttg tctatatgtg  3480
attttccacc atattgccgt cttttggcaa tgtgagggcc cggaaacctg gccctgtctt  3540
cttgacgagc attcctaggg gtctttcccc tctcgccaaa ggaatgcaag gtctgttgaa  3600
tgtcgtgaag gaagcagttc ctctggaagc ttcttgaaga caaacaacgt ctgtagcgac  3660
cctttgcagg cagcggaacc ccccacctgg cgacaggtgc ctctgcggcc aaaagccacg  3720
tgtataagat acacctgcaa aggcggcaca accccagtgc cacgttgtga gttggatagt  3780
tgtggaaaga gtcaaatggc tctcctcaag cgtattcaac aaggggctga aggatgccca  3840
gaaggtaccc cattgtatgg gatctgatct ggggcctcgg tgcacatgct ttacatgtgt  3900
ttagtcgagg ttaaaaaaac gtctaggccc cccgaaccac ggggacgtgg ttttcctttg  3960
aaaaacacga tgataagctt gccacaaccc ttaccggtcg ccaccatgag cgagctgatt  4020
aaggagaaca tgcacatgaa gctgtacatg gagggcaccg tggacaacca tcacttcaag  4080
tgcacatccg agggcgaagg caagccctac gagggcaccc agaccatgag aatcaaggtg  4140
gtcgagggcg gccctctccc cttcgccttc gacatcctgg ctactagctt cctctacggc  4200
agcaagacct tcatcaacca cacccagggc atccccgact tcttcaagca gtccttccct  4260
gagggcttca catgggagag agtcaccaca tacgaagacg gggggcgtgct gaccgctacc  4320
caggacacca gcctccagga cggctgcctc atctacaacg tcaagatcag aggggtgaac  4380
ttcacatcca acggccctgt gatgcagaag aaaacactcg gctgggaggc cttcaccgag  4440
acgctgtacc ccgctgacgg cggcctggaa ggcagaaacg acatggccct gaagctcgtg  4500
ggcgggagcc atctgatcgc aaacatcaag accacatata gatccaagaa acccgctaag  4560
aacctcaaga tgcctggcgt ctactatgtg gactacagac tggaaagaat caaggaggcc  4620
aacaacgaga cctacgtcga gcagcacgag gtggcagtgg ccagatactg cgacctccct  4680
agcaaactgg ggcacaagct taattgattc tagagtcgac cgagcatctt accgccattt  4740
atacccatat ttgttctgtt tttcttgatt tgggtataca tttaaatgtt aatagaacaa  4800
aatggtgggg caatcattta cattttttagg gatatgtaat tactagttca ggtgtattgc  4860
cacaagacaa acatgttaag aaactttccc gttatttacg ctctgttcct gttaatcaac  4920
```

```
ctctggatta caaaatttgt gaaagattga ctgatattct taactatgtt gctcctttta  4980
cgctgtgtgg atatgctgct ttatagcctc tgtatctagc tattgcttcc cgtacggctt  5040
tcgttttctc ctccttgtat aaatcctggt tgctgtctct tttagaggag ttgtggcccg  5100
ttgtccgtca acgtggcgtg gtgtgctctg tgtttgctga cgcaaccccc actggctggg  5160
gcattgccac cacctgtcaa ctcctttctg ggactttcgc tttccccctc ccgatcgcca  5220
cggcagaact catcgccgcc tgccttgccc gctgctggac aggggctagg ttgctgggca  5280
ctgataattc cgtggtgttg tcatcggtac ctttttaaaa gaaaaggggg gactggaagg  5340
gctaattcac tcccaacgaa gacaagatat cataacttcg tatagcatac attatacgaa  5400
gttataattt atttgtgaaa tttgtgatgc tattgcttta tttgtaacca tatgtttatt  5460
tgtgaaattt gtgatgctat tgctttattt gtaaccattg ctttttgctt gtactgggtc  5520
tctctggtta gaccagatct gagcctggga gctctctggc taactaggga acccactgct  5580
taagcctcaa taaagcttgc ctcgaccagc ctcgactgtg ccttctagtt gccagccatc  5640
tgttgtttgc ccctcccccg tgccttcctt gaccctggaa ggtgccactc ccactgtcct  5700
ttcctaataa aatgaggaaa ttgcatcgca ttgtctgagt aggtgtcatt ctattctggg  5760
gggtggggtg gggcaggaca gcaaggggga ggattgggaa gacaatagca ggcatgctgg  5820
ggatgcggtg ggctctatgg cctgcagctg cattaatgaa tcggccaacg cgcggggaga  5880
ggcggtttgc gtattgggcg ctcttccgct tcctcgctca ctgactcgct gcgctcggtc  5940
gttcggctgc ggcgagcggt atcagctcac tcaaaggcgg taatacggtt atccacagaa  6000
tcaggggata acgcaggaaa gaacatgtga gcaaaaggcc agcaaaaggc caggaaccgt  6060
aaaaaggccg cgttgctggc gtttttccat aggctccgcc cccctgacga gcatcacaaa  6120
aatcgacgct caagtcagag gtggcgaaac ccgacaggac tataaagata ccaggcgttt  6180
ccccctggaa gctccctcgt gcgctctcct gttccgaccc tgccgcttac cggatacctg  6240
tccgcctttc tcccttcggg aagcgtggcg ctttctcata gctcacgctg taggtatctc  6300
agttcggtgt aggtcgttcg ctccaagctg ggctgtgtgc acgaaccccc cgttcagccc  6360
gaccgctgcg ccttatccgg taactatcgt cttgagtcca acccggtaag acacgactta  6420
tcgccactgg cagcagccac tggtaacagg attagcagag cgaggtatgt aggcggtgct  6480
acagagttct tgaagtggtg gcctaactac ggctacacta gaaggacagt atttggtatc  6540
tgcgctctgc tgaagccagt taccttcgga aaaagagttg gtagctcttg atccggcaaa  6600
caaaccaccg ctggtagcgg tggttttttt gtttgcaagc agcagattac gcgcagaaaa  6660
aaaggatctc aagaagatcc tttgatcttt tctacggggt ctgacgctca gtggaacgaa  6720
aactcacgtt aagggatttt ggtcatgaga ttatcaaaaa ggatcttcac ctagatcctt  6780
ttaaattaaa aatgaagttt taaatcaatc taaagtatat atgagtaaac ttggtctgac  6840
agttaccaat gcttaatcag tgaggcacct atctcagcga tctgtctatt tcgttcatcc  6900
atagttgcct gactccccgt cgtgtagata actacgatac gggagggctt accatctggc  6960
cccagtgctg caatgatacc gcgagaccca cgctcaccgg ctccagattt atcagcaata  7020
aaccagccag ccggaagggc cgagcgcaga agtggtcctg caactttatc cgcctccatc  7080
cagtctatta attgttgccg ggaagctaga gtaagtagtt cgccagttaa tagtttgcgc  7140
aacgttgttg ccattgctac aggcatcgtg gtgtcacgct cgtcgtttgg tatggcttca  7200
ttcagctccg gttcccaacg atcaaggcga gttacatgat cccccatgtt gtgcaaaaaa  7260
gcggttagct ccttcggtcc tccgatcgtt gtcagaagta agttggccgc agtgttatca  7320
ctcatggtta tggcagcact gcataattct cttactgtca tgccatccgt aagatgcttt  7380
tctgtgactg gtgagtactc aaccaagtca ttctgagaat agtgtatgcg gcgaccgagt  7440
tgctcttgcc cggcgtcaat acgggataat accgcgccac atagcagaac tttaaaagtg  7500
ctcatcattg gaaaacgttc ttcggggcga aaactctcaa ggatcttacc gctgttgaga  7560
tccagttcga tgtaacccac tcgtgcaccc aactgatctt cagcatcttt tactttcacc  7620
agcgtttctg ggtgagcaaa aacaggaagg caaaatgccg caaaaaaggg aataagggcg  7680
acacggaaat gttgaatact catactcttc ctttttcaat attattgaag catttatcag  7740
ggttattgtc tcatgagcgg atacatattt gaatgtattt agaaaaataa acaaataggg  7800
gttccgcgca catttccccg aaaagtgcca cct                               7833
```

```
SEQ ID NO: 128          moltype = DNA  length = 8607
FEATURE                 Location/Qualifiers
misc_feature            1..8607
                        note = Plasmid pCVL.SFFV.HA.NLS.I-LTR
                         I.T2A.Trex2.IRES.mTagBFP
source                  1..8607
                        mol_type = other DNA
                        organism = synthetic construct
SEQUENCE: 128
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc caggggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
```

-continued

```
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcttc ccagttcaag ctagaaacga  2460
caacatctct ccatggacta tcactggttt cgctgacgct gaatcttctt tcatgttgac  2520
tgtttctaag gactctaaga gaaacactgg ttggtctgtt agaccaagat tcagaatcgg  2580
tttgcacaac aaggacgtga ctatcttgaa gtctatcaga gaatacttgg gcgccggtat  2640
catcacttct gacaaggacg ctagaatcag attcgaatct ttgaaggaat tggaagttgt  2700
tatcaaccac ttcgacaagt acccattgat cactcaaaag agagctgact acttgttgtt  2760
caagaaggct ttctacttaa ttaagaacaa ggaacacttg actgaagaag gtttgaacca  2820
aatcttgact ttgaaggctt ctttgaactt gggtttgtct gaagaattga aggaagcatt  2880
cccaaacact atcccagctg aaaagttact agttactggt caagaaatcc cagactctaa  2940
ctgggttgct ggtttcactg ctggtgaagg ttctttctac atcagaatcg ctaagaactc  3000
tactttgaag actggttacc aagttcaatc tgttttccaa atcactcaag acacgcgtga  3060
catcgaattg atgaagaact tgatctctta cttgaactgt ggtaacatca gaatcagaaa  3120
gtacaagggt tctgaaggta tccacgacac ttgtgttgac ttggttgtta ctaacttgaa  3180
cgacatcaag gaaaagatca tcccattctt caacaagaac cacatcatcg gtgttaagtt  3240
gcaagactac agagactggt gtaaggttgt tactttgatc gacaacaagg aacacttgac  3300
ttctgaaggt ttggaaaaga tccaaaagat caaggaaggt atgaacagag gtagatcttt  3360
gggatccggt gagggcagag gaagtcttct aacatgcggt gacgtggagg agaatccggg  3420
cccctccgga tctgagccac ctcgggctga gacctttgta ttcctggacc tagaagccac  3480
tgggctccca aacatggacc ctgagattgc agagatatcc ctttttgctg ttcaccgctc  3540
ttccctggag aacccagaac gggatgattc tggttccttg gtgctgcccc gtgttctgga  3600
caagctcaca ctgtgcatgt gcccggagcg cccctttact gccaaggcca gtgagattac  3660
tggtttgagc agcgaaagcc tgatgcactg cgggaaggct ggtttcaatg gcgctgtggt  3720
aaggacactg cagggcttcc taagccgcca ggagggcccc atctgccttg tggcccacaa  3780
tggcttcgat tatgacttcc cactgctgtg cacggagcta caacgtctgg gtgcccatct  3840
gccccaagac actgtctgcc tggacacact gcctgcattg cggggcctgg accgtgctca  3900
cagccacggc accagggctc aaggccgcaa aagctacagc ctggccagtc tcttccaccg  3960
ctacttccag gctgaaccca gtgctgccca ttcagcagaa ggtgatgtgc acaccctgct  4020
tctgatcttc ctgcatcgtg ctcctgagct gctcgcctgg gcagatgagc aggcccgcag  4080
ctgggctcat attgagccca tgtacgtgcc acctgatggt ccaagcctcg aagcctgacc  4140
tgcaggtcga gcatgcatct agggcggcca attccgcccc tctccctccc ccccccctaa  4200
cgttactggc cgaagccgct tggaataagg ccggtgtgcg tttgtctata tgtgattttc  4260
caccatattg ccgtcttttg gcaatgtgag ggcccggaaa cctggccctg tcttcttgac  4320
gagcattcct aggggtcttt cccctctcgc caaaggaatg caaggtctgt tgaatgtcgt  4380
gaaggaagca gttcctctgg aagcttcttg aagacaaaca acgtctgtag cgaccctttg  4440
caggcagcgg aacccccac ctggcgacag gtgcctctgc ggccaaaagc cacgtgtata  4500
agatacacct gcaaaggcgg cacaacccca gtgccacgtt gtgagttgga tagttgtgga  4560
aagagtcaaa tggctctcct caagcgtatt caacaagggg ctgaaggatg cccagaaggt  4620
accccattgt atgggatctg atctggggcc tcggtgcaca tgctttacat gtgtttagtc  4680
gaggttaaaa aaacgtctag gccccccgaa ccacggggac gtggttttcc tttgaaaaac  4740
acgatgataa gcttgccaca acccttaccg gtcgccacca tgagcgagct gattaaggag  4800
aacatgcaca tgaagctgta catggagggc accgtggaca accatcactt caagtgcaca  4860
tccgagggcg aaggcaagcc ctacgagggc acccagacca tgagaatcaa ggtggtcgag  4920
ggcggccctc tcccttcgc cttcgacatc ctggctacta gcttcctcta cggcagcaag  4980
accttcatca accacaccca gggcatcccc gacttcttca agcagtcctt ccctgagggc  5040
ttcacatggg agagagtcac cacatacgaa gacgggggcg tgctgaccgc tacccaggac  5100
accagcctcc aggacggctg cctcatctac aacgtcaaga tcagaggggt gaacttcaca  5160
tccaacggcc ctgtgatgca gaagaaaaca ctcggctggg aggccttcac cgagacgctg  5220
taccccgctg acggcggcct ggaaggcaga aacgacatgg ccctgaagct cgtgggcggg  5280
agccatctga tcgcaaacat caagaccaca tatagatcca agaaacccgc taagaacctc  5340
aagatgcctg gcgtctacta tgtggactac agactggaaa gaatcaagga ggccaacaac  5400
gagacctacg tcgagcagca cgaggtggca gtggccagat actgcgacct ccctagcaaa  5460
ctggggcaca agcttaattg attctagagt cgaccgagca tcttaccgcc atttataccc  5520
atatttgttc tgtttttctt gatttgggta tacatttaaa tgttaataga acaaaatggt  5580
ggggcaatca tttacatttt tagggatatg taattactag ttcaggtgta ttgccacaag  5640
acaaacatgt taagaaactt tcccgttatt tacgctctgt tcctgttaat caacctctgg  5700
attacaaaat ttgtgaaaga ttgactgata ttcttaacta tgttgctcct tttacgctgt  5760
gtggatatgc tgctttatag cctctgtatc tagctattgc ttcccgtacg gctttcgttt  5820
tctcctcctt gtataaatcc tggttgctgt ctcttttaga ggagttgtgg cccgttgtcc  5880
gtcaacgtgg cgtggtgtgc tctgtgtttg ctgacgcaac ccccactggc tggggcattg  5940
```

-continued

```
ccaccacctg tcaactcctt tctgggactt tcgctttccc cctcccgatc gccacggcag  6000
aactcatcgc cgcctgcctt gcccgctgct ggacaggggc taggttgctg ggcactgata  6060
attccgtggt gttgtcatcg gtacctttt aaaagaaaag gggggactgg aagggctaat  6120
tcactcccaa cgaagacaag atatcataac ttcgtatagc atacattata cgaagttata  6180
atttatttgt gaaatttgtg atgctattgc tttatttgta accatatgtt tatttgtgaa  6240
atttgtgatg ctattgcttt atttgtaacc attgcttttt gcttgtactg ggtctctctg  6300
gttagaccag atctgagcct gggagctctc tggctaacta gggaacccac tgcttaagcc  6360
tcaataaagc ttgcctcgac cagcctcgac tgtgccttct agttgccagc catctgttgt  6420
ttgcccctcc cccgtgcctt ccttgaccct ggaaggtgcc actcccactg tcctttccta  6480
ataaaatgag gaaattgcat cgcattgtct gagtaggtgt cattctattc tggggggtgg  6540
ggtggggcag gacagcaagg gggaggattg ggaagacaat agcaggcatg ctggggatgc  6600
ggtgggctct atggcctgca gctgcattaa tgaatcggcc aacgcgcggg gagaggcggt  6660
ttgcgtattg ggcgctcttc cgcttcctcg ctcactgact cgctgcgctc ggtcgttcgg  6720
ctgcggcgag cggtatcagc tcactcaaag gcggtaatac ggttatccac agaatcaggg  6780
gataacgcag gaaagaacat gtgagcaaaa ggccagcaaa aggccaggaa ccgtaaaaag  6840
gccgcgttgc tggcgttttt ccataggctc cgcccccctg acgagcatca caaaaatcga  6900
cgctcaagtc agaggtggcg aaacccgaca ggactataaa gataccaggc gtttccccct  6960
ggaagctccc tcgtgcgctc tcctgttccg accctgccgc ttaccggata cctgtccgcc  7020
tttctccctt cgggaagcgt ggcgctttct catagctcac gctgtaggta tctcagttcg  7080
gtgtaggtcg ttcgctccaa gctgggctgt gtgcacgaac cccccgttca gcccgaccgc  7140
tgcgccttat ccggtaacta tcgtcttgag tccaacccgg taagacacga cttatcgcca  7200
ctggcagcag ccactggtaa caggattagc agagcgaggt atgtaggcgg tgctacagag  7260
ttcttgaagt ggtggcctaa ctacggctac actagaagga cagtatttgg tatctgcgct  7320
ctgctgaagc cagttacctt cggaaaaaga gttggtagct cttgatccgg caaacaaacc  7380
accgctggta gcggtggttt ttttgtttgc aagcagcaga ttacgcgcag aaaaaaagga  7440
tctcaagaag atcctttgat cttttctacg gggtctgacg ctcagtggaa cgaaaactca  7500
cgttaaggga ttttggtcat gagattatca aaaaggatct tcacctagat ccttttaaat  7560
taaaaatgaa gttttaaatc aatctaaagt atatatgagt aaacttggtc tgacagttac  7620
caatgcttaa tcagtgaggc acctatctca gcgatctgtc tatttcgttc atccatagtt  7680
gcctgactcc ccgtcgtgta gataactacg atacgggagg gcttaccatc tggccccagt  7740
gctgcaatga taccgcgaga cccacgctca ccggctccag atttatcagc aataaaccag  7800
ccagccggaa gggccgagcg cagaagtggt cctgcaactt tatccgcctc catccagtct  7860
attaattgtt gccgggaagc tagagtaagt agttcgccag ttaatagttt gcgcaacgtt  7920
gttgccattg ctacaggcat cgtggtgtca cgctcgtcgt ttggtatggc ttcattcagc  7980
tccggttccc aacgatcaag gcgagttaca tgatccccca tgttgtgcaa aaaagcggtt  8040
agctccttcg gtcctccgat cgttgtcaga agtaagttgg ccgcagtgtt atcactcatg  8100
gttatggcag cactgcataa ttctcttact gtcatgccat ccgtaagatg cttttctgtg  8160
actggtgagt actcaaccaa gtcattctga gaatagtgta tgcggcgacc gagttgctct  8220
tgcccggcgt caatacggga taataccgcg ccacatagca gaactttaaa agtgctcatc  8280
attggaaaac gttcttcggg gcgaaaactc tcaaggatct taccgctgtt gagatccagt  8340
tcgatgtaac ccactcgtgc acccaactga tcttcagcat cttttacttt caccagcgtt  8400
tctgggtgag caaaaacagg aaggcaaaat gccgcaaaaa agggaataag ggcgacacgg  8460
aaatgttgaa tactcatact cttccttttt caatattatt gaagcattta tcagggttat  8520
tgtctcatga gcggatacat atttgaatgt atttagaaaa ataaacaaat aggggttccg  8580
cgcacatttc cccgaaaagt gccacct                                     8607

SEQ ID NO: 129         moltype = DNA  length = 7818
FEATURE                Location/Qualifiers
misc_feature           1..7818
                       note = Plasmid pCVL.SFFV.HA.NLS.I-GPI I.IRES.mTagBFP
source                 1..7818
                       mol_type = other DNA
                       organism = synthetic construct
SEQUENCE: 129
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
```

-continued

```
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgct actgttactc cattgatcga  2460
cccatggttc atcactggtt tcgctgacgc tgaatcttct ttcgttgttt ctatcaagag  2520
aaacaagaag atcaagtgtg gttggaacgt tgttactaga ttccaaatcg ccttaagtca  2580
aaaggacttg gctttgttgg aaagaatcaa gtcttacttc aaggacgctg gtaacatcta  2640
catcaagtct gacaaggttt ctgttgactg gcacgttact tctgttaagg acttgaagat  2700
catccttgat cacttcgaca agtacccatt gaagactgaa aagttggctg actacatctt  2760
gttcaaggaa gttttcaaca tcatcttgac taagcaacac ttgactgttg aaggtatcca  2820
aaagatcgtt gctatcagag cttctatcaa caagggtttg tacggtgaat tgaaggctgc  2880
attcccaaac atcatcccag ttcaaaggcc taagatcgac gacagattca tcatcgatat  2940
ccaaccatgg tgggttgctg gtttcactga aggtgaaggt tgtttctctg ttgttgttac  3000
taactctcca tctactaagt ctggtttctc tgcttctttg atcttccaaa tcactcaaca  3060
ctctcgtgac atcgttttga tgcaaaacat catcaagttc ctaggttgtg gtagaatcca  3120
caagagatct aaggaagaag ctgttgacat cttggttact aagttctctg acttgactga  3180
aaaggttatc ccattcttcg aatctatccc attgcaaggt ttgaagttga agaacttcac  3240
tgacttctct aaggctgctg acatcatcaa ggttaagggt cacttgactc caaagggttt  3300
ggacaagatc ttgcaaatca agttgggtat gaacactaga agaatctagc ctgcaggtcg  3360
agcatgcatc tagggcggcc aattccgccc ctctccctcc cccccccta acgttactgg  3420
ccgaagccgc ttggaataag gccggtgtgc gtttgtctat atgtgatttt ccaccatatt  3480
gccgtctttt ggcaatgtga gggcccggaa acctggccct gtcttcttga cgagcattcc  3540
taggggtctt tcccctctcg ccaaaggaat gcaaggtctg ttgaatgtcg tgaaggaagc  3600
agttcctctg gaagcttctt gaagacaaac aacgtctgta gcgacccttt gcaggcagcg  3660
gaacccccca cctggcgaca ggtgcctctg cggccaaaag ccacgtgtat aagatacacc  3720
tgcaaaggcg gcacaacccc agtgccacgt tgtgagttgg atagttgtgg aaagagtcaa  3780
atggctctcc tcaagcgtat tcaacaaggg gctgaaggat gcccagaagg taccccattg  3840
tatgggatct gatctggggc ctcggtgcac atgctttaca tgtgtttagt cgaggttaaa  3900
aaaacgtcta ggccccccga accacgggga cgtggttttc ctttgaaaaa cacgatgata  3960
agcttgccac aacccttacc ggtcgccacc atgagcgagc tgattaagga gaacatgcac  4020
atgaagctgt acatggaggg caccgtggac aaccatcact tcaagtgcac atccgagggc  4080
gaaggcaagc cctacgaggg cacccagacc atgagaatca aggtggtcga gggcggccct  4140
ctccccttcg ccttcgacat cctggctact agcttcctct acggcagcaa gaccttcatc  4200
aaccacaccc agggcatccc cgacttcttc aagcagtcct tccctgaggg cttcacatgg  4260
gagagagtca ccacatacga agacgggggc gtgctgaccg ctacccagga caccagcctc  4320
caggacggct gcctcatcta caacgtcaag atcagagggg tgaacttcac atccaacggc  4380
cctgtgatgc agaagaaaac actcggctgg gaggccttca ccgagacgct gtaccccgct  4440
gacggcggcc tggaaggcag aaacgacatg gccctgaagc tcgtgggcgg gagccatctg  4500
atcgcaaaca tcaagaccac atatagatcc aagaaacccg ctaagaacct caagatgcct  4560
ggcgtctact atgtggacta cagactggaa agaatcaagg aggccaacaa cgagacctac  4620
gtcgagcagc acgaggtggc agtggccaga tactgcgacc tccctagcaa actggggcac  4680
aagcttaatt gattctagag tcgaccgagc atcttaccgc catttatacc catatttgtt  4740
ctgtttttct tgatttgggt atacatttaa atgttaatag aacaaaatgg tggggcaatc  4800
atttacattt ttagggatat gtaattacta gttcaggtgt attgccacaa gacaaacatg  4860
ttaagaaact ttcccgttat ttacgctctg ttcctgttaa tcaacctctg gattacaaaa  4920
tttgtgaaag attgactgat attcttaact atgttgctcc ttttacgctg tgtggatatg  4980
ctgctttata gcctctgtat ctagctattg cttcccgtac ggctttcgtt ttctcctcct  5040
tgtataaatc ctggttgctg tctcttttag aggagttgtg gcccgttgtc cgtcaacgtg  5100
gcgtggtgtg ctctgtgttt gctgacgcaa cccccactgg ctggggcatt gccaccacct  5160
gtcaactcct ttctgggact ttcgctttcc ccctcccgat cgccacggca gaactcatcg  5220
ccgcctgcct tgcccgctgc tggacagggg ctaggttgct gggcactgat aattccgtgg  5280
tgttgtcatc ggtacctttt taaaagaaaa ggggggactg gaagggctaa ttcactccca  5340
acgaagacaa gatatcataa cttcgtatag catacattat acgaagttat aatttatttg  5400
tgaaatttgt gatgctattg ctttatttgt aaccatatgt ttatttgtga aatttgtgat  5460
gctattgctt tatttgtaac cattgctttt tgcttgtact gggtctctct ggttagacca  5520
gatctgagcc tgggagctct ctggctaact agggaaccca ctgcttaagc ctcaataaag  5580
cttgcctcga ccagcctcga ctgtgccttc tagttgccag ccatctgttg tttgcccctc  5640
ccccgtgcct tccttgaccc tggaaggtgc cactcccact gtcctttcct aataaaatga  5700
ggaaattgca tcgcattgtc tgagtaggtg tcattctatt ctggggggtg gggtggggca  5760
ggacagcaag ggggaggatt gggaagacaa tagcaggcat gctggggatg cggtgggctc  5820
tatggcctgc agctgcatta atgaatcggc caacgcgcgg ggagaggcgg tttgcgtatt  5880
gggcgctctt ccgcttcctc gctcactgac tcgctgcgct cggtcgttcg gctgcggcga  5940
gcggtatcag ctcactcaaa ggcggtaata cggttatcca cagaatcagg ggataacgca  6000
ggaaagaaca tgtgagcaaa aggccagcaa aaggccagga accgtaaaaa ggccgcgttg  6060
ctggcgtttt tccataggct ccgcccccct gacgagcatc acaaaaatcg acgctcaagt  6120
cagaggtggc gaaacccgac aggactataa agataccagg cgtttccccc tggaagctcc  6180
ctcgtgcgct ctcctgttcc gaccctgccg cttaccggat acctgtccgc ctttctccct  6240
```

```
tcgggaagcg tggcgctttc tcatagctca cgctgtaggt atctcagttc ggtgtaggtc  6300
gttcgctcca agctgggctg tgtgcacgaa ccccccgttc agcccgaccg ctgcgcctta  6360
tccggtaact atcgtcttga gtccaacccg gtaagacacg acttatcgcc actggcagca  6420
gccactggta acaggattag cagagcgagg tatgtaggcg gtgctacaga gttcttgaag  6480
tggtggccta actacggcta cactagaagg acagtatttg gtatctgcgc tctgctgaag  6540
ccagttacct tcggaaaaag agttggtagc tcttgatccg gcaaacaaac caccgctggt  6600
agcggtggtt tttttgtttg caagcagcag attacgcgca gaaaaaaagg atctcaagaa  6660
gatcctttga tcttttctac ggggtctgac gctcagtgga acgaaaactc acgttaaggg  6720
attttggtca tgagattatc aaaaaggatc ttcacctaga tccttttaaa ttaaaaatga  6780
agttttaaat caatctaaag tatatatgag taaacttggt ctgacagtta ccaatgctta  6840
atcagtgagg cacctatctc agcgatctgt ctatttcgtt catccatagt tgcctgactc  6900
cccgtcgtgt agataactac gatacgggag ggcttaccat ctggccccag tgctgcaatg  6960
ataccgcgag acccacgctc accggctcca gatttatcag caataaacca gccagccgga  7020
agggccgagc gcagaagtgg tcctgcaact ttatccgcct ccatccagtc tattaattgt  7080
tgccgggaag ctagagtaag tagttcgcca gttaatagtt tgcgcaacgt tgttgccatt  7140
gctacaggca tcgtggtgtc acgctcgtcg tttggtatgg cttcattcag ctccggttcc  7200
caacgatcaa ggcgagttac atgatccccc atgttgtgca aaaaagcggt tagctccttc  7260
ggtcctccga tcgttgtcag aagtaagttg gccgcagtgt tatcactcat ggttatggca  7320
gcactgcata attctcttac tgtcatgcca tccgtaagat gcttttctgt gactggtgag  7380
tactcaacca agtcattctg agaatagtgt atgcggcgac cgagttgctc ttgcccggcg  7440
tcaatacggg ataataccgc gccacatagc agaactttaa aagtgctcat cattggaaaa  7500
cgttcttcgg ggcgaaaact ctcaaggatc ttaccgctgt tgagatccag ttcgatgtaa  7560
cccactcgtg cacccaactg atcttcagca tcttttactt tcaccagcgt ttctgggtga  7620
gcaaaaacag gaaggcaaaa tgccgcaaaa aagggaataa gggcgacacg gaaatgttga  7680
atactcatac tcttcctttt tcaatattat tgaagcattt atcagggtta ttgtctcatg  7740
agcggataca tatttgaatg tatttagaaa aataaacaaa taggggttcc gcgcacattt  7800
ccccgaaaag tgccacct                                               7818

SEQ ID NO: 130          moltype = DNA  length = 8592
FEATURE                 Location/Qualifiers
misc_feature            1..8592
                        note = Plasmid pCVL.SFFV.HA.NLS.I-GPI
                         I.T2A.Trex2.IRES.mTagBFP
source                  1..8592
                        mol_type = other DNA
                        organism = synthetic construct
SEQUENCE: 130
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgct actgttactc cattgatcga  2460
cccatggttc atcactggtt tcgctgacgc tgaatcttct ttcgttgttt ctatcaagag  2520
```

-continued

```
aaacaagaag atcaagtgtg gttggaacgt tgttactaga ttccaaatcg ccttaagtca  2580
aaaggacttg gctttgttgg aaagaatcaa gtcttacttc aaggacgctg gtaacatcta  2640
catcaagtct gacaaggttt ctgttgactg gcacgttact tctgttaagg acttgaagat  2700
catccttgat cacttcgaca agtacccatt gaagactgaa aagttggctg actacatctt  2760
gttcaaggaa gttttcaaca tcatcttgac taagcaacac ttgactgttg aaggtatcca  2820
aaagatcgtt gctatcagag cttctatcaa caagggtttg tacggtgaat tgaaggctgc  2880
attcccaaac atcatcccag ttcaaaggcc taagatcgac gacagattca tcatcgatat  2940
ccaaccatgg tgggttgctg gtttcactga aggtgaaggt tgtttctctg ttgttgttac  3000
taactctcca tctactaagt ctggtttctc tgcttctttg atcttccaaa tcactcaaca  3060
ctctcgtgac atcgttttga tgcaaaacat catcaagttc ctaggttgtg gtagaatcca  3120
caagagatct aaggaagaag ctgttgacat cttggttact aagttctctg acttgactga  3180
aaaggttatc ccattcttcg aatctatccc attgcaaggt ttgaagttga agaacttcac  3240
tgacttctct aaggctgctg acatcatcaa ggttaagggt cacttgactc caaagggttt  3300
ggacaagatc ttgcaaatca agttgggtat gaacactaga agaatcggat ccggtgaggg  3360
cagaggaagt cttctaacat gcggtgacgt ggaggagaat ccgggcccct ccggatctga  3420
gccacctcgg gctgagacct ttgtattcct ggacctagaa gccactgggc tcccaaacat  3480
ggaccctgag attgcagaga tatccctttt tgctgttcac cgctcttccc tggagaaccc  3540
agaacgggat gattctggtt ccttggtgct gccccgtgtt ctggacaagc tcacactgtg  3600
catgtgcccg gagcgcccct ttactgccaa ggccagtgag attactggtt tgagcagcga  3660
aagcctgatg cactgcggga aggctggttt caatggcgct gtggtaagga cactgcaggg  3720
cttcctaagc cgccaggagg gccccatctg ccttgtggcc cacaatggct tcgattatga  3780
cttcccactg ctgtgcacgg agctacaacg tctgggtgcc catctgcccc aagacactgt  3840
ctgcctggac acactgcctg cattgcgggg cctggaccgt gctcacagcc acggcaccag  3900
ggctcaaggc cgcaaaagct acagcctggc cagtctcttc caccgctact tccaggctga  3960
acccagtgct gcccattcag cagaaggtga tgtgcacacc ctgcttctga tcttcctgca  4020
tcgtgctcct gagctgctcg cctgggcaga tgagcaggcc cgcagctggg ctcatattga  4080
gcccatgtac gtgccacctg atggtccaag cctcgaagcc tgacctgcag gtcgagcatg  4140
catctagggc ggccaattcc gcccctctcc ctcccccccc cctaacgtta ctggccgaag  4200
ccgcttggaa taaggccggt gtgcgtttgt ctatatgtga ttttccacca tattgccgtc  4260
ttttggcaat gtgagggccc ggaaacctgg ccctgtcttc ttgacgagca ttcctagggg  4320
tctttcccct ctcgccaaag gaatgcaagg tctgttgaat gtcgtgaagg aagcagttcc  4380
tctggaagct tcttgaagac aaacaacgtc tgtagcgacc ctttgcaggc agcggaaccc  4440
cccacctggc gacaggtgcc tctgcggcca aaagccacgt gtataagata cacctgcaaa  4500
ggcggcacaa ccccagtgcc acgttgtgag ttggatagtt gtggaaagag tcaaatggct  4560
ctcctcaagc gtattcaaca aggggctgaa ggatgcccag aaggtacccc attgtatggg  4620
atctgatctg gggcctcggt gcacatgctt tacatgtgtt tagtcgaggt taaaaaaacg  4680
tctaggcccc ccgaaccacg gggacgtggt tttcctttga aaaacacgat gataagcttg  4740
ccacaaccct taccggtcgc caccatgagc gagctgatta aggagaacat gcacatgaag  4800
ctgtacatgg agggcaccgt ggacaaccat cacttcaagt gcacatccga gggcgaaggc  4860
aagccctacg agggcaccca gaccatgaga atcaaggtgg tcgagggcgg ccctctcccc  4920
ttcgccttcg acatcctggc tactagcttc ctctacggca gcaagacctt catcaaccac  4980
acccagggca tccccgactt cttcaagcag tccttccctg agggcttcac atgggagaga  5040
gtcaccacat acgaagacgg gggcgtgctg accgctaccc aggacaccag cctccaggac  5100
ggctgcctca tctacaacgt caagatcaga ggggtgaact tcacatccaa cggccctgtg  5160
atgcagaaga aaacactcgg ctgggaggcc ttcaccgaga cgctgtaccc cgctgacggc  5220
ggcctggaag gcagaaacga catggccctg aagctcgtgg gcgggagcca tctgatcgca  5280
aacatcaaga ccacatatag atccaagaaa cccgctaaga acctcaagat gcctggcgtc  5340
tactatgtgg actacagact ggaaagaatc aaggaggcca acaacgagac ctacgtcgag  5400
cagcacgagg tggcagtggc cagatactgc gacctcccta gcaaactggg gcacaagctt  5460
aattgattct agagtcgacc gagcatctta ccgccattta tacccatatt tgttctgttt  5520
ttcttgattt gggtatacat ttaaatgtta atagaacaaa atggtggggc aatcatttac  5580
atttttaggg atatgtaatt actagttcag gtgtattgcc acaagacaaa catgttaaga  5640
aactttcccg ttatttacgc tctgttcctg ttaatcaacc tctggattac aaaatttgtg  5700
aaagattgac tgatattctt aactatgttg ctccttttac gctgtgtgga tatgctgctt  5760
tatagcctct gtatctagct attgcttccc gtacggcttt cgttttctcc tccttgtata  5820
aatcctggtt gctgtctctt ttagaggagt tgtggcccgt tgtccgtcaa cgtggcgtgg  5880
tgtgctctgt gtttgctgac gcaaccccca ctggctgggg cattgccacc acctgtcaac  5940
tcctttctgg gactttcgct ttccccctcc cgatcgccac ggcagaactc atcgccgcct  6000
gccttgcccg ctgctggaca ggggctaggt tgctgggcac tgataattcc gtggtgttgt  6060
catcggtacc tttttaaaag aaaagggggg actggaaggg ctaattcact cccaacgaag  6120
acaagatatc ataacttcgt atagcataca ttatacgaag ttataattta tttgtgaaat  6180
ttgtgatgct attgctttat ttgtaaccat atgtttattt gtgaaatttg tgatgctatt  6240
gctttatttg taaccattgc tttttgcttg tactgggtct ctctggttag accagatctg  6300
agcctgggag ctctctggct aactagggaa cccactgctt aagcctcaat aaagcttgcc  6360
tcgaccagcc tcgactgtgc cttctagttg ccagccatct gttgtttgcc cctcccccgt  6420
gccttccttg accctggaag gtgccactcc cactgtcctt tcctaataaa atgaggaaat  6480
tgcatcgcat tgtctgagta ggtgtcattc tattctgggg ggtggggtgg ggcaggacag  6540
caagggggag gattgggaag acaatagcag gcatgctggg gatgcggtgg gctctatggc  6600
ctgcagctgc attaatgaat cggccaacgc gcggggagag gcggtttgcg tattgggcgc  6660
tcttccgctt cctcgctcac tgactcgctg cgctcggtcg ttcggctgcg gcgagcggta  6720
tcagctcact caaaggcggt aatacggtta tccacagaat caggggataa cgcaggaaag  6780
aacatgtgag caaaaggcca gcaaaaggcc aggaaccgta aaaaggccgc gttgctggcg  6840
tttttccata ggctccgccc ccctgacgag catcacaaaa atcgacgctc aagtcagagg  6900
tggcgaaacc cgacaggact ataaagatac caggcgtttc cccctggaag ctccctcgtg  6960
cgctctcctg ttccgaccct gccgcttacc ggatacctgt ccgcctttct cccttcggga  7020
agcgtggcgc tttctcatag ctcacgctgt aggtatctca gttcggtgta ggtcgttcgc  7080
tccaagctgg gctgtgtgca cgaacccccc gttcagcccg accgctgcgc cttatccggt  7140
aactatcgtc ttgagtccaa cccggtaaga cacgacttat cgccactggc agcagccact  7200
ggtaacagga ttagcagagc gaggtatgta ggcggtgcta cagagttctt gaagtggtgg  7260
```

```
cctaactacg gctacactag aaggacagta tttggtatct gcgctctgct gaagccagtt  7320
accttcggaa aaagagttgg tagctcttga tccggcaaac aaaccaccgc tggtagcggt  7380
ggtttttttg tttgcaagca gcagattacg cgcagaaaaa aaggatctca agaagatcct  7440
ttgatctttt ctacggggtc tgacgctcag tggaacgaaa actcacgtta agggattttg  7500
gtcatgagat tatcaaaaag gatcttcacc tagatccttt taaattaaaa atgaagtttt  7560
aaatcaatct aaagtatata tgagtaaact tggtctgaca gttaccaatg cttaatcagt  7620
gaggcaccta tctcagcgat ctgtctattt cgttcatcca tagttgcctg actccccgtc  7680
gtgtagataa ctacgatacg ggagggctta ccatctggcc ccagtgctgc aatgataccg  7740
cgagacccac gctcaccggc tccagattta tcagcaataa accagccagc cggaagggcc  7800
gagcgcagaa gtggtcctgc aactttatcc gcctccatcc agtctattaa ttgttgccgg  7860
gaagctagag taagtagttc gccagttaat agtttgcgca acgttgttgc cattgctaca  7920
ggcatcgtgg tgtcacgctc gtcgtttggt atggcttcat tcagctccgg ttcccaacga  7980
tcaaggcgag ttacatgatc ccccatgttg tgcaaaaaag cggttagctc cttcggtcct  8040
ccgatcgttg tcagaagtaa gttggccgca gtgttatcac tcatggttat ggcagcactg  8100
cataattctc ttactgtcat gccatccgta agatgctttt ctgtgactgg tgagtactca  8160
accaagtcat tctgagaata gtgtatgcgg cgaccgagtt gctcttgccc ggcgtcaata  8220
cgggataata ccgcgccaca tagcagaact ttaaaagtgc tcatcattgg aaaacgttct  8280
tcggggcgaa aactctcaag gatcttaccg ctgttgagat ccagttcgat gtaacccact  8340
cgtgcaccca actgatcttc agcatctttt actttcacca gcgtttctgg gtgagcaaaa  8400
acaggaaggc aaaatgccgc aaaaaaggga ataagggcga cacggaaatg ttgaatactc  8460
atactcttcc tttttcaata ttattgaagc atttatcagg gttattgtct catgagcgga  8520
tacatatttg aatgtattta gaaaaataaa caaatagggg ttccgcgcac atttccccga  8580
aaagtgccac ct                                                       8592

SEQ ID NO: 131          moltype = DNA  length = 7818
FEATURE                 Location/Qualifiers
misc_feature            1..7818
                        note = Plasmid pCVL.SFFV.HA.NLS.I-GZE I.IRES.mTagBFP
source                  1..7818
                        mol_type = other DNA
                        organism = synthetic construct
SEQUENCE: 131
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgct agctctttgg aacaatcttc  2460
tttgccacca aagttggacc catcttacgt tactggtttc actgacggtg aaggttcttt  2520
catcttgact atcatcaagg acaacaagta caagttgggt tggagagttg catgcagatt  2580
cgttatctct ttgcacaaga aggacttggt tttgttgaac tctttgaaga acttcttcaa  2640
cactggttct gttttcttga tgggtaaggg cgccgctcaa tacagagttg aatctttgac  2700
tggtttgtct atcatcatca accacttcga cagataccca ttgaacacta agaagcaagc  2760
tgactacatg ttgttcaagt tggcttacaa cttgatcatc aacaagtctc acttgactga  2820
```

-continued

```
aaagggtttg tctgaactag tttctttgaa ggctgttatg aacaacggtt tgaaggacga  2880
attgaagatc gcttacccaa acatcactcc agttttgagg cctgaaatcc cattgtcttt  2940
gaacatcgat ccattgtggt tggctggttt cactgacgct gaaggttgtt tctctgttgt  3000
tgttttcaag tctaagactt ctaagatcgg tgaagctgtt aagttgtctt tcatcatcac  3060
tcaatctgtt agagacgaat ttttaattaa gtctttgatc gaatacttgg gttgtggtta  3120
cacttctttg gacggtagag gtgctatcga cttcaaggtt tctgacttct cttctcttaa  3180
gaacatcatc atcccattct acgacaagta ctacatccac ggtaacaagt ctttggactt  3240
caaggacttc tctcgtgttg ttactttgat ggaaaacaag aagcacttga ctaagcaagg  3300
tttggacgaa atcaagaaga tcagaaacgc tatgaacact aacagatagc ctgcaggtcg  3360
agcatgcatc tagggcggcc aattccgccc ctctccctcc cccccccccta acgttactgg  3420
ccgaagccgc ttggaataag gccggtgtgc gtttgtctat atgtgatttt ccaccatatt  3480
gccgtctttt ggcaatgtga gggcccggaa acctggccct gtcttcttga cgagcattcc  3540
taggggtctt tcccctctcg ccaaaggaat gcaaggtctg ttgaatgtcg tgaaggaagc  3600
agttcctctg gaagcttctt gaagacaaac aacgtctgta gcgacccttt gcaggcagcg  3660
gaacccccca cctggcgaca ggtgcctctg cggccaaaag ccacgtgtat aagatacacc  3720
tgcaaaggcg gcacaacccc agtgccacgt tgtgagttgg atagttgtgg aaagagtcaa  3780
atggctctcc tcaagcgtat tcaacaaggg gctgaaggat gcccagaagg taccccattg  3840
tatgggatct gatctggggc ctcggtgcac atgctttaca tgtgtttagt cgaggttaaa  3900
aaaacgtcta ggccccccga accacgggga cgtggttttc ctttgaaaaa cacgatgata  3960
agcttgccac aacccttacc ggtcgccacc atgagcgagc tgattaagga gaacatgcac  4020
atgaagctgt acatggaggg caccgtggac aaccatcact tcaagtgcac atccgagggc  4080
gaaggcaagc cctacgaggg cacccagacc atgagaatca aggtggtcga gggcggccct  4140
ctccccttcg ccttcgacat cctggctact agcttcctct acggcagcaa gaccttcatc  4200
aaccacaccc agggcatccc cgacttcttc aagcagtcct tccctgaggg cttcacatgg  4260
gagagagtca ccacatacga agacgggggc gtgctgaccg ctacccagga caccagcctc  4320
caggacggct gcctcatcta caacgtcaag atcagagggg tgaacttcac atccaacggc  4380
cctgtgatgc agaagaaaac actcggctgg gaggccttca ccgagacgct gtaccccgct  4440
gacggcggcc tggaaggcag aaacgacatg gccctgaagc tcgtgggcgg gagccatctg  4500
atcgcaaaca tcaagaccac atatagatcc aagaaacccg ctaagaacct caagatgcct  4560
ggcgtctact atgtggacta cagactggaa agaatcaagg aggccaacaa cgagacctac  4620
gtcgagcagc acgaggtggc agtggccaga tactgcgacc tccctagcaa actggggcac  4680
aagcttaatt gattctagag tcgaccgagc atcttaccgc catttatacc catatttgtt  4740
ctgtttttct tgatttgggt atacatttaa atgttaatag aacaaaatgg tggggcaatc  4800
atttacattt ttagggatat gtaattacta gttcaggtgt attgccacaa gacaaacatg  4860
ttaagaaact ttcccgttat ttacgctctg ttcctgttaa tcaacctctg gattacaaaa  4920
tttgtgaaag attgactgat attcttaact atgttgctcc ttttacgctg tgtggatatg  4980
ctgctttata gcctctgtat ctagctattg cttcccgtac ggctttcgtt ttctcctcct  5040
tgtataaatc ctggttgctg tctcttttag aggagttgtg gcccgttgtc cgtcaacgtg  5100
gcgtggtgtg ctctgtgttt gctgacgcaa cccccactgg ctggggcatt gccaccacct  5160
gtcaactcct ttctgggact ttcgctttcc ccctcccgat cgccacggca gaactcatcg  5220
ccgcctgcct tgcccgctgc tggacagggg ctaggttgct gggcactgat aattccgtgg  5280
tgttgtcatc ggtacctttt taaaagaaaa ggggggactg gaagggctaa ttcactccca  5340
acgaagacaa gatatcataa cttcgtatag catacattat acgaagttat aatttatttg  5400
tgaaatttgt gatgctattg ctttatttgt aaccatatgt ttatttgtga aatttgtgat  5460
gctattgctt tatttgtaac cattgctttt tgcttgtact gggtctctct ggttagacca  5520
gatctgagcc tgggagctct ctggctaact agggaaccca ctgcttaagc ctcaataaag  5580
cttgcctcga ccagcctcga ctgtgccttc tagttgccag ccatctgttg tttgcccctc  5640
ccccgtgcct tccttgaccc tggaaggtgc cactcccact gtcctttcct aataaaatga  5700
ggaaattgca tcgcattgtc tgagtaggtg tcattctatt ctggggggtg gggtggggca  5760
ggacagcaag ggggaggatt gggaagacaa tagcaggcat gctggggatg cggtgggctc  5820
tatggcctgc agctgcatta atgaatcggc caacgcgcgg ggagaggcgg tttgcgtatt  5880
gggcgctctt ccgcttcctc gctcactgac tcgctgcgct cggtcgttcg gctgcggcga  5940
gcggtatcag ctcactcaaa ggcggtaata cggttatcca cagaatcagg ggataacgca  6000
ggaaagaaca tgtgagcaaa aggccagcaa aaggccagga accgtaaaaa ggccgcgttg  6060
ctggcgtttt tccataggct ccgcccccct gacgagcatc acaaaaatcg acgctcaagt  6120
cagaggtggc gaaacccgac aggactataa agataccagg cgtttccccc tggaagctcc  6180
ctcgtgcgct ctcctgttcc gaccctgccg cttaccggat acctgtccgc ctttctccct  6240
tcgggaagcg tggcgctttc tcatagctca cgctgtaggt atctcagttc ggtgtaggtc  6300
gttcgctcca agctgggctg tgtgcacgaa ccccccgttc agcccgaccg ctgcgcctta  6360
tccggtaact atcgtcttga gtccaacccg gtaagacacg acttatcgcc actggcagca  6420
gccactggta acaggattag cagagcgagg tatgtaggcg gtgctacaga gttcttgaag  6480
tggtggccta actacggcta cactagaagg acagtatttg gtatctgcgc tctgctgaag  6540
ccagttacct tcggaaaaag agttggtagc tcttgatccg gcaaacaaac caccgctggt  6600
agcggtggtt tttttgtttg caagcagcag attacgcgca gaaaaaaagg atctcaagaa  6660
gatcctttga tcttttctac ggggtctgac gctcagtgga acgaaaactc acgttaaggg  6720
attttggtca tgagattatc aaaaaggatc ttcacctaga tccttttaaa ttaaaaatga  6780
agttttaaat caatctaaag tatatatgag taaacttggt ctgacagtta ccaatgctta  6840
atcagtgagg cacctatctc agcgatctgt ctatttcgtt catccatagt tgcctgactc  6900
cccgtcgtgt agataactac gatacgggag ggcttaccat ctggccccag tgctgcaatg  6960
ataccgcgag acccacgctc accggctcca gatttatcag caataaacca gccagccgga  7020
agggccgagc gcagaagtgg tcctgcaact ttatccgcct ccatccagtc tattaattgt  7080
tgccgggaag ctagagtaag tagttcgcca gttaatagtt tgcgcaacgt tgttgccatt  7140
gctacaggca tcgtggtgtc acgctcgtcg tttggtatgg cttcattcag ctccggttcc  7200
caacgatcaa ggcgagttac atgatccccc atgttgtgca aaaaagcggt tagctccttc  7260
ggtcctccga tcgttgtcag aagtaagttg gccgcagtgt tatcactcat ggttatggca  7320
gcactgcata attctcttac tgtcatgcca tccgtaagat gcttttctgt gactggtgag  7380
tactcaacca agtcattctg agaatagtgt atgcggcgac cgagttgctc ttgcccggcg  7440
tcaatacggg ataataccgc gccacatagc agaactttaa aagtgctcat cattggaaaa  7500
cgttcttcgg ggcgaaaact ctcaaggatc ttaccgctgt tgagatccag ttcgatgtaa  7560
```

```
cccactcgtg cacccaactg atcttcagca tcttttactt tcaccagcgt ttctgggtga  7620
gcaaaaacag gaaggcaaaa tgccgcaaaa aagggaataa gggcgacacg gaaatgttga  7680
atactcatac tcttcctttt tcaatattat tgaagcattt atcagggtta ttgtctcatg  7740
agcggataca tatttgaatg tatttagaaa aataaacaaa taggggttcc gcgcacattt  7800
ccccgaaaag tgccacct                                                7818

SEQ ID NO: 132          moltype = DNA  length = 8592
FEATURE                 Location/Qualifiers
misc_feature            1..8592
                        note = Plasmid pCVL.SFFV.HA.NLS.I-GZE
                         I.T2A.Trex2.IRES.mTagBFP
source                  1..8592
                        mol_type = other DNA
                        organism = synthetic construct
SEQUENCE: 132
gacgtcaatg tagtcttatg caatactctt gtagtcttgc aacatggtaa cgatgagtta  60
gcaacatgcc ttacaaggag agaaaaagca ccgtgcatgc cgattggtgg aagtaaggtg  120
gtacgatcgt gccttattag gaaggcaaca gacgggtctg acatggattg gacgaaccac  180
tgaattgccg cattgcagag atattgtatt taagtgccta gctcgataca taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagaccctt ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga gatgggtgcg agagcgtcag tattaagcgg  600
gggagaatta gatcgcgatg ggaaaaaatt cggttaaggc cagggggaaa gaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca agatagagga agagcaaaac  900
aaaagtaaga ccaccgcaca gcaagcggcc ctgatcttca gacctggagg aggagatatg  960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctggggatt  1320
tggggttgct ctggaaaact catttgcacc actgctgtgc cttggaatgc tagttggagt  1380
aatgaatctc tggaacagat ttggaatcac acgacctgga tggagtggga cagagaaatt  1440
aacaattaca caagcttaat acactcctta attgaagaat cgcaaaacca gcaagaaaag  1500
aatgaacaag aattattgga attagataaa tgggcaagtt tgtggaattg gtttaacata  1560
acaaattggc tgtggtatat aaaattattc ataatgatag taggaggctt ggtaggttta  1620
agaatagttt ttgctgtact ttctatagtg aatagagtta ggcagggata ttcaccatta  1680
tcgtttcaga cccacctccc aaccccgagg ggacccgaca ggcccgaagg aatagaagaa  1740
gaaggtggag agagagacag agacagatcc attcgattag tgaacggatc tcgacggtat  1800
cggttaactt ttaaaagaaa aggggggatt ggggggtaca gtgcagggga aagaatagta  1860
gacataatag caacagacat acaaactaaa gaattacaaa aacaaattac aaaaattcaa  1920
aattttatcg attacgcgtc acgtgctagc tgcagtaacg ccattttgca aggcatggaa  1980
aaataccaaa ccaagaatag agaagttcag atcaagggcg ggtacatgaa aatagctaac  2040
gttgggccaa acaggatatc tgcggtgagc agtttcggcc ccggcccggg gccaagaaca  2100
gatggtcacc gcagtttcgg ccccggcccg aggccaagaa cagatggtcc ccagatatgg  2160
cccaaccctc agcagtttct taagacccat cagatgtttc caggctcccc caaggacctg  2220
aaatgaccct gcgccttatt tgaattaacc aatcagcctg cttctcgctt ctgttcgcgc  2280
gcttctgctt cccgagctct ataaaagagc tcacaacccc tcactcggcg cgccagtcct  2340
ccgacagact gagtcgcccg ctcgagccgc caccatggga tatccatacg atgtcccaga  2400
ttatgcgcca cctaagaaga aacgcaaagt cgaattcgct agctctttgg aacaatcttc  2460
tttgccacca aagttggacc catcttacgt tactggtttc actgacggtg aaggttcttt  2520
catcttgact atcatcaagg acaacaagta caagttgggt tggagagttg catgcagatt  2580
cgttatctct ttgcacaaga aggacttggt tttgttgaac tctttgaaga acttcttcaa  2640
cactggttct gttttcttga tgggtaaggg cgccgctcaa tacagagttg aatctttgac  2700
tggtttgtct atcatcatca accacttcga cagataccca ttgaacacta agaagcaagc  2760
tgactacatg ttgttcaagt tggcttacaa cttgatcatc aacaagtctc acttgactga  2820
aaagggtttg tctgaactag tttctttgaa ggctgttatg aacaacggtt tgaaggacga  2880
attgaagatc gcttacccaa acatcactcc agttttgagg cctgaaatcc cattgtcttt  2940
gaacatcgat ccattgtggt tggctggttt cactgacgct gaaggttgtt tctctgttgt  3000
tgttttcaag tctaagactt ctaagatcgg tgaagctgtt aagttgtctt tcatcatcac  3060
tcaatctgtt agagacgaat ttttaattaa gtctttgatc gaatacttgg gttgtggtta  3120
cacttctttg gacggtagag gtgctatcga cttcaaggtt tctgacttct cttctcttaa  3180
gaacatcatc atcccattct acgacaagta ctacatccac ggtaacaagt ctttggactt  3240
caaggacttc tctcgtgttg ttactttgat ggaaaacaag aagcacttga ctaagcaagg  3300
tttggacgaa atcaagaaga tcagaaacgc tatgaacact aacagaggat ccggtgaggg  3360
cagaggaagt cttctaacat gcggtgacgt ggaggagaat ccgggcccct ccggatctga  3420
gccacctcgg gctgagacct ttgtattcct ggacctagaa gccactgggc tcccaaacat  3480
ggaccctgag attgcagaga tatccctttt tgctgttcac cgctcttccc tggagaaccc  3540
agaacgggat gattctggtt ccttggtgct gccccgtgtt ctggacaagc tcacactgtg  3600
catgtgcccg gagcgcccct ttactgccaa ggccagtgag attactggtt tgagcagcga  3660
aagcctgatg cactgcggga aggctggttt caatggcgct gtggtaagga cactgcaggg  3720
cttcctaagc cgccaggagg gccccatctg ccttgtggcc cacaatggct tcgattatga  3780
cttcccactg ctgtgcacgg agctacaacg tctgggtgcc catctgcccc aagacactgt  3840
```

-continued

```
ctgcctggac acactgcctg cattgcgggg cctggaccgt gctcacagcc acggcaccag  3900
ggctcaaggc cgcaaaagct acagcctggc cagtctcttc caccgctact tccaggctga  3960
acccagtgct gcccattcag cagaaggtga tgtgcacacc ctgcttctga tcttcctgca  4020
tcgtgctcct gagctgctcg cctgggcaga tgagcaggcc cgcagctggg ctcatattga  4080
gcccatgtac gtgccacctg atggtccaag cctcgaagcc tgacctgcag gtcgagcatg  4140
catctagggc ggccaattcc gcccctctcc ctcccccccc cctaacgtta ctggccgaag  4200
ccgcttggaa taaggccggt gtgcgtttgt ctatatgtga ttttccacca tattgccgtc  4260
ttttggcaat gtgagggccc ggaaacctgg ccctgtcttc ttgacgagca ttcctagggg  4320
tctttcccct ctcgccaaag gaatgcaagg tctgttgaat gtcgtgaagg aagcagttcc  4380
tctggaagct tcttgaagac aaacaacgtc tgtagcgacc ctttgcaggc agcggaaccc  4440
cccacctggc gacaggtgcc tctgcggcca aaagccacgt gtataagata cacctgcaaa  4500
ggcggcacaa ccccagtgcc acgttgtgag ttggatagtt gtggaaagag tcaaatggct  4560
ctcctcaagc gtattcaaca aggggctgaa ggatgcccag aaggtacccc attgtatggg  4620
atctgatctg gggcctcggt gcacatgctt tacatgtgtt tagtcgaggt taaaaaaacg  4680
tctaggcccc ccgaaccacg gggacgtggt tttcctttga aaaacacgat gataagcttg  4740
ccacaaccct taccggtcgc caccatgagc gagctgatta aggagaacat gcacatgaag  4800
ctgtacatgg agggcaccgt ggacaaccat cacttcaagt gcacatccga gggcgaaggc  4860
aagccctacg agggcaccca gaccatgaga atcaaggtgg tcgagggcgg ccctctcccc  4920
ttcgccttcg acatcctggc tactagcttc ctctacggca gcaagacctt catcaaccac  4980
acccagggca tccccgactt cttcaagcag tccttccctg agggcttcac atgggagaga  5040
gtcaccacat acgaagacgg gggcgtgctg accgctaccc aggacaccag cctccaggac  5100
ggctgcctca tctacaacgt caagatcaga ggggtgaact tcacatccaa cggccctgtg  5160
atgcagaaga aaacactcgg ctgggaggcc ttcaccgaga cgctgtaccc cgctgacggc  5220
ggcctggaag gcagaaacga catggccctg aagctcgtgg gcgggagcca tctgatcgca  5280
aacatcaaga ccacatatag atccaagaaa cccgctaaga acctcaagat gcctggcgtc  5340
tactatgtgg actacagact ggaaagaatc aaggaggcca acaacgagac ctacgtcgag  5400
cagcacgagg tggcagtggc cagatactgc gacctcccta gcaaactggg gcacaagctt  5460
aattgattct agagtcgacc gagcatctta ccgccattta tacccatatt tgttctgttt  5520
ttcttgattt gggtatacat ttaaatgtta atagaacaaa atggtggggc aatcatttac  5580
atttttaggg atatgtaatt actagttcag gtgtattgcc acaagacaaa catgttaaga  5640
aactttcccg ttatttacgc tctgttcctg ttaatcaacc tctggattac aaaatttgtg  5700
aaagattgac tgatattctt aactatgttg ctccttttac gctgtgtgga tatgctgctt  5760
tatagcctct gtatctagct attgcttccc gtacggcttt cgttttctcc tccttgtata  5820
aatcctggtt gctgtctctt ttagaggagt tgtggcccgt tgtccgtcaa cgtggcgtgg  5880
tgtgctctgt gtttgctgac gcaaccccca ctggctgggg cattgccacc acctgtcaac  5940
tcctttctgg gactttcgct ttccccctcc cgatcgccac ggcagaactc atcgccgcct  6000
gccttgcccg ctgctggaca ggggctaggt tgctgggcac tgataattcc gtggtgttgt  6060
catcggtacc tttttaaaag aaaagggggg actggaaggg ctaattcact cccaacgaag  6120
acaagatatc ataacttcgt atagcataca ttatacgaag ttataattta tttgtgaaat  6180
ttgtgatgct attgctttat ttgtaaccat atgtttattt gtgaaatttg tgatgctatt  6240
gctttatttg taaccattgc tttttgcttg tactgggtct ctctggttag accagatctg  6300
agcctgggag ctctctggct aactagggaa cccactgctt aagcctcaat aaagcttgcc  6360
tcgaccagcc tcgactgtgc cttctagttg ccagccatct gttgtttgcc cctcccccgt  6420
gccttccttg accctggaag gtgccactcc cactgtcctt tcctaataaa atgaggaaat  6480
tgcatcgcat tgtctgagta ggtgtcattc tattctgggg ggtggggtgg ggcaggacag  6540
caagggggag gattgggaag acaatagcag gcatgctggg gatgcggtgg gctctatggc  6600
ctgcagctgc attaatgaat cggccaacgc gcggggagag gcggtttgcg tattgggcgc  6660
tcttccgctt cctcgctcac tgactcgctg cgctcggtcg ttcggctgcg gcgagcggta  6720
tcagctcact caaaggcggt aatacggtta tccacagaat caggggataa cgcaggaaag  6780
aacatgtgag caaaaggcca gcaaaaggcc aggaaccgta aaaaggccgc gttgctggcg  6840
tttttccata ggctccgccc ccctgacgag catcacaaaa atcgacgctc aagtcagagg  6900
tggcgaaacc cgacaggact ataaagatac caggcgtttc cccctggaag ctccctcgtg  6960
cgctctcctg ttccgaccct gccgcttacc ggatacctgt ccgcctttct cccttcggga  7020
agcgtggcgc tttctcatag ctcacgctgt aggtatctca gttcggtgta ggtcgttcgc  7080
tccaagctgg gctgtgtgca cgaacccccc gttcagcccg accgctgcgc cttatccggt  7140
aactatcgtc ttgagtccaa cccggtaaga cacgacttat cgccactggc agcagccact  7200
ggtaacagga ttagcagagc gaggtatgta ggcggtgcta cagagttctt gaagtggtgg  7260
cctaactacg gctacactag aaggacagta tttggtatct gcgctctgct gaagccagtt  7320
accttcggaa aaagagttgg tagctcttga tccggcaaac aaaccaccgc tggtagcggt  7380
ggtttttttg tttgcaagca gcagattacg cgcagaaaaa aaggatctca agaagatcct  7440
ttgatctttt ctacggggtc tgacgctcag tggaacgaaa actcacgtta agggattttg  7500
gtcatgagat tatcaaaaag gatcttcacc tagatccttt taaattaaaa atgaagtttt  7560
aaatcaatct aaagtatata tgagtaaact tggtctgaca gttaccaatg cttaatcagt  7620
gaggcaccta tctcagcgat ctgtctattt cgttcatcca tagttgcctg actccccgtc  7680
gtgtagataa ctacgatacg ggagggctta ccatctggcc ccagtgctgc aatgataccg  7740
cgagacccac gctcaccggc tccagattta tcagcaataa accagccagc cggaagggcc  7800
gagcgcagaa gtggtcctgc aactttatcc gcctccatcc agtctattaa ttgttgccgg  7860
gaagctagag taagtagttc gccagttaat agtttgcgca acgttgttgc cattgctaca  7920
ggcatcgtgg tgtcacgctc gtcgtttggt atggcttcat tcagctccgg ttcccaacga  7980
tcaaggcgag ttacatgatc ccccatgttg tgcaaaaaag cggttagctc cttcggtcct  8040
ccgatcgttg tcagaagtaa gttggccgca gtgttatcac tcatggttat ggcagcactg  8100
cataattctc ttactgtcat gccatccgta agatgctttt ctgtgactgg tgagtactca  8160
accaagtcat tctgagaata gtgtatgcgg cgaccgagtt gctcttgccc ggcgtcaata  8220
cgggataata ccgcgccaca tagcagaact ttaaaagtgc tcatcattgg aaaacgttct  8280
tcggggcgaa aactctcaag gatcttaccg ctgttgagat ccagttcgat gtaacccact  8340
cgtgcaccca actgatcttc agcatctttt actttcacca gcgtttctgg gtgagcaaaa  8400
acaggaaggc aaaatgccgc aaaaaaggga ataagggcga cacggaaatg ttgaatactc  8460
atactcttcc tttttcaata ttattgaagc atttatcagg gttattgtct catgagcgga  8520
tacatatttg aatgtattta gaaaaataaa caaatagggg ttccgcgcac atttccccga  8580
```

-continued

```
aaagtgccac ct                                                     8592

SEQ ID NO: 133          moltype = DNA  length = 6955
FEATURE                 Location/Qualifiers
misc_feature            1..6955
                        note = pExodus ExoI
source                  1..6955
                        mol_type = other DNA
                        organism = synthetic construct
SEQUENCE: 133
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggggatac agggattgct acaatttatc aaagaagctt cagaacccat ccatgtgagg  960
aagtataaag ggcaggtagt agctgtggat acatattgct ggcttcacaa aggagctatt  1020
gcttgtgctg aaaaactagc caaaggtgaa cctactgata ggtatgtagg attttgtatg  1080
aaatttgtaa atatgttact atctcatggg atcaagccta ttctcgtatt tgatggatgt  1140
actttacctt ctaaaaagga agtagagaga tctagaagag aaagacgaca agccaatctt  1200
cttaagggaa agcaacttct tcgtgagggg aaagtctcgg aagctcgaga gtgtttcacc  1260
cggtctatca atatcacaca tgccatggcc cacaaagtaa ttaaagctgc ccggtctcag  1320
ggggtagatt gcctcgtggc tccctatgaa gctgatgcgc agttggccta tcttaacaaa  1380
gcgggaattg tgcaagccat aattacagag gactcggatc tcctagcttt tggctgtaaa  1440
aaggtaattt taaagatgga ccagtttgga aatggacttg aaattgatca agctcggcta  1500
ggaatgtgca gacagcttgg ggatgtattc acggaagaga agtttcgtta catgtgtatt  1560
ctttcaggtt gtgactacct gtcatcactg cgtgggattg gattagcaaa ggcatgcaaa  1620
gtcctaagac tagccaataa tccagatata gtaaaggtta tcaagaaaat tggacattat  1680
ctcaagatga atatcacggt accagaggat tacatcaacg ggtttattcg ggccaacaat  1740
accttcctct atcagctagt ttttgatccc atcaaaagga aacttattcc tctgaacgcc  1800
tatgaagatg atgttgatcc tgaaacacta agctacgctg ggcaatatgt tgatgattcc  1860
atagctcttc aaatagcact tggaaataaa gatataaata cttttgaaca gatcgatgac  1920
tacaatccag acactgctat gcctgcccat tcaagaagtc atagttggga tgacaaaaca  1980
tgtcaaaagt cagctaatgt tagcagcatt tggcatagga attactctcc cagaccagag  2040
tcgggtactg tttcagatgc cccacaattg aaggaaaatc caagtactgt gggagtggaa  2100
cgagtgatta gtactaaagg gttaaatctc ccaaggaaat catccattgt gaaaagacca  2160
agaagtgcag agctgtcaga agatgacctg ttgagtcagt attctctttc atttacgaag  2220
aagaccaaga aaaatagctc tgaaggcaat aaatcattga gcttttctga agtgtttgtg  2280
cctgacctgg taaatggacc tactaacaaa aagagtgtaa gcactccacc taggacgaga  2340
aataaatttg caacattttt acaaaggaaa aatgaagaaa gtggtgcagt tgtggttcca  2400
gggaccagaa gcaggttttt ttgcagttca gattctactg actgtgtatc aaacaaagtg  2460
agcatccagc ctctggatga aactgctgtc acagataaag agaacaatct gcatgaatca  2520
gagtatggag accaagaagg caagagactg gttgacacag atgtagcacg taattcaagt  2580
gatgacattc cgaataatca tattccaggt gatcatattc cagacaaggc aacagtgttt  2640
acagatgaag agtcctactc ttttgagagc agcaaattta caaggaccat ttcaccaccc  2700
actttgggaa cactaagaag ttgttttagt tggtctggag gtcttggaga tttttcaaga  2760
acgccgagcc cctctccaag cacagcattg cagcagttcc gaagaaagag cgattccccc  2820
acctctttgc ctgagaataa tatgtctgat gtgtcgcagt taaagagcga ggagtccagt  2880
gacgatgagt ctcatccctt acgagaaggg gcatgttctt cacagtccca ggaaagtgga  2940
gaattctcac tgcagagttc aaatgcatca aagctttctc agtgctctag taaggactct  3000
gattcagagg aatctgattg caatattaag ttacttgaca gtcaaagtga ccagacctcc  3060
aagctatgtt tatctcattt ctcaaaaaaa gacacacctc taaggaacaa ggttcctggg  3120
ctatataagt ccagttctgc agactctctt tctacaacca agatcaaacc tctaggacct  3180
gccagagcca gtgggctgag caagaagccg gcaagcatcc agaagagaaa gcatcataat  3240
gccgagaaca agccggggtt acagatcaaa ctcaatgagc tctggaaaaa ctttggattt  3300
aaaaaagatt ctgaaaagct tcctccttgt aagaaacccc tgtccccagt cagagataac  3360
atccaactaa ctccagaagc ggaagaggat atatttaaca aacctgaatg tggccgtgtt  3420
caaagagcaa tattccagtg aggatccact agtccagtgt ggtggaattc tgcagatatc  3480
cagcacagtg gcggccgctc gagtctagag ggcccgttta aacccgctga tcagcctcga  3540
ctgtgccttc tagttgccag ccatctgttg tttgcccctc ccccgtgcct tccttgaccc  3600
tggaaggtgc cactcccact gtcctttcct aataaaatga ggaaattgca tcgcattgtc  3660
tgagtaggtg tcattctatt ctggggggtg gggtggggca ggacagcaag ggggaggatt  3720
gggaagacaa tagcaggcat gctggggatg cggtgggctc tatggcttct gaggcggaaa  3780
gaaccagctg gggctctagg gggtatcccc acgcgccctg tagcggcgca ttaagcgcgg  3840
cgggtgtggt ggttacgcgc agcgtgaccg ctacacttgc cagcgcccta gcgcccgctc  3900
ctttcgcttt cttcccttcc tttctcgcca cgttcgccgg ctttccccgt caagctctaa  3960
atcgggggct ccctttaggg ttccgattta gtgctttacg gcacctcgac cccaaaaaac  4020
ttgattaggg tgatggttca cgtagtgggc catcgccctg atagacggtt tttcgccctt  4080
tgacgttgga gtccacgttc tttaatagtg gactcttgtt ccaaactgga acaacactca  4140
```

```
accctatctc ggtctattct tttgatttat aagggatttt gccgatttcg gcctattggt  4200
taaaaaatga gctgatttaa caaaaattta acgcgaatta attctgtgga atgtgtgtca  4260
gttagggtgt ggaaagtccc caggctcccc agcaggcaga agtatgcaaa gcctatcagg  4320
acatagcgtt ggctacccgt gatattgctg aagagcttgg cggcgaatgg gctgaccgct  4380
tcctcgtgct ttacggtatc gccgctcccg attcgcagcg catcgccttc tatcgccttc  4440
ttgacgagtt cttctgagcg ggactctggg gttcgaaatg accgaccaag cgacgcccaa  4500
cctgccatca cgagatttcg attccaccgc cgccttctat gaaaggttgg gcttcggaat  4560
cgttttccgg gacgccggct ggatgatcct ccagcgcggg gatctcatgc tggagttctt  4620
cgcccacccc aacttgttta ttgcagctta taatggttac aaataaagca atagcatcac  4680
aaatttcaca aataaagcat ttttttcact gcattctagt tgtggtttgt ccaaactcat  4740
caatgtatct tatcatgtct gtataccgtc gacctctagc tagagcttgg cgtaatcatg  4800
gtcatagctg tttcctgtgt gaaattgtta tccgctcaca attccacaca acatacgagc  4860
cggaagcata aagtgtaaag cctggggtgc ctaatgagtg agctaactca cattaattgc  4920
gttgcgctca ctgcccgctt tccagtcggg aaacctgtcg tgccagctgc attaatgaat  4980
cggccaacgc gcggggagag gcggtttgcg tattgggcgc tcttccgctt cctcgctcac  5040
tgactcgctg cgctcggtcg ttcggctgcg gcgagcggta tcagctcact caaaggcggt  5100
aatacggtta tccacagaat caggggataa cgcaggaaag aacatgtgag caaaaggcca  5160
gcaaaaggcc aggaaccgta aaaaggccgc gttgctggcg tttttccata ggctccgccc  5220
ccctgacgag catcacaaaa atcgacgctc aagtcagagg tggcgaaacc cgacaggact  5280
ataaagatac caggcgtttc cccctggaag ctccctcgtg cgctctcctg ttccgaccct  5340
gccgcttacc ggatacctgt ccgcctttct cccttcggga agcgtggcgc tttctcatag  5400
ctcacgctgt aggtatctca gttcggtgta ggtcgttcgc tccaagctgg gctgtgtgca  5460
cgaacccccc gttcagcccg accgctgcgc cttatccggt aactatcgtc ttgagtccaa  5520
cccggtaaga cacgacttat cgccactggc agcagccact ggtaacagga ttagcagagc  5580
gaggtatgta ggcggtgcta cagagttctt gaagtggtgg cctaactacg gctacactag  5640
aagaacagta tttggtatct gcgctctgct gaagccagtt accttcggaa aaagagttgg  5700
tagctcttga tccggcaaac aaaccaccgc tggtagcggt ttttttgttt gcaagcagca  5760
gattacgcgc agaaaaaaag gatctcaaga agatcctttg atcttttcta cggggtctga  5820
cgctcagtgg aacgaaaact cacgttaagg gattttggtc atgagattat caaaaaggat  5880
cttcacctag atccttttaa attaaaaatg aagttttaaa tcaatctaaa gtatatatga  5940
gtaaacttgg tctgacagtt accaatgctt aatcagtgag gcacctatct cagcgatctg  6000
tctatttcgt tcatccatag ttgcctgact ccccgtcgtg tagataacta cgatacggga  6060
gggcttacca tctggcccca gtgctgcaat gataccgcga gacccacgct caccggctcc  6120
agatttatca gcaataaacc agccagccgg aagggccgag cgcagaagtg gtcctgcaac  6180
tttatccgcc tccatccagt ctattaattg ttgccgggaa gctagagtaa gtagttcgcc  6240
agttaatagt ttgcgcaacg ttgttgccat tgctacaggc atcgtggtgt cacgctcgtc  6300
gtttggtatg gcttcattca gctccggttc ccaacgatca aggcgagtta catgatcccc  6360
catgttgtgc aaaaaagcgg ttagctcctt cggtcctccg atcgttgtca gaagtaagtt  6420
ggccgcagtg ttatcactca tggttatggc agcactgcat aattctctta ctgtcatgcc  6480
atccgtaaga tgcttttctg tgactggtga gtactcaacc aagtcattct gagaatagtg  6540
tatgcggcga ccgagttgct cttgcccggc gtcaatacgg gataataccg cgccacatag  6600
cagaacttta aaagtgctca tcattggaaa acgttcttcg gggcgaaaac tctcaaggat  6660
cttaccgctg ttgagatcca gttcgatgta acccactcgt gcacccaact gatcttcagc  6720
atcttttact ttcaccagcg tttctgggtg agcaaaaaca ggaaggcaaa atgccgcaaa  6780
aaagggaata agggcgacac ggaaatgttg aatactcata ctcttccttt ttcaatatta  6840
ttgaagcatt tatcagggtt attgtctcat gagcggatac atatttgaat gtatttagaa  6900
aaataaacaa ataggggttc cgcgcacatt tccccgaaaa gtgccacctg acgtc       6955

SEQ ID NO: 134          moltype = DNA  length = 5036
FEATURE                 Location/Qualifiers
misc_feature            1..5036
                        note = pExodus Lambda exonuclease
source                  1..5036
                        mol_type = other DNA
                        organism = synthetic construct
SEQUENCE: 134
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atgacacccg acattattct ccagcggaca ggtattgacg tgagggccgt ggaacagggg  960
gatgatgctt ggcacaaact gaggctcggc gtgatcaccg catctgaggt gcacaacgtc  1020
attgccaaac cccgctctgg aaagaaatgg cctgacatga agatgagtta cttccatact  1080
ctgctcgccg aggtgtgcac cggagtcgct cccgaagtga acgccaaggc tctggcatgg  1140
ggtaaacagt acgagaatga cgctcgaacc ctcttcgagt tcaccagtgg ggtgaacgtc  1200
acagagtcac caatcatcta ccgggatgaa agcatgcgca ctgcatgctc ccccgacggt  1260
ctgtgttctg atgggaatgg tctggagctc aagtgtcctt tcacctcccg agatttcatg  1320
aagttcaggc tcggcggatt tgaagctatc aagagcgcat acatggccca ggtccagtat  1380
```

-continued

```
tccatgtggg tgacaagaaa aaacgcttgg tactttgcaa attatgaccc taggatgaag  1440
agagagggcc tgcactacgt ggtcatcgag cgggacgaaa aatatatggc cagcttcgat  1500
gaaatcgtgc cagagtttat tgaaaagatg gatgaggccc tggctgaaat tggcttcgtg  1560
tttggagagc agtggcggct cgagtctaga gggcccgttt aaacccgctg atcagcctcg  1620
actgtgcctt ctagttgcca gccatctgtt gtttgcccct cccccgtgcc ttccttgacc  1680
ctggaaggtg ccactcccac tgtcctttcc taataaaatg aggaaattgc atcgcattgt  1740
ctgagtaggt gtcattctat tctggggggt ggggtggggc aggacagcaa gggggaggat  1800
tgggaagaca atagcaggca tgctggggat gcggtgggct ctatggcttc tgaggcggaa  1860
agaaccagct ggggctctag ggggtatccc cacgcgccct gtagcggcgc attaagcgcg  1920
gcgggtgtgg tggttacgcg cagcgtgacc gctacacttg ccagcgccct agcgcccgct  1980
cctttcgctt tcttcccttc ctttctcgcc acgttcgccg gctttccccg tcaagctcta  2040
aatcgggggc tccctttagg gttccgattt agtgctttac ggcacctcga ccccaaaaaa  2100
cttgattagg gtgatggttc acgtagtggg ccatcgccct gatagacggt ttttcgccct  2160
ttgacgttgg agtccacgtt ctttaatagt ggactcttgt tccaaactgg aacaacactc  2220
aaccctatct cggtctattc ttttgattta taagggattt tgccgatttc ggcctattgg  2280
ttaaaaaatg agctgattta acaaaaattt aacgcgaatt aattctgtgg aatgtgtgtc  2340
agttagggtg tggaaagtcc ccaggctccc cagcaggcag aagtatgcaa agcctatcag  2400
gacatagcgt tggctacccg tgatattgct gaagagcttg gcggcgaatg ggctgaccgc  2460
ttcctcgtgc tttacggtat cgccgctccc gattcgcagc gcatcgcctt ctatcgcctt  2520
cttgacgagt tcttctgagc gggactctgg ggttcgaaat gaccgaccaa gcgacgccca  2580
acctgccatc acgagatttc gattccaccg ccgccttcta tgaaaggttg ggcttcggaa  2640
tcgttttccg ggacgccggc tggatgatcc tccagcgcgg ggatctcatg ctggagttct  2700
tcgcccaccc caacttgttt attgcagctt ataatggtta caaataaagc aatagcatca  2760
caaatttcac aaataaagca tttttttcac tgcattctag ttgtggtttg tccaaactca  2820
tcaatgtatc ttatcatgtc tgtataccgt cgacctctag ctagagcttg gcgtaatcat  2880
ggtcatagct gtttcctgtg tgaaattgtt atccgctcac aattccacac aacatacgag  2940
ccggaagcat aaagtgtaaa gcctggggtg cctaatgagt gagctaactc acattaattg  3000
cgttgcgctc actgcccgct ttccagtcgg gaaacctgtc gtgccagctg cattaatgaa  3060
tcggccaacg cgcggggaga ggcggtttgc gtattgggcg ctcttccgct tcctcgctca  3120
ctgactcgct gcgctcggtc gttcggctgc ggcgagcggt atcagctcac tcaaaggcgg  3180
taatacggtt atccacagaa tcaggggata acgcaggaaa gaacatgtga gcaaaaggcc  3240
agcaaaaggc caggaaccgt aaaaaggccg cgttgctggc gtttttccat aggctccgcc  3300
cccctgacga gcatcacaaa aatcgacgct caagtcagag gtggcgaaac ccgacaggac  3360
tataaagata ccaggcgttt ccccctggaa gctccctcgt gcgctctcct gttccgaccc  3420
tgccgcttac cggatacctg tccgcctttc tcccttcggg aagcgtggcg ctttctcata  3480
gctcacgctg taggtatctc agttcggtgt aggtcgttcg ctccaagctg ggctgtgtgc  3540
acgaaccccc cgttcagccc gaccgctgcg ccttatccgg taactatcgt cttgagtcca  3600
acccggtaag acacgactta tcgccactgg cagcagccac tggtaacagg attagcagag  3660
cgaggtatgt aggcggtgct acagagttct tgaagtggtg gcctaactac ggctacacta  3720
gaagaacagt atttggtatc tgcgctctgc tgaagccagt taccttcgga aaaagagttg  3780
gtagctcttg atccggcaaa caaaccaccg ctggtagcgg tttttttgtt tgcaagcagc  3840
agattacgcg cagaaaaaaa ggatctcaag aagatccttt gatcttttct acggggtctg  3900
acgctcagtg gaacgaaaac tcacgttaag ggattttggt catgagatta tcaaaaagga  3960
tcttcaccta gatcctttta aattaaaaat gaagttttaa atcaatctaa agtatatatg  4020
agtaaacttg gtctgacagt taccaatgct taatcagtga ggcacctatc tcagcgatct  4080
gtctatttcg ttcatccata gttgcctgac tccccgtcgt gtagataact acgatacggg  4140
agggcttacc atctggcccc agtgctgcaa tgataccgcg agacccacgc tcaccggctc  4200
cagatttatc agcaataaac cagccagccg gaagggccga gcgcagaagt ggtcctgcaa  4260
ctttatccgc ctccatccag tctattaatt gttgccggga agctagagta agtagttcgc  4320
cagttaatag tttgcgcaac gttgttgcca ttgctacagg catcgtggtg tcacgctcgt  4380
cgtttggtat ggcttcattc agctccggtt cccaacgatc aaggcgagtt acatgatccc  4440
ccatgttgtg caaaaaagcg gttagctcct tcggtcctcc gatcgttgtc agaagtaagt  4500
tggccgcagt gttatcactc atggttatgg cagcactgca taattctctt actgtcatgc  4560
catccgtaag atgcttttct gtgactggtg agtactcaac caagtcattc tgagaatagt  4620
gtatgcggcg accgagttgc tcttgcccgg cgtcaatacg ggataatacc gcgccacata  4680
gcagaacttt aaaagtgctc atcattggaa aacgttcttc ggggcgaaaa ctctcaagga  4740
tcttaccgct gttgagatcc agttcgatgt aacccactcg tgcacccaac tgatcttcag  4800
catcttttac tttcaccagc gtttctgggt gagcaaaaac aggaaggcaa aatgccgcaa  4860
aaaagggaat aagggcgaca cggaaatgtt gaatactcat actcttcctt tttcaatatt  4920
attgaagcat ttatcagggt tattgtctca tgagcggata catatttgaa tgtatttaga  4980
aaaataaaca aataggggtt ccgcgcacat ttccccgaaa agtgccacct gacgtc      5036

SEQ ID NO: 135          moltype = DNA  length = 5816
FEATURE                 Location/Qualifiers
misc_feature            1..5816
                        note = pExodus Sox
source                  1..5816
                        mol_type = other DNA
                        organism = synthetic construct
SEQUENCE: 135
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
```

-continued

```
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggaagcaa cccctacacc cgccgacctg tttagcgaag attacctcgt ggataccctc  960
gacggactga ttgtggatga ccagcaggct gtgctggcat ctctcagttt ctcaaagttt  1020
ctgaaacacg ccaaggtgcg agattggtgc gcacaggcca agatccagcc aagcatgccc  1080
gccctcagga tggcttacaa ttatttcctg ttttccaaag tgggcgagtt cattggatct  1140
gaagacgtct gcaacttctt tgtggataga gtctttggag gagtgcggct gctcgacgtg  1200
gcctctgtct acgccgcttg tagtcagatg aatgctcatc agaggcacca tatctgctgt  1260
ctggtggaga gagcaacaag ctcccagtcc ctcaacccag tctgggacgc actgcgagat  1320
gggatcattt ctagttcaaa attccactgg gccgtgaagc agcagaatac aagcaagaaa  1380
atcttttccc cctggcctat tactaacaat catttcgtgg caggacccct cgcctttgga  1440
ctgcgatgcg aggaagtggt caagacactg ctcgctactc tgctccaccc cgacgaggca  1500
aactgtctgg attacggctt catgcagagt cctcagaatg ggatcttcgg tgtgtccctg  1560
gactttgcag ccaacgtcaa aactgatacc gagggacggc tgcagttcga ccccaactgc  1620
aaggtgtacg aaatcaaatg tcgcttcaag tatacttttg ctaaaatgga gtgcgatcct  1680
atctacgctg catatcagag gctgtatgaa gccccaggaa aactggctct caaggacttc  1740
ttttacagca tctccaaacc agccgtggag tatgtcggcc tgggaaagct cccctctgaa  1800
agtgactacc tggtggccta cgaccaggag tgggaagcct gcccccggaa gaaacgcaag  1860
ctgacccctc tccacaacct gatcagagag tgtattctgc ataatagtac cacagaatca  1920
gacgtgtacg tcctgaccga ccctcaggat acacgcgggc agatcagcat caaggctcga  1980
ttcaaggcaa acctgtttgt gaatgtcaga cacagctact tctatcaggt gctgctccag  2040
agctccatcg tcgaggaata cattgggctc gattcaggta tcccacggct gggtagcccc  2100
aaatactata ttgctaccgg gttctttagg aagagaggtt atcaggaccc tgtgaactgt  2160
acaatcggag gtgacgccct ggacccccac gtcgagatcc caactctgct cattgtgacc  2220
cccgtctact tccccagggg cgctaagcac aggctgctcc atcaggccgc taatttttgg  2280
tcacggagcg caaaagatac cttcccatac attaagtggg acttttccta tctgtctgcc  2340
aacgtgcctc attctccact cgagtctaga gggcccgttt aaacccgctg atcagcctcg  2400
actgtgcctt ctagttgcca gccatctgtt gtttgcccct cccccgtgcc ttccttgacc  2460
ctggaaggtg ccactcccac tgtcctttcc taataaaatg aggaaattgc atcgcattgt  2520
ctgagtaggt gtcattctat tctggggggt ggggtggggc aggacagcaa gggggaggat  2580
tgggaagaca atagcaggca tgctggggat gcggtgggct ctatggcttc tgaggcggaa  2640
agaaccagct ggggctctag ggggtatccc cacgcgccct gtagcggcgc attaagcgcg  2700
gcgggtgtgg tggttacgcg cagcgtgacc gctacacttg ccagcgccct agcgcccgct  2760
cctttcgctt tcttcccttc ctttctcgcc acgttcgccg gctttccccg tcaagctcta  2820
aatcgggggc tccctttagg gttccgattt agtgctttac ggcacctcga ccccaaaaaa  2880
cttgattagg gtgatggttc acgtagtggg ccatcgccct gatagacggt ttttcgccct  2940
ttgacgttgg agtccacgtt ctttaatagt ggactcttgt tccaaactgg aacaacactc  3000
aaccctatct cggtctattc ttttgattta taagggattt tgccgatttc ggcctattgg  3060
ttaaaaaatg agctgattta acaaaaattt aacgcgaatt aattctgtgg aatgtgtgtc  3120
agttagggtg tggaaagtcc ccaggctccc cagcaggcag aagtatgcaa agcctatcag  3180
gacatagcgt tggctacccg tgatattgct gaagagcttg gcggcgaatg ggctgaccgc  3240
ttcctcgtgc tttacggtat cgccgctccc gattcgcagc gcatcgcctt ctatcgcctt  3300
cttgacgagt tcttctgagc gggactctgg ggttcgaaat gaccgaccaa gcgacgccca  3360
acctgccatc acgagatttc gattccaccg ccgccttcta tgaaaggttg ggcttcggaa  3420
tcgttttccg ggacgccggc tggatgatcc tccagcgcgg ggatctcatg ctggagttct  3480
tcgcccaccc caacttgttt attgcagctt ataatggtta caaataaagc aatagcatca  3540
caaatttcac aaataaagca tttttttcac tgcattctag ttgtggtttg tccaaactca  3600
tcaatgtatc ttatcatgtc tgtataccgt cgacctctag ctagagcttg gcgtaatcat  3660
ggtcatagct gtttcctgtg tgaaattgtt atccgctcac aattccacac aacatacgag  3720
ccggaagcat aaagtgtaaa gcctggggtg cctaatgagt gagctaactc acattaattg  3780
cgttgcgctc actgcccgct ttccagtcgg gaaacctgtc gtgccagctg cattaatgaa  3840
tcggccaacg cgcggggaga ggcggtttgc gtattgggcg ctcttccgct tcctcgctca  3900
ctgactcgct gcgctcggtc gttcggctgc ggcgagcggt atcagctcac tcaaaggcgg  3960
taatacggtt atccacagaa tcaggggata acgcaggaaa gaacatgtga gcaaaaggcc  4020
agcaaaaggc caggaaccgt aaaaaggccg cgttgctggc gtttttccat aggctccgcc  4080
cccctgacga gcatcacaaa aatcgacgct caagtcagag gtggcgaaac ccgacaggac  4140
tataaagata ccaggcgttt ccccctggaa gctccctcgt gcgctctcct gttccgaccc  4200
tgccgcttac cggatacctg tccgcctttc tcccttcggg aagcgtggcg ctttctcata  4260
gctcacgctg taggtatctc agttcggtgt aggtcgttcg ctccaagctg ggctgtgtgc  4320
acgaaccccc cgttcagccc gaccgctgcg ccttatccgg taactatcgt cttgagtcca  4380
acccggtaag acacgactta tcgccactgg cagcagccac tggtaacagg attagcagag  4440
cgaggtatgt aggcggtgct acagagttct tgaagtggtg gcctaactac ggctacacta  4500
gaagaacagt atttggtatc tgcgctctgc tgaagccagt taccttcgga aaaagagttg  4560
gtagctcttg atccggcaaa caaaccaccg ctggtagcgg tttttttgtt tgcaagcagc  4620
agattacgcg cagaaaaaaa ggatctcaag aagatccttt gatcttttct acggggtctg  4680
acgctcagtg gaacgaaaac tcacgttaag ggattttggt catgagatta tcaaaaagga  4740
tcttcaccta gatcctttta aattaaaaat gaagttttaa atcaatctaa agtatatatg  4800
agtaaacttg gtctgacagt taccaatgct taatcagtga ggcacctatc tcagcgatct  4860
gtctatttcg ttcatccata gttgcctgac tccccgtcgt gtagataact acgatacggg  4920
agggcttacc atctggcccc agtgctgcaa tgataccgcg agacccacgc tcaccggctc  4980
cagatttatc agcaataaac cagccagccg gaagggccga gcgcagaagt ggtcctgcaa  5040
ctttatccgc ctccatccag tctattaatt gttgccggga agctagagta agtagttcgc  5100
cagttaatag tttgcgcaac gttgttgcca ttgctacagg catcgtggtg tcacgctcgt  5160
cgtttggtat ggcttcattc agctccggtt cccaacgatc aaggcgagtt acatgatccc  5220
ccatgttgtg caaaaaagcg gttagctcct tcggtcctcc gatcgttgtc agaagtaagt  5280
```

-continued

```
tggccgcagt gttatcactc atggttatgg cagcactgca taattctctt actgtcatgc  5340
catccgtaag atgcttttct gtgactggtg agtactcaac caagtcattc tgagaatagt  5400
gtatgcggcg accgagttgc tcttgcccgg cgtcaatacg ggataatacc gcgccacata  5460
gcagaacttt aaaagtgctc atcattggaa aacgttcttc ggggcgaaaa ctctcaagga  5520
tcttaccgct gttgagatcc agttcgatgt aacccactcg tgcacccaac tgatcttcag  5580
catcttttac tttcaccagc gtttctgggt gagcaaaaac aggaaggcaa aatgccgcaa  5640
aaaagggaat aagggcgaca cggaaatgtt gaatactcat actcttcctt tttcaatatt  5700
attgaagcat ttatcagggt tattgtctca tgagcggata catatttgaa tgtatttaga  5760
aaaataaaca aataggggtt ccgcgcacat ttccccgaaa agtgccacct gacgtc      5816

SEQ ID NO: 136          moltype = DNA  length = 6236
FEATURE                 Location/Qualifiers
misc_feature            1..6236
                        note = pExodus UL12
source                  1..6236
                        mol_type = other DNA
                        organism = synthetic construct
SEQUENCE: 136
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tggaactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggaaagca ctgggggtcc tgcctgtcct cctgggcgaa ccgtgactaa aaggtcctgg  960
gctctggctg aagatacacc aagggggcct gacagccccc ctaagaggcc aagacccaac  1020
tccctgccac tcaccacaac tttcaggcca ctgccaccac ctccacagac cacaagtgcc  1080
gtcgatccaa gctcccactc acccgtgaat ccccccaggg accagcatgc cactgacacc  1140
gctgatgaga aacctcgcgc cgcttcacca gcactgtctg atgccagtgg accacccacc  1200
cccgacattc ctctgagccc aggcggaaca cacgcaagag acccagatgc cgaccccgat  1260
agccctgacc tggattccat gtggagtgct tcagtgattc ccaacgcact ccctagccac  1320
atcctggccg agaccttcga acgacatctg aggggactgc tcagaggggt gcgggcaccc  1380
ctcgctatcg gacctctgtg ggcccggctg gattacctct gctccctggc cgtggtgctg  1440
gaggaagctg gaatggtgga ccgaggactg ggacgccacc tctggcgact gaccaggaga  1500
gcacctccag cagccgctga tgcagtggca cctcggccac tgatgggttt ctatgaggca  1560
gccactcaga atcaggcaga ctgccagctg tgggcactgc tccgacgagg actcactacc  1620
gcctctaccc tgcgatgggg accacagggt ccctgttttt ctccccagtg gctcaagcat  1680
aacgctagtc tgcggcctga cgtgcagtct agtgcagtca tgttcggacg agtgaatgag  1740
ccaacagcac ggagcctgct ctttcgctac tgcgtgggtc gagctgacga tgggggcgag  1800
gctggcgcag atactcgaag gttcatcttt cacgaaccta gtgacctggc cgaggaaaac  1860
gtccacacat gcggggtgct gatggatggc catactggaa tggtcggggc ttctctcgat  1920
attctggtgt gtccaaggga catccacggc tacctggcac ccgtgcctaa aactcccctg  1980
gctttctacg aggtcaagtg tagagcaaaa tatgcctttg accctatgga cccctctgac  2040
cccacagcca gtgcttacga ggacctgatg gcccacagat cccctgaggc cttcagggcc  2100
ttcatcagat caattccaaa gcccagcgtc aggtatttcg ctccaggtag agtgcctggc  2160
ccagaggaag ctctggtcac ccaggatcag gcatggtccg aggcacacgc ctctggtgaa  2220
aaaagacgat gcagcgctgc agaccgagca ctcgtggagc tgaacagtgg cgtggtctca  2280
gaagtgctgc tctttggagc tcctgatctg ggcgcccata caatctcacc agtgagctgg  2340
tcaagcggcg acctggtccg ccgagagcca gtgttcgcca accctcggca cccaaatttt  2400
aagcagattc tcgtgcaggg atacgtcctg gattcccatt tccccgactg tcccccctcac  2460
cctcatctgg tgaccttcat cggacggcac cgcacttctg ccgaggaaagg ggtgaccttc  2520
aggctggagg atggagctgg tgcactgggt gcagctggac catccaaggc ttctattctc  2580
ccaaatcagg ctgtgcccat cgcactgatc attacccctg tcaggatcga cccagaaatc  2640
tacaaagcaa tccagcgctc ctctcgactg gcctttgacg atacactcgc cgagctgtgg  2700
gccagcagga gcccaggccc tggaccagca gccgctgaaa caactagttc aagccctacc  2760
acaggaagga gcagcaggct cgagtctaga gggcccgttt aaacccgctg atcagcctcg  2820
actgtgcctt ctagttgcca gccatctgtt gtttgcccct cccccgtgcc ttccttgacc  2880
ctggaaggtg ccactcccac tgtcctttcc taataaaatg aggaaattgc atcgcattgt  2940
ctgagtaggt gtcattctat tctggggggt ggggtggggc aggacagcaa gggggaggat  3000
tgggaagaca atagcaggca tgctggggat gcggtgggct ctatggcttc tgaggcggaa  3060
agaaccagct ggggctctag ggggtatccc cacgcgccct gtagcggcgc attaagcgcg  3120
gcgggtgtgg tggttacgcg cagcgtgacc gctacacttg ccagcgccct agcgcccgct  3180
cctttcgctt tcttcccttc ctttctcgcc acgttcgccg gctttccccg tcaagctcta  3240
aatcgggggc tccctttagg gttccgattt agtgctttac ggcacctcga ccccaaaaaa  3300
cttgattagg gtgatggttc acgtagtggg ccatcgccct gatagacggt ttttcgccct  3360
ttgacgttgg agtccacgtt ctttaatagt ggactcttgt tccaaactgg aacaacactc  3420
aaccctatct cggtctattc ttttgattta taagggattt tgccgatttc ggcctattgg  3480
ttaaaaaatg agctgattta acaaaaattt aacgcgaatt aattctgtgg aatgtgtgtc  3540
agttagggtg tggaaagtcc ccaggctccc cagcaggcag aagtatgcaa agcctatcag  3600
gacatagcgt tggctacccg tgatattgct gaagagcttg gcggcgaatg ggctgaccgc  3660
```

-continued

```
ttcctcgtgc tttacggtat cgccgctccc gattcgcagc gcatcgcctt ctatcgcctt  3720
cttgacgagt tcttctgagc gggactctgg ggttcgaaat gaccgaccaa gcgacgccca  3780
acctgccatc acgagatttc gattccaccg ccgccttcta tgaaaggttg ggcttcggaa  3840
tcgttttccg ggacgccggc tggatgatcc tccagcgcgg ggatctcatg ctggagttct  3900
tcgcccaccc caacttgttt attgcagctt ataatggtta caaataaagc aatagcatca  3960
caaatttcac aaataaagca tttttttcac tgcattctag ttgtggtttg tccaaactca  4020
tcaatgtatc ttatcatgtc tgtataccgt cgacctctag ctagagcttg gcgtaatcat  4080
ggtcatagct gtttcctgtg tgaaattgtt atccgctcac aattccacac aacatacgag  4140
ccggaagcat aaagtgtaaa gcctggggtg cctaatgagt gagctaactc acattaattg  4200
cgttgcgctc actgcccgct ttccagtcgg gaaacctgtc gtgccagctg cattaatgaa  4260
tcggccaacg cgcggggaga ggcggtttgc gtattgggcg ctcttccgct tcctcgctca  4320
ctgactcgct gcgctcggtc gttcggctgc ggcgagcggt atcagctcac tcaaaggcgg  4380
taatacggtt atccacagaa tcaggggata acgcaggaaa gaacatgtga gcaaaaggcc  4440
agcaaaaggc caggaaccgt aaaaaggccg cgttgctggc gtttttccat aggctccgcc  4500
cccctgacga gcatcacaaa aatcgacgct caagtcagag gtggcgaaac ccgacaggac  4560
tataaagata ccaggcgttt ccccctggaa gctccctcgt gcgctctcct gttccgaccc  4620
tgccgcttac cggatacctg tccgcctttc tcccttcggg aagcgtggcg ctttctcata  4680
gctcacgctg taggtatctc agttcggtgt aggtcgttcg ctccaagctg ggctgtgtgc  4740
acgaaccccc cgttcagccc gaccgctgcg ccttatccgg taactatcgt cttgagtcca  4800
acccggtaag acacgactta tcgccactgg cagcagccac tggtaacagg attagcagag  4860
cgaggtatgt aggcggtgct acagagttct tgaagtggtg gcctaactac ggctacacta  4920
gaagaacagt atttggtatc tgcgctctgc tgaagccagt taccttcgga aaaagagttg  4980
gtagctcttg atccggcaaa caaaccaccg ctggtagcgg tttttttgtt tgcaagcagc  5040
agattacgcg cagaaaaaaa ggatctcaag aagatccttt gatcttttct acggggtctg  5100
acgctcagtg gaacgaaaac tcacgttaag ggattttggt catgagatta tcaaaaagga  5160
tcttcaccta gatcctttta aattaaaaat gaagttttaa atcaatctaa agtatatatg  5220
agtaaacttg gtctgacagt taccaatgct taatcagtga ggcacctatc tcagcgatct  5280
gtctatttcg ttcatccata gttgcctgac tccccgtcgt gtagataact acgatacggg  5340
agggcttacc atctggcccc agtgctgcaa tgataccgcg agacccacgc tcaccggctc  5400
cagatttatc agcaataaac cagccagccg gaagggccga gcgcagaagt ggtcctgcaa  5460
ctttatccgc ctccatccag tctattaatt gttgccggga agctagagta agtagttcgc  5520
cagttaatag tttgcgcaac gttgttgcca ttgctacagg catcgtggtg tcacgctcgt  5580
cgtttggtat ggcttcattc agctccggtt cccaacgatc aaggcgagtt acatgatccc  5640
ccatgttgtg caaaaaagcg gttagctcct tcggtcctcc gatcgttgtc agaagtaagt  5700
tggccgcagt gttatcactc atggttatgg cagcactgca taattctctt actgtcatgc  5760
catccgtaag atgcttttct gtgactggtg agtactcaac caagtcattc tgagaatagt  5820
gtatgcggcg accgagttgc tcttgcccgg cgtcaatacg ggataatacc gcgccacata  5880
gcagaacttt aaaagtgctc atcattggaa aacgttcttc ggggcgaaaa ctctcaagga  5940
tcttaccgct gttgagatcc agttcgatgt aacccactcg tgcacccaac tgatcttcag  6000
catcttttac tttcaccagc gtttctgggt gagcaaaaac aggaaggcaa aatgccgcaa  6060
aaaagggaat aagggcgaca cggaaatgtt gaatactcat actcttcctt tttcaatatt  6120
attgaagcat ttatcagggt tattgtctca tgagcggata catatttgaa tgtatttaga  6180
aaaataaaca aataggggtt ccgcgcacat ttccccgaaa agtgccacct gacgtc      6236

SEQ ID NO: 137          moltype = DNA  length = 5954
FEATURE                 Location/Qualifiers
misc_feature            1..5954
                        note = pExodus Apollo
source                  1..5954
                        mol_type = other DNA
                        organism = synthetic construct
SEQUENCE: 137
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atgaacggcg tgctgattcc tcacactcct attgctgtgg acttctggtc tctccggcga  960
gctgggactg cccgactctt ctttctgagt cacatgcatt cagatcacac tgtgggactg  1020
agctccacct gggcccgacc actgtactgc tcccccatca cagctcatct gctccacagg  1080
catctgcagg tgagcaagca gtggattcag gccctggagg tcggcgaatc ccacgtcctg  1140
cctctcgatg agatcggaca ggaaaccatg acagtgactc tgctcgacgc taatcattgc  1200
ccagggtccg tcatgttcct gtttgagggc tacttcggaa caattctgta tactggcgat  1260
tttcggtaca ctccatctat gctgaaggaa cccgccctga ccctcggaaa acagatccac  1320
acactgtacc tcgacaacac taattgtaac cctgctctgg tgctcccatc caggcaggag  1380
gccgctcacc agatcgtcca gctgattaga aagcacccac agcataacat caaaattggg  1440
ctgtatagtc tcggcaagga gtcactgctc gaacagctgg ccctggagtt ccagacatgg  1500
gtggtcctgt ctcccaggag actggaactc gtgcagctgc tcgggctggc tgatgtgttt  1560
actgtcgagg aaaaggctgg tagaatccac gcagtggacc acatggagat ttgtcacagc  1620
```

-continued

```
aatatgctga gatggaacca gacccatcct acaatcgcca ttctgccaac tagccggaag  1680
atccactcta gtcatcccga tatccacgtg attccttatt ctgaccattc aagctacagt  1740
gagctgcgag cattcgtggc agccctcaag ccatgccagg tggtccctat cgtcagccgg  1800
cgcccttgtg gaggatttca ggattcactg agcccacgca tctcagtgcc actgattccc  1860
gacagcgtcc agcagtacat gtcctctagt tcacgaaagc ccagcctgct ctggctgctg  1920
gagcgaaggc tgaaacgccc ccgaacccag ggagtggtct tcgaaagccc tgaggaatcc  1980
gccgatcagt ctcaggctga tagggactcc aagaaagcaa agaaagagaa gctgtctccc  2040
tggcctgccg atctcgaaaa acagcccagc caccatcctc tgaggatcaa gaaacagctg  2100
ttcccagacc tctattctaa ggagtggaac aaggctgtgc ccttttgcga aagtcagaag  2160
agagtcacta tgctgaccgc acctctcggc ttcagcgtgc acctgcggtc caccgacgag  2220
gagttcatca gtcagaaaac acgcgaggaa attggcctgg gatcacctct cgtgccaatg  2280
ggcgacgatg acgggggtcc agaggcaacc ggaaatcaga gcgcctggat ggggcacggt  2340
tccccactgt ctcatagctc caaggggacc cccctgctcg ctacagagtt caggggtctg  2400
gcactcaaat atctgctcac acccgtgaac ttctttcagg ccggctactc tagtagacgg  2460
tttgaccagc aggtcgagaa gtatcacaaa ccttgtctcg agtctagagg gcccgtttaa  2520
acccgctgat cagcctcgac tgtgccttct agttgccagc catctgttgt ttgcccctcc  2580
cccgtgcctt ccttgaccct ggaaggtgcc actcccactg tcctttccta ataaaatgag  2640
gaaattgcat cgcattgtct gagtaggtgt cattctattc tggggggtgg ggtggggcag  2700
gacagcaagg gggaggattg ggaagacaat agcaggcatg ctggggatgc ggtgggctct  2760
atggcttctg aggcggaaag aaccagctgg ggctctaggg ggtatcccca cgcgccctgt  2820
agcggcgcat taagcgcggc gggtgtggtg gttacgcgca gcgtgaccgc tacacttgcc  2880
agcgccctag cgcccgctcc tttcgctttc ttcccttcct ttctcgccac gttcgccggc  2940
tttccccgtc aagctctaaa tcgggggctc cctttagggt tccgatttag tgctttacgg  3000
cacctcgacc ccaaaaaact tgattagggt gatggttcac gtagtgggcc atcgccctga  3060
tagacggttt ttcgcccttt gacgttggag tccacgttct ttaatagtgg actcttgttc  3120
caaactggaa caacactcaa ccctatctcg gtctattctt ttgatttata agggattttg  3180
ccgatttcgg cctattggtt aaaaaatgag ctgatttaac aaaaatttaa cgcgaattaa  3240
ttctgtggaa tgtgtgtcag ttagggtgtg gaaagtcccc aggctcccca gcaggcagaa  3300
gtatgcaaag cctatcagga catagcgttg gctacccgtg atattgctga agagcttggc  3360
ggcgaatggg ctgaccgctt cctcgtgctt tacggtatcg ccgctcccga ttcgcagcgc  3420
atcgccttct atcgccttct tgacgagttc ttctgagcgg gactctgggg ttcgaaatga  3480
ccgaccaagc gacgcccaac ctgccatcac gagatttcga ttccaccgcc gccttctatg  3540
aaaggttggg cttcggaatc gttttccggg acgccggctg gatgatcctc cagcgcgggg  3600
atctcatgct ggagttcttc gcccacccca acttgtttat tgcagcttat aatggttaca  3660
aataaagcaa tagcatcaca aatttcacaa ataaagcatt tttttcactg cattctagtt  3720
gtggtttgtc caaactcatc aatgtatctt atcatgtctg tataccgtcg acctctagct  3780
agagcttggc gtaatcatgg tcatagctgt ttcctgtgtg aaattgttat ccgctcacaa  3840
ttccacacaa catacgagcc ggaagcataa agtgtaaagc ctggggtgcc taatgagtga  3900
gctaactcac attaattgcg ttgcgctcac tgcccgcttt ccagtcggga aacctgtcgt  3960
gccagctgca ttaatgaatc ggccaacgcg cggggagagg cggtttgcgt attgggcgct  4020
cttccgcttc ctcgctcact gactcgctgc gctcggtcgt tcggctgcgg cgagcggtat  4080
cagctcactc aaaggcggta atacggttat ccacagaatc aggggataac gcaggaaaga  4140
acatgtgagc aaaaggccag caaaaggcca ggaaccgtaa aaaggccgcg ttgctggcgt  4200
ttttccatag gctccgcccc cctgacgagc atcacaaaaa tcgacgctca agtcagaggt  4260
ggcgaaaccc gacaggacta taaagatacc aggcgtttcc ccctggaagc tccctcgtgc  4320
gctctcctgt tccgaccctg ccgcttaccg gatacctgtc cgcctttctc ccttcgggaa  4380
gcgtggcgct ttctcatagc tcacgctgta ggtatctcag ttcggtgtag gtcgttcgct  4440
ccaagctggg ctgtgtgcac gaaccccccg ttcagcccga ccgctgcgcc ttatccggta  4500
actatcgtct tgagtccaac ccggtaagac acgacttatc gccactggca gcagccactg  4560
gtaacaggat tagcagagcg aggtatgtag gcggtgctac agagttcttg aagtggtggc  4620
ctaactacgg ctacactaga agaacagtat ttggtatctg cgctctgctg aagccagtta  4680
ccttcggaaa aagagttggt agctcttgat ccggcaaaca aaccaccgct ggtagcggtt  4740
tttttgtttg caagcagcag attacgcgca gaaaaaaagg atctcaagaa gatcctttga  4800
tcttttctac ggggtctgac gctcagtgga acgaaaactc acgttaaggg attttggtca  4860
tgagattatc aaaaaggatc ttcacctaga tccttttaaa ttaaaaatga agttttaaat  4920
caatctaaag tatatatgag taaacttggt ctgacagtta ccaatgctta atcagtgagg  4980
cacctatctc agcgatctgt ctatttcgtt catccatagt tgcctgactc cccgtcgtgt  5040
agataactac gatacgggag ggcttaccat ctggccccag tgctgcaatg ataccgcgag  5100
acccacgctc accggctcca gatttatcag caataaacca gccagccgga agggccgagc  5160
gcagaagtgg tcctgcaact ttatccgcct ccatccagtc tattaattgt tgccgggaag  5220
ctagagtaag tagttcgcca gttaatagtt tgcgcaacgt tgttgccatt gctacaggca  5280
tcgtggtgtc acgctcgtcg tttggtatgg cttcattcag ctccggttcc caacgatcaa  5340
ggcgagttac atgatccccc atgttgtgca aaaaagcggt tagctccttc ggtcctccga  5400
tcgttgtcag aagtaagttg gccgcagtgt tatcactcat ggttatggca gcactgcata  5460
attctcttac tgtcatgcca tccgtaagat gcttttctgt gactggtgag tactcaacca  5520
agtcattctg agaatagtgt atgcggcgac cgagttgctc ttgcccggcg tcaatacggg  5580
ataataccgc gccacatagc agaactttaa aagtgctcat cattggaaaa cgttcttcgg  5640
ggcgaaaact ctcaaggatc ttaccgctgt tgagatccag ttcgatgtaa cccactcgtg  5700
cacccaactg atcttcagca tcttttactt tcaccagcgt ttctgggtga gcaaaaacag  5760
gaaggcaaaa tgccgcaaaa aagggaataa gggcgacacg gaaatgttga atactcatac  5820
tcttcctttt tcaatattat tgaagcattt atcagggtta ttgtctcatg agcggataca  5880
tatttgaatg tatttagaaa aataaacaaa taggggttcc gcgcacattt ccccgaaaag  5940
tgccacctga cgtc                                                    5954
```

```
SEQ ID NO: 138          moltype = DNA  length = 5498
FEATURE                 Location/Qualifiers
misc_feature            1..5498
                        note = pExodus FenI
source                  1..5498
```

-continued mol_type = other DNA
organism = synthetic construct
SEQUENCE: 138
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
atgggcatcc aggggctcgc aaaactcatc gcagacgtgg ctccttccgc aattagagag 960
aacgacatca agtcctattt cggcagaaag gtggctatcg acgcatctat gagtatctac 1020
cagttcctga ttgccgtgag gcagggcgga gatgtcctcc agaacgagga aggcgagacc 1080
acaagccacc tgatgggaat gttctacaga acaatccgga tgatggagaa tggcattaag 1140
ccagtgtatg tctttgacgg gaaacccccct cagctgaagt caggcgagct cgccaaaaga 1200
agcgaaagga gagccgaagc tgagaagcag ctgcagcagg cacaggcagc tggagccgaa 1260
caggaggtgg aaaaattcac aaagcggctg gtgaaagtca ctaagcagca caacgacgag 1320
tgcaagcatc tgctcagcct gatgggaatc cccctacctcg atgctccttc cgaggcagaa 1380
gcctcttgcg cagccctggt gaaagcaggg aaggtctatg ctgcagccac cgaggacatg 1440
gattgtctga catttggttc ccctgtgctg atgcgacacc tcaccgcctc tgaggctaag 1500
aaactgccaa tccaggagtt ccatctgtcc cgcattctcc aggagctggg gctcaatcag 1560
gaacagtttg tggacctgtg catcctgctc ggtagtgatt actgtgagtc aatcaggggg 1620
attggtccca agagagctgt ggacctgatt cagaaacata agtctatcga ggaaattgtg 1680
aggaggctgg accccaacaa atatccagtc cccgagaatt ggctccacaa ggaagcccat 1740
cagctgttcc tggagccaga agtgctggac cccgagagcg tcgaactcaa gtggtccgag 1800
cccaacgagg aagagctgat caaattcatg tgtggcgaga agcagttttc tgaagagcga 1860
attaggagtg gagtgaaacg cctgtcaaag agccgacagg ggagtactca gggtcggctg 1920
gacgatttct ttaaggtcac cggcagcctc agctccgcta aacgcaagga gcctgaacca 1980
aaaggaagca ctaagaaaaa ggccaagacc ggcgctgccg gcaagttcaa gagaggaaag 2040
ctcgagtcta gagggcccgt ttaaacccgc tgatcagcct cgactgtgcc ttctagttgc 2100
cagccatctg ttgtttgccc ctcccccgtg ccttccttga ccctggaagg tgccactccc 2160
actgtccttt cctaataaaa tgaggaaatt gcatcgcatt gtctgagtag gtgtcattct 2220
attctggggg gtggggtggg gcaggacagc aagggggagg attgggaaga caatagcagg 2280
catgctgggg atgcggtggg ctctatggct tctgaggcgg aaagaaccag ctggggctct 2340
agggggtatc cccacgcgcc ctgtagcggc gcattaagcg cggcgggtgt ggtggttacg 2400
cgcagcgtga ccgctacact tgccagcgcc ctagcgcccg ctcctttcgc tttcttccct 2460
tcctttctcg ccacgttcgc cggctttccc cgtcaagctc taaatcgggg gctcccttta 2520
gggttccgat ttagtgcttt acggcacctc gaccccaaaa aacttgatta gggtgatggt 2580
tcacgtagtg ggccatcgcc ctgatagacg gtttttcgcc ctttgacgtt ggagtccacg 2640
ttctttaata gtggactctt gttccaaact ggaacaacac tcaaccctat ctcggtctat 2700
tcttttgatt tataagggat tttgccgatt tcggcctatt ggttaaaaaa tgagctgatt 2760
taacaaaaat ttaacgcgaa ttaattctgt ggaatgtgtg tcagttaggg tgtggaaagt 2820
ccccaggctc cccagcaggc agaagtatgc aaagcctatc aggacatagc gttggctacc 2880
cgtgatattg ctgaagagct tggcggcgaa tgggctgacc gcttcctcgt gctttacggt 2940
atcgccgctc ccgattcgca gcgcatcgcc ttctatcgcc ttcttgacga gttcttctga 3000
gcgggactct ggggttcgaa atgaccgacc aagcgacgcc caacctgcca tcacgagatt 3060
tcgattccac cgccgccttc tatgaaaggt tgggcttcgg aatcgttttc cgggacgccg 3120
gctggatgat cctccagcgc ggggatctca tgctggagtt cttcgcccac cccaacttgt 3180
ttattgcagc ttataatggt tacaaataaa gcaatagcat cacaaatttc acaaataaag 3240
catttttttc actgcattct agttgtggtt tgtccaaact catcaatgta tcttatcatg 3300
tctgtatacc gtcgacctct agctagagct tggcgtaatc atggtcatag ctgtttcctg 3360
tgtgaaattg ttatccgctc acaattccac acaacatacg agccggaagc ataaagtgta 3420
aagcctgggg tgcctaatga gtgagctaac tcacattaat tgcgttgcgc tcactgcccg 3480
ctttccagtc gggaaacctg tcgtgccagc tgcattaatg aatcggccaa cgcgcgggga 3540
gaggcggttt gcgtattggg cgctcttccg cttcctcgct cactgactcg ctgcgctcgg 3600
tcgttcggct gcggcgagcg gtatcagctc actcaaaggc ggtaatacgg ttatccacag 3660
aatcagggga taacgcagga aagaacatgt gagcaaaagg ccagcaaaag gccaggaacc 3720
gtaaaaaggc cgcgttgctg gcgtttttcc ataggctccg cccccctgac gagcatcaca 3780
aaaatcgacg ctcaagtcag aggtggcgaa acccgacagg actataaaga taccaggcgt 3840
ttccccctgg aagctccctc gtgcgctctc ctgttccgac cctgccgctt accggatacc 3900
tgtccgcctt tctcccttcg ggaagcgtgg cgctttctca tagctcacgc tgtaggtatc 3960
tcagttcggt gtaggtcgtt cgctccaagc tgggctgtgt gcacgaaccc cccgttcagc 4020
ccgaccgctg cgccttatcc ggtaactatc gtcttgagtc caacccggta agacacgact 4080
tatcgccact ggcagcagcc actggtaaca ggattagcag agcgaggtat gtaggcggtg 4140
ctacagagtt cttgaagtgg tggcctaact acggctacac tagaagaaca gtatttggta 4200
tctgcgctct gctgaagcca gttaccttcg gaaaaagagt tggtagctct tgatccggca 4260
aacaaaccac cgctggtagc ggtttttttg tttgcaagca gcagattacg cgcagaaaaa 4320
aaggatctca agaagatcct ttgatctttt ctacggggtc tgacgctcag tggaacgaaa 4380
actcacgtta agggattttg gtcatgagat tatcaaaaag gatcttcacc tagatccttt 4440
taaattaaaa atgaagtttt aaatcaatct aaagtatata tgagtaaact tggtctgaca 4500
gttaccaatg cttaatcagt gaggcaccta tctcagcgat ctgtctattt cgttcatcca 4560

```
tagttgcctg actccccgtc gtgtagataa ctacgatacg ggagggctta ccatctggcc  4620
ccagtgctgc aatgataccg cgagacccac gctcaccggc tccagattta tcagcaataa  4680
accagccagc cggaagggcc gagcgcagaa gtggtcctgc aactttatcc gcctccatcc  4740
agtctattaa ttgttgccgg gaagctagag taagtagttc gccagttaat agtttgcgca  4800
acgttgttgc cattgctaca ggcatcgtgg tgtcacgctc gtcgtttggt atggcttcat  4860
tcagctccgg ttcccaacga tcaaggcgag ttacatgatc ccccatgttg tgcaaaaaag  4920
cggttagctc cttcggtcct ccgatcgttg tcagaagtaa gttggccgca gtgttatcac  4980
tcatggttat ggcagcactg cataattctc ttactgtcat gccatccgta agatgctttt  5040
ctgtgactgg tgagtactca accaagtcat tctgagaata gtgtatgcgg cgaccgagtt  5100
gctcttgccc ggcgtcaata cgggataata ccgcgccaca tagcagaact ttaaaagtgc  5160
tcatcattgg aaaacgttct tcggggcgaa aactctcaag gatcttaccg ctgttgagat  5220
ccagttcgat gtaacccact cgtgcaccca actgatcttc agcatctttt actttcacca  5280
gcgtttctgg gtgagcaaaa acaggaaggc aaaatgccgc aaaaaaggga ataagggcga  5340
cacggaaatg ttgaatactc atactcttcc tttttcaata ttattgaagc atttatcagg  5400
gttattgtct catgagcgga tacatatttg aatgtattta gaaaaataaa caaatagggg  5460
ttccgcgcac atttccccga aaagtgccac ctgacgtc                          5498

SEQ ID NO: 139          moltype = DNA  length = 6341
FEATURE                 Location/Qualifiers
misc_feature            1..6341
                        note = pExodus RecE
source                  1..6341
                        mol_type = other DNA
                        organism = synthetic construct
SEQUENCE: 139
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atgtccacta aacccctctt cctcctgaga aaagccaaaa aatcaagcgg cgaacccgat  960
gtcgtcctct gggcaagcaa tgacttcgag tctacatgcg ctactctgga ctacctcatc  1020
gtgaagagtg ggaagaaact gagctcctat ttcaaagctg tcgcaacaaa ttttccagtg  1080
gtcaacgacc tgcctgcaga gggagaaatt gatttcacct ggtccgagag ataccagctg  1140
tccaaggact ctatgacatg ggaactgaaa ccaggagccg ctcccgataa tgctcactat  1200
cagggaaaca ccaatgtgaa cggggaggac atgacagaaa tcgaggaaaa catgctgctc  1260
ccaatctctg gacaggagct gcccattaga tggctcgccc agcacgggag tgaaaagcct  1320
gtgacccatg tctcaaggga cggtctgcag gctctccata ttgccagagc tgaggaactg  1380
ccagcagtga ctgcactggc cgtcagtcac aagacctcac tgctcgatcc cctggagatc  1440
cgggaactgc ataagctcgt gcgcgatact gacaaagtct ttccaaaccc cggaaatagc  1500
aacctggggc tcattaccgc tttctttgag gcatacctga atgccgatta tacagaccgc  1560
ggactgctca ctaaggaatg gatgaaaggg aacagggtgt ctcacatcac aagaactgcc  1620
agtggggcta atgcaggcgg agggaacctg acagaccgag gcgagggctt cgtgcatgac  1680
ctgacatcac tcgctcgcga tgtggcaact ggcgtcctgg ctcgaagcat ggatctggac  1740
atctacaatc tccaccccgc ccatgctaag cggattgagg aaatcattgc cgagaacaag  1800
ccccctttct ccgtgtttcg ggacaagttc atcaccatgc ctggtggcct ggattactca  1860
cgcgccattg tggtcgccag cgtgaaggag gcccctatcg gaattgaagt gatcccagct  1920
cacgtcacag agtatctgaa caaggtgctc accgaaacag atcatgcaaa ccctgaccca  1980
gagatcgtcg atattggatg cggcaggagc agcgcaccaa tgcctcagcg ggtgaccgag  2040
gaaggcaagc aggacgatga ggaaaaacca cagccctctg gcaccacagc agtggagcag  2100
ggagaggcag aaacaatgga gcccgacgcc acagaacacc atcaggacac tcagcctctg  2160
gatgcacaga gccaggtgaa cagcgtcgat gccaagtacc aggagctgcg agctgagctc  2220
cacgaagcaa ggaagaatat ccctagcaaa aacccagtgg acgatgacaa actgctcgca  2280
gccagccgag gtgagttcgt ggacggcatc tccgatccca acgaccctaa gtgggtgaaa  2340
ggcatccaga ctagggactg tgtctaccag aatcagcccg agaccgaaaa gacaagtcct  2400
gatatgaacc agcctgagcc agtggtccag caggagcctg aaatcgcatg caatgcctgt  2460
gggcagaccg gaggggataa ctgcccagac tgtggagccg tgatgggggga cgctacttat  2520
caggagacct ttgatgagga atcccaggtc gaggccaagg aaaacgaccc tgaggaaatg  2580
gagggtgctg aacacccaca taatgagaac gcaggctccg atccccacag ggattgctct  2640
gacgagaccg gagaagtggc tgacccagtg atcgtcgagg atattgaacc cggtatctac  2700
tatggcattt ctaatgagaa ctaccatgcc ggtccaggca tctcaaagag ccagctggat  2760
gacattgcag acacacctgc cctgtatctc tggagaaaaa acgccccagt ggacactacc  2820
aagactaaaa ccctggatct cggcactgct ttccactgtc gggtgctgga gcccgaggaa  2880
tttctcgagt ctagagggcc cgtttaaacc cgctgatcag cctcgactgt gccttctagt  2940
tgccagccat ctgttgtttg cccctccccc gtgccttcct tgaccctgga aggtgccact  3000
cccactgtcc tttcctaata aaatgaggaa attgcatcgc attgtctgag taggtgtcat  3060
tctattctgg ggggtggggt ggggcaggac agcaaggggg aggattggga agacaatagc  3120
aggcatgctg ggatgcggt gggctctatg gcttctgagg cggaaagaac cagctggggc  3180
tctagggggt atccccacgc gccctgtagc ggcgcattaa gcgcggcggg tgtggtggtt  3240
```

```
acgcgcagcg tgaccgctac acttgccagc gccctagcgc ccgctccttt cgctttcttc  3300
ccttcctttc tcgccacgtt cgccggcttt ccccgtcaag ctctaaatcg ggggctccct  3360
ttagggttcc gatttagtgc tttacggcac ctcgacccca aaaaacttga ttagggtgat  3420
ggttcacgta gtgggccatc gccctgatag acggtttttc gccctttgac gttggagtcc  3480
acgttcttta atagtggact cttgttccaa actggaacaa cactcaaccc tatctcggtc  3540
tattcttttg atttataagg gattttgccg atttcggcct attggttaaa aaatgagctg  3600
atttaacaaa aatttaacgc gaattaattc tgtggaatgt gtgtcagtta gggtgtggaa  3660
agtccccagg ctccccagca ggcagaagta tgcaaagcct atcaggacat agcgttggct  3720
acccgtgata ttgctgaaga gcttggcggc gaatgggctg accgcttcct cgtgctttac  3780
ggtatcgccg ctcccgattc gcagcgcatc gccttctatc gccttcttga cgagttcttc  3840
tgagcgggac tctggggttc gaaatgaccg accaagcgac gcccaacctg ccatcacgag  3900
atttcgattc caccgccgcc ttctatgaaa ggttgggctt cggaatcgtt ttccgggacg  3960
ccggctggat gatcctccag cgcggggatc tcatgctgga gttcttcgcc caccccaact  4020
tgtttattgc agcttataat ggttacaaat aaagcaatag catcacaaat ttcacaaata  4080
aagcattttt ttcactgcat tctagttgtg gtttgtccaa actcatcaat gtatcttatc  4140
atgtctgtat accgtcgacc tctagctaga gcttggcgta atcatggtca tagctgtttc  4200
ctgtgtgaaa ttgttatccg ctcacaattc cacacaacat acgagccgga agcataaagt  4260
gtaaagcctg gggtgcctaa tgagtgagct aactcacatt aattgcgttg cgctcactgc  4320
ccgctttcca gtcgggaaac ctgtcgtgcc agctgcatta atgaatcggc caacgcgcgg  4380
ggagaggcgg tttgcgtatt gggcgctctt ccgcttcctc gctcactgac tcgctgcgct  4440
cggtcgttcg gctgcggcga gcggtatcag ctcactcaaa ggcggtaata cggttatcca  4500
cagaatcagg ggataacgca ggaaagaaca tgtgagcaaa aggccagcaa aaggccagga  4560
accgtaaaaa ggccgcgttg ctggcgtttt tccataggct ccgcccccct gacgagcatc  4620
acaaaaatcg acgctcaagt cagaggtggc gaaacccgac aggactataa agataccagg  4680
cgtttccccc tggaagctcc ctcgtgcgct ctcctgttcc gaccctgccg cttaccggat  4740
acctgtccgc ctttctccct tcgggaagcg tggcgctttc tcatagctca cgctgtaggt  4800
atctcagttc ggtgtaggtc gttcgctcca agctgggctg tgtgcacgaa ccccccgttc  4860
agcccgaccg ctgcgcctta tccggtaact atcgtcttga gtccaacccg gtaagacacg  4920
acttatcgcc actggcagca gccactggta acaggattag cagagcgagg tatgtaggcg  4980
gtgctacaga gttcttgaag tggtggccta actacggcta cactagaaga acagtatttg  5040
gtatctgcgc tctgctgaag ccagttacct tcggaaaaag agttggtagc tcttgatccg  5100
gcaaacaaac caccgctggt agcggttttt ttgtttgcaa gcagcagatt acgcgcagaa  5160
aaaaaggatc tcaagaagat cctttgatct tttctacggg gtctgacgct cagtggaacg  5220
aaaactcacg ttaagggatt ttggtcatga gattatcaaa aaggatcttc acctagatcc  5280
ttttaaatta aaaatgaagt tttaaatcaa tctaaagtat atatgagtaa acttggtctg  5340
acagttacca atgcttaatc agtgaggcac ctatctcagc gatctgtcta tttcgttcat  5400
ccatagttgc ctgactcccc gtcgtgtaga taactacgat acgggagggc ttaccatctg  5460
gccccagtgc tgcaatgata ccgcgagacc cacgctcacc ggctccagat ttatcagcaa  5520
taaaccagcc agccggaagg gccgagcgca gaagtggtcc tgcaacttta tccgcctcca  5580
tccagtctat taattgttgc cgggaagcta gagtaagtag ttcgccagtt aatagtttgc  5640
gcaacgttgt tgccattgct acaggcatcg tggtgtcacg ctcgtcgttt ggtatggctt  5700
cattcagctc cggttcccaa cgatcaaggc gagttacatg atcccccatg ttgtgcaaaa  5760
aagcggttag ctccttcggt cctccgatcg ttgtcagaag taagttggcc gcagtgttat  5820
cactcatggt tatggcagca ctgcataatt ctcttactgt catgccatcc gtaagatgct  5880
tttctgtgac tggtgagtac tcaaccaagt cattctgaga atagtgtatg cggcgaccga  5940
gttgctcttg cccggcgtca atacgggata ataccgcgcc acatagcaga actttaaaag  6000
tgctcatcat tggaaaacgt tcttcggggc gaaaactctc aaggatctta ccgctgttga  6060
gatccagttc gatgtaaccc actcgtgcac ccaactgatc ttcagcatct tttactttca  6120
ccagcgtttc tgggtgagca aaaacaggaa ggcaaaatgc cgcaaaaaag ggaataaggg  6180
cgacacggaa atgttgaata ctcatactct tcctttttca atattattga agcatttatc  6240
agggttattg tctcatgagc ggatacatat ttgaatgtat ttagaaaaat aaacaaatag  6300
gggttccgcg cacatttccc cgaaaagtgc cacctgacgt c                        6341
```

```
SEQ ID NO: 140         moltype = DNA  length = 6434
FEATURE                Location/Qualifiers
misc_feature           1..6434
                       note = pExodus Artemis
source                 1..6434
                       mol_type = other DNA
                       organism = synthetic construct
SEQUENCE: 140
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atgtcctcat ttgaagggca gatggcagaa taccccacca ttagcattga tagatttgat  960
agggaaaacc tcagggcacg ggcttatttc ctgagccact gccataagga ccacatgaaa  1020
gggctcaggg cacctaccct caagaggaga ctggagtgct ccctcaaagt ctacctgtat  1080
```

-continued

```
tgttctccag tgacaaagga gctgctcctg acttccccca aatatcgctt ttggaagaaa  1140
cgaatcattt ctatcgagat tgaaactcca acccagatca gtctggtgga tgaggcttca  1200
ggcgaaaagg aggaaattgt ggtcaccctc ctgccagcag gacactgtcc aggtagcgtc  1260
atgttcctgt ttcagggcaa caatggaacc gtgctgtaca caggcgactt ccgcctcgct  1320
cagggagagg cagctcgaat ggaactcctg cattctggcg gacgggtcaa ggatatccag  1380
agtgtgtatc tggacaccac attctgcgat ccccggtttt accagattcc tagccgcgag  1440
gaatgtctgt ccggagtgct ggagctggtg aggtcatgga tcaccagaag cccatatcac  1500
gtggtctggc tgaactgcaa ggcagcctac gggtatgagt acctcttcac aaatctgtcc  1560
gaggaactcg gtgtgcaggt ccatgtgaac aaactggaca tgtttcgcaa tatgcccgag  1620
atcctccacc atctgactac cgataggaac acccagattc acgcttgcag acatcccaag  1680
gcagaggaat acttccagtg gagtaaactg ccttgtggca tcacttcacg gaaccgcatt  1740
cccctccaca tcattagcat caagccttcc accatgtggt ttggcgagcg atccaggaaa  1800
accaatgtca ttgtgcgaac aggagaaagc tcctataggg cctgcttctc ttttcattct  1860
agttacagtg agatcaagga cttcctctct tatctgtgtc ctgtgaacgc ttaccctaat  1920
gtcatcccag tgggcacaac tatggataag gtggtcgaga ttctcaaacc actgtgtcgg  1980
tcaagccaga gcacagaacc caagtacaaa cctctcggaa agctgaaaag agcccggact  2040
gtgcaccgag acagcgagga agaggacgat tatctgtttg acgatcccct gcctatccca  2100
ctcagacaca aggtgcccta ccctgagact ttccatcccg aagtcttttc catgaccgct  2160
gtgtctgaga agcagccaga aaaactgaga cagaccccag gatgctgtcg agcagagtgc  2220
atgcagtcct ctaggttcac aaactttgtg gactgtgaag agtccaattc tgagagtgaa  2280
gaggaagtgg gcatccccgc ctcactgcag ggggatctcg gtagcgtgct ccacctgcag  2340
aaggctgacg gcgacgtccc acagtgggag gtgttcttta aaagaaacga cgaaatcacc  2400
gatgagtccc tggaaaattt ccctagttca acagtggccg ggggttcaca gagcccaaag  2460
ctgttttccg actctgatgg ggagtctact cacatcagct cccagaactc tagtcagagc  2520
acacatatta ctgagcaggg ctcccaggga tgggacagtc agtcagatac agtcctggtg  2580
tcaagccagg agcggaacag tggtgacatc acatcactgg acaaggcaga ttatcgccct  2640
actatcaaag agaacattcc agccagcctg atggaacaga atgtgatttg ccctaaggac  2700
acctactctg atctgaagag tagagacaaa gatgtcacta tcgtgcctag caccggcgag  2760
ccaaccacac tgtcctctga aactcacatt cccgaggaaa agagcctcct gaacctgtcc  2820
accaatgcag actctcagag ttcaagcgat ttcgaggtgc catctacacc cgaggccgaa  2880
ctgcctaagc gggaacatct ccagtatctg tacgagaaac tggccacagg agaaagcatc  2940
gctgtgaaga aacgcaagtg tagcctcctg gacactctcg agtctagagg gcccgtttaa  3000
acccgctgat cagcctcgac tgtgccttct agttgccagc catctgttgt ttgcccctcc  3060
cccgtgcctt ccttgaccct ggaaggtgcc actcccactg tcctttccta ataaaatgag  3120
gaaattgcat cgcattgtct gagtaggtgt cattctattc tggggggtgg ggtggggcag  3180
gacagcaagg gggaggattg ggaagacaat agcaggcatg ctggggatgc ggtgggctct  3240
atggcttctg aggcggaaag aaccagctgg ggctctaggg ggtatcccca cgcgccctgt  3300
agcggcgcat taagcgcggc gggtgtggtg gttacgcgca gcgtgaccgc tacacttgcc  3360
agcgccctag cgcccgctcc tttcgctttc ttcccttcct ttctcgccac gttcgccggc  3420
tttccccgtc aagctctaaa tcgggggctc cctttagggt tccgatttag tgctttacgg  3480
cacctcgacc ccaaaaaact tgattagggt gatggttcac gtagtgggcc atcgccctga  3540
tagacggttt ttcgcccttt gacgttggag tccacgttct ttaatagtgg actcttgttc  3600
caaactggaa caacactcaa ccctatctcg gtctattctt ttgatttata agggattttg  3660
ccgatttcgg cctattggtt aaaaaatgag ctgatttaac aaaaatttaa cgcgaattaa  3720
ttctgtggaa tgtgtgtcag ttagggtgtg gaaagtcccc aggctcccca gcaggcagaa  3780
gtatgcaaag cctatcagga catagcgttg gctacccgtg atattgctga agagcttggc  3840
ggcgaatggg ctgaccgctt cctcgtgctt tacggtatcg ccgctcccga ttcgcagcgc  3900
atcgccttct atcgccttct tgacgagttc ttctgagcgg gactctgggg ttcgaaatga  3960
ccgaccaagc gacgcccaac ctgccatcac gagatttcga ttccaccgcc gccttctatg  4020
aaaggttggg cttcggaatc gttttccggg acgccggctg gatgatcctc cagcgcgggg  4080
atctcatgct ggagttcttc gcccacccca acttgtttat tgcagcttat aatggttaca  4140
aataaagcaa tagcatcaca aatttcacaa ataaagcatt tttttcactg cattctagtt  4200
gtggtttgtc caaactcatc aatgtatctt atcatgtctg tataccgtcg acctctagct  4260
agagcttggc gtaatcatgg tcatagctgt ttcctgtgtg aaattgttat ccgctcacaa  4320
ttccacacaa catacgagcc ggaagcataa agtgtaaagc ctggggtgcc taatgagtga  4380
gctaactcac attaattgcg ttgcgctcac tgcccgcttt ccagtcggga aacctgtcgt  4440
gccagctgca ttaatgaatc ggccaacgcg cggggagagg cggtttgcgt attgggcgct  4500
cttccgcttc ctcgctcact gactcgctgc gctcggtcgt tcggctgcgg cgagcggtat  4560
cagctcactc aaaggcggta atacggttat ccacagaatc aggggataac gcaggaaaga  4620
acatgtgagc aaaaggccag caaaaggcca ggaaccgtaa aaaggccgcg ttgctggcgt  4680
ttttccatag gctccgcccc cctgacgagc atcacaaaaa tcgacgctca agtcagaggt  4740
ggcgaaaccc gacaggacta taaagatacc aggcgtttcc ccctggaagc tccctcgtgc  4800
gctctcctgt tccgaccctg ccgcttaccg gatacctgtc cgcctttctc ccttcgggaa  4860
gcgtggcgct ttctcatagc tcacgctgta ggtatctcag ttcggtgtag gtcgttcgct  4920
ccaagctggg ctgtgtgcac gaaccccccg ttcagcccga ccgctgcgcc ttatccggta  4980
actatcgtct tgagtccaac ccggtaagac acgacttatc gccactggca gcagccactg  5040
gtaacaggat tagcagagcg aggtatgtag gcggtgctac agagttcttg aagtggtggc  5100
ctaactacgg ctacactaga agaacagtat ttggtatctg cgctctgctg aagccagtta  5160
ccttcggaaa aagagttggt agctcttgat ccggcaaaca aaccaccgct ggtagcggtt  5220
tttttgtttg caagcagcag attacgcgca gaaaaaaagg atctcaagaa gatcctttga  5280
tcttttctac ggggtctgac gctcagtgga acgaaaactc acgttaaggg attttggtca  5340
tgagattatc aaaaaggatc ttcacctaga tccttttaaa ttaaaaatga agttttaaat  5400
caatctaaag tatatatgag taaacttggt ctgacagtta ccaatgctta atcagtgagg  5460
cacctatctc agcgatctgt ctatttcgtt catccatagt tgcctgactc cccgtcgtgt  5520
agataactac gatacgggag ggcttaccat ctggccccag tgctgcaatg ataccgcgag  5580
acccacgctc accggctcca gatttatcag caataaacca gccagccgga agggccgagc  5640
gcagaagtgg tcctgcaact ttatccgcct ccatccagtc tattaattgt tgccgggaag  5700
ctagagtaag tagttcgcca gttaatagtt tgcgcaacgt tgttgccatt gctacaggca  5760
tcgtggtgtc acgctcgtcg tttggtatgg cttcattcag ctccggttcc caacgatcaa  5820
```

-continued

```
ggcgagttac atgatccccc atgttgtgca aaaaagcggt tagctccttc ggtcctccga  5880
tcgttgtcag aagtaagttg gccgcagtgt tatcactcat ggttatggca gcactgcata  5940
attctcttac tgtcatgcca tccgtaagat gcttttctgt gactggtgag tactcaacca  6000
agtcattctg agaatagtgt atgcggcgac cgagttgctc ttgcccggcg tcaatacggg  6060
ataataccgc gccacatagc agaactttaa aagtgctcat cattggaaaa cgttcttcgg  6120
ggcgaaaact ctcaaggatc ttaccgctgt tgagatccag ttcgatgtaa cccactcgtg  6180
cacccaactg atcttcagca tcttttactt tcaccagcgt ttctgggtga gcaaaaacag  6240
gaaggcaaaa tgccgcaaaa aagggaataa gggcgacacg gaaatgttga atactcatac  6300
tcttcctttt tcaatattat tgaagcattt atcagggtta ttgtctcatg agcggataca  6360
tatttgaatg tatttagaaa aataaacaaa taggggttcc gcgcacattt ccccgaaaag  6420
tgccacctga cgtc                                                    6434

SEQ ID NO: 141         moltype = DNA  length = 6419
FEATURE                Location/Qualifiers
misc_feature           1..6419
                       note = pExodus Dna2
source                 1..6419
                       mol_type = other DNA
                       organism = synthetic construct
SEQUENCE: 141
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggaacagc tcaacgaact ggaactcctc atggagaagt ccttttggga agaagccgaa  960
ctgcctgccg aactgtttca gaagaaggtg gtcgcttctt tcccccgcac cgtgctgagt  1020
acagggatgg acaaccgata cctcgtcctg gcagtgaata ccgtccagaa caaagagggt  1080
aattgcgaaa agcgactggt catcacagcc agccagtccc tggagaataa ggaactgtgc  1140
attctcagaa acgactggtg ttccgtgcca gtcgagcccg gcgatatcat tcacctggaa  1200
ggagactgca catctgatac ttggatcatt gacaaggatt tcggctacct catcctgtat  1260
cctgacatgc tgattagcgg aacttccatc gccagctcca ttaggtgtat gaggagagct  1320
gtgctgagcg agacctttcg ctctagtgat cccgctaccc gacagatgct catcggcaca  1380
gtgctgcacg aggtcttcca gaaagccatt aacaatagct ttgctcctga gaagctgcag  1440
gaactcgcat ttcagacaat ccaggagatt aggcatctga aagaaatgta cagactcaat  1500
ctgtctcagg acgagatcaa gcaggaggtg gaagattatc tgccaagttt ctgcaaatgg  1560
gccggagact ttatgcataa gaacactagc accgatttcc cacagatgca gctctctctg  1620
cccagtgaca actcaaaaga taattccacc tgtaacatcg aggtggtcaa gcctatggac  1680
atcgaggaaa gcatttggtc cccacggttt gggctgaagg gtaaaatcga tgtgactgtc  1740
ggggtgaaga ttcaccgcgg ttacaagacc aaatataaga tcatgcccct ggagctgaag  1800
acaggcaagg agtctaacag tattgaacat cggtcccagg tggtcctgta cacactgctc  1860
tctcaggagc gacgagccga ccccgaagct ggactgctcc tgtacctgaa gactggacag  1920
atgtatcccg tgcctgcaaa tcacctggat aaaagagagc tcctgaagct gcggaaccag  1980
atggccttca gcctgtttca tcggatctca aaaagcgcaa ctcgccagaa gacccagctg  2040
gccagcctcc ctcagatcat tgaggaagag aaaacatgca agtactgtag tcagatcgga  2100
aattgcgcac tgtattcaag agccgtggag cagcagatgg actgttcaag cgtgcccatc  2160
gtcatgctgc ctaaaattga agaggaaaca cagcacctca agcagactca tctggagtat  2220
ttctccctct ggtgcctcat gctgaccctc gaatcccagt ctaaggacaa caagaaaaat  2280
caccagaaca tctggctgat gcctgcttct gagatggaaa agagtggctc atgtatcgga  2340
aacctgatta ggatggagca tgtgaagatt gtctgcgacg ggcagtacct gcacaatttc  2400
cagtgtaagc atggtgctat cccagtgacc aacctgatgg caggggatag agtcattgtg  2460
tctggcgagg aacgaagtct gtttgccctc tcaaggggat atgtgaagga gatcaatatg  2520
accacagtca catgcctcct ggacaggaac ctgagcgtgc tcccagaatc cactctgttc  2580
agactcgatc aggaggagaa gaactgtgac atcgatactc ccctggggaa tctcagcaag  2640
ctgatggaga acacctttgt gtccaagaaa ctcagagacc tgatcattga tttccgggaa  2700
ccccagttta tctcctacct ctcctctgtg ctgcctcacg acgctaagga taccgtcgca  2760
tgcattctca aagggctgaa caagcctcag cggcaggcta tgaagaaagt gctcctgtct  2820
aaagactata ctctgatcgt cggcatgcca ggcaccggaa agactaccac aatctgtaca  2880
ctggtgcgct tccgaaggtt tattcagctc agttcaaatc tgcagtcaaa gaaattcgcc  2940
gatcagagcc ctctgaaccc actcgagtct agagggcccg tttaaacccg ctgatcagcc  3000
tcgactgtgc cttctagttg ccagccatct gttgtttgcc cctcccccgt gccttccttg  3060
accctggaag gtgccactcc cactgtcctt tcctaataaa atgaggaaat tgcatcgcat  3120
tgtctgagta ggtgtcattc tattctgggg ggtggggtgg ggcaggacag caagggggag  3180
gattgggaag acaatagcag gcatgctggg gatgcggtgg gctctatggc ttctgaggcg  3240
gaaagaacca gctggggctc taggggtat ccccacgcgc cctgtagcgg cgcattaagc  3300
gcggcgggtg tggtggttac gcgcagcgtg accgctacac ttgccagcgc cctagcgccc  3360
gctcctttcg ctttcttccc ttcctttctc gccacgttcg ccggctttcc ccgtcaagct  3420
ctaaatcggg ggctcccttt agggttccga tttagtgctt tacggcacct cgaccccaaa  3480
aaacttgatt agggtgatgg ttcacgtagt gggccatcgc cctgatagac ggtttttcgc  3540
```

-continued

```
cctttgacgt tggagtccac gttctttaat agtggactct tgttccaaac tggaacaaca  3600
ctcaacccta tctcggtcta ttcttttgat ttataaggga ttttgccgat ttcggcctat  3660
tggttaaaaa atgagctgat ttaacaaaaa tttaacgcga attaattctg tggaatgtgt  3720
gtcagttagg gtgtggaaag tccccaggct ccccagcagg cagaagtatg caaagcctat  3780
caggacatag cgttggctac ccgtgatatt gctgaagagc ttggcggcga atgggctgac  3840
cgcttcctcg tgctttacgg tatcgccgct cccgattcgc agcgcatcgc cttctatcgc  3900
cttcttgacg agttcttctg agcgggactc tggggttcga aatgaccgac caagcgacgc  3960
ccaacctgcc atcacgagat ttcgattcca ccgccgcctt ctatgaaagg ttgggcttcg  4020
gaatcgtttt ccgggacgcc ggctggatga tcctccagcg cggggatctc atgctggagt  4080
tcttcgccca ccccaacttg tttattgcag cttataatgg ttacaaataa agcaatagca  4140
tcacaaattt cacaaataaa gcattttttt cactgcattc tagttgtggt ttgtccaaac  4200
tcatcaatgt atcttatcat gtctgtatac cgtcgacctc tagctagagc ttggcgtaat  4260
catggtcata gctgtttcct gtgtgaaatt gttatccgct cacaattcca cacaacatac  4320
gagccggaag cataaagtgt aaagcctggg gtgcctaatg agtgagctaa ctcacattaa  4380
ttgcgttgcg ctcactgccc gctttccagt cgggaaacct gtcgtgccag ctgcattaat  4440
gaatcggcca acgcgcgggg agaggcggtt tgcgtattgg gcgctcttcc gcttcctcgc  4500
tcactgactc gctgcgctcg gtcgttcggc tgcggcgagc ggtatcagct cactcaaagg  4560
cggtaatacg gttatccaca gaatcagggg ataacgcagg aaagaacatg tgagcaaaag  4620
gccagcaaaa ggccaggaac cgtaaaaagg ccgcgttgct ggcgtttttc cataggctcc  4680
gcccccctga cgagcatcac aaaaatcgac gctcaagtca gaggtggcga aacccgacag  4740
gactataaag ataccaggcg tttccccctg gaagctccct cgtgcgctct cctgttccga  4800
ccctgccgct taccggatac ctgtccgcct ttctcccttc gggaagcgtg gcgctttctc  4860
atagctcacg ctgtaggtat ctcagttcgg tgtaggtcgt tcgctccaag ctgggctgtg  4920
tgcacgaacc ccccgttcag cccgaccgct gcgccttatc cggtaactat cgtcttgagt  4980
ccaacccggt aagacacgac ttatcgccac tggcagcagc cactggtaac aggattagca  5040
gagcgaggta tgtaggcggt gctacagagt tcttgaagtg gtggcctaac tacggctaca  5100
ctagaagaac agtatttggt atctgcgctc tgctgaagcc agttaccttc ggaaaaagag  5160
ttggtagctc ttgatccggc aaacaaacca ccgctggtag cggttttttt gtttgcaagc  5220
agcagattac gcgcagaaaa aaaggatctc aagaagatcc tttgatcttt tctacggggt  5280
ctgacgctca gtggaacgaa aactcacgtt aagggatttt ggtcatgaga ttatcaaaaa  5340
ggatcttcac ctagatcctt ttaaattaaa aatgaagttt taaatcaatc taaagtatat  5400
atgagtaaac ttggtctgac agttaccaat gcttaatcag tgaggcacct atctcagcga  5460
tctgtctatt tcgttcatcc atagttgcct gactccccgt cgtgtagata actacgatac  5520
gggagggctt accatctggc cccagtgctg caatgatacc gcgagaccca cgctcaccgg  5580
ctccagattt atcagcaata aaccagccag ccggaagggc cgagcgcaga agtggtcctg  5640
caactttatc cgcctccatc cagtctatta attgttgccg ggaagctaga gtaagtagtt  5700
cgccagttaa tagtttgcgc aacgttgttg ccattgctac aggcatcgtg gtgtcacgct  5760
cgtcgtttgg tatggcttca ttcagctccg gttcccaacg atcaaggcga gttacatgat  5820
cccccatgtt gtgcaaaaaa gcggttagct ccttcggtcc tccgatcgtt gtcagaagta  5880
agttggccgc agtgttatca ctcatggtta tggcagcact gcataattct cttactgtca  5940
tgccatccgt aagatgcttt tctgtgactg gtgagtactc aaccaagtca ttctgagaat  6000
agtgtatgcg gcgaccgagt tgctcttgcc cggcgtcaat acgggataat accgcgccac  6060
atagcagaac tttaaaagtg ctcatcattg gaaaacgttc ttcggggcga aaactctcaa  6120
ggatcttacc gctgttgaga tccagttcga tgtaacccac tcgtgcaccc aactgatctt  6180
cagcatcttt tactttcacc agcgtttctg ggtgagcaaa aacaggaagg caaaatgccg  6240
caaaaaaggg aataagggcg acacggaaat gttgaatact catactcttc ctttttcaat  6300
attattgaag catttatcag ggttattgtc tcatgagcgg atacatattt gaatgtattt  6360
agaaaaataa acaaataggg gttccgcgca catttccccg aaaagtgcca cctgacgtc   6419
```

```
SEQ ID NO: 142         moltype = DNA  length = 6482
FEATURE                Location/Qualifiers
misc_feature           1..6482
                       note = pExodus MreII
source                 1..6482
                       mol_type = other DNA
                       organism = synthetic construct
SEQUENCE: 142
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atgagcaccg cagacgccct ggacgatgag aacacattca aaatcctggt cgcaacagac  960
attcacctcg ggtttatgga gaaagacgcc gtgagaggga acgatacttt cgtcaccctg  1020
gacgagatcc tgcggctcgc tcaggagaac gaagtggatt tcattctgct cggcggagac  1080
ctgtttcacg aaaataagcc aagcagaaaa acactccata cttgcctgga gctgctccgc  1140
aagtactgta tgggcgatcg accagtgcag ttcgagatcc tgtctgacca gagtgtcaac  1200
ttcggatttt ccaagtttcc ctgggtgaat tatcaggatg ggaacctgaa tatctcaatt  1260
cccgtgttca gcatccacgg caaccatgac gatcctaccg gagcagatgc cctgtgcgcc  1320
```

-continued

```
ctcgacatcc tgagctgtgc tgggttcgtg aatcactttg gcaggtccat gtctgtggag  1380
aagatcgaca tttctcccgt cctgctccag aagggcagta ccaaaatcgc cctctacggc  1440
ctgggaagca ttcctgatga gcgcctctat cgaatgtttg tgaacaagaa agtcacaatg  1500
ctgcgcccaa aggaggacga aaactcctgg ttcaatctct ttgtgatcca ccagaaccgg  1560
tctaaacatg gcagtacaaa tttcattcct gagcagttcc tcgacgattt tatcgacctg  1620
gtcatctggg gacacgagca tgaatgcaag atcgctccaa caaaaaacga acagcagctg  1680
ttttacattt ctcagcctgg gagctccgtg gtcactagtc tgtcaccagg cgaggcagtg  1740
aagaaacacg tcggcctgct ccggatcaag ggacgcaaaa tgaacatgca caagattccc  1800
ctgcatactg tgagacagtt ctttatggag gatatcgtcc tggccaatca tcctgatatt  1860
ttcaacccccg acaatcctaa ggtgacccag gctatccaga gcttttgtct cgaaaaaatt  1920
gaggaaatgc tggagaacgc agagcgcgaa cgactgggaa attcccacca gccagaaaag  1980
cccctcgtga ggctgagagt ggactattct ggggggtttcg agccattttc cgtgctgaga  2040
ttctctcaga agtttgtgga tcgggtcgct aaccccaaag acatcattca cttctttcgg  2100
catcgcgagc agaaggaaaa aacaggggag gaaatcaatt tcggcaagct gattactaaa  2160
ccttctgaag ggaccacact cagggtggag gacctggtca agcagtactt tcagaccgcc  2220
gagaagaacg tgcagctgag cctgctcaca gagagaggga tgggtgaagc tgtgcaggag  2280
ttcgtcgata aggaggaaaa agacgcaatc gaggaactcg tgaagtatca gctggagaaa  2340
acccagcgat tcctcaagga aaggcacatc gacgctctgg aggataaaat tgacgaggaa  2400
gtcaggaggt tcagggagac cagacagaag aacacaaatg aggaagacga tgaggtgcgc  2460
gaagcaatga cacgagctag ggcactgagg agccagtccg aggaatctgc cagtgctttc  2520
agtgccgacg atctcatgtc aatcgatctg gctgagcaga tggcaaacga ctccgacgat  2580
tcaatcagcg ccgctactaa taagggcaga ggacgggggc gcggtcggcg cggcggacgc  2640
ggacagaact ccgcatctag ggggggttct cagcgaggca gggcagatac tggactggag  2700
acctcaacaa gaagccggaa ctccaagacc gcagtgagtg cctcacggaa tatgagcatc  2760
attgacgcct tcaagagcac cagacagcag ccctcccgga acgtcactac caaaaattac  2820
tcagaagtga tcgaagtcga tgagagcgac gtggaggaag atattttcc tacaactagt  2880
aagactgacc agaggtggtc tagtacctca agctccaaga tcatgagcca gtcccaggtg  2940
tccaaaggag tggacttcga atctagtgag gacgatgacg atgacccctt catgaacaca  3000
tcaagcctgc gaaggaatag acggctcgag tctagagggc ccgtttaaac ccgctgatca  3060
gcctcgactg tgccttctag ttgccagcca tctgttgttt gcccctcccc cgtgccttcc  3120
ttgaccctgg aaggtgccac tcccactgtc ctttcctaat aaaatgagga aattgcatcg  3180
cattgtctga gtaggtgtca ttctattctg gggggtgggg tggggcagga cagcaagggg  3240
gaggattggg aagacaatag caggcatgct ggggatgcgg tgggctctat ggcttctgag  3300
gcggaaagaa ccagctgggg ctctaggggg tatccccacg cgccctgtag cggcgcatta  3360
agcgcggcgg gtgtggtggt tacgcgcagc gtgaccgcta cacttgccag cgccctagcg  3420
cccgctcctt tcgctttctt cccttccttt ctcgccacgt tcgccggctt tccccgtcaa  3480
gctctaaatc gggggctccc tttagggttc cgatttagtg ctttacggca cctcgacccc  3540
aaaaaacttg attagggtga tggttcacgt agtgggccat cgccctgata gacggttttt  3600
cgccctttga cgttggagtc cacgttcttt aatagtggac tcttgttcca aactggaaca  3660
acactcaacc ctatctcggt ctattctttt gatttataag ggattttgcc gatttcggcc  3720
tattggttaa aaaatgagct gatttaacaa aaatttaacg cgaattaatt ctgtggaatg  3780
tgtgtcagtt agggtgtgga aagtccccag gctccccagc aggcagaagt atgcaaagcc  3840
tatcaggaca tagcgttggc tacccgtgat attgctgaag agcttggcgg cgaatgggct  3900
gaccgcttcc tcgtgcttta cggtatcgcc gctcccgatt cgcagcgcat cgccttctat  3960
cgccttcttg acgagttctt ctgagcggga ctctggggtt cgaaatgacc gaccaagcga  4020
cgcccaacct gccatcacga gatttcgatt ccaccgccgc cttctatgaa aggttgggct  4080
tcggaatcgt tttccgggac gccggctgga tgatcctcca gcgcggggat ctcatgctgg  4140
agttcttcgc ccaccccaac ttgtttattg cagcttataa tggttacaaa taaagcaata  4200
gcatcacaaa tttcacaaat aaagcatttt tttcactgca ttctagttgt ggtttgtcca  4260
aactcatcaa tgtatcttat catgtctgta taccgtcgac ctctagctag agcttggcgt  4320
aatcatggtc atagctgttt cctgtgtgaa attgttatcc gctcacaatt ccacacaaca  4380
tacgagccgg aagcataaag tgtaaagcct ggggtgccta atgagtgagc taactcacat  4440
taattgcgtt gcgctcactg cccgctttcc agtcgggaaa cctgtcgtgc cagctgcatt  4500
aatgaatcgg ccaacgcgcg gggagaggcg gtttgcgtat tgggcgctct tccgcttcct  4560
cgctcactga ctcgctgcgc tcggtcgttc ggctgcggcg agcggtatca gctcactcaa  4620
aggcggtaat acggttatcc acagaatcag gggataacgc aggaaagaac atgtgagcaa  4680
aaggccagca aaaggccagg aaccgtaaaa aggccgcgtt gctggcgttt ttccataggc  4740
tccgcccccc tgacgagcat cacaaaaatc gacgctcaag tcagaggtgg cgaaacccga  4800
caggactata aagataccag gcgtttcccc ctggaagctc cctcgtgcgc tctcctgttc  4860
cgaccctgcc gcttaccgga tacctgtccg cctttctccc ttcgggaagc gtggcgcttt  4920
ctcatagctc acgctgtagg tatctcagtt cggtgtaggt cgttcgctcc aagctgggct  4980
gtgtgcacga accccccgtt cagcccgacc gctgcgcctt atccggtaac tatcgtcttg  5040
agtccaaccc ggtaagacac gacttatcgc cactggcagc agccactggt aacaggatta  5100
gcagagcgag gtatgtaggc ggtgctacag agttcttgaa gtggtggcct aactacggct  5160
acactagaag aacagtattt ggtatctgcg ctctgctgaa gccagttacc ttcggaaaaa  5220
gagttggtag ctcttgatcc ggcaaacaaa ccaccgctgg tagcggtttt tttgtttgca  5280
agcagcagat tacgcgcaga aaaaaaggat ctcaagaaga tcctttgatc ttttctacgg  5340
ggtctgacgc tcagtggaac gaaaactcac gttaagggat tttggtcatg agattatcaa  5400
aaaggatctt cacctagatc cttttaaatt aaaaatgaag ttttaaatca atctaaagta  5460
tatatgagta aacttggtct gacagttacc aatgcttaat cagtgaggca cctatctcag  5520
cgatctgtct atttcgttca tccatagttg cctgactccc cgtcgtgtag ataactacga  5580
tacgggaggg cttaccatct ggccccagtg ctgcaatgat accgcgagac ccacgctcac  5640
cggctccaga tttatcagca ataaaccagc cagccggaag ggccgagcgc agaagtggtc  5700
ctgcaacttt atccgcctcc atccagtcta ttaattgttg ccgggaagct agagtaagta  5760
gttcgccagt taatagtttg cgcaacgttg ttgccattgc tacaggcatc gtggtgtcac  5820
gctcgtcgtt tggtatggct tcattcagct ccggttccca acgatcaagg cgagttacat  5880
gatcccccat gttgtgcaaa aaagcggtta gctccttcgg tcctccgatc gttgtcagaa  5940
gtaagttggc cgcagtgtta tcactcatgg ttatggcagc actgcataat tctcttactg  6000
tcatgccatc cgtaagatgc ttttctgtga ctggtgagta ctcaaccaag tcattctgag  6060
```

```
aatagtgtat gcggcgaccg agttgctctt gcccggcgtc aatacgggat aataccgcgc  6120
cacatagcag aactttaaaa gtgctcatca ttggaaaacg ttcttcgggg cgaaaactct  6180
caaggatctt accgctgttg agatccagtt cgatgtaacc cactcgtgca cccaactgat  6240
cttcagcatc ttttactttc accagcgttt ctgggtgagc aaaaacagga aggcaaaatg  6300
ccgcaaaaaa gggaataagg gcgacacgga aatgttgaat actcatactc ttcctttttc  6360
aatattattg aagcatttat cagggttatt gtctcatgag cggatacata tttgaatgta  6420
tttagaaaaa taaacaaata ggggttccgc gcacatttcc ccgaaaagtg ccacctgacg  6480
tc                                                                 6482

SEQ ID NO: 143          moltype = DNA  length = 5885
FEATURE                 Location/Qualifiers
misc_feature            1..5885
                        note = pExodus TdT
source                  1..5885
                        mol_type = other DNA
                        organism = synthetic construct
SEQUENCE: 143
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggacccac caagggcatc acatctctcc cccaggaaga aaagaccaag acagacaggc  960
gctctcatgg caagttcacc tcaggatatc aagttccagg acctcgtggt ctttattctg  1020
gaaaagaaaa tgggaaccac aaggagagca ttcctcatgg agctggcccg gcgcaagggg  1080
tttagggtgg aaaacgagct gtccgactct gtcacacaca tcgtggctga gaacaatagt  1140
ggttcagatg tgctcgaatg gctgcaggca cagaaggtgc aggtcagctc ccagcccgag  1200
ctgctcgatg tcagctggct gatcgaatgc attagagctg gcaagcctgt ggagatgact  1260
ggcaaacatc agctggtggt ccgaagggac tacagcgatt ccactaaccc aggaccacct  1320
aagaccccac caatcgctgt gcagaaaatt agtcagtatg catgccagag acggactacc  1380
ctgaacaatt gtaatcagat tttcaccgac gcctttgata ttctggctga aaactgcgag  1440
ttccgagaaa atgaggactc ctgtgtcacc ttcatgagag ccgcttccgt gctcaagtct  1500
ctgccttca caatcatctc aatgaaggat actgagggca tcccatgcct gggaagcaag  1560
gtgaaaggga tcattgagga aatcattgaa gacggagagt ctagtgaagt caaggccgtg  1620
ctgaacgatg agagatacca gagcttcaag ctgttcacct cagtcttcgg ggtgggtctg  1680
aagacatccg agaaatggtt cagaatggga tttcggactc tctctaaggt gcggtctgac  1740
aagagtctga aattcacccg catgcagaaa gcagggtttc tctactatga ggatctggtc  1800
tcttgtgtga cccgcgcaga agccgaggct gtgagtgtcc tcgtgaagga ggctgtctgg  1860
gcattcctgc ctgacgcctt tgtgacaatg actggcggat tccgccgagg gaagaaaatg  1920
ggtcacgacg tggattttct gatcacctca ccaggtagca cagaagacga ggaacagctg  1980
ctccagaaag tgatgaatct gtgggagaag aaaggcctgc tcctgtacta tgatctggtc  2040
gagagcactt tcgaaaagct ccgcctgcca tcccgaaaag tggacgccct ggatcatttt  2100
cagaagtgct tcctcatctt taaactgccc cgacagaggg tggactctga tcagtcaagc  2160
tggcaggaag gaaagacctg gaaagctatt cgggtggacc tggtgctgtg tccctacgag  2220
aggagagcat tcgcactcct gggatggaca ggcagcaggc agtttgaaag ggacctgcgg  2280
cgctacgcaa ctcacgagcg gaagatgatc ctcgacaacc atgccctgta tgataagaca  2340
aaacgcattt tcctgaaggc cgagagcgag gaagaaatct tcgctcacct cggcctggac  2400
tatattgagc cttgggaaag aaatgctctc gagtctagag ggcccgttta aacccgctga  2460
tcagcctcga ctgtgccttc tagttgccag ccatctgttg tttgcccctc ccccgtgcct  2520
tccttgaccc tggaaggtgc cactcccact gtcctttcct aataaaatga ggaaattgca  2580
tcgcattgtc tgagtaggtg tcattctatt ctggggggtg gggtggggca ggacagcaag  2640
ggggaggatt gggaagacaa tagcaggcat gctggggatg cggtgggctc tatggcttct  2700
gaggcggaaa gaaccagctg gggctctagg gggtatcccc acgcgccctg tagcggcgca  2760
ttaagcgcgg cgggtgtggt ggttacgcgc agcgtgaccg ctacacttgc cagcgcccta  2820
gcgcccgctc ctttcgcttt cttcccttcc tttctcgcca cgttcgccgg ctttccccgt  2880
caagctctaa atcgggggct ccctttaggg ttccgattta gtgctttacg gcacctcgac  2940
cccaaaaaac ttgattaggg tgatggttca cgtagtgggc catcgccctg atagacggtt  3000
tttcgccctt tgacgttgga gtccacgttc tttaatagtg gactcttgtt ccaaactgga  3060
acaacactca accctatctc ggtctattct tttgatttat aagggatttt gccgatttcg  3120
gcctattggt taaaaaatga gctgatttaa caaaaattta acgcgaatta attctgtgga  3180
atgtgtgtca gttagggtgt ggaaagtccc caggctcccc agcaggcaga agtatgcaaa  3240
gcctatcagg acatagcgtt ggctacccgt gatattgctg aagagcttgg cggcgaatgg  3300
gctgaccgct tcctcgtgct ttacggtatc gccgctcccg attcgcagcg catcgccttc  3360
tatcgccttc ttgacgagtt cttctgagcg ggactctggg gttcgaaatg accgaccaag  3420
cgacgcccaa cctgccatca cgagatttcg attccaccgc cgccttctat gaaaggttgg  3480
gcttcggaat cgttttccgg gacgccggct ggatgatcct ccagcgcggg gatctcatgc  3540
tggagttctt cgcccacccc aacttgttta ttgcagctta taatggttac aaataaagca  3600
atagcatcac aaatttcaca aataaagcat ttttttcact gcattctagt tgtggtttgt  3660
ccaaactcat caatgtatct tatcatgtct gtataccgtc gacctctagc tagagcttgg  3720
```

-continued

```
cgtaatcatg gtcatagctg tttcctgtgt gaaattgtta tccgctcaca attccacaca  3780
acatacgagc cggaagcata aagtgtaaag cctggggtgc ctaatgagtg agctaactca  3840
cattaattgc gttgcgctca ctgcccgctt tccagtcggg aaacctgtcg tgccagctgc  3900
attaatgaat cggccaacgc gcggggagag gcggtttgcg tattgggcgc tcttccgctt  3960
cctcgctcac tgactcgctg cgctcggtcg ttcggctgcg gcgagcggta tcagctcact  4020
caaaggcggt aatacggtta tccacagaat caggggataa cgcaggaaag aacatgtgag  4080
caaaaggcca gcaaaaggcc aggaaccgta aaaaggccgc gttgctggcg tttttccata  4140
ggctccgccc ccctgacgag catcacaaaa atcgacgctc aagtcagagg tggcgaaacc  4200
cgacaggact ataaagatac caggcgtttc cccctggaag ctccctcgtg cgctctcctg  4260
ttccgaccct gccgcttacc ggatacctgt ccgcctttct cccttcggga agcgtggcgc  4320
tttctcatag ctcacgctgt aggtatctca gttcggtgta ggtcgttcgc tccaagctgg  4380
gctgtgtgca cgaacccccc gttcagcccg accgctgcgc cttatccggt aactatcgtc  4440
ttgagtccaa cccggtaaga cacgacttat cgccactggc agcagccact ggtaacagga  4500
ttagcagagc gaggtatgta ggcggtgcta cagagttctt gaagtggtgg cctaactacg  4560
gctacactag aagaacagta tttggtatct gcgctctgct gaagccagtt accttcggaa  4620
aaagagttgg tagctcttga tccggcaaac aaaccaccgc tggtagcggt ttttttgttt  4680
gcaagcagca gattacgcgc agaaaaaaag gatctcaaga agatcctttg atcttttcta  4740
cggggtctga cgctcagtgg aacgaaaact cacgttaagg gattttggtc atgagattat  4800
caaaaaggat cttcacctag atccttttaa attaaaaatg aagttttaaa tcaatctaaa  4860
gtatatatga gtaaacttgg tctgacagtt accaatgctt aatcagtgag gcacctatct  4920
cagcgatctg tctatttcgt tcatccatag ttgcctgact ccccgtcgtg tagataacta  4980
cgatacggga gggcttacca tctggcccca gtgctgcaat gataccgcga gacccacgct  5040
caccggctcc agatttatca gcaataaacc agccagccgg aagggccgag cgcagaagtg  5100
gtcctgcaac tttatccgcc tccatccagt ctattaattg ttgccgggaa gctagagtaa  5160
gtagttcgcc agttaatagt ttgcgcaacg ttgttgccat tgctacaggc atcgtggtgt  5220
cacgctcgtc gtttggtatg gcttcattca gctccggttc ccaacgatca aggcgagtta  5280
catgatcccc catgttgtgc aaaaaagcgg ttagctcctt cggtcctccg atcgttgtca  5340
gaagtaagtt ggccgcagtg ttatcactca tggttatggc agcactgcat aattctctta  5400
ctgtcatgcc atccgtaaga tgcttttctg tgactggtga gtactcaacc aagtcattct  5460
gagaatagtg tatgcggcga ccgagttgct cttgcccggc gtcaatacgg gataataccg  5520
cgccacatag cagaacttta aaagtgctca tcattggaaa acgttcttcg gggcgaaaac  5580
tctcaaggat cttaccgctg ttgagatcca gttcgatgta acccactcgt gcacccaact  5640
gatcttcagc atcttttact ttcaccagcg tttctgggtg agcaaaaaca ggaaggcaaa  5700
atgccgcaaa aaagggaata agggcgacac ggaaatgttg aatactcata ctcttccttt  5760
ttcaatatta ttgaagcatt tatcagggtt attgtctcat gagcggatac atatttgaat  5820
gtatttagaa aaataaacaa ataggggttc cgcgcacatt tccccgaaaa gtgccacctg  5880
acgtc                                                              5885
```

```
SEQ ID NO: 144          moltype = DNA  length = 7412
FEATURE                 Location/Qualifiers
misc_feature            1..7412
                        note = pExodus Vaccinia Polymerase
source                  1..7412
                        mol_type = other DNA
                        organism = synthetic construct
SEQUENCE: 144
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggatgtcc gctgtattaa ctggtttgaa tctcatggtg aaaatcggtt cctgtatctg  960
aaaagtcggt gtagaaatgg cgagaccgtg ttcatcaggt ttcctcacta cttttactat  1020
gtggtcactg acgaaatcta ccagtctctg agtccccctc cattcaatgc tcgcccactc  1080
gggaagatgc gaactatcga cattgatgag accatcagtt acaacctgga cattaaggat  1140
cgaaaatgct cagtggcaga catgtggctg atcgaggaac caaagaaacg cagcattcag  1200
aacgccacaa tggatgaatt tctgaatatc tcctggttct atatcagtaa cgggatttca  1260
cccgacggtt gctacagcct ggatgagcag tatctcacta agatcaacaa tggatgctac  1320
cattgtgacg atcctagaaa ctgttttgca aagaaaatcc cccgattcga cattcctagg  1380
agctatctgt tcctcgacat cgagtgccac ttcgataaga aatttccaag cgtgttcatc  1440
aatcccatct cccatacatc ttactgttac attgatctga gcggcaagcg gctgctcttc  1500
actctgatca acgaggaaat gctcaccgag caggaaattc aggaggcagt ggaccgagga  1560
tgcctgcgca tccagtctct catggagatg gattacgaga gggaactggt gctctgtagt  1620
gaaatcgtcc tgctcagaat tgccaagcag ctgctggagc tgacatttga ctacgtggtc  1680
acttttaacg ggcacaattt cgatctgaga tatatcacca acaggctgga gctgctcaca  1740
ggtgaaaaga tcattttccg gtcccccgac aagaaagagg ctgtgtacct gtgcatctat  1800
gaacgcaatc agagctccca caaaggcgtg ggcggaatgg caaacaccac atttcatgtc  1860
aacaataaca atggaaccat cttctttgac ctgtacagct tcattcagaa gtccgaaaaa  1920
ctggactctt ataagctcga ttcaatcagc aagaacgctt tttcttgtat gggcaaggtg  1980
```

-continued

```
ctgaacaggg gagtcagaga gatgacattc attggggacg atactaccga cgccaagggt  2040
aaagccgctg catttgccaa agtgctgaca actggcgctg ataacaattt cacccaggag  2100
acagctactg gtaactacgt gactgtggac gaggacatta tctgtaaagt gattagaaag  2160
gacatttggg agaacggctt caaggtggtg ctcctgtgcc ccactctccc taacgacacc  2220
tacaaactca gcttcggaaa ggacgatgtg gacctggccc agatgtacaa ggattataac  2280
ctgaatatcg ccctcgacat ggctaggtac tgtattcacg atgcttgcct gtgtcagtat  2340
ctctgggagt actatggggt ggaaactaag accgatgccg gtgcttctac ctacgtcctg  2400
cctcagagta tggtgtttga gtatcgagca tccacagtca tcaaagggcc actgctcaag  2460
ctgctcctgg agacaaagac tattctggtg aggagcgaga ccaaacagaa gttcccttac  2520
gaaggcggaa aggtcttcgc tccaaaacag aagatgtttt caaacaatgt gctcatcttc  2580
gactacaaca gcctgtatcc caatgtctgc atttttggca acctgtcccc tgagactctc  2640
gtgggagtgg tcgtgtctac caataggctg gaggaagaga tcaacaatca gctcctgctc  2700
cagaagtacc cccctccaag gtatatcaca gtgcattgtg agccaagact gcccaacctc  2760
attagtgaaa tcgccatttt tgacagatca atcgagggca ccattccacg actgctcagg  2820
acattcctgg ctgaacgagc aaggtacaag aaaatgctga aacaggctac cagctccaca  2880
gagaaggcaa tctacgattc catgcagtac acatataaga ttgtcgcaaa cagtgtgtat  2940
gggctcatgg gcttcaggaa cagcgccctg tacagttatg catcagccaa gagctgcact  3000
tccatcggga ggagaatgat tctgtacctg gagagcgtgc tgaacggcgc cgaactctcc  3060
aatggaatgc tgcggtttgc taaccctctg tctaatccat tctatatgga cgatcgcgac  3120
atcaacccaa ttgtcaagac cagcctgccc atcgattaca gattccggtt tcgctcagtc  3180
tatggtgaca cagatagcgt gtttactgaa atcgacagcc aggacgtgga taaatccatc  3240
gagattgcca aggaactgga gagactcatt aacaatcggg tcctgttcaa caattttaaa  3300
atcgagttcg aggctgtgta caagaacctg attatgcaga gcaagaaaaa gtacaccaca  3360
atgaaatatt ccgcatctag taactccaag tctgtccccg agaggatcaa caaggggact  3420
tccgaaaccc ggcgcgacgt gtctaagttc cacaagaaca tgatcaaaac atataagact  3480
cggctgtctg agatgctcag tgaaggtcgc atgaactcta atcaagtgtg tatcgatatt  3540
ctgaggagcc tggagaccga cctgcgctca gaatttgata gccgatcaag ccctctggag  3600
ctcttcatgc tgagccgcat gcaccattcc aactacaagt ctgccgacaa cccaaatatg  3660
tacctggtga cagagtataa caagaacaat cccgaaacta tcgagctggg cgaacggtac  3720
tattttgcat acatttgccc cgccaacgtc ccttggacaa aaaagctggt gaatatcaag  3780
acctatgaga caatcattga ccgaagtttc aaactgggat cagatcagag gatcttctac  3840
gaagtgtatt ttaagagact gacttccgag atcgtcaacc tgctcgataa caaggtgctg  3900
tgtatttctt tctttgaacg catgttcgga agtaaaccca ccttttacga ggctctcgag  3960
tctagagggc ccgtttaaac ccgctgatca gcctcgactg tgccttctag ttgccagcca  4020
tctgttgttt gcccctcccc cgtgccttcc ttgaccctgg aaggtgccac tcccactgtc  4080
ctttcctaat aaaatgagga aattgcatcg cattgtctga gtaggtgtca ttctattctg  4140
gggggtgggg tggggcagga cagcaagggg gaggattggg aagacaatag caggcatgct  4200
ggggatgcgg tgggctctat ggcttctgag gcggaaagaa ccagctgggg ctctaggggg  4260
tatccccacg cgccctgtag cggcgcatta agcgcggcgg gtgtggtggt tacgcgcagc  4320
gtgaccgcta cacttgccag cgccctagcg cccgctcctt tcgctttctt cccttccttt  4380
ctcgccacgt tcgccggctt tccccgtcaa gctctaaatc gggggctccc tttagggttc  4440
cgatttagtg ctttacggca cctcgacccc aaaaaacttg attagggtga tggttcacgt  4500
agtgggccat cgccctgata gacggttttt cgccctttga cgttggagtc cacgttcttt  4560
aatagtggac tcttgttcca aactggaaca acactcaacc ctatctcggt ctattctttt  4620
gatttataag ggattttgcc gatttcggcc tattggttaa aaaatgagct gatttaacaa  4680
aaatttaacg cgaattaatt ctgtggaatg tgtgtcagtt agggtgtgga aagtccccag  4740
gctccccagc aggcagaagt atgcaaagcc tatcaggaca tagcgttggc tacccgtgat  4800
attgctgaag agcttggcgg cgaatgggct gaccgcttcc tcgtgcttta cggtatcgcc  4860
gctcccgatt cgcagcgcat cgccttctat cgccttcttg acgagttctt ctgagcggga  4920
ctctggggtt cgaaatgacc gaccaagcga cgcccaacct gccatcacga gatttcgatt  4980
ccaccgccgc cttctatgaa aggttgggct tcggaatcgt tttccgggac gccggctgga  5040
tgatcctcca gcgcggggat ctcatgctgg agttcttcgc ccaccccaac ttgtttattg  5100
cagcttataa tggttacaaa taaagcaata gcatcacaaa tttcacaaat aaagcatttt  5160
tttcactgca ttctagttgt ggtttgtcca aactcatcaa tgtatcttat catgtctgta  5220
taccgtcgac ctctagctag agcttggcgt aatcatggtc atagctgttt cctgtgtgaa  5280
attgttatcc gctcacaatt ccacacaaca tacgagccgg aagcataaag tgtaaagcct  5340
ggggtgccta atgagtgagc taactcacat taattgcgtt gcgctcactg cccgctttcc  5400
agtcgggaaa cctgtcgtgc cagctgcatt aatgaatcgg ccaacgcgcg gggagaggcg  5460
gtttgcgtat tgggcgctct tccgcttcct cgctcactga ctcgctgcgc tcggtcgttc  5520
ggctgcggcg agcggtatca gctcactcaa aggcggtaat acggttatcc acagaatcag  5580
gggataacgc aggaaagaac atgtgagcaa aaggccagca aaaggccagg aaccgtaaaa  5640
aggccgcgtt gctggcgttt ttccataggc tccgcccccc tgacgagcat cacaaaaatc  5700
gacgctcaag tcagaggtgg cgaaacccga caggactata aagataccag gcgtttcccc  5760
ctggaagctc cctcgtgcgc tctcctgttc cgaccctgcc gcttaccgga tacctgtccg  5820
cctttctccc ttcgggaagc gtggcgcttt ctcatagctc acgctgtagg tatctcagtt  5880
cggtgtaggt cgttcgctcc aagctgggct gtgtgcacga accccccgtt cagcccgacc  5940
gctgcgcctt atccggtaac tatcgtcttg agtccaaccc ggtaagacac gacttatcgc  6000
cactggcagc agccactggt aacaggatta gcagagcgag gtatgtaggc ggtgctacag  6060
agttcttgaa gtggtggcct aactacggct acactagaag aacagtattt ggtatctgcg  6120
ctctgctgaa gccagttacc ttcggaaaaa gagttggtag ctcttgatcc ggcaaacaaa  6180
ccaccgctgg tagcggtttt tttgtttgca agcagcagat tacgcgcaga aaaaaaggat  6240
ctcaagaaga tcctttgatc ttttctacgg ggtctgacgc tcagtggaac gaaaactcac  6300
gttaagggat tttggtcatg agattatcaa aaaggatctt cacctagatc cttttaaatt  6360
aaaaatgaag ttttaaatca atctaaagta tatatgagta aacttggtct gacagttacc  6420
aatgcttaat cagtgaggca cctatctcag cgatctgtct atttcgttca tccatagttg  6480
cctgactccc cgtcgtgtag ataactacga tacgggaggg cttaccatct ggccccagtg  6540
ctgcaatgat accgcgagac ccacgctcac cggctccaga tttatcagca ataaaccagc  6600
cagccggaag ggccgagcgc agaagtggtc ctgcaacttt atccgcctcc atccagtcta  6660
ttaattgttg ccgggaagct agagtaagta gttcgccagt taatagtttg cgcaacgttg  6720
```

-continued

```
ttgccattgc tacaggcatc gtggtgtcac gctcgtcgtt tggtatggct tcattcagct  6780
ccggttccca acgatcaagg cgagttacat gatcccccat gttgtgcaaa aaagcggtta  6840
gctccttcgg tcctccgatc gttgtcagaa gtaagttggc cgcagtgtta tcactcatgg  6900
ttatggcagc actgcataat tctcttactg tcatgccatc cgtaagatgc ttttctgtga  6960
ctggtgagta ctcaaccaag tcattctgag aatagtgtat gcggcgaccg agttgctctt  7020
gcccggcgtc aatacgggat aataccgcgc cacatagcag aactttaaaa gtgctcatca  7080
ttggaaaacg ttcttcgggg cgaaaactct caaggatctt accgctgttg agatccagtt  7140
cgatgtaacc cactcgtgca cccaactgat cttcagcatc ttttactttc accagcgttt  7200
ctgggtgagc aaaaacagga aggcaaaatg ccgcaaaaaa gggaataagg gcgacacgga  7260
aatgttgaat actcatactc ttcctttttc aatattattg aagcatttat cagggttatt  7320
gtctcatgag cggatacata tttgaatgta tttagaaaaa taaacaaata ggggttccgc  7380
gcacatttcc ccgaaaagtg ccacctgacg tc                                 7412

SEQ ID NO: 145          moltype = DNA  length = 5601
FEATURE                 Location/Qualifiers
misc_feature            1..5601
                        note = pExodus Rad2
source                  1..5601
                        mol_type = other DNA
                        organism = synthetic construct
SEQUENCE: 145
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
atggggatac agggattgct acaatttatc aaagaagctt cagaacccat ccatgtgagg  960
aagtataaag ggcaggtagt agctgtggat acatattgct ggcttcacaa aggagctatt  1020
gcttgtgctg aaaaactagc caaaggtgaa cctactgata ggtatgtagg attttgtatg  1080
aaatttgtaa atatgttact atctcatggg atcaagccta ttctcgtatt tgatggatgt  1140
actttacctt ctaaaaagga agtagagaga tctagaagag aaagacgaca agccaatctt  1200
cttaagggaa agcaacttct tcgtgagggg aaagtctcgg aagctcgaga gtgtttcacc  1260
cggtctatca atatcacaca tgccatggcc cacaaagtaa ttaaagctgc ccggtctcag  1320
ggggtagatt gcctcgtggc tccctatgaa gctgatgcgc agttggccta tcttaacaaa  1380
gcgggaattg tgcaagccat aattacagag gactcggatc tcctagcttt tggctgtaaa  1440
aaggtaattt taaagatgga ccagtttgga aatggacttg aaattgatca agctcggcta  1500
ggaatgtgca gacagcttgg ggatgtattc acggaagaga agtttcgtta catgtgtatt  1560
ctttcaggtt gtgactacct gtcatcactg cgtgggattg gattagcaaa ggcatgcaaa  1620
gtcctaagac tagccaataa tccagatata gtaaaggtta tcaagaaaat tggacattat  1680
ctcaagatga atatcacggt accagaggat tacatcaacg ggtttattcg ggccaacaat  1740
accttcctct atcagctagt ttttgatccc atcaaaagga aacttattcc tctgaacgcc  1800
tatgaagatg atgttgatcc tgaaacacta agctacgctg ggcaatatgt tgatgattcc  1860
atagctcttc aaatagcact tggaaataaa gatataaata cttttgaaca gatcgatgac  1920
tacaatccag acactgctat gcctgcccat tcaagaagtc atagttggga tgacaaaaca  1980
tgtcaaaagt cagctaatgt tagcagcatt tggcatagga attactctcc cagaccagag  2040
tcgggtactg tttcagatgc cccacaattg aaggaaaatc caagtgagga tccactagtc  2100
cagtgtggtg gaattctgca gatatccagc acagtggcgg ccgctcgagt ctagagggcc  2160
cgtttaaacc cgctgatcag cctcgactgt gccttctagt tgccagccat ctgttgtttg  2220
cccctccccc gtgccttcct tgaccctgga aggtgccact cccactgtcc tttcctaata  2280
aaatgaggaa attgcatcgc attgtctgag taggtgtcat tctattctgg ggggtggggt  2340
ggggcaggac agcaaggggg aggattggga agacaatagc aggcatgctg gggatgcggt  2400
gggctctatg gcttctgagg cggaaagaac cagctggggc tctagggggt atccccacgc  2460
gccctgtagc ggcgcattaa gcgcggcggg tgtggtggtt acgcgcagcg tgaccgctac  2520
acttgccagc gccctagcgc ccgctccttt cgctttcttc ccttcctttc tcgccacgtt  2580
cgccggcttt ccccgtcaag ctctaaatcg ggggctccct ttagggttcc gatttagtgc  2640
tttacggcac ctcgacccca aaaaacttga ttagggtgat ggttcacgta gtgggccatc  2700
gccctgatag acggtttttc gccctttgac gttggagtcc acgttcttta atagtggact  2760
cttgttccaa actggaacaa cactcaaccc tatctcggtc tattcttttg atttataagg  2820
gattttgccg atttcggcct attggttaaa aaatgagctg atttaacaaa aatttaacgc  2880
gaattaattc tgtggaatgt gtgtcagtta gggtgtggaa agtccccagg ctccccagca  2940
ggcagaagta tgcaaagcct atcaggacat agcgttggct acccgtgata ttgctgaaga  3000
gcttggcggc gaatgggctg accgcttcct cgtgctttac ggtatcgccg ctcccgattc  3060
gcagcgcatc gccttctatc gccttcttga cgagttcttc tgagcgggac tctggggttc  3120
gaaatgaccg accaagcgac gcccaacctg ccatcacgag atttcgattc caccgccgcc  3180
ttctatgaaa ggttgggctt cggaatcgtt ttccgggacg ccggctggat gatcctccag  3240
cgcggggatc tcatgctgga gttcttcgcc caccccaact tgtttattgc agcttataat  3300
ggttacaaat aaagcaatag catcacaaat ttcacaaata aagcattttt ttcactgcat  3360
tctagttgtg gtttgtccaa actcatcaat gtatcttatc atgtctgtat accgtcgacc  3420
tctagctaga gcttggcgta atcatggtca tagctgtttc ctgtgtgaaa ttgttatccg  3480
```

-continued

```
ctcacaattc cacacaacat acgagccgga agcataaagt gtaaagcctg gggtgcctaa  3540
tgagtgagct aactcacatt aattgcgttg cgctcactgc ccgctttcca gtcgggaaac  3600
ctgtcgtgcc agctgcatta atgaatcggc caacgcgcgg ggagaggcgg tttgcgtatt  3660
gggcgctctt ccgcttcctc gctcactgac tcgctgcgct cggtcgttcg gctgcggcga  3720
gcggtatcag ctcactcaaa ggcggtaata cggttatcca cagaatcagg ggataacgca  3780
ggaaagaaca tgtgagcaaa aggccagcaa aaggccagga accgtaaaaa ggccgcgttg  3840
ctggcgtttt tccataggct ccgcccccct gacgagcatc acaaaaatcg acgctcaagt  3900
cagaggtggc gaaacccgac aggactataa agataccagg cgtttccccc tggaagctcc  3960
ctcgtgcgct ctcctgttcc gaccctgccg cttaccggat acctgtccgc ctttctccct  4020
tcgggaagcg tggcgctttc tcatagctca cgctgtaggt atctcagttc ggtgtaggtc  4080
gttcgctcca agctgggctg tgtgcacgaa ccccccgttc agcccgaccg ctgcgcctta  4140
tccggtaact atcgtcttga gtccaacccg gtaagacacg acttatcgcc actggcagca  4200
gccactggta acaggattag cagagcgagg tatgtaggcg gtgctacaga gttcttgaag  4260
tggtggccta actacggcta cactagaaga acagtatttg gtatctgcgc tctgctgaag  4320
ccagttacct tcggaaaaag agttggtagc tcttgatccg gcaaacaaac caccgctggt  4380
agcggttttt ttgtttgcaa gcagcagatt acgcgcagaa aaaaaggatc tcaagaagat  4440
cctttgatct tttctacggg gtctgacgct cagtggaacg aaaactcacg ttaagggatt  4500
ttggtcatga gattatcaaa aaggatcttc acctagatcc ttttaaatta aaaatgaagt  4560
tttaaatcaa tctaaagtat atatgagtaa acttggtctg acagttacca atgcttaatc  4620
agtgaggcac ctatctcagc gatctgtcta tttcgttcat ccatagttgc ctgactcccc  4680
gtcgtgtaga taactacgat acgggagggc ttaccatctg gccccagtgc tgcaatgata  4740
ccgcgagacc cacgctcacc ggctccagat ttatcagcaa taaaccagcc agccggaagg  4800
gccgagcgca gaagtggtcc tgcaacttta tccgcctcca tccagtctat taattgttgc  4860
cgggaagcta gagtaagtag ttcgccagtt aatagtttgc gcaacgttgt tgccattgct  4920
acaggcatcg tggtgtcacg ctcgtcgttt ggtatggctt cattcagctc cggttcccaa  4980
cgatcaaggc gagttacatg atcccccatg ttgtgcaaaa aagcggttag ctccttcggt  5040
cctccgatcg ttgtcagaag taagttggcc gcagtgttat cactcatggt tatggcagca  5100
ctgcataatt ctcttactgt catgccatcc gtaagatgct tttctgtgac tggtgagtac  5160
tcaaccaagt cattctgaga atagtgtatg cggcgaccga gttgctcttg cccggcgtca  5220
atacgggata ataccgcgcc acatagcaga actttaaaag tgctcatcat tggaaaacgt  5280
tcttcggggc gaaaactctc aaggatctta ccgctgttga gatccagttc gatgtaaccc  5340
actcgtgcac ccaactgatc ttcagcatct tttactttca ccagcgtttc tgggtgagca  5400
aaaacaggaa ggcaaaatgc cgcaaaaaag ggaataaggg cgacacggaa atgttgaata  5460
ctcatactct tcctttttca atattattga agcatttatc agggttattg tctcatgagc  5520
ggatacatat ttgaatgtat ttagaaaaat aaacaaatag gggttccgcg cacatttccc  5580
cgaaaagtgc cacctgacgt c                                           5601

SEQ ID NO: 146         moltype = DNA  length = 30
FEATURE                Location/Qualifiers
misc_feature           1..30
                       note = Cleavage site for I-SceI
source                 1..30
                       mol_type = other DNA
                       organism = synthetic construct
SEQUENCE: 146
agttacgcta gggataacag ggtaatatag                                  30

SEQ ID NO: 147         moltype = DNA  length = 24
FEATURE                Location/Qualifiers
misc_feature           1..24
                       note = Target site for zinc finger nuclease VF2468.
source                 1..24
                       mol_type = other DNA
                       organism = synthetic construct
SEQUENCE: 147
accatcttct tcaaggacga cggc                                        24
```

COUPLING ENDONUCLEASES WITH END-PROCESSING ENZYMES DRIVES HIGH EFFICIENCY GENE DISRUPTION

RELATED APPLICATION

The present application is a continuation application of U.S. application Ser. No. 17/244,190, filed Apr. 29, 2021, which is a continuation application of U.S. application Ser. No. 15/215,405, filed Jul. 20, 2016, now issued as U.S. patent Ser. No. 11/008,565, which is a continuation application of U.S. application Ser. No. 14/949,744, filed Nov. 23, 2015, now issued as U.S. patent Ser. No. 10/995,332, which is a divisional application of U.S. application Ser. No. 14/173,705, filed on Feb. 5, 2014, which is a divisional application of U.S. Application No. 13,405,183, filed on Feb. 24, 2012, now issued as U.S. Pat. No. 8,673,557, which in turn claims the benefit of priority to U.S. Provisional Patent Application No. 61/447,672, filed Feb. 28, 2011, and the disclosures for each of these related applications are incorporated herein by reference in their entireties.

STATEMENT REGARDING FEDERALLY SPONSORED R&D

This invention was made with government support under grant numbers CA133832, GM007270, DE019582, HL075453, HL092557, HL092553, HL092554, and AI096111 awarded by the National Institutes of Health. The government has certain rights in the invention.

INCORPORATION-BY-REFERENCE OF SEQUENCE LISTING

The instant application contains a Sequence Listing which has been submitted via EFS-Web and is hereby incorporated by reference in its entirety. Said Sequence Listing, created on Dec. 1, 2023, is named "4475-105US12.xml" and is 466,944 bytes in size.

FIELD

The present disclosure relates to molecular and cellular biology. Some embodiments relate to genome engineering and the introduction of targeted, site-specific DNA breaks mediated by endonucleases to achieve gene disruption or site-specific recombination. Several embodiments relate to compositions and methods for partial or complete inactivation of a target gene. Some embodiments relate to inactivation of a targeted gene for therapeutic purposes and/or to produce cell lines in which a target gene is inactivated.

BACKGROUND

Targeted gene disruption has wide applicability for research, therapeutic, agricultural, and industrial uses. One strategy for producing targeted gene disruption is through the generation of double-strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. One limitation of the zinc finger endonucleases is that low specificity for a target site or the presence of multiple target sites in a genome can result in off-target cleavage events. As Fok1 endonuclease cleaves as a dimer, one strategy to prevent off-target cleavage events has been to design zinc finger domains that bind at adjacent 9 base pair sites.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

The mutagenicity of the double strand DNA breaks generated by both the naturally occurring and artificial endonucleases depend upon the precision of DNA repair. The double strand breaks caused by endonucleases are commonly repaired through non-homologous end joining (NHEJ), which is the major DNA double-strand break repair pathway for many organisms. NHEJ is referred to as "non-homologous" because the break ends are ligated directly without the need for a homologous template, in contrast to homologous recombination, which utilizes a homologous sequence to guide repair. Imprecise repair through this pathway can result in mutations at the break site, such as DNA base deletions and insertions as well as translocations and telomere fusion. When the mutations are made within the coding sequence of a gene, they can render the gene and its subsequent protein product non-functional, creating a targeted gene disruption or "knockout" of the gene.

Double strand DNA break repair through the NHEJ pathway is often not mutagenic. The majority of endonuclease-induced breaks repaired by the NHEJ pathway involve precise re-ligation, resulting in the restoration of the original DNA sequence. This is especially true of the types of DNA breaks created by the current endonuclease platforms available for engineering site-specificity, namely homing endonucleases (meganucleases) and zinc finger nucleases. Both of these types of enzymes leave compatible base pair overhangs that do not require processing prior to re-ligation by the NHEJ pathway. When the overhangs are compatible, NHEJ repairs the break with a high degree of accuracy. Thus, from a genome engineering standpoint, many of the cleavage events generated by the current site-specific endonuclease platforms are unproductive.

The need for additional solutions to these problems is manifest.

SUMMARY

Mutagenesis of cellular DNA can occur when a DNA cleavage event is followed by imprecise end joining during DNA repair. As disclosed herein, one strategy for increasing the frequency of imprecise DNA repair events is by modifying compatible overhangs generated at double-strand DNA breaks with an end-processing enzyme. The methods and compositions described herein are broadly applicable and may involve any agent of interest which generates either blunt ends or compatible overhangs upon cleaving double stranded DNA, for example, nucleases, ionizing radiation, such as x-rays and gamma rays, as well as drugs such as bleomycin, cisplatin, and mitomycin C. Several embodiments disclosed herein relate to methods for coupling the generation of double-strand DNA breaks to modification of compatible overhangs generated at the cleavage site with a DNA end-processing enzyme. Several embodiments disclosed herein relate to methods for coupling the generation of double-strand DNA breaks to modification of blunt ends generated at the cleavage site with an end-processing enzyme. Some embodiments disclosed herein relate to methods for coupling the generation of double-strand DNA breaks to cleavage of the exposed phosphodiester bonds at the DNA break site by an exonuclease. Some embodiments disclosed herein relate to methods for coupling the generation of double-strand DNA breaks to the addition of DNA bases to an exposed DNA end by a non-template polymerase.

In yet another aspect, the methods and compositions described herein are broadly applicable and may involve any agent of interest which generates breaks in a polynucleatide. Several embodiments disclosed herein relate to methods for coupling the generation of polynucleotide breaks to modification of polynucleotide ends generated at the cleavage site with an end-processing enzyme. In some embodiments, the polynucleotide may be double stranded DNA, single stranded DNA, stranded RNA, single stranded RNA, double stranded DNA/RNA hybrids and synthetic polynucleotides.

Several embodiments disclosed herein relate to a strategy for increasing the frequency of imprecise DNA repair events by modifying compatible overhangs generated at exonuclease-induced DNA breaks with a DNA end-processing enzyme. Several embodiments disclosed herein relate to methods for coupling site-specific cleavage of a targeted DNA sequence to modification of compatible overhangs generated at the cleavage site with a DNA end-processing enzyme. Several embodiments disclosed herein relate to methods for coupling site-specific cleavage of a targeted DNA sequence to modification of blunt DNA ends generated at the cleavage site with a DNA end-processing enzyme. Some embodiments disclosed herein relate to methods for coupling site-specific cleavage of a targeted DNA sequence by an endonuclease to cleavage of the exposed phosphodiester bonds at the DNA cleavage site by an exonuclease. Some embodiments disclosed herein relate to methods for coupling site-specific cleavage of a targeted DNA sequence by an endonuclease to the addition of DNA bases to an exposed DNA end by a non-template polymerase. Some embodiments disclosed herein relate to methods for coupling site-specific cleavage of a targeted DNA sequence by an endonuclease to removal of a 5'phosphate at the DNA cleavage site by a 5'-phosphatase. Some embodiments disclosed herein relate to methods for coupling site-specific cleavage of a targeted DNA sequence by an endonuclease to removal of a 3'phosphate at the DNA cleavage site by a 3'phosphatase. Further disclosed herein are fusion proteins, comprising one or more site-specific endonuclease domains tethered to one or more DNA end-processing domains.

Non-limiting examples of endonucleases include homing endonucleases (meganucleases), zinc finger nucleases and TAL effector nucleases. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion).

Non-limiting examples of DNA end-processing enzymes include 5-3'exonucleases, 3-5'exonucleases, 5-3' alkaline exonucleases, 5' flap endonucleases, helicases, phosphatases, hydrolases and template-independent DNA polymerases. The exonucleases may comprise heterologous DNA-binding and end-processing domains (e.g., a zinc finger and an exonuclease domain).

Several embodiments relate to co-expression of one or more endonucleases (enzymes that incise DNA at a specific internal target site) with one or more end-processing enzymes, in order to achieve enhanced processing of the polynucleotide ends produced by endonuclease-mediated polynucleotide cleavage. Several embodiments relate to co-expression of one or more endonucleases with one or more exonucleases (enzymes that catalyzes the removal of polynucleotide bases from an exposed polynucleotide end) in order to achieve enhanced processing of the polynucleotide ends produced by endonuclease-mediated polynucleotide cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the polynucleotide ends produced by endonuclease-mediated polynucleotide cleavage. Several embodiments relate to co-expression of one or more endonucleases with one or more phosphatases that catalyze the removal of a 3' phosphate in order to achieve enhanced processing of the polynucleotide ends produced by endonuclease-mediated polynucleotide cleavage. In some embodiments, an endonuclease is coupled to an end-processing enzyme.

Several embodiments relate to co-expression of one or more endonucleases (enzymes that incise DNA at a specific internal target site) with one or more DNA end-processing enzymes, in order to achieve enhanced processing of the DNA ends produced by endonuclease-mediated DNA cleavage. Several embodiments relate to co-expression of one or more endonucleases with one or more exonucleases (enzymes that catalyzes the removal of DNA bases from an exposed DNA end) in order to achieve enhanced processing of the DNA ends produced by endonuclease-mediated DNA cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the DNA ends produced by endonuclease-mediated DNA cleavage. Several embodiments relate to co-expression of one or more endonucleases with one or more phosphatases that catalyze the removal of a 3' phosphate in order to achieve enhanced processing of the DNA ends produced by endonuclease-mediated DNA cleavage. In some embodiments, an endonuclease is coupled to a DNA end-processing enzyme.

In one aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting a site-specific endonuclease which cleaves the sequence within the region of interest; and (c) delivering one or more fusion proteins to the cell, the fusion protein(s) comprising one or more site-specific endonuclease domains and one or more DNA end-processing domains; wherein the endonuclease domain cleaves the DNA in the region of interest. In some embodiments, a fusion protein can be delivered to a cell by delivering a polynucleotide encoding the fusion protein to a cell. In some embodiments the polynucleotide is DNA. In other embodiments, the polynucleotide is RNA. In some embodiments, a fusion protein can be expressed in a cell by delivering a DNA vector encoding the fusion protein to a cell, wherein the DNA vector is transcribed and the mRNA transcription product is translated to generate the fusion protein. In some embodiments, a fusion protein can be expressed in a cell by delivering an RNA molecule encoding the fusion protein to the cell wherein the RNA molecule is translated to generate the fusion protein. In some embodiments, a fusion protein may be delivered directly to the cell.

In another aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting one or more site-specific endonucleases which cleaves the sequence within the region of interest; and (c) co-expressing the one or more selected endonuclease and one or more end-processing enzyme in the cell; wherein the endonuclease cleaves the DNA in the region of interest and the end-processing enzyme modifies the DNA ends exposed by the endonuclease. The nucleases and end-processing enzymes can be expressed in a cell, e.g., by delivering the proteins to the cell or by delivering one or more polynucleotides encoding the nucleases to a cell. In some embodiments, a single polynucleotide encodes both the one or more endonucleases and the one or more end-processing enzymes under the control of a single promoter. In some embodiments, one or more endonucleases and one or more end-processing enzymes are coupled by one or more T2A "skip" peptide motifs. In some embodiments, one or more endonucleases and one or more end-processing enzymes are encoded by separate polynucleotides. In some embodiments, expression of the DNA end-processing enzyme precedes that of the endonuclease.

In yet another aspect, a method for improving the mutation frequency associated with endonuclease mediated cleavage of cellular DNA in multiple regions of interest (e.g., a method for targeted disruption of multiple genomic sequences) is provided, the method comprising: (a) selecting a first sequence in a first region of interest; (b) selecting a first site-specific endonuclease which cleaves the first sequence within the first region of interest; (c) selecting a second sequence in a second region of interest; (d) selecting a second site-specific endonuclease which cleaves the second sequence within the second region of interest and (c) co-expressing the selected endonucleases and one or more end-processing enzymes in the cell; wherein the first endonuclease cleaves the DNA in the first region of interest, the second endonuclease cleaves the DNA in the second region of interest and the one or more end-processing enzymes modify the exposed DNA ends. The nucleases and end-processing enzyme(s) can be expressed in a cell, e.g., by delivering the proteins to the cell or by delivering one or more polynucleotides encoding the nucleases and end-processing enzyme(s) to a cell. In some embodiments, a single polynucleotide encodes both the first and second endonucleases and the one or more end-processing enzyme under the control of a single promoter. In some embodiments, the endonucleases and the end-processing enzyme(s) are coupled by one or more T2A "skip" peptide motifs. In some embodiments, the first and second regions of interest are in the same gene. In other embodiments, the first and second regions of interest are in different genes. In some embodiments the method further comprises co-expression of a third, fourth, fifth, sixth, seventh, eighth, ninth, and/or tenth endonuclease in the cell.

In yet another aspect, the disclosure provides a method for treating or preventing, or inhibiting HIV infection or ameliorating a condition associated with HIV in a subject, the method comprising: (a) introducing, into a cell, a first nucleic acid encoding a first polypeptide, wherein the first polypeptide comprises: (i) a zinc finger DNA-binding domain that is engineered to bind to a first target site in the CCR5 gene; and (ii) a cleavage domain; and (iii) an end-processing domain under conditions such that the polypeptide is expressed in the cell, whereby the polypeptide binds to the target site and cleaves the CCR5 gene and end-processing enzyme domain modifies the endonuclease cleavage site; and (b) introducing the cell into the subject. In certain embodiments, the cell is selected from the group consisting of a hematopoietic stem cell, a T-cell, a macrophage, a dendritic cell, and an antigen-presenting cell.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide and a second polypeptide, wherein the first polypeptide comprises: (i) a zinc finger DNA-binding domain that is engineered to bind to a first target site in the CCR5 gene; and (ii) a cleavage domain; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the cell is selected from the group consisting of a hematopoietic stem cell, a T-cell, a macrophage, a dendritic cell and an antigen-presenting cell.

In another aspect, the disclosure provides a method for treating or preventing or inhibiting HIV infection or ameliorating a condition associated with HIV in a subject, the method comprising: (a) introducing, into a cell, a nucleic acid encoding a polypeptide, wherein the polypeptide comprises: (i) a homing endonuclease domain that is engineered to bind to a first target site in the CCR5 gene; and (ii) a end-processing domain under conditions such that the polypeptide is expressed in the cell, whereby the polypeptide binds to the target site and cleaves the CCR5 gene and modifies the exposed DNA ends created at the cleavage site; and (b) introducing the cell into the subject. In certain embodiments, the DNA end-processing domain comprises an exonuclease.

In another aspect, the disclosure provides a method for treating or preventing or inhibiting HIV infection or ameliorating a condition associated with HIV in a subject, the method comprising: (a) introducing, into a cell, a nucleic acid encoding a first polypeptide and a second polypeptide, wherein the first polypeptide comprises a homing endonuclease that is engineered to bind to a target site in the CCR5 gene; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, the homing endonuclease and the end-processing enzyme are coupled by one or more T2A "skip" peptide motifs.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide, wherein the first polypeptide comprises: a homing endonuclease that is engineered to bind to a first target site in the CCR5 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, expression of the end-processing enzyme precedes that of the endonuclease.

In another aspect, the disclosure provides a method for treating or preventing or inhibiting hyper IGE syndrome or ameliorating a condition associated with hyper IGE syndrome a subject, the method comprising: (a) introducing, into one or more cells, a nucleic acid encoding a polypeptide, wherein the polypeptide comprises: (i) a homing endonuclease domain that is engineered to bind to a first target site in the Stat3 gene; and (ii) a end-processing domain under conditions such that the polypeptide is expressed in the cell, whereby the polypeptide binds to the target site and cleaves the Stat3 gene and modifies the exposed DNA ends created at the endonuclease cleavage site. In certain embodiments, the end-processing enzyme domain comprises an exonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a first nucleic acid encoding a first polypeptide, wherein the first polypeptide comprises: a homing endonuclease that is engineered to bind to a first target site in the STAT3 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the expression of the end-processing enzyme precedes that of the endonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a nucleic acid encoding a first polypeptide and a second polypeptide, wherein the first polypeptide comprises a homing endonuclease that is engineered to bind to a first target site in the STAT3 gene and the second polypeptide comprises a end-processing enzyme; under conditions such that the polypeptides are co-expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the homing endonuclease and the end-processing enzyme are coupled by one or more T2A "skip" peptide motifs.

BRIEF DESCRIPTION OF THE DRAWINGS

FIGS. 6A and 6B shows the results of DNA sequencing of amplicons surrounding the I-SceI target site in HEK293 Traffic Light Reporter cells treated with I-SceI-IRES-BFP or I-SceI-T2A-Trex2-IRES-BFP.

FIG. $17A_1$ and FIG. $17A_2$ show representative flow plots of HEK293 Traffic Light Reporter cells following co-transfection of I-SceI-IRES-BFP and an expression plasmid coding for the indicated end-processing enzyme.

DETAILED DESCRIPTION

Definitions

Figure 1A:
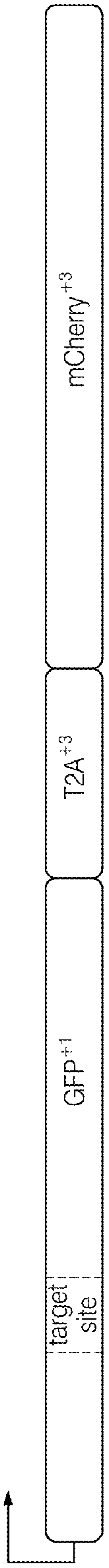
FIG. 1A shows a schematic of the Traffic Light Reporter system (TLR) for measuring the effectiveness of exonuclease induced gene disruption. mCherry positive cells represent a proportion of the total cells that have undergone gene disruption.
Figure 1B:
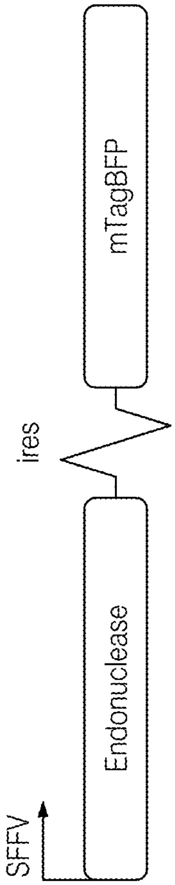
FIGS. 1B-1H show schematic representations of expression vectors for delivery of endonucleases and DNA end-processing enzymes.
Figure 1C:
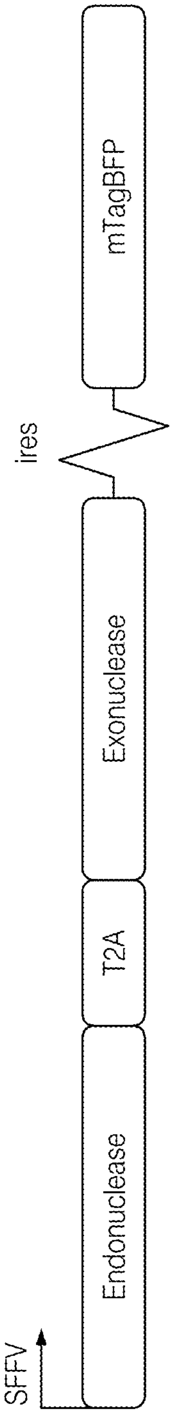
Figure 1D:
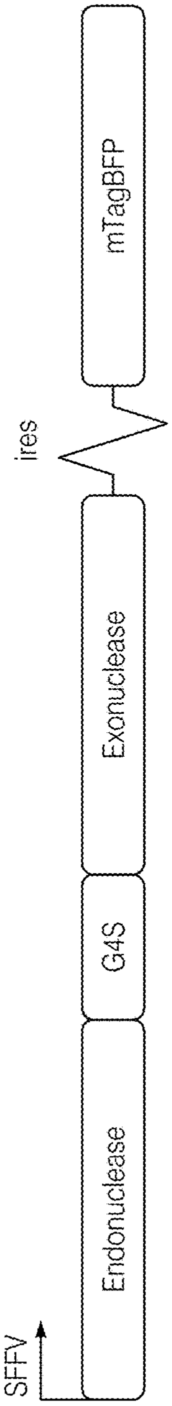
Figure 1E:
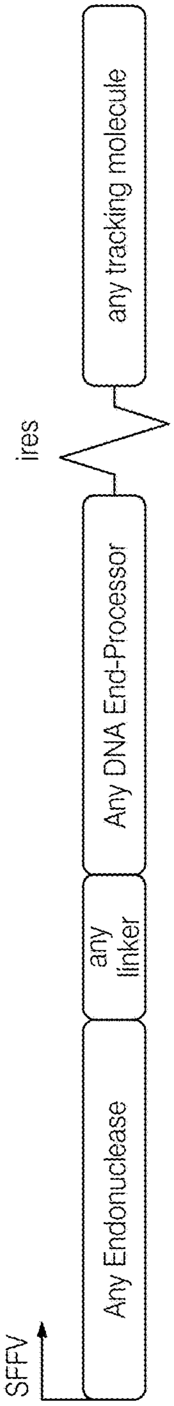
Figure 1F:
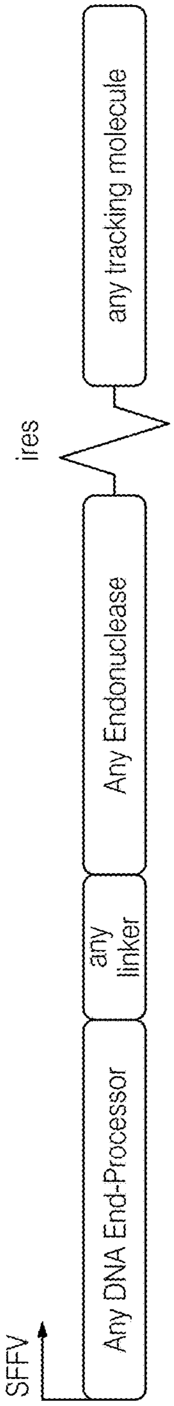
Figure 1G:
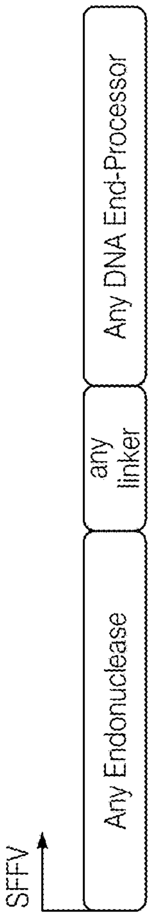
Figure 1H:
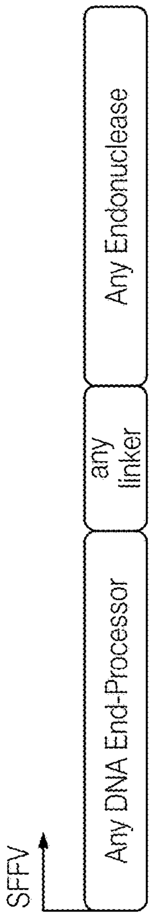

In the description that follows, a number of terms are used extensively. The following definitions are provided to facilitate understanding of the present embodiments.

As used herein, "a" or "an" may mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (e.g., GAU and GAC triplets each encode Asp). It will be understood that, as a result of the degeneracy of the genetic code, a multitude of nucleotide sequences encoding a given protein such as an endonuclease, end-processing enzyme, or endonuclease/end-processing enzyme fusion protein of the present embodiments may be produced.

The term "complementary to" means that the complementary sequence is homologous to all or a portion of a reference polynucleotide sequence. For illustration, the nucleotide sequence "CATTAG" corresponds to a reference sequence "CATTAG" and is complementary to a reference sequence "GTAATC."

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another non-limiting example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art may also use the term "cDNA" to refer to a double-stranded DNA molecule consisting of such a single-stranded DNA molecule and its complementary DNA strand. The term "cDNA" may also refer to a clone of a cDNA molecule synthesized from an RNA template.

A "promoter" is a nucleotide sequence that directs the transcription of a structural gene. In some embodiments, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, Gene Expr. 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). As used herein, a promoter may be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (e.g., endogenous DNA) so long as that host DNA is combined with non-host DNA (e.g., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptide components, such as carbohydrate groups. Carbohydrates and other non-peptide substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present embodiments, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, plastome, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transduced with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, "transient transfection" refers to the introduction of exogenous nucleic acid(s) into a host cell by a method that does not generally result in the integration of the exogenous nucleic into the genome of the transiently transfected host cell.

By the term "host cell" is meant a cell that contains one or more nucleases, for example endonucleases, end-processing enzymes, and/or endonuclease/end-processing enzyme fusion proteins encompassed by the present embodiments or a vector encoding the same that supports the replication, and/or transcription or transcription and translation (expression) of one or more nucleases, for example endonucleases, end-processing enzymes, and/or endonuclease/end-processing enzyme fusion proteins. Host cells for use in the present invention can be prokaryotic cells or eukaryotic cells. Examples of prokaryotic host cells include, but are not limited to *E. coli*, nitrogen fixing bacteria, *Staphylococcus aureus, Staphylococcus albus, Lactobacillus acidophilus, Bacillus anthracis, Bacillus subtilis, Bacillus thuringiensis, Clostridium tetani, Clostridium botulinum, Streptococcus mutans, Streptococcus pneumoniae*, mycoplasmas, and cyanobacteria. Examples of eukaryotic host cells include, but are not limited to, protozoa, fungi, algae, plant, insect, amphibian, avian and mammalian cells.

"Integrative transformants" are recombinant host cells, in which heterologous DNA has become integrated into the genomic DNA of the cells.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, e.g., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, or alternatively glycosylated or derivative forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "gene expression" refers to the biosynthesis of a gene product. For example, in the case of a structural gene, gene expression involves transcription of the structural gene into mRNA and the translation of mRNA into one or more polypeptides.

The term "endonuclease" refers to enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases.

The term "homing endonuclease" refers to double stranded DNases that have large, asymmetric recognition sites (12-40 base pairs). Homing endonuclease recognition sites are extremely rare. For example, an 18 base pair recognition sequence will occur only once in every $7\times10^{10}$ base pairs of random sequence. This is equivalent to only one site in 20 mammalian-sized genomes. Unlike standard restriction endonucleases, however, homing endonucleases tolerate some sequence degeneracy within their recognition sequence. As a result, their observed sequence specificity is typically in the range of 10-12 base pairs. Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. Examples of homing endonucleases include, but are not limited to, I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII. Their recognition sequences are known. The specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66. The methods and compositions described herein may be applied to cleavage sites generated by homing endonucleases.

The term "TAL effector nuclease" (TALEN) refers to a nuclease comprising a TAL-effector domain fused to a nuclease domain. TAL-effector DNA binding domains, isolated from the plant pathogen *Xanthomonas* have been described (see Boch et al., (2009) Science 29 Oct. 2009 (10.1126/science.117881) and Moscou and Bogdanove, (2009) Science 29 Oct. 2009 (10.1126/science.1178817)). These DNA binding domains may be engineered to bind to a desired target and fused to a nuclease domain, such as the Fok1 nuclease domain, to derive a TAL effector domain-nuclease fusion protein. The methods and compositions described herein may be applied to cleavage sites generated by TAL effector nucleases.

The term "Zinc-finger nuclease" (ZFN) refers to artificial restriction enzymes generated by fusing a zinc finger DNA-binding domain to a DNA-cleavage domain. Zinc finger domains can be engineered to bind to a desired target site. In some embodiments, the cleavage domain comprises the non-specific cleavage domain of FokI. In other embodiments, the cleavage domain comprises all or an active portion of another nuclease. In some embodiments, the cleavage domain may comprise Trex2 or an active fragment thereof. The methods and compositions described herein may be applied to cleavage sites generated by zinc-finger nucleases The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. A end-processing enzyme may modify may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents. DNA end-processing enzyme may modify exposed DNA ends by adding one or more nucleotides, removing one or more nucleotides, removing or modifying a phosphate group and/or removing or modifying a hydroxyl group. Non-limiting examples of types of DNA end-processing enzymes include 5-3' exonucleases, 5-3' alkaline exonucleases, 3-5' exonucleases, 5' flap endonucleases, helicases, phosphatases, hydrolases and template-independent DNA polymerases. Examples of DNA end-processing enzymes include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgsl, Sae2, CtIP, Pol mu, Pol lambda, MUS81, EME1, EME2, SLX1, SLX4 and UL-12. Many DNA end-processing enzymes are highly conserved throughout evolution, and thus likely to function in several different species. Further, homologues of DNA end-processing enzymes may be readily identifiable in organisms of biotechnological interest, including plants, animals, and algae. Contemplated herein are methods of modifying DNA end-processing enzymes to optimize activity or processivity.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8 (Yoon J-H, et al., Characterization of the 3' to 5' exonuclease activity found in human nucleoside diphosphate kinase 1 (NDK1) and several of its homologues. *Biochemistry* 2005: 44(48):15774-15786), WRN (Ahn, B., et al., Regulation of WRN helicase activity in human base excision repair. *J. Biol. Chem.* 2004, 279:53465-53474) and Three prime repair exonuclease 2 (Trex2) (Mazur, D. J., Perrino, F. W., Excision of 3' termini by the Trex1 and TREX2 3'->5' exonucleases. Characterization of the recombinant proteins. *J. Biol. Chem.* 2001, 276:17022-17029). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "target site" or "target sequence" refers to a nucleic acid sequence that defines a portion of a nucleic acid to which a binding molecule will bind, provided sufficient conditions for binding exist. For example, the target sites for several homing endonucleases are shown in Table 1.

TABLE 1

Examples of Homing Endonucleases and their Target Sites.

| Homing Endonucleases | Target |
|---|---|
| I-SceI | TAGGGATAACAGGGTAAT (SEQ ID No. 1) |
| I-LtrI | AATGCTCCTATACGACGTTTAG (SEQ ID No. 2) |
| I-GpiI | TTTTCCTGTATATGACTTAAAT (SEQ ID No. 3) |
| I-GzeI | GCCCCTCATAACCCGTATCAAG (SEQ ID No. 4) |
| I-xMpeMI | TAGATAACCATAAGTGCTAAT (SEQ ID No. 5) |
| I-PanMI | GCTCCTCATAATCCTTATCAAG (SEQ ID No. 6) |
| I-CreI | TCAAAACGTCGTGAGACAGTTTGG (SEQ ID No. 7) |
| I-OnuI | TTTCCACTTATTCAACCTTTTA (SEQ ID No. 8) |
| I-HjeMI | TTGAGGAGGTTTCTCTGTTAAT (SEQ ID No. 9) |
| I-AniI | TGAGGAGGTTTCTCTGTAAA (SEQ ID No. 10) |

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a host cell as a single protein. A fusion protein can comprise at least part of one polypeptide fused with another polypeptide. In some embodiments, a fusion protein can comprise at least a part of one polypeptide fused with at least a part of the same polypeptide. One example of a fusion protein is monomorized Trex2 (at least a part of Trex2 fused to at least a part of Trex2).

The term "endonuclease/end-processing enzyme fusion protein" or "fusion protein having endonuclease and end-processing activity" refers to an enzyme, which has an endonuclease catalytic domain and an end-processing catalytic domain and exhibits endonuclease and end-processing activity.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., an endonuclease domain, a polynucleotide binding domain, such as a DNA-binding domain, or an end-processing domain).

"Prokaryotic" cells lack a true nuclease. Examples of prokaryotic cells are bacteria (e.g., cyanobacteria, *Lactobacillus acidophilus*, Nitrogen-Fixing Bacteria, *Helicobacter pylori, Bifidobacterium, Staphylococcus aureus, Bacillus anthrax, Clostridium tetani, Streptococcus pyogenes, Staphylococcus pneumoniae, Klebsiella pneumoniae* and *Escherichia coli*) and archaea (e.g., Crenarchaeota, Euryarchaeota, and Korarchaeota).

"Eukaryotic" cells include, but are not limited to, algae cells, fungal cells (such as yeast), plant cells, animal cells, mammalian cells, and human cells (e.g., T-cells).

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

"Algae" are predominantly aquatic organisms that carry out oxygen-evolving photosynthesis but lack specialized water-conducting and food-conducting tissues. Algae may be unicellular or multicellular. Algae may be adapted to live in salt water, fresh water and on land. Example of algae include, but are not limited to, diatoms, chlorophyta (for example, volvox, spirogyra), euglenophyta, dinoflagellata, chrysophyta, phaephyta (for example, fucus, kelp, sargassum), and rhodophyta (for example, lemanae).

The term "subject" as used herein includes all members of the animal kingdom including non-human primates and humans.

Overview

Several embodiments described herein relate to a method of improving the rate of gene disruptions caused by imprecise repair of DNA double-strand breaks. In some embodiments, DNA end-processing enzymes are provided to enhance the rate of gene disruption. Some aspects of the present embodiments include, without limitation, enhanced rates of DNA end-processing enzyme-mediated processing of DNA ends at the site of a double-strand break.

Targeted DNA double-strand breaks introduced by rare-cleaving endonucleases can be harnessed for gene disruption applications in diverse cell types by engaging non-homologous end joining DNA repair pathways. However, endonucleases create chemically clean breaks that are often subject to precise repair, limiting the efficiency of targeted gene disruption. Several embodiments described herein relate to a method of improving the rate of targeted gene disruptions caused by imprecise repair of endonuclease-induced site-specific DNA double-strand breaks. In some embodiments, site specific endonucleases are coupled with end-processing enzymes to enhance the rate of targeted gene disruption. Coupling may be, for example, physical, spatial, and/or temporal.

Some aspects of the present embodiments include, without limitation, enhanced rates of end-processing enzyme-mediated processing of endonuclease-produced DNA ends, leading to enhanced targeted gene disruption at the genomic target site. Using this strategy, embodiments described herein show over 25 fold increased endonuclease-induced disruption rates. Certain embodiments described herein can achieve complete knockout of a target gene within a population. This technology further has the potential to dramatically increase the utility of rare-cleaving endonucleases for genetic knockout applications. Improving the mutation rate associated with endonucleases facilitates endonuclease engineering, as enzymes with different levels of activity can be utilized. In some embodiments, endo-end-processor coupling is used modify DNA ends for endonuclease-induced genome engineering. In some embodiments, expression of exonucleases capable of processive 5' end resection coupled with manipulation of the DNA repair environment can be used to enhance homologous recombination-mediated gene targeting.

Not to be bound by any particular theory, the resolution of a double-strand DNA breaks by "error-prone" non-homologous end-joining (NHEJ) can be harnessed to create targeted disruptions and genetic knockouts, as the NHEJ process can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, and ligates ends back together with minimal processing. As the DNA breaks created by designer endonuclease platforms (zinc-finger nucleases (ZFNs), TAL effector nucleases (TALENs), and homing endonucleases (HEs)) all leave chemically clean, compatible overhang breaks that do not require processing prior to ligation, they are excellent substrates for precise repair by the cNHEJ pathway. In the absence or failure of the classical NHEJ pathway to resolve a break, alternative NHEJ pathways (altNHEJ) can substitute: however, these pathways are considerably more mutagenic.

Not to be bound by any particular theory, modification of DNA double-strand breaks by end-processing enzymes may bias repair towards an altNHEJ pathway. Further, different subsets of end-processing enzymes may enhance disruption by different mechanisms. For example, Trex2, an exonuclease that specifically hydrolyzes the phosphodiester bonds which are exposed at 3' overhangs, biases repair at break sites toward mutagenic deletion. By contrast, terminal deoxynucleotidyl transferase (TdT), a non-templative polymerase, is expected to bias repair at break sites toward mutagenic insertions by promoting the addition of nucleotide bases to alter DNA ends prior to ligation. Accordingly, one of skill in the art may use end-processing enzymes with different activities to provide for a desired engineering outcome. Further one of skill in the art may use synergy between different end-processing enzymes to achieve maximal or unique types of knockout effects.

Several embodiments described herein couple DNA breaks created by endonucleases with end-processing enzymes is a robust way to improve the rates of targeted disruption in a variety of cell types and species, without associated toxicity to the host. This is an important advance at least because: 1) Double-strand breaks (DSBs) trigger cell cycle checkpoints to arrest division until the break has been resolved; in the case of a "persistent break" (a repetitive cycle of cleaving and precise repair), cells may arrest indefinitely, leading to apoptosis. 2) Engineering applications often utilize transient delivery of an endonuclease, providing only a short window in which enzyme concentration is sufficient to achieve breaks. 3) Persistent breaks can be a source of translocations. Coupling endonucleases to end-processing enzymes prevents the establishment of a persistent break and reduces the incidence of gross chromosomal rearrangements, thereby potentially improving the safety of endonuclease-induced targeted disruption. 4) Multiple changes in a single round of mutagenesis may be achieved, for use for example, in multi-allelic knockouts and multiplexing, as data described herein suggests that coupling endonucleases to end-processing enzymes improves the mutagenic rate of two given endonucleases 5-fold at their respective targets, a 25-fold improvement may be realized in disrupting both targets simultaneously.

Any suitable method may be used to provide endonucleases, end-processing enzymes, and/or fusion proteins having endonuclease and end-processing activity to host cells. In some embodiments one or more polypeptides having endonuclease and/or end-processing activity may be provided directly to cells. In some embodiments, expression of endonucleases, end-processing enzymes and/or fusion proteins having endonuclease and end-processing activity in a host cell can result from delivery of one or more polynucleotides encoding one or more endonucleases, end-processing enzymes, and/or fusion proteins having endonuclease and end-processing activity to the host cell. In some embodiments, one or more polynucleotides is a DNA expression vector. In some embodiments, one or more polynucleotides is an RNA expression vector. In some embodiments, trans-splicing, polypeptide cleavage and/or polypeptide ligation can be involved in expression of one or more proteins in a cell. Methods for polynucleotide and polypeptide delivery to cells are well known in the art.

The compositions and methods described herein are useful for generating targeted disruptions of the coding sequences of genes and in some embodiments, creating gene knockouts. Targeted cleavage by the compositions and methods described herein can also be used to alter non-coding sequences (e.g., regulatory sequences such as promoters, enhancers, initiators, terminators, splice sites) to alter the levels of expression of a gene product. Such methods can be used, for example, for biological research, for biotechnology applications such as crop modification, for therapeutic purposes, functional genomics, and/or target validation studies.

Targeted mutations resulting from the methods and compositions described herein include, but are not limited to, point mutations (e.g., conversion of a single base pair to a different base pair), substitutions (e.g., conversion of a plurality of base pairs to a different sequence of identical length), insertions of one or more base pairs, deletions of one or more base pairs and any combination of the aforementioned sequence alterations.

Some embodiments relate to coupling the activity of one or more site-specific endonucleases with one or more end-processing enzymes. In some embodiments, the endonucleases and end-processing enzymes are provided as separate proteins. In some embodiments, the endonucleases and end-processing enzymes are co-expressed in a cell. If expression of the separate endonucleases and end-processing enzymes is by polynucleotide delivery, each of the endonucleases and end-processing enzymes can be encoded by separate polynucleotides, or by a single polynucleotide.

In some embodiments, the endonucleases and end-processing enzymes are encoded by a single polynucleotide and expressed by a single promoter. In some embodiments, an endonuclease and end-processing enzymes are linked by a T2A sequence which allows for two separate proteins to be produced from a single translation. In some embodiments, a different linker sequence can be used. In other embodiments a single polynucleotide encodes the endonucleases and end-processing enzymes separated by an Internal Ribosome Entry Sequence (IRES).

Several embodiments relate to coupling the activity of one or more site-specific endonucleases selected from the group consisting of: homing endonucleases (meganucleases) (including engineered homing edonucleases), zinc finger nucleases, and TAL effector nucleases with one or more end-processing enzymes. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion). In some embodiments, the endonucleases and end-processing enzymes are provided as a fusion protein. In some embodiments, the endonucleases and end-processing enzymes are provided as separate proteins. In some embodiments, the endonucleases and end-processing enzymes are co-expressed in a cell.

Several embodiments relate to coupling the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgsl, Sae2, CtIP, Pol mu, Pol lambda, MUS81, EME1, EME2, SLX1, SLX4 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Several embodiments relate to coupling the activity of one or more ZFNs with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgsl, Sae2, CtIP, Pol mu, Pol lambda, MUS81, EME1, EME2, SLX1, SLX4 and UL-12. In some embodiments, the ZFNs and DNA end-processing enzymes are provided as a fusion protein. In some embodiments, the ZFNs and DNA end-processing enzymes are provided as separate proteins. In some embodiments, the ZFNs and DNA end-processing enzymes are co-expressed in a host cell.

Several embodiments relate to coupling the activity of one or more TALENs with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgsl, Sae2, CtIP, Pol mu, Pol lambda, MUS81, EME1, EME2, SLX1, SLX4 and UL-12. In some embodiments, the TALENs and DNA end-processing enzymes are provided as a fusion protein. In some embodiments, the TALENs and DNA end-processing enzymes are provided as separate proteins. In some embodiments, the TALENs and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Apollo, Artemis, Dna2, Exo1, Mre11, Rad2, RecE, Lambda exonuclease, Sox, exonuclease VII, T7-exonuclease Gene 6 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Sox and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Trex2, Vaccinia DNA polymerase, Mre11, exonuclease I, exonuclease III, NDK1, NDK5, NDK7, NDK8, and WRN. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of Fen1. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of TdT. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Some embodiments relate to coupling the activity of multiple site-specific endonucleases with the activity of one or more end-processing enzymes. The site specific endonucleases may cleave target sites within the same gene or in different genes. In some embodiments, 1, 2, 3, 4, 5, 6, 7, 8, 9, or 10 site-specific endonucleases may be provided to a cell along with one or more end-processing enzymes. In some embodiments, a combination of homing endonucleases, zinc finger endonucleases, and/or TAL effector endonucleases may be provided to a cell with one or more end-processing enzymes. In some embodiments, the end-processing enzyme is an exonuclease. In some embodiments, a 5' and a 3' exonuclease may be provided. If expression of the multiple endonucleases and one or more exonucleases is by polynucleotide delivery, each of the endonucleases and exonucleases can be encoded by separate polynucleotides, or by a single polynucleotide. In some embodiments, the endonucleases and exonucleases are encoded by a single polynucleotide and expressed by a single promoter. In some embodiments, the endonucleases and exonucleases are linked by a T2A sequence which allows for separate proteins to be produced from a single translation. In some embodiments, different linker sequences can be used. In other embodiments, a single polynucleotide encodes the endonucleases and exonucleases separated by IRESs.

Several embodiments relate to a heterologous fusion protein, which comprises an endonuclease domain and an end-processing domain or portions thereof. Several embodiments relate to a heterologous fusion construct, which encodes a fusion protein having endonuclease and end-processing activity. The present embodiments also relate to vectors and host cells comprising the heterologous fusion construct as well as methods for producing a fusion protein having endonuclease and end-processing activity and compositions thereof. In one embodiment, the endonuclease domain is coupled to the end-processing domain by recombinant means (e.g., the fusion protein is generated by translation of a nucleic acid in which a polynucleotide encoding all or a portion of a endonuclease is joined in-frame with a polynucleotide encoding all or a portion of a end-processing enzyme). In other embodiments, the endonuclease domain and end-processing domain of a fusion protein may be linked chemically. This chemical linkage can be carried out, for example, by using bifunctional linker molecules, such as, BS3 (Bis[sulfosuccinimidyl] suberate).

Some embodiments relate to a fusion protein comprising an endonuclease domain and exonuclease domain. In some embodiments the fusion protein comprises at least a fragment or variant of a homing endonuclease and at least a fragment or variant of an exonuclease, for example a 3' exonuclease, which are associated with one another by genetic or chemical conjugation to one another. In several embodiments, the 3' exonuclease is a Trex2 monomer, dimer, or a variant thereof. In other embodiments, the fusion protein comprises at least a fragment or variant of a zinc finger endonuclease and at least a fragment or variant of a 5' exonuclease, which are associated with one another, by genetic fusion or chemical conjugation to one another. The endonuclease and exonuclease, once part of the fusion protein, may be referred to as a “portion”, “region,” “domain” or “moiety” of the endo/exo-nuclease fusion protein.

In some embodiments, an end-processing enzyme (or fragment or variant thereof) is fused directly to an endonuclease (or fragment or variant thereof). The end-processing enzyme (or fragment or variant thereof) may be fused to the amino terminus or the carboxyl terminus of the endonuclease (or fragment or variant thereof).

An endonuclease/end-processing enzyme fusion protein may optionally include a linker peptide between the endonuclease and end-processing enzyme domains to provide greater physical separation between the moieties and thus maximize the accessibility of the endonuclease portion, for instance, for binding to its target sequence. The linker peptide may consist of amino acids selected to make it more flexible or more rigid depending on the relevant function. The linker sequence may be cleavable by a protease or cleavable chemically to yield separate endonuclease and end-processing enzyme moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the endonuclease moiety with respect to the end-processing enzyme moiety so that the endonuclease domain can recognize and cleave its target sequence and the end-processing domain can modify the DNA ends exposed at the cleavage site. The linker may also be a simple amino acid sequence of a sufficient length to prevent any steric hindrance between the endonuclease domain and the end-processing domain. In addition, the linker sequence may provide for post-translational modification including, but not limited to, e.g., phosphorylation sites, biotinylation sites, sulfation sites, 7-carboxylation sites, and the like.

In some embodiments the linker sequence comprises from about 4 to 30 amino acids, more preferably from about 8 to 22 amino acids. That is, the linker sequence can be any number of amino acids from about 4 to 30, such as at least or equal to 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a T2A linker sequence allows for two separate proteins to be produced from a single translation. Suitable linker sequences can be readily identified empirically. Additionally, suitable size and sequences of linker sequences also can be determined by conventional computer modeling techniques.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are well known in the art.

A variety of DNA molecules encoding the above-described endonucleases, end-processing enzymes and fusion proteins may be constructed for providing the selected proteins or peptides to a cell. The DNA molecules encoding the endonucleases, end-processing enzyme, and fusion proteins may be modified to contain different codons to optimize expression in a selected host cell, as is known in the art.

A variety of RNA molecules encoding the above-described endonucleases, end-processing enzymes and fusion proteins may be constructed for providing the selected proteins or peptides to a cell. The RNA molecules encoding the endonucleases, end-processing enzyme, and fusion proteins may be modified to contain different codons to optimize expression in a selected host cell, as is known in the art.

Several embodiments relate to the prevention of precise cNHEJ mediated repair of endonuclease-induced double strand breaks by simultaneous expression of end-processing enzymes capable of recognizing the post-endonuclease break structure, resulting in the modification of DNA ends prior to ligation, promoting a mutagenic outcome. Some embodiments relate to the simultaneous expression exonucleases capable of recognizing the post-endonuclease break structure, resulting in the trimming of DNA ends prior to ligation, promoting a mutagenic outcome. Simultaneous expression of a site-specific endonuclease and an end-processing enzyme improves the efficiency of targeted gene disruption by up to ~70 fold, essentially fixing a mutagenic outcome in 100% of a population of cells containing the target site in less than 72 hours.

In some embodiments, effective amounts of endonucleases and end-processing enzymes or an effective amount of a fusion protein are delivered to a cell either directly by contacting the cell will the protein(s) or by transient expression from an expression construct. In such embodiments, cell division reduces the concentration of the nucleases to sub-active levels within a few cell divisions.

Several embodiments relate to a method of conferring site specificity on a DNA end-processing enzyme by physically tethering an end-processing enzyme domain to a site specific DNA binding domain. In some embodiments, the end-processing enzyme domain is tethered to a DNA binding domain through a linker peptide. The composition and structure of the linker peptide is not especially limited and in some embodiments the linker may be chemically or enzymaticly cleavable. The linker peptide may be flexible or rigid and may comprise from about 4 to 30 amino acids. In other embodiments, the end-processing enzyme domain is chemically fused to a DNA binding domain. Not wishing to be bound by a particular theory, imparting site specificity to a end-processing enzyme through tethering the end-processing enzyme to a site specific DNA binding domain decreases toxicity associated with indiscriminate end-processing activity, such as exonuclease activity, and reduces the effective amount of end-processing enzyme required for efficient modification of the exposed double stranded DNA break caused by endonuclease activity compared to untethered end-processing enzyme. In some embodiments, the end-processing enzyme is tethered to a homing endonuclease. In other embodiments, the end-processing enzyme is tethered to zinc finger endonuclease. In some embodiments, an end-processing enzyme domain is tethered to a zinc finger DNA binding domain which binds to a DNA sequence adjacent to the cleavage site of a homing endonuclease or zinc finger endonuclease.

Figure 11A:
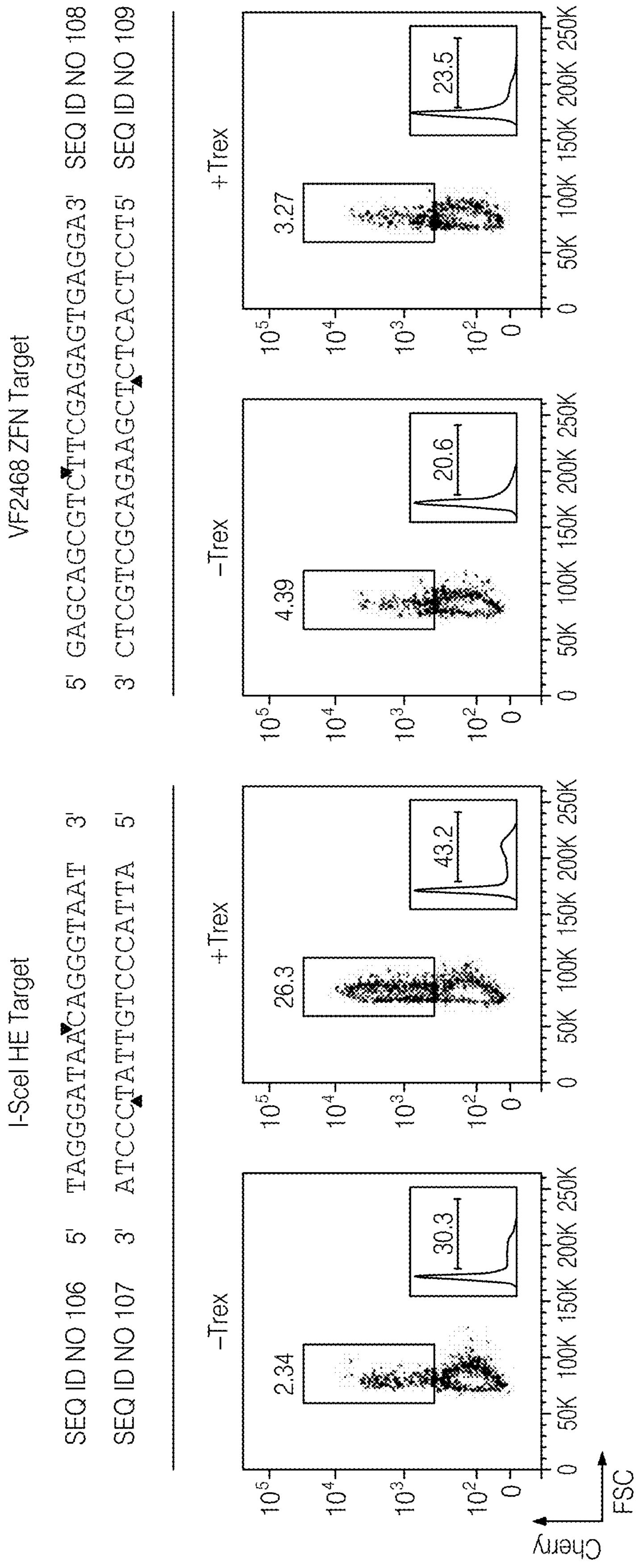
FIG. 11A shows representative flow plots and targets sites of HEK293 Traffic Light Reporter cells following transfection with a homing endonuclease with and without Trex2 and a zinc finger nuclease with and without Trex2.
Figure 11B:
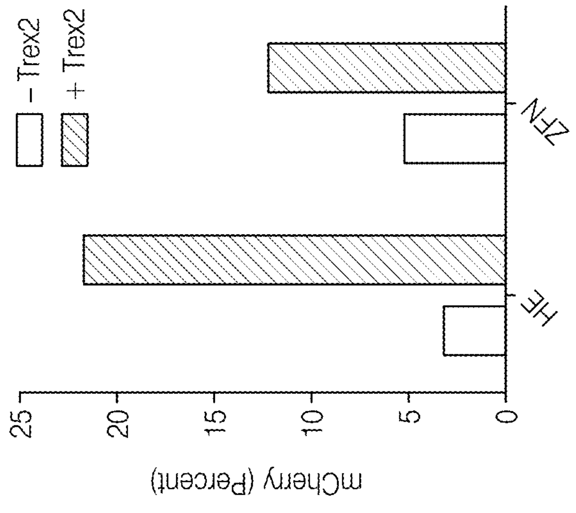
FIG. 11B shows a graph of an independent experiment examining cleavage site mutation for I-SceI and Zinc Finger Nuclease in the presence and absence of Trex2.
Figure 11C:
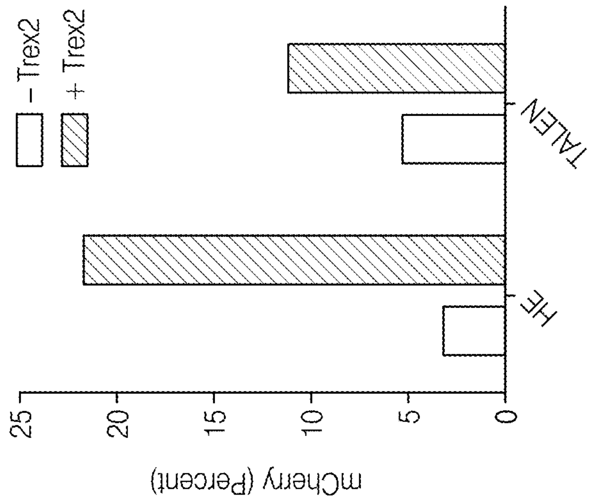
FIG. 11C shows a graph of HEK293 Traffic Light Reporter cells following co-transfection of an HE with Trex2 or a TALEN with Trex2.

Several embodiments relate to coupling the activity of one or more site-specific endonucleases with Trex2. Trex2 may be provided as a monomer or dimer. The Trex2 enzyme specifically hydrolyzes the phosphodiester bonds which are exposed at 3' overhangs. While the homing endonucleases generate 3' overhangs which are susceptible to Trex2 exonuclease activity, the zinc finger nucleases, which utilize the Fok1 cleavage domain, generate double strand DNA breaks with 5' overhangs. The homing endonucleases and zinc finger nucleases generate mutations at their cleavage sites at a baseline rate. Co-expression of Trex2 with homing endonucleases increased the mutation rate ~70 fold. Co-expression of Trex2 with zinc finger endonucleases was also observed to effect on the rate of mutation. See FIGS. 11A and 11B. Accordingly, several embodiments described herein relate to improving the mutation rate associated zinc finger endonuclease targeted cleavage events by coupling zinc finger endonuclease to exonucleases which cleave 5' overhangs. Some embodiments relate to coupling 3' exonucleases to zinc finger endonucleases wherein the nuclease domain of the zinc finger endonuclease generates 3' overhangs.

Some embodiments relate to the co-expression of a homing endonuclease and the exonuclease, Trex2, via a single promoter linked by a T2A sequence that enables separate polypeptides to be produced from a single translation event. In this way, the endonuclease and exonuclease are provided in a 1 to 1 ratio. Higher rates of modification are achieved using T2A linked expression of the homing endonuclease, I-SceI, and Trex2 than is achieved through co-transduction of separate I-SceI, and Trex2 expression constructs. In some embodiments, a fusion protein comprising one or more endonuclease domains and one or more Trex2 domains may be provided.

In another aspect, methods of co-expressing an end-processing enzyme with a zinc finger endonuclease capable of mutating the CCR-5 gene and/or inactivating CCR-5 function in a cell or cell line are provided. In some embodiments, a method for improving the inactivation of a CCR-5 gene in a human cell is provided, the method comprising administering to the cell any site specific endonuclease having a target site in a CCR5 coupled to an end-processing enzyme. In some embodiments, a method for improving the inactivation of a CCR-5 gene in a human cell is provided, the method comprising administering to the cell any site specific endonuclease having a target site in a CCR5 coupled to an exonuclease capable of cleaving the phosphodiester bonds created at the site of endonuclease cleavage. In some embodiments, a method for improving the inactivation of a CCR-5 gene in a human cell is provided, the method comprising administering to the cell any site specific endonuclease having a target site in a CCR5 and contemporaneously administering an exonuclease capable of cleaving the phosphodiester bonds created at the site of endonuclease cleavage. Examples of suitable endonucleases include engineered homing endonucleases and meganucleases, which have very long recognition sequences, some of which are likely to be present, on a statistical basis, once in a human-sized genome. Any such nuclease having a unique target site in a CCR5 gene can be used instead of, or in addition to, a zinc finger nuclease, in conjunction with an exonuclease for targeted cleavage in a CCR5 gene. Some embodiments relate to administration of a fusion protein comprising a CCR5-site-specific endonuclease and an exonuclease capable of cleaving the phosphodiester bonds created at the site of endonuclease cleavage.

Expression Vectors

Expression constructs can be readily designed using methods known in the art. Examples of nucleic acid expression vectors include, but are not limited to: recombinant viruses, lentiviruses, adenoviruses, plasmids, bacterial artificial chromosomes, yeast artificial chromosomes, human artificial chromosomes, minicircle DNA, episomes, cDNA, RNA, and PCR products. In some embodiments, nucleic acid expression vectors encode a single peptide (e.g., an endonuclease, an end-processing enzyme, or a fusion protein having endonuclease and end-processing activity). In some embodiments, nucleic acid expression vectors encode one or more endonucleases and one or more end-processing enzymes in a single, polycistronic expression cassette. In some embodiments, one or more endonucleases and one or more end-processing enzymes are linked to each other by a 2A peptide sequence or equivalent "autocleavage" sequence. In some embodiments, a polycistronic expression cassette may incorporate one or more internal ribosomal entry site (IRES) sequences between open reading frames. In some embodiments, the nucleic acid expression vectors are DNA expression vectors. In some embodiments, the nucleic acid expression vectors are RNA expression vectors.

In some embodiments, a nucleic acid expression vector may further comprise one or more selection markers that facilitate identification or selection of host cells that have received and express the endonuclease(s), end-processing enzyme(s), and/or fusion protein(s) having endonuclease and end-processing activity along with the selection marker. Examples of selection markers include, but are not limited to, genes encoding fluorescent proteins, e.g., EGFP, DS-Red, YFP, and CFP; genes encoding proteins conferring resistance to a selection agent, e.g., $Puro^R$ gene, $Zeo^R$ gene, $Hygro^R$ gene, $neo^R$ gene, and the blasticidin resistance gene. In some cases, the selection marker comprises a fluorescent reporter and a selection marker.

In some embodiments, a DNA expression vector may comprise a promoter capable of driving expression of one or more endonuclease(s), end-processing enzyme(s), and/or fusion protein(s) having endonuclease and end-processing activity. Examples of promoters include, but are not limited to, retroviral LTR elements; constitutive promoters such as CMV, HSV1-TK, SV40, EF-1a, β-actin; inducible promoters, such as those containing Tet-operator elements; and tissue specific promoters. Suitable bacterial and eukaryotic promoters are well known in the art and described, e.g., in Sambrook et al., Molecular Cloning, A Laboratory Manual (2nd ed. 2001); Kriegler, Gene Transfer and Expression: A Laboratory Manual (1990); and Current Protocols in Molecular Biology (2010). Non-limiting examples of plant promoters include promoter sequences derived from *A. thaliana* ubiquitin-3 (ubi-3).

In some embodiments, a nucleic acid encoding one or more endonucleases, end-processing enzymes, and/or fusion proteins having endonuclease and end-processing activity can be cloned into a vector for transformation into prokaryotic or eukaryotic cells. In some embodiments, nucleic acids encoding different endonucleases and end-processing enzymes are cloned into the same vector. In such cases, the nucleic acids encoding different endonucleases and end-processing enzymes may optionally be separated by T2A or IRES sequences. Vectors can be prokaryotic vectors, e.g., plasmids, or shuttle vectors, insect vectors, or eukaryotic vectors, including plant vectors described herein. Expression of the nucleases and fusion proteins may be under the control of a constitutive promoter or an inducible promoter.

Introduction of polypeptides having endonuclease and/or end-processing activity and/or polynucleotides encoding polypeptides having endonuclease and/or end-processing activity into host cells may use any suitable methods for nucleic acid or protein delivery as described herein or as would be known to one of ordinary skill in the art. The polypeptides and polynucleotides described herein can be delivered into cultured cells in vitro, as well as in situ into tissues and whole organisms. Introduction of the polypeptides and polynucleotides of the present embodiments into a host cell can be accomplished chemically, biologically, or mechanically. This may include, but is not limited to, electroporation, sonoporation, use of a gene gun, lipotransfection, calcium phosphate transfection, use of dendrimers, microinjection, polybrene, protoplast fusion, the use of viral vectors including adenoviral, AAV, and retroviral vectors, and group II ribozymes.

Organisms

The present invention is applicable to any prokaryotic or eukaryotic organism in which it is desired to create a targeted genetic mutation. Examples of eukaryotic organisms include, but are not limited to, algae, plants, animals (e.g., mammals such as mice, rats, primates, pigs, cows, sheep, rabbits, etc.), fish, and insects. In some embodiments, isolated cells from the organism can be genetically modified as described herein. In some embodiments, the modified cells can develop into reproductively mature organisms. Eukaryotic (e.g., algae, yeast, plant, fungal, piscine, avian, and mammalian cells) cells can be used. Cells from organisms containing one or more additional genetic modifications can also be used.

Examples of mammalian cells include any cell or cell line of the organism of interest, for example oocytes, somatic cells, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells and myeloma cells like SP2 or NSO. Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, muscle stem cells, skin stem cells, and neuronal stem cells.

Examples of target plants and plant cells include, but are not limited to, monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, *Avena, Brassica, Citrus, Citrullus, Capsicum, Cucurbita, Daucus*, Erigeron, Glycine, *Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, roots, etc. The present disclosure also encompasses seeds of the plants described above. The present disclosure further encompasses the progeny, clones, cell lines, or cells of the plants described.

Generating Homozygously Modified Organisms

Cells in which one or more endonucleases are co-expressed with one or more end-processing enzyme(s) and/or cells in which one or more fusion proteins having endonuclease and end-processing activity are expressed are then assayed for the presence of mutations at the endonuclease cleavage site(s). Such modified cells can be identified using any suitable method known to the skilled artisan, including sequencing, PCR analysis, southern blotting, and the like. In some embodiments, an amplicon spanning the endonuclease target site is generated by PCR. The amplicon is then exposed to the endonuclease and the ability of the endonuclease to cut the amplicon is assessed. Mutation of the target site is indicated by the absence of endonuclease generated cleavage products.

Subsequently, cells containing the mutated target site(s) are cultured or otherwise treated such that they generate a whole organism with the mutated target site. For example, traditional methods of pro-nuclear injection or oocyte injection can be used to generate animals with the mutated target site. Likewise, plant cells containing the mutated target site(s) can be cultured to regenerate a whole plant which possesses the mutant genotype and thus the desired phenotype. Regeneration can also be obtained from plant callus, explants, organs, pollens, embryos, or parts thereof. Once the heterozygous organisms containing the mutated target site(s) reach reproductive maturity, they can be crossed to each other, or in some instances, spores may be grown into haploids. Of the resulting progeny from crosses, approximately 25% will be homozygous mutant/mutant at the target locus.

Pharmaceutical Compositions and Administration

Endonucleases, end-processing enzymes and fusion proteins having endonuclease and end-processing activity and expression vectors encoding endonucleases, end-processing enzymes and fusion proteins having endonuclease and end-processing activity can be administered directly to a patient for targeted cleavage of a DNA sequence and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia and the like. In some embodiments, the compositions described herein (e.g., endonucleases, end-processing enzymes and fusion proteins having endonuclease and end-processing activity and expression vectors encoding endonucleases, end-processing enzymes and fusion proteins having endonuclease and end-processing activity) can be used in methods of treating, preventing, or inhibiting a disease (e.g., cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia) or ameliorating a disease condition or symptom associated with a disease, such as, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis or ameliorate a disease condition or symptom associated with an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a disease caused by misregulation of genes. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a cancer, such as BCL-2, Bcl-XI, and FLIP, or ameliorate a disease condition or symptom associated with a cancer, such as BCL-2, Bcl-XI, and FLIP, by, for example, increasing the mutation rate of genes with anti-apoptotic activity.

Examples of microorganisms that can be inhibited (e.g., inhibiting the growth or infection) by provision of endonucleases, end-processing enzymes and fusion proteins having endonuclease and end-processing activity include pathogenic bacteria, e.g., *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria; infectious fungus, e.g., *Aspergillus, Candida* species; protozoa such as sporozoa (e.g., Plasmodia), rhizopods (e.g., *Entamoeba*) and *flagellates*

(*Trypanosoma, Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing homing endonucleases or zinc finger endonucleases into ultimate contact with the tissue to be treated. The endonucleases, end-processing enzymes and fusion proteins having endonuclease and end-processing activity are administered in any suitable manner, and in some embodiments with pharmaceutically acceptable carriers. Suitable methods of administering such proteins or polynucleotides are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences).

The endonucleases, end-processing enzymes and fusion proteins having endonuclease and end-processing activity or vectors encoding endonucleases, end-processing enzymes and fusion proteins having endonuclease and end-processing activity, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Kits

Also provided are kits for performing any of the above methods. The kits typically contain one or more endonucleases, end-processing enzymes and/or fusion proteins having endonuclease and end-processing activity or expression vectors encoding endonucleases, end-processing enzymes and/or fusion proteins having endonuclease and end-processing activity as described herein. The kits may also contain a reporter construct, such as the mCherry+ reporter construct described herein, containing a cloning site for insertion of the target site for a selected endonuclease of interest. In some embodiments, kits may contain one or more plasmids according to SEQ ID NOs: 110-145. For example, kits for screening mutagenesis produced by coupled endonuclease and end-processing activity and/or fusion proteins with activity to a particular gene are provided with one or more reporter constructs containing the desired target site(s). Similarly, kits for enriching cells for a population of cells having a endonuclease-mediated genomic modification may comprise a reporter construct comprising a target site present in the genome of the cells and one or more endonuclease specific to the target site of interest and one or more selected end-processing enzymes and/or one or more fusion proteins specific to the target site of interest.

The kits can also contain cells, buffers for transformation of cells, culture media for cells, and/or buffers for performing assays. Typically, the kits also contain a label, which includes any material such as instructions, packaging or advertising leaflet that is attached to or otherwise accompanies the other components of the kit.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The present embodiments should therefore not be limited by the above described embodiment, method, and examples, but by all embodiments and methods within the scope and spirit of the present embodiments.

The following Examples are presented for the purposes of illustration and should not be construed as limitations.

Example 1

Co-Expression of the Homing Endonuclease, I-SceI, and Trex2 Exonuclease Increases the Rate at which I-SceI Induces Mutations To determine if coupling an exonuclease with a site-specific endonuclease could enhance targeted gene disruption efficiency, we assessed the effect of Trex2 on the mutagenic repair of DSBs generated by I-SceI. To ensure that Trex2 would be co-expressed with I-SceI, we developed expression vectors that drive coupled expression of both an endonuclease and an end-processing enzyme from a single promoter via a T2A "skip" peptide motif. We also included mTagBFP fluorescent protein co-expression by an internal ribosomal entry site (IRES) for tracking transfection efficiency.

To measure the rate of nuclease-induced targeted disruption, a mutNHEJ reporter construct (Traffic Light Reporter (TLR)) was constructed by placing the I-SceI target site, SEQ ID NO: 146 5'-AGTTACGCTAGGGATAACAGGGTAATATAG-3', in front of the mCherry fluorescent protein ORF in the +3 reading frame. See FIG. 1A. When an endonuclease-induced DNA cleavage event results in a frameshift into the +3 reading frame, the mCherry fluorescent protein is placed in frame and correctly translated, resulting in red fluorescent cells that may be easily detected by flow cytometry. HEK cell lines harboring the TLR were generated by plating $0.1\times10^6$ HEK293 cells 24 hrs prior to transduction in a 24 well plate. mutNHEJ (TLR) reporter cell lines were made by transducing HEK293 cells at limiting titer (~5%) with ~25 ngs of an integrating lentivirus containing the reporter construct with 4 ug/ml polybrene. Media was changed 24 hrs after transduction.

Expression vectors comprising the homing endonuclease, I-SceI, a fluorescent protein (BFP), and optionally Trex2 with either a T2A or G4S linker peptide were constructed according to the schematics provided in FIGS. 1B-H.

$0.1\times10^{6}$ HEK293 cells containing a genomically-integrated mutNHEJ (TLR) reporter cassette were plated 24 hrs prior to transfection in a 24 well plate. The HEK 293 cells were transfected with expression constructs comprising the I-SceI mutant D44A alone, the I-SceI mutant D44A coupled to Trex2 via a T2A linker, I-SceI alone or I-SceI coupled to Trex2 via a T2A linker using Fugene transfection reagent according to manufacture's protocol. 72 hours following transduction of the cell line with the expression vectors, the cells were analyzed by flow cytometry on a BD LSRII or BD FACS ARIAII. The mCherry fluorophore was excited using a 561 nm laser and acquired with a 610/20 filter. The mTagBFP fluorophore was excited on a 405 nm laser with a 450/50 filter. Data was analyzed using FlowJo software (FlowJo, Ashland OR).

Figure 2A:
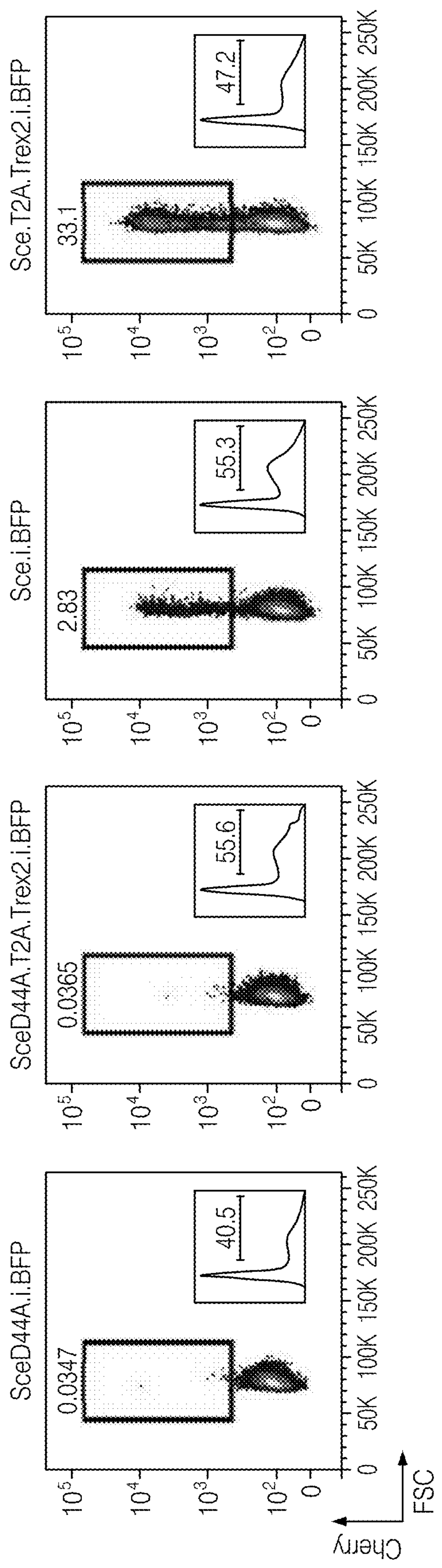
FIG. 2A shows representative flow plots of HEK293 cells harboring Traffic light Reporter transfected with expression vectors encoding SceD44A-IRES-BFP, SceD44A-T2A-Trex2-IRES-BFP, I-SceI-IRES-BFP, and I-SceI-T2A-Trex2-IRES-BFP. SceD44A corresponds to an inactive mutant form of I-SceI.
Figure 2B:
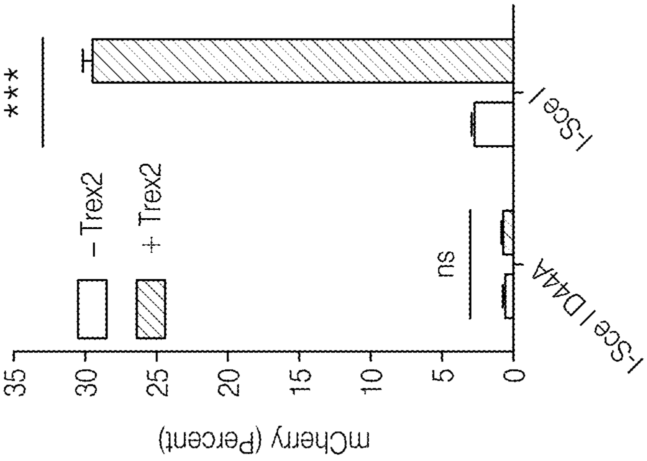
FIG. 2B shows quantification of gene disruption in three independent transfections of the vectors indicated in FIG. 2A. Error bars represent standard error of the mean (SEM), and p-values (with * representing $p<0.05$, $p<0.005$, and *$p<0.0005$) were calculated using the Student's two-tailed unpaired t-test to compare the samples indicated in this and all subsequent figures.

The plot shown in FIG. 2A demonstrates that I-SceI expression induced mutagenic NHEJ events as visualized by mCherry+ expression and that the rate of mutagenic NHEJ events (mCherry+) was significantly increased following co-expression of I-SceI with the exonuclease Trex2. See FIG. 2A. While neither I-SceI D44A (catalytically inactive) nor I-SceI D44A coupled to Trex2 was able to induce any measurable gene disruption, I-SceI coupled to Trex2 via T2A linkage exhibited a substantial increase in mCherry positive cells compared to I-SceI alone. See FIG. 2A.

Following co-expression of I-SceI endonuclease and Trex2 exonuclease, genomic DNA was extracted from the HEK 293 reporter cells using Qiagen's DNA easy kit. Amplicons spanning the I-SceI target site were generated by PCR, cloned into a shuttle vector and subjected to DNA sequencing of the I-SceI target site. The sequencing demonstrated that essentially every cell in the population contains a mutated I-SceI target site, as predicted by the reporter readout. See FIGS. 6A and 6B.

Figure 21A:
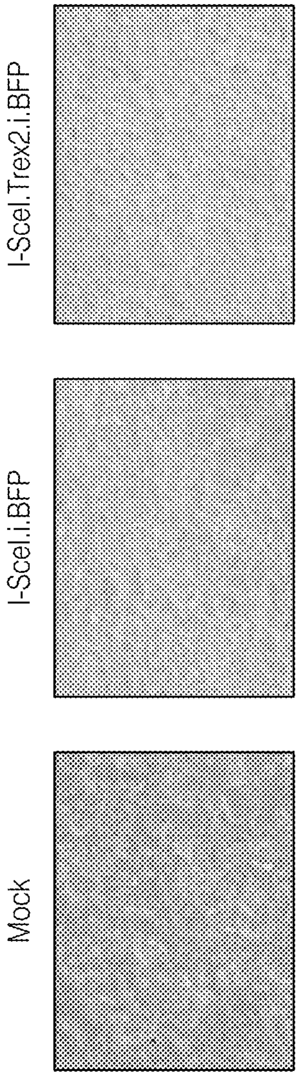
FIG. 21A shows live cell image of cells 72 hrs post mock transfection or transfection with an expression vectors encoding I-SceI-IRES-BFP or I-SceI-T2A-Trex2-IRES-BFP.
Figure 21B:
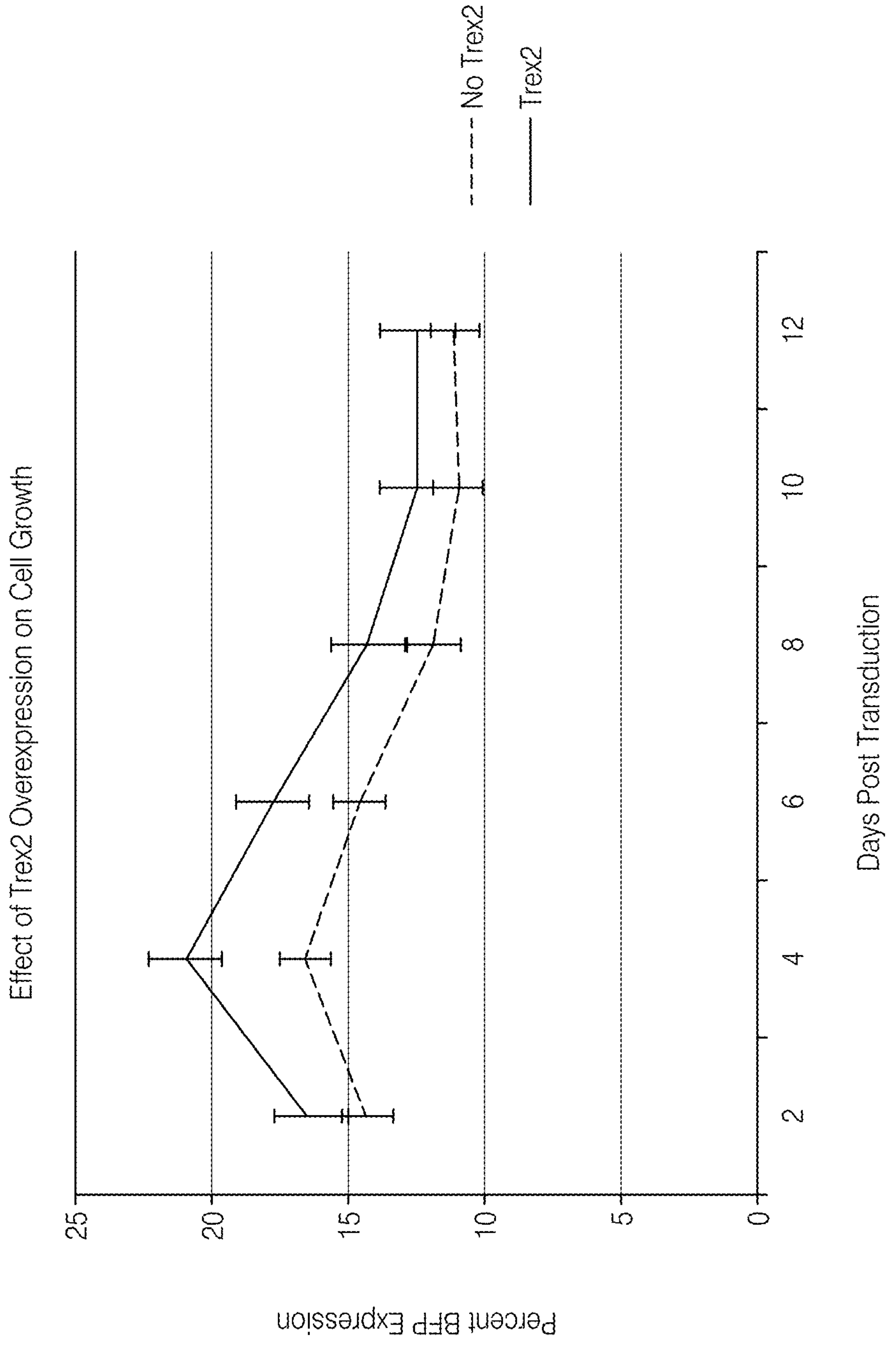
FIG. 21B shows a graph depicting maintenance of BFP expression in cells transduced with an integrating lentivirus containing BFP alone (no Trex2) or Trex2-BFP.

HEK 293 cells were transduced with expression constructs comprising the I-SceI mutant D44A alone, I-SceI alone or I-SceI coupled to Trex2 via a T2A linker. Following transduction of the cell line with the expression vectors, the cells were analyzed by visual inspection daily. Live cell images were taken 72 hours post transduction with the expression vectors. The cells treated in each manner appeared indistinguishable, and there is no overt toxicity associated with Trex2 co-expression. See FIG. 21B.

Figure 4A:
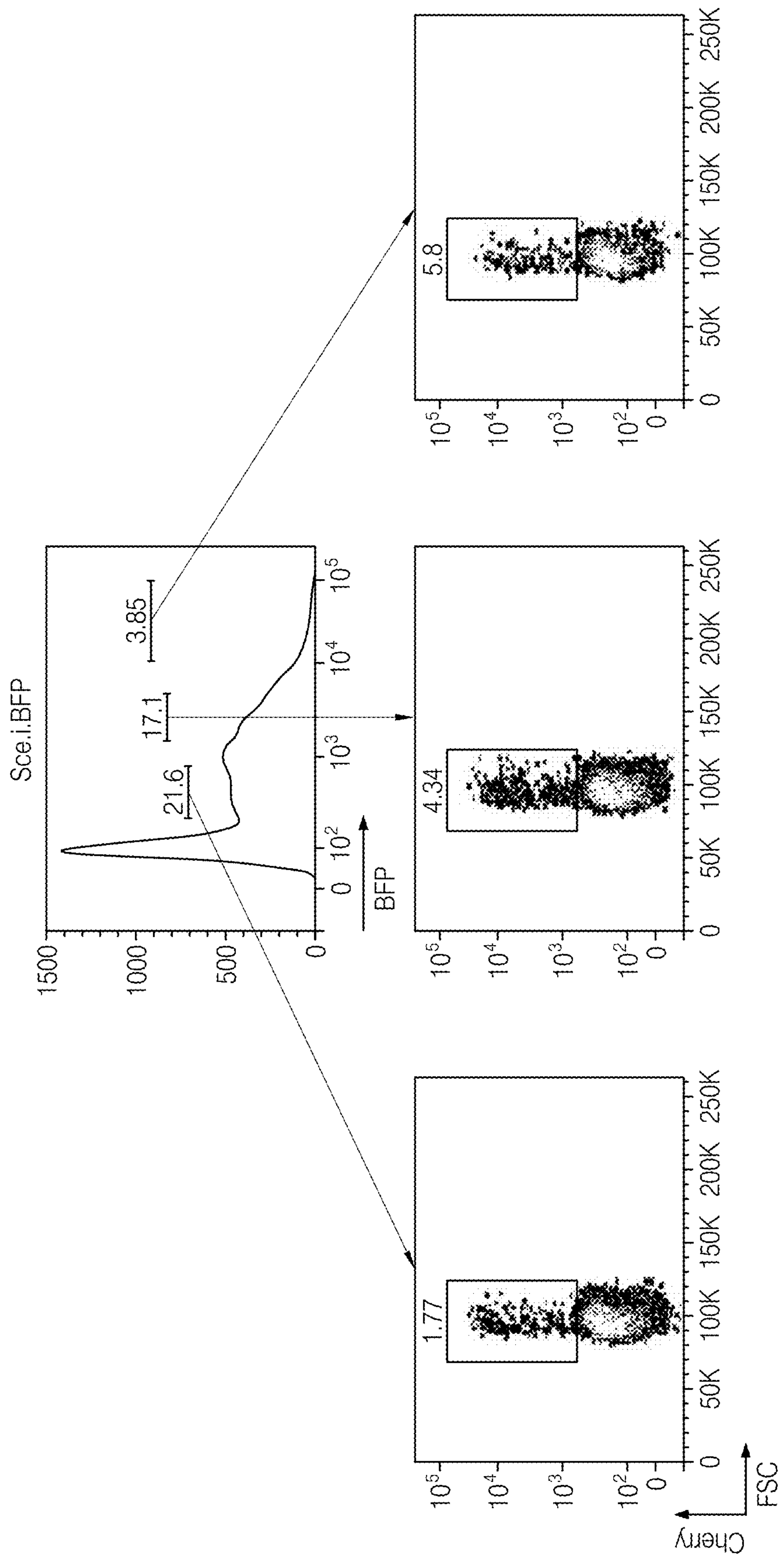
FIG. 4A shows gating analysis of HEK293 cells harboring Traffic Light Reporter transfected with I-SceI-IRES-BFP.
Figure 4B:
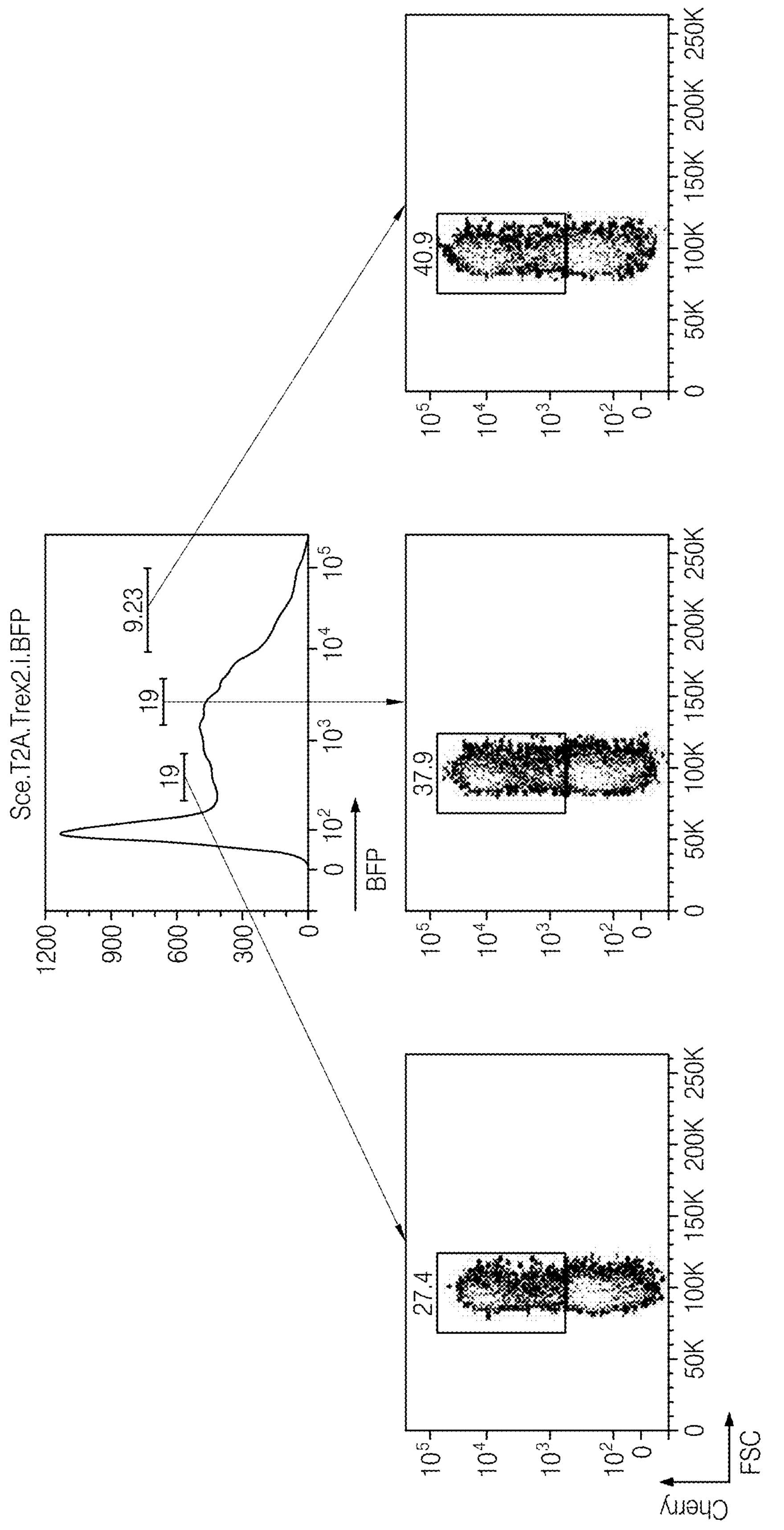
FIG. 4B shows a gating analysis of HEK293 cells harboring Traffic Light Reporter transfected with I-SceI-T2A-Trex2-IRES-BFP expression vectors.

To assess the total gene disruption rate, I-SceI and I-SceI-T2A-Trex2 transfected cells were sorted based on varying BFP expression levels. HEK 293 cells containing a genomically-integrated cassette corresponding to the targeted disruption reporter illustrated in FIG. 1A (TLR) were transduced with expression constructs comprising I-SceI-IRES-BFP (blue fluorescent protein) or I-SceI-T2A-Trex2-IRES-BFP. Expression of I-SceI-IRES-BFP and I-SceI-T2A-Trex2-IRES-BFP was measured in the transduced cells by a gating analysis of flow cytometry plots of BFP activity. Cells with low, low-medium, medium and high levels of BFP expression (corresponding to different levels of I-SceI endonuclease or I-SceI endonuclease/Trex2 exonuclease expression) were then assayed for induced mutagenic NHEJ events as visualized by mCherry+ expression. The data demonstrated that low levels of I-SceI alone resulted in lower mutation levels, while expression of I-SceI in combination with Trex2 result in high modification rates even at low levels of expression from the I-SceI-T2A-Trex2-IRES-BFP construct. See FIGS. 4A and 4B.

Figure 5A:
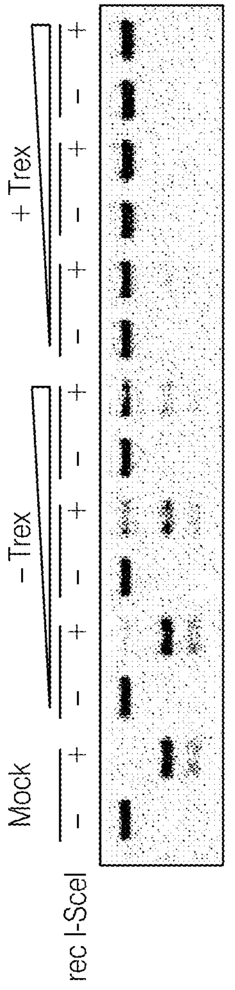
FIG. 5A shows an I-SceI restriction digest of amplicons flanking the I-SceI target site from HEK293 cells harboring traffic light reporter sorted by BFP expression levels follow transfection with expression constructs as indicated in FIG. 4A and FIG. 4B.
Figure 5B:
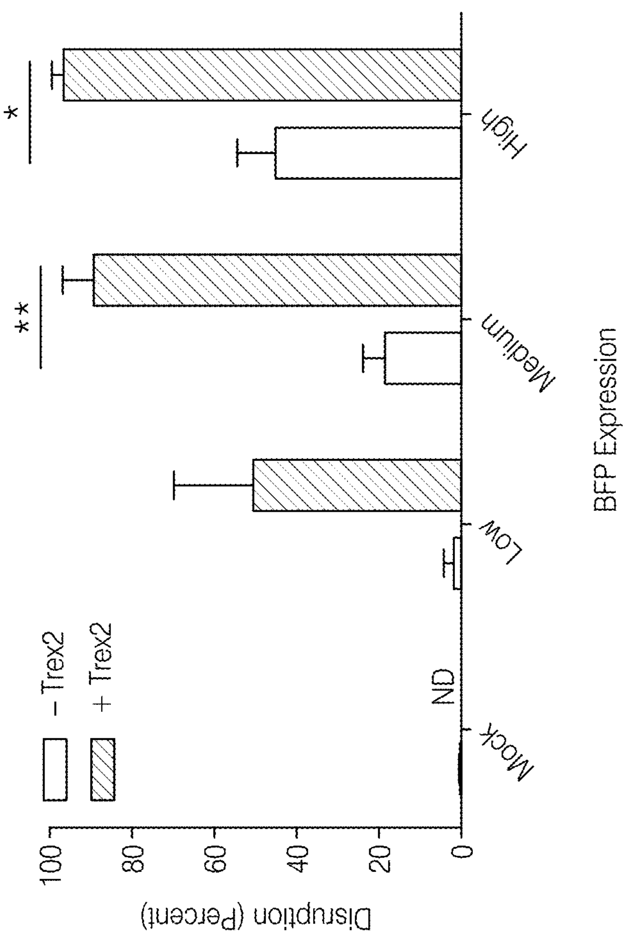
FIG. 5B shows quantification of three independent experiments as described in FIG. 5A.

After the I-SceI and I-SceI-T2A-Trex2 transfected cells were sorted based on varying BFP expression levels, the area flanking the I-SceI target was amplified from each of the populations by PCR. 100 ng of each PCR product was digested in vitro with recombinant I-SceI (New England Biolabs) for 6 hours at 37° C. DNA was separated using a 1% agarose gel stained with ethidium bromide to look for a resistant band, indicative of a mutagenic event at the locus that destroyed the I-SceI target site. See FIG. 5A. Percent disruption was calculated by quantifying band intensity using Image J software, and dividing the intensity of the undigested band by the total. At low endonuclease expression levels, a 25-fold increase in total gene disruption between I-SceI and I-SceI coupled to Trex2 (2.2 to 50.2% respectively) was observed, and nearly 100% of targets were disrupted in the medium and high expression gates of I-SceI T2A Trex2 (90.3, and 97.1% respectively) See FIG. 5B.

Figure 7:
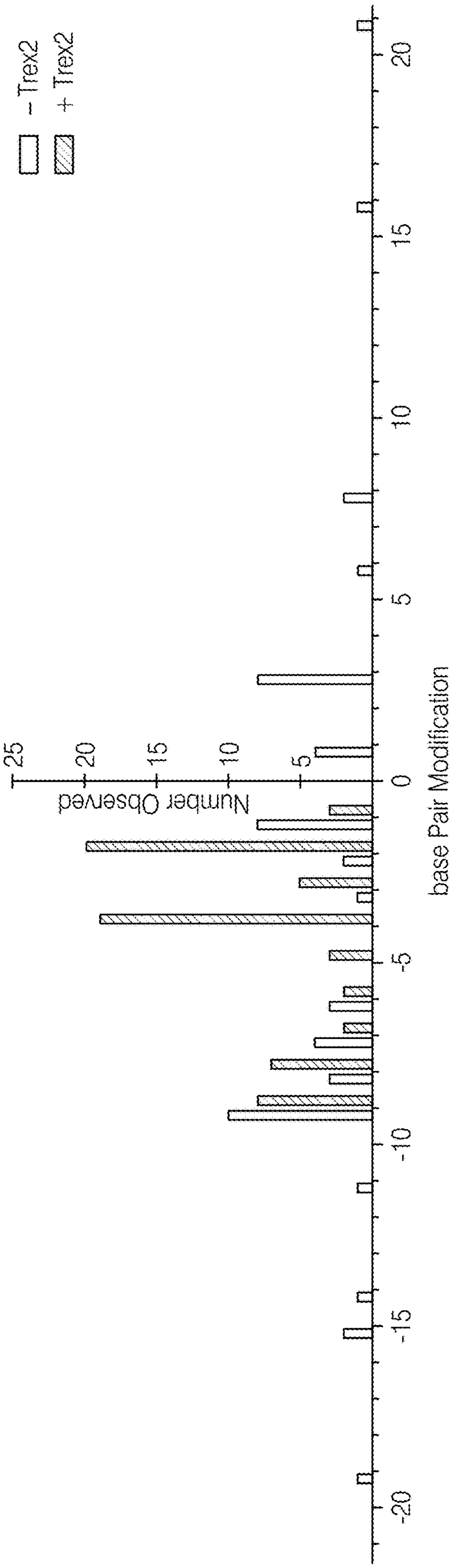
FIG. 7 shows a graph scoring observed mutations (deletions are negative, insertions are positive) at the I-SceI target site following transfection of HEK293 Traffic Light Reporter cells with I-SceI-IRES-BFP or I-SceI-T2A-Trex2-IRES-BFP as described in FIG. 5.
Figure 8A:
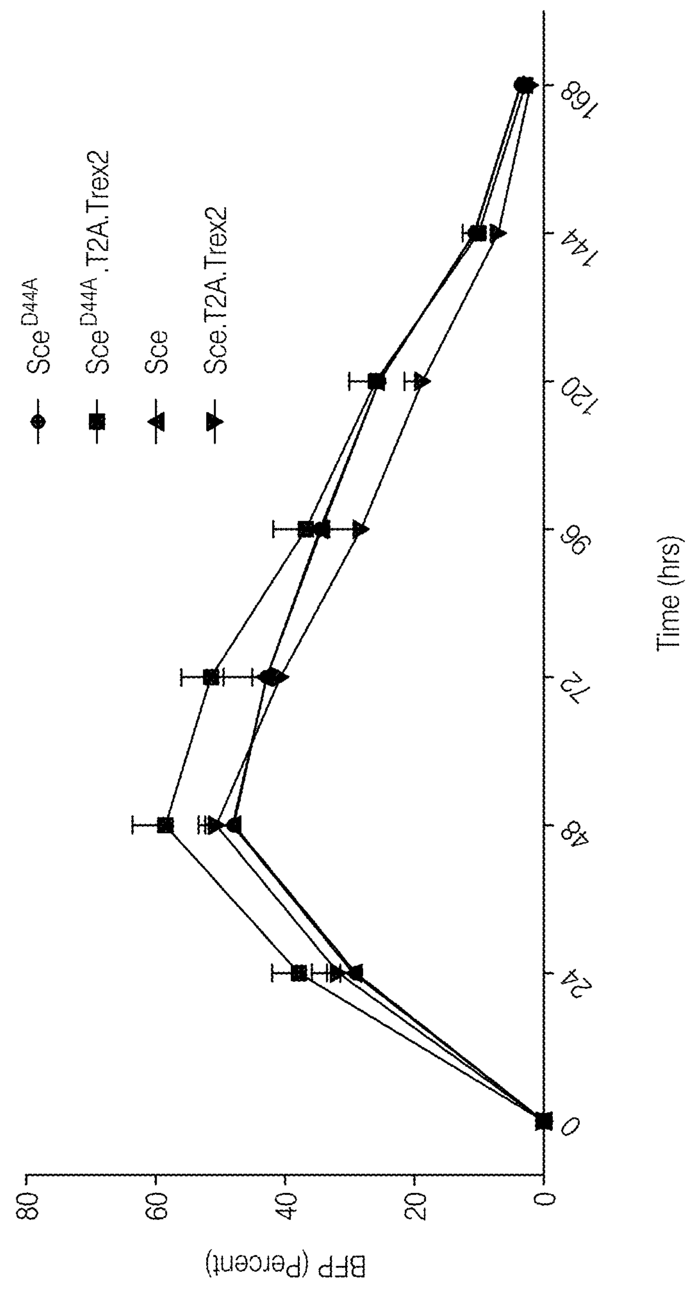
FIG. 8A shows a kinetic time course analysis demonstrating transient expression of I-SceI-T2A-Trex2-IRES-BFP after transfection into HEK293 cells harboring Traffic Light Reporter. The constructs shown are tagged to BFP by an IRES sequence downstream of either I-SceI or Trex2.
Figure 8B:
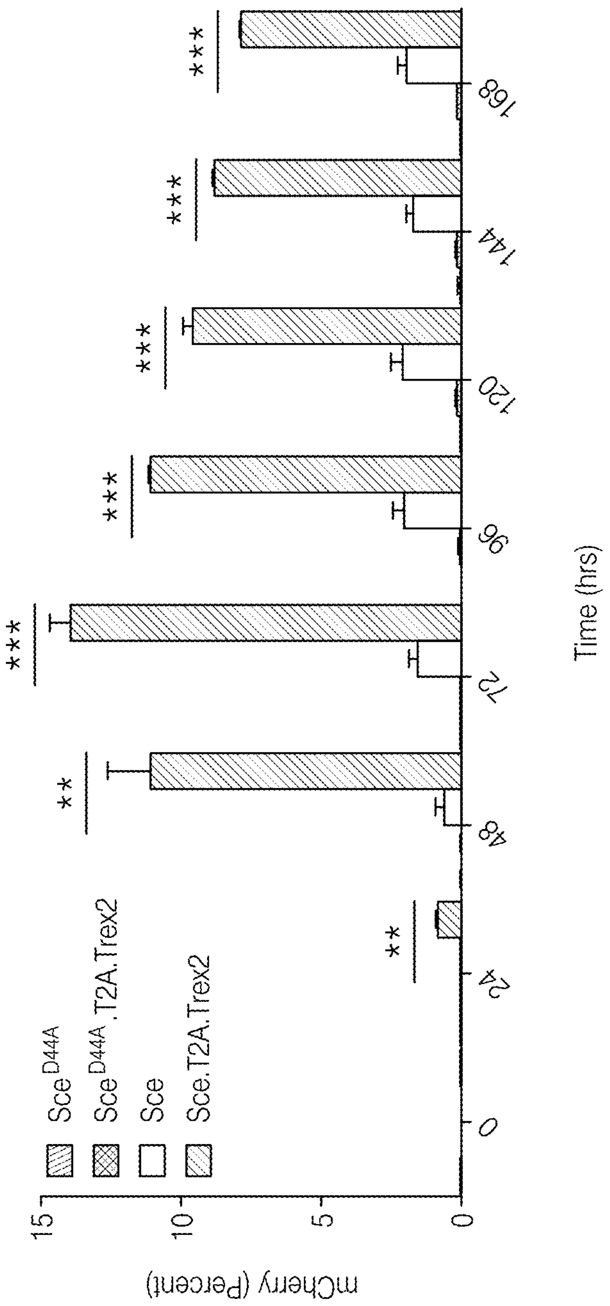
FIG. 8B shows a graph quantifying 3 experiments of HEK293T cells transfected with the vectors indicated in FIG. 8A, analyzed at the indicated time-points. Cherry indicates gene disruption rates observed in transfected cells.

These experiments indicate that while I-SceI exhibits a dose dependent increase in gene disruption, I-SceI coupled to Trex2 quickly becomes saturated. Sequence analysis of the I-SceI target site in high expressing cells confirmed that 100% of cells were modified in the I-SceI-T2A-Trex2 treated cells. See FIGS. 6A and 6B. Comparison of the mutation spectra between I-SceI alone and I-SceI.T2A.Trex2 showed a trend towards small deletion events in the exonuclease treated cells. See FIGS. 6A, 6B and 7. In a kinetic analysis, while all constructs exhibited similar expression patterns, Trex2 expression coincided with the appearance of disruption events at earlier time-points. See FIGS. 8A and 8B. In sum, coupling of endonucleases to Trex2 expression in a single open reading frame resulted in up to 25-fold enhancement in the efficiency of targeted gene disruption in cells from multiple species and in primary cell types, and is able to drive targeted knockout rates to near completion within 72 hrs.

Example 2

Trex2 Exonuclease Increases the Mutation Rate of a Variety of Homing Endonucleases The applicability of Trex2-enhanced disruption to multiple different nuclease scaffolds was evaluated. Targeted disruption reporter cassettes (mutNHEJ reporter cassettes) with target cleavage sites for I-Ltr, I-Gpi, I-Gze, I-MpeMI, I-PanMI, I-Cre, I-OnuI, I-HjeMI, and I-AniI (See Table 1) were generated by placing the endonuclease target site of interest placed in front of the mCherry fluorescent protein ORF in the +3 reading frame. HEK293T Reporter cell lines containing genomically-integrated I-Ltr, I-Gpi, I-Gze, I-MpeMI, I-PanMI, I-Cre, I-OnuI, I-HjeMI, and I-AniI TLR reporter cassettes were then generated. Each cell line was transfected with an expression construct for its respective enzyme with or without co-transfection of an expression construct encoding Trex2, and disruption rates were measured.

Figure 10:
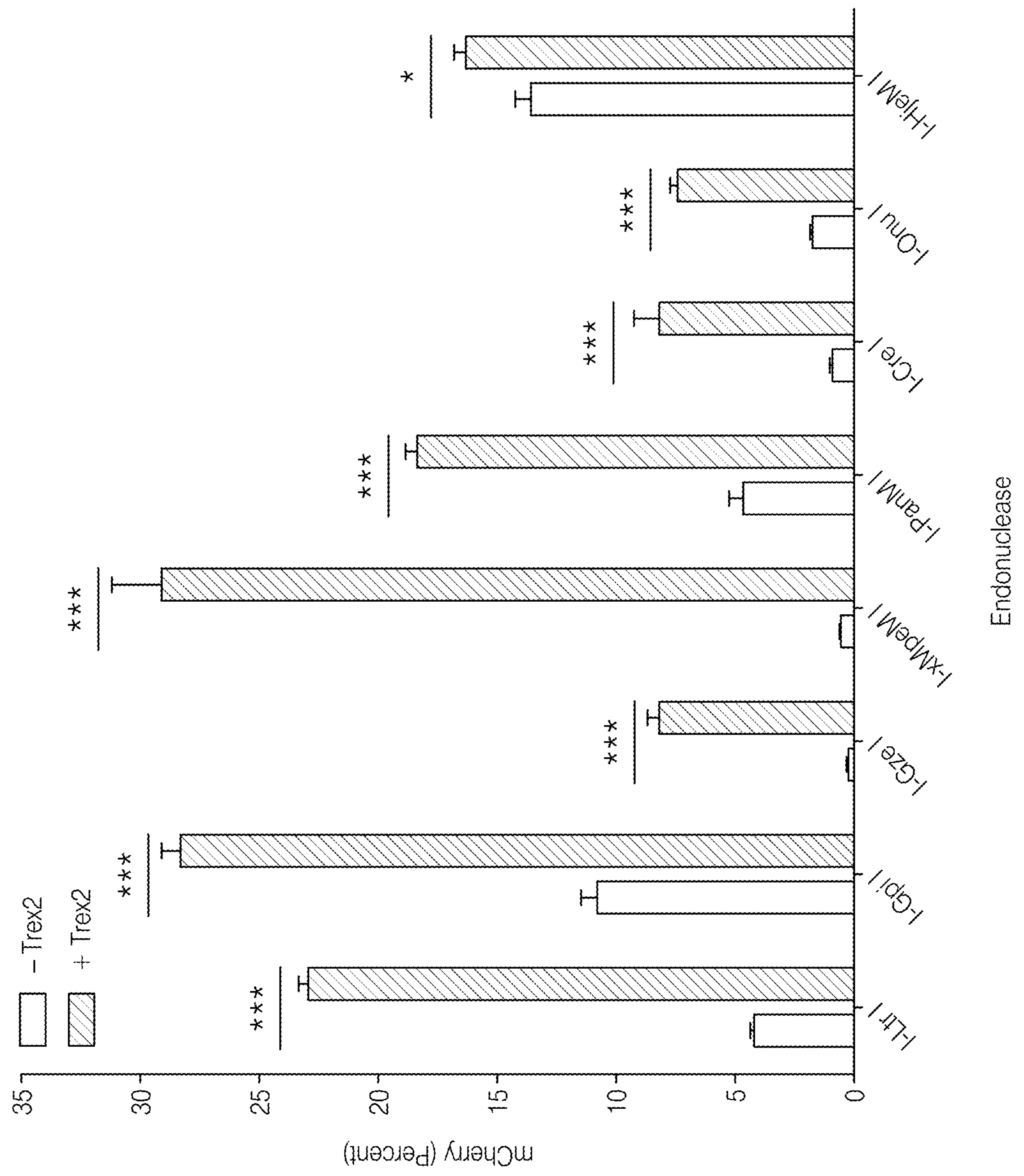
FIG. 10 shows a graph quantifying gene disruption rates of several different homing endonucleases with and without Trex2 exonuclease as measured by HEK293 cells harboring Traffic Light Reporters with respective target sites for the indicated homing endonucleases.

The effect of Trex2 co-expression with each of I-Ltr, I-Gpi, I-Gze, I-MpeMI, I-PanMI, I-Cre, I-OnuI, I-HjeMI, and I-AniI homing endonucleases was analyzed by flow cytometry. For each of the different Homing Endonucleases tested, disruption rates increased when coupled to Trex2, demonstrating that the Trex2 exonuclease can facilitate gene disruption from breaks generated by a variety of different homing endonucleases, which leave different 3' 4 bp overhangs and possess varying enzyme kinetics. See FIG. 10. This data demonstrates that Trex2 expression increases the mutagenesis rates associated with targeted DNA cleavage by a variety of homing endonucleases. Further, co-expression of Trex2 with I-Gze increased mCherry+ expression significantly over the background levels observed with I-Gze expression alone. See FIG. 10.

Homing Endonucleases in the panel having very low activity were rescued by coupling to Trex2. See FIG. 10. This suggests that Homing Endonucleases that appear inactive may be generating breaks at an undetectable rate, and that addition of Trex2 reveals these breaks by catalyzing end processing prior to break ligation. This is consistent with the observation that Trex2 can increase disruption rates of a higher activity enzyme, such as I-SceI, even at very low expression levels.

Figure 12A:
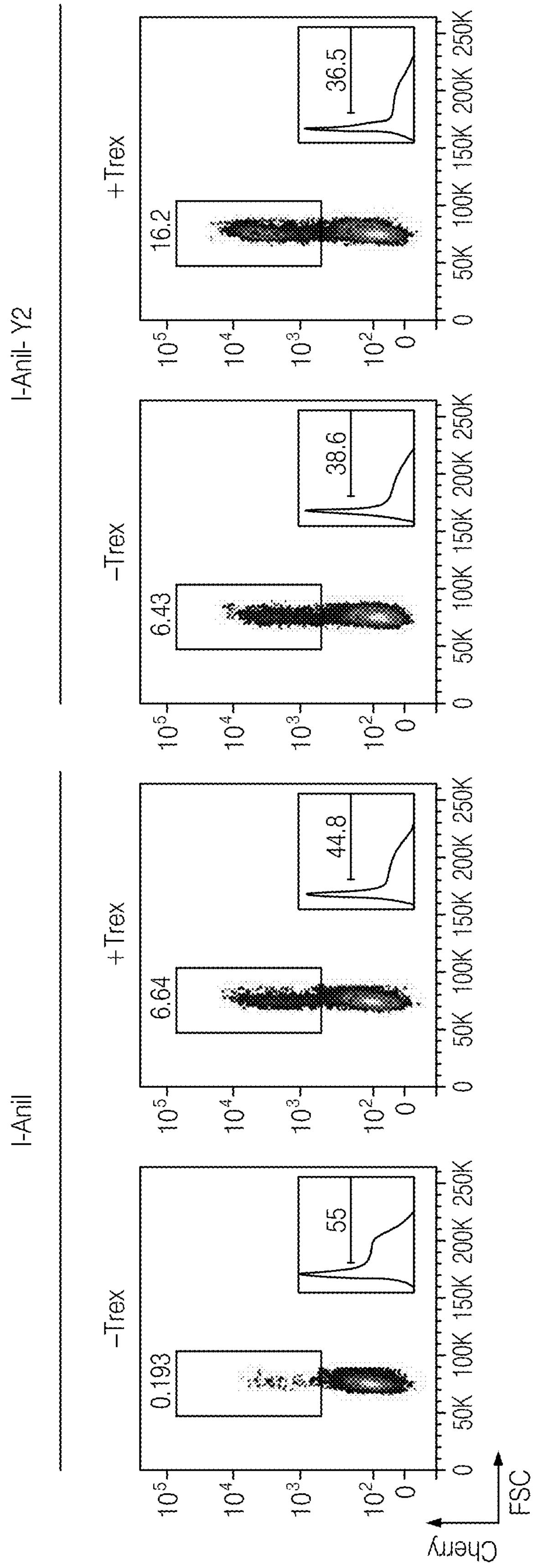
FIG. 12A shows representative flow plots of HEK293 cells harboring Traffic Light Reporters with an I-AniI target site following transfection with either I-AniI-IRES-BFP, I-AniI-T2A-Trex2-IRES-BFP, I-AniIY2-IRES-BFP, I-AniIY2-T2A-Trex2-IRES-BFP.
Figure 12B:
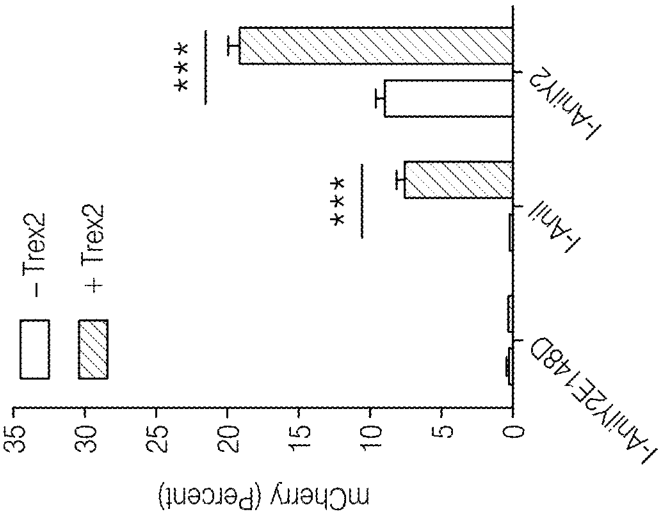
FIG. 12B shows a graph quantitating 3 independent experiments as performed in FIG. 12A.
Figure 13:
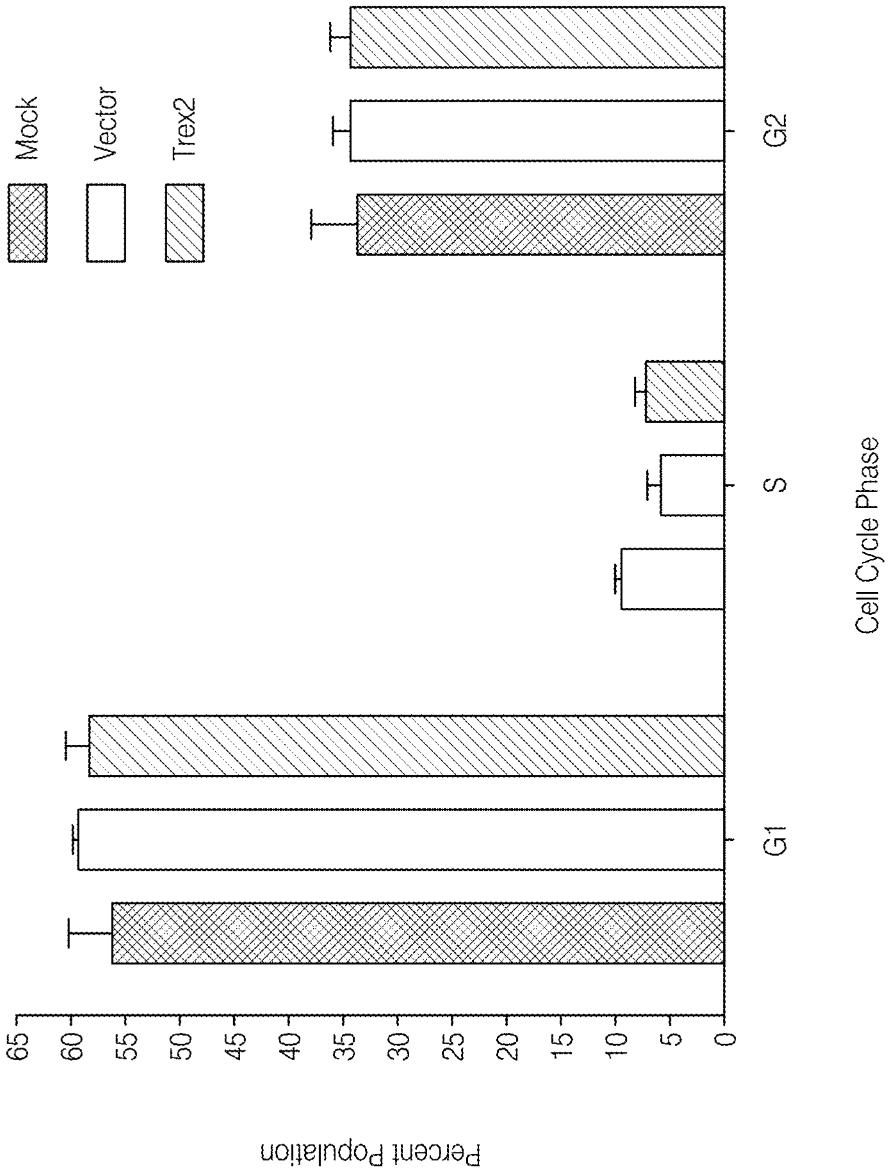
FIG. 13 shows graph depicting cell cycle analysis of murine embryonic fibroblasts transduced with Mock, I-SceI-IRES-BFP, or I-SceI-T2A-Trex2-IRES-BFP viruses.
Figure 14:
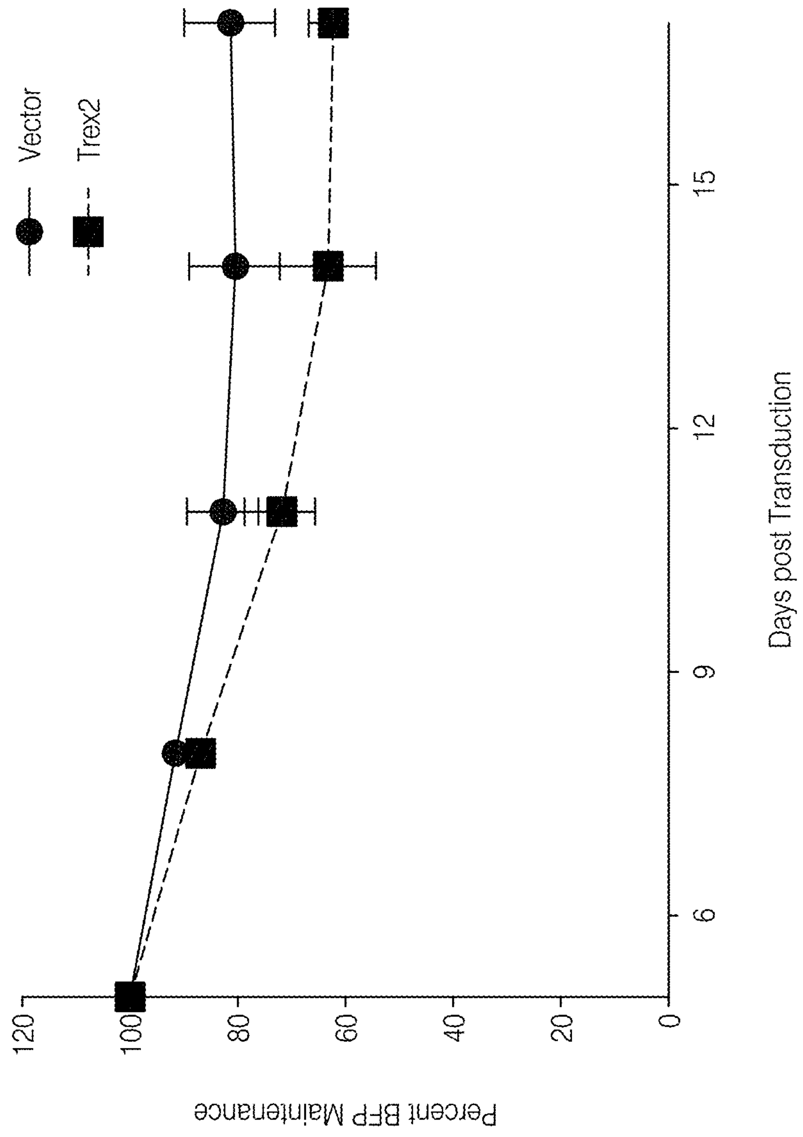
FIG. 14 shows a graph depicting maintenance of BFP expression in cells transduced with an integrating lentivirus containing I-SceID44A-IRES-BFP or I-SceID44A-T2A-Trex2-IRES-BFP.
Figure 15A:
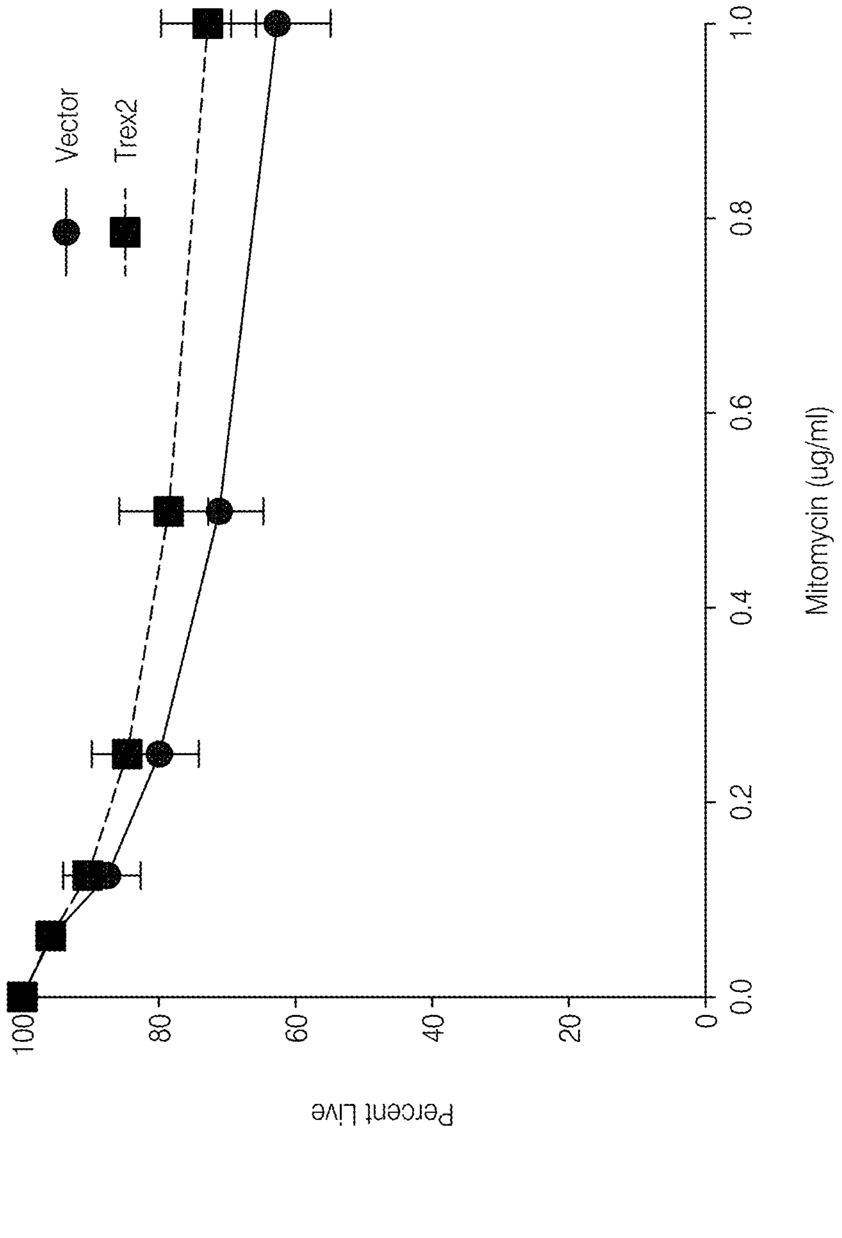
FIG. 15A shows a graph measuring human CD34+ hematopietic stem cell survival when transduced with I-SceID44A-IRES-BFP or I-SceID44A-T2A-Trex2-IRES-BFP and challenged with Mitomycin C.
Figure 15B:
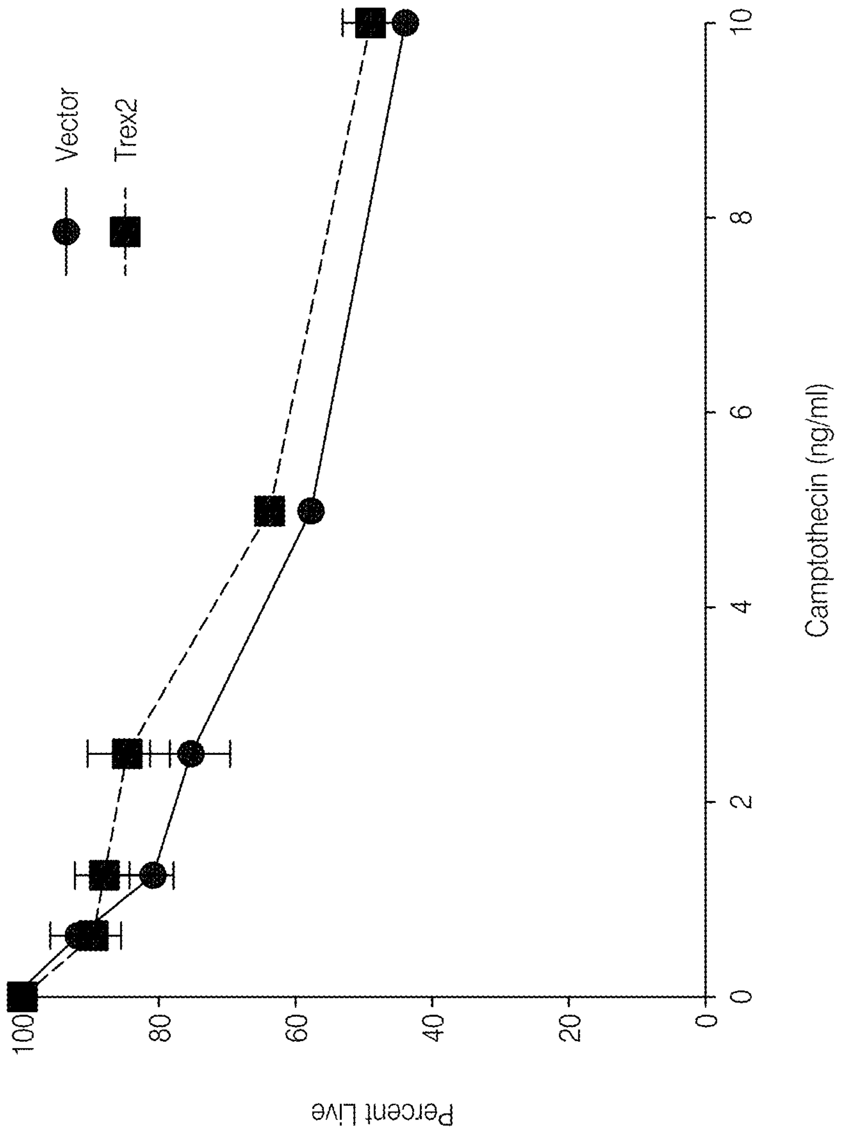
FIG. 15B shows a graph measuring human CD34+ hematopietic stem cell survival when transduced with I-SceID44A-IRES-BFP or I-SceID44A-T2A-Trex2-IRES-BFP and challenged with camptothecin.
Figure 15C:
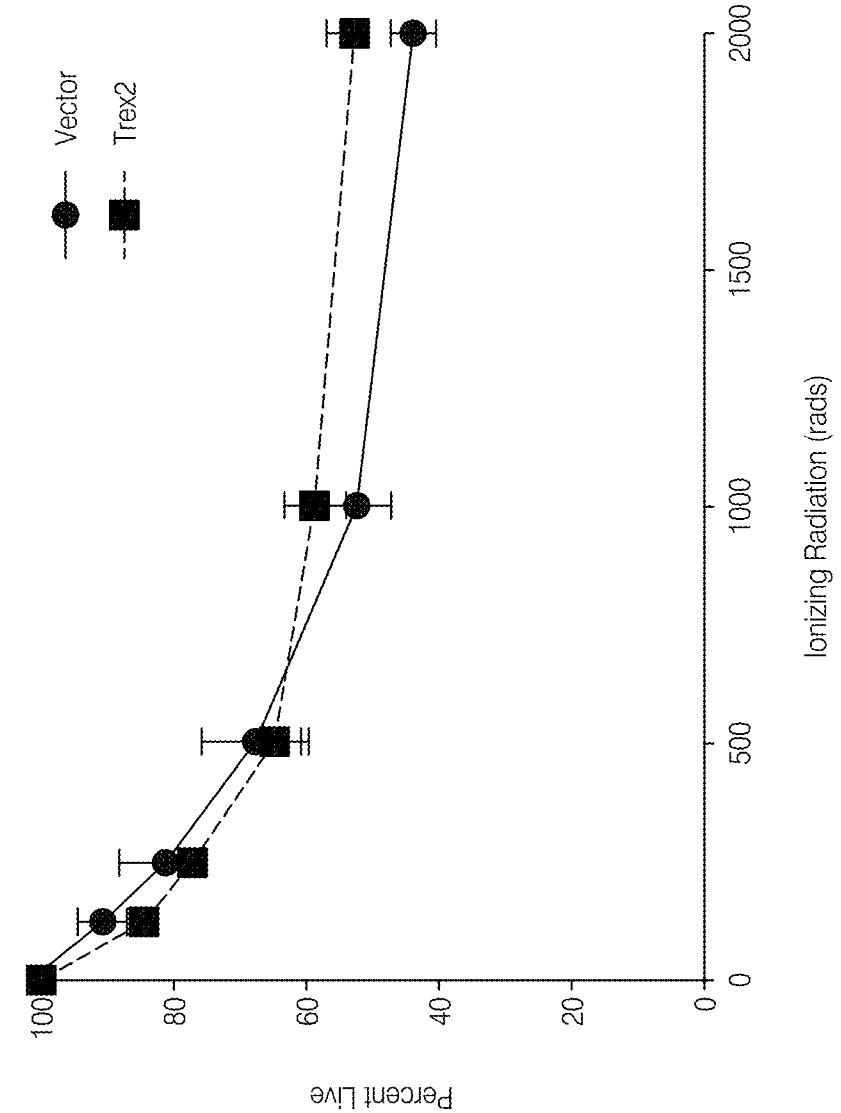
FIG. 15C shows a graph measuring human CD34+ hematopietic stem cell survival when transduced with I-SceID44A-IRES-BFP or I-SceID44A-T2A-Trex2-IRES-BFP and challenged with ionizing radiation.
Figure 16A:
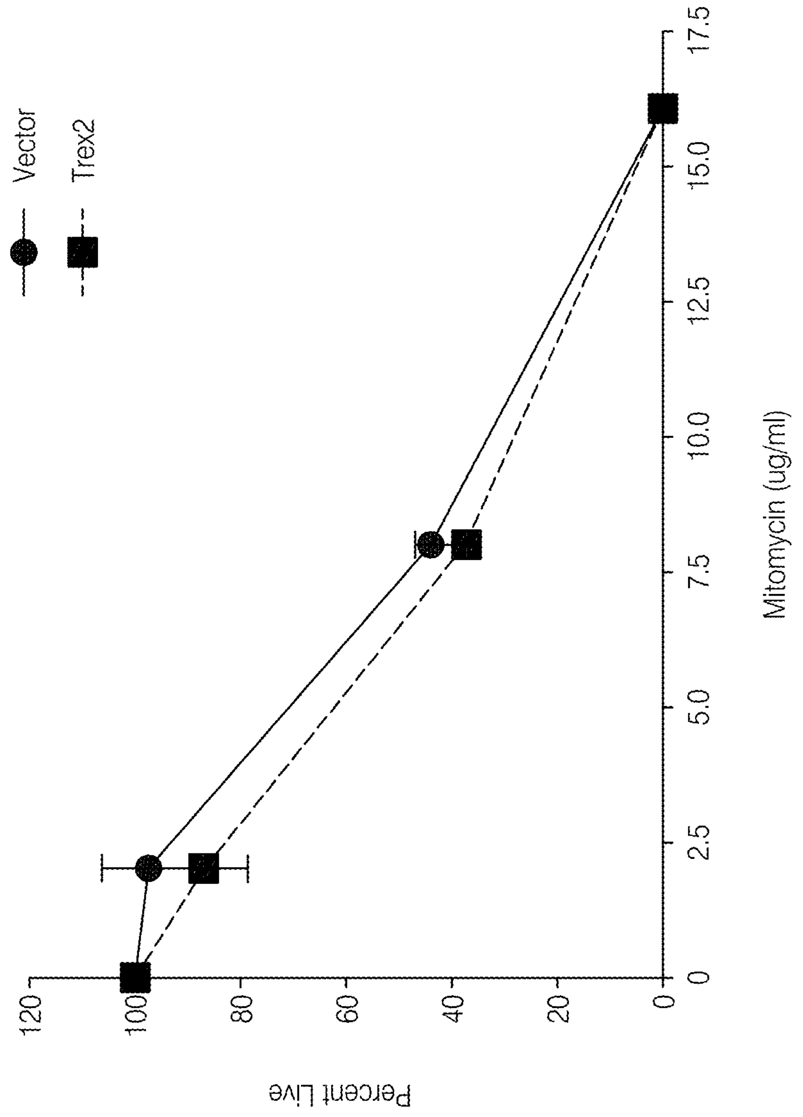
FIG. 16A shows a graph measuring murine embryonic fibroblast cell survival when transduced with I-SceID44A-IRES-BFP or I-SceID44A-T2A-Trex2-IRES-BFP and challenged with Mitomycin C.
Figure 16B:
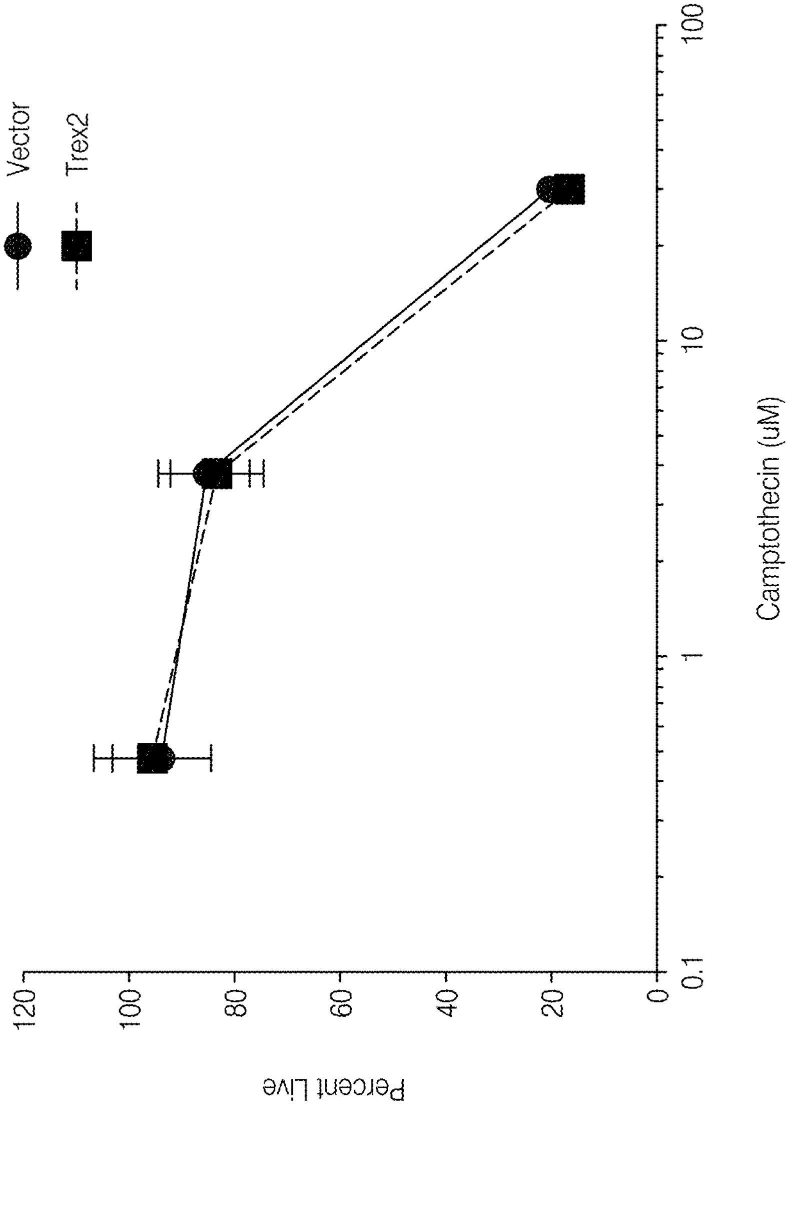
FIG. 16B shows a graph measuring murine embryonic fibroblast cell survival when transduced with I-SceID44A-IRES-BFP or I-SceID44A-T2A-Trex2-IRES-BFP and challenged with camptothecin.

To test the ability of Trex2 to reveal breaks caused by Homing Endonucleases having very low activity, the effect of coupling Trex2 on the gene disruption rate of the I-AniI Homing Endonucleases was analyzed by flow cytometry. WT I-AniI exhibits very little activity in cells and expression of WT I-AniI alone does not exhibit targeted disruption activity. See FIGS. 12A and 12B. Coupling of Trex2 to WT I-AniI increases its gene disruption capacity to that of the highly active I-AniI variant, I-AniI Y2. See FIGS. 12A and 12B. I-AniI Y2 was subjected to several rounds of directed evolution to improve its activity. Coupling of Trex2 to an inactive form of I-AniI, I-AniI E148D, shows no increase in reporter expression. This data demonstrates that Trex2 expression increases the mutagenesis rates associated with targeted DNA cleavage by sub-active homing endonucleases.

Together, these results show that Trex2 can increase disruption rates for a variety of homing endonucleases and rescue low-activity endonucleases, effectively lowering the engineering bar for enzymes designed to produce gene disruption at novel target sites.

Example 3

Co-Expression of Trex2 Exonuclease Affects the Mutation Rate Associated with FokI Zinc Finger Nuclease Mediated Breaks A reporter cell line was generated that harbors a 5' ACC ATC TTC ttcaag GAC GAC GGC 3' (SEQ ID NO. 147) target site for a corresponding zinc finger nuclease containing a FokI nuclease domain. Expression vectors encoding the zinc finger nuclease were transduced into reporter cell lines harboring the TLR-FokI reporter cassette with and without Trex2. Co-expression of Trex2 with the zinc finger nuclease results in an increased mutation rate. See FIG. 11B.

Example 4

The Chimeric I-SceI-G4s-Trex2 Endo/Exo-Nuclease Fusion Protein Improves the Rate of Targeted Disruption Expression vectors comprising HA-I-SceI-BFP, (HA-I-SceI)-T2A-Trex2-BFP or (HA-I-SceI)-G4S-Trex2-BFP were constructed as described in Example 1. The I-SceI gene used to construct the expression vectors further encoded an N-terminal HA epitope tag. The (HA-I-SceI)-T2A-(HA-Trex2-BFP) expression vector expresses HA-I-SceI and Trex2 in a 1 to 1 ratio from a single promoter, but the T2A linker sequence allows for two separate proteins to be produced from a single translation. The (HA-I-SceI)-G4S-(HA-Trex2)-BFP expression vector produces an endo/exo-nuclease fusion protein where HA-I-SceI and Trex2 proteins are coupled together by a G4S linker peptide. The HA-I-SceI-BFP, (HA-I-SceI)-T2A-Trex2-BFP and (HA-I-SceI)-G4S-Trex2-BFP expression vectors were transduced into HEK293 cells containing a genomically-integrated cassette corresponding to the targeted disruption reporter illustrated in FIG. 1A.

Figure 3A:
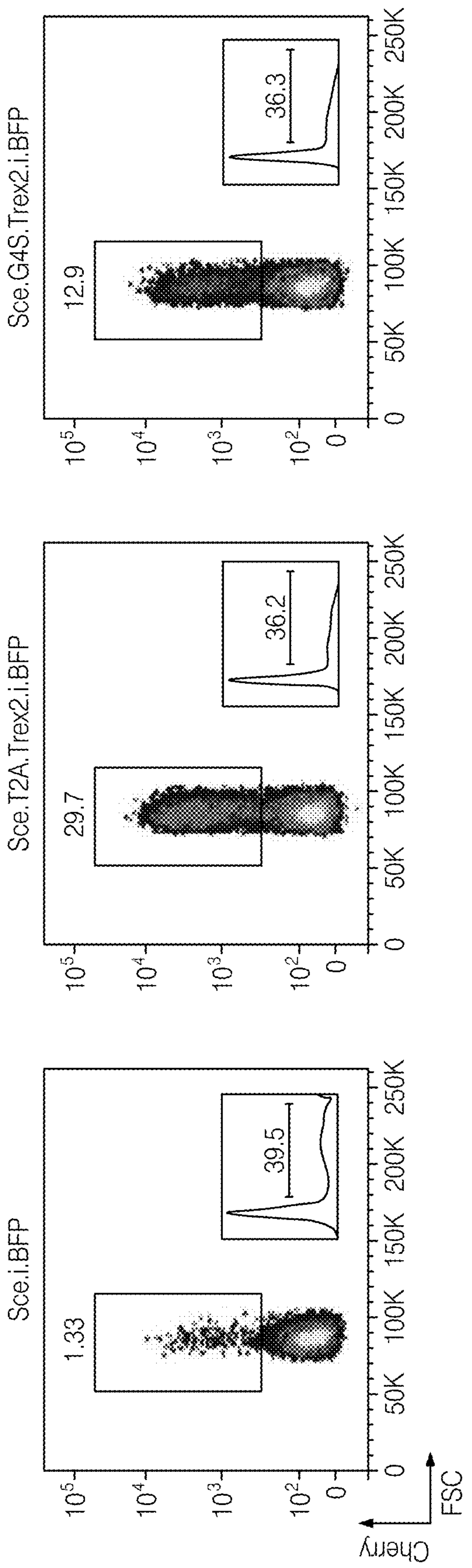
FIG. 3A shows representative flow plots of HEK293 cells harboring Traffic light Reporter transfected with expression vectors encoding I-SceI-IRES-BFP, I-SceI-T2A-Trex2-BFP, or I-SceI-G4S-Trex2-IRES BFP.

Following transduction of the cell line with the expression vectors, the cells were analyzed for mCherry+ expression by flow cytometry. The plot shown in FIG. 3A demonstrated that I-SceI-G4S-Trex2 endo/exo fusion proteins are active and increase targeted disruption rates over provision of I-SceI alone. See FIGS. 3A-C.

However, Sce-G4S-Trex2, despite stable fusion protein expression, was inferior at inducing gene disruption compared to Sce-T2A-Trex2, possibly due to steric hindrance. See FIG. 3A.

Figure 3B:
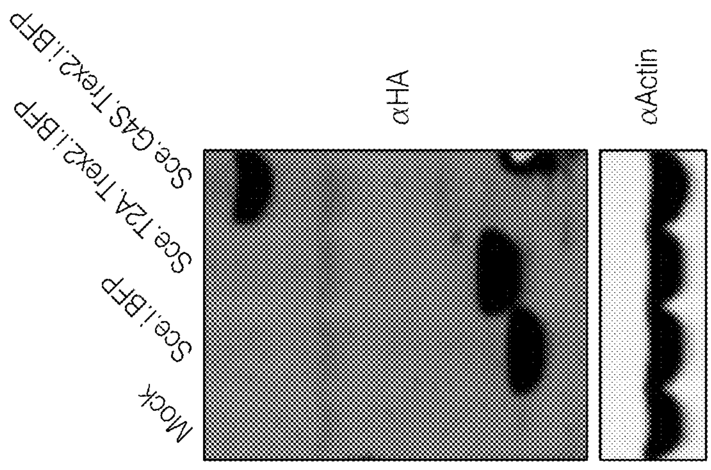
FIG. 3B shows an anti-HA western blot demonstrating equal expression of endonucleases, and stability of the (HA-)I-SceI, (HA-)I-SceI-T2A and (HA-)I-SceI-G4S-Trex2 proteins from FIG. 3A.
Figure 3C:
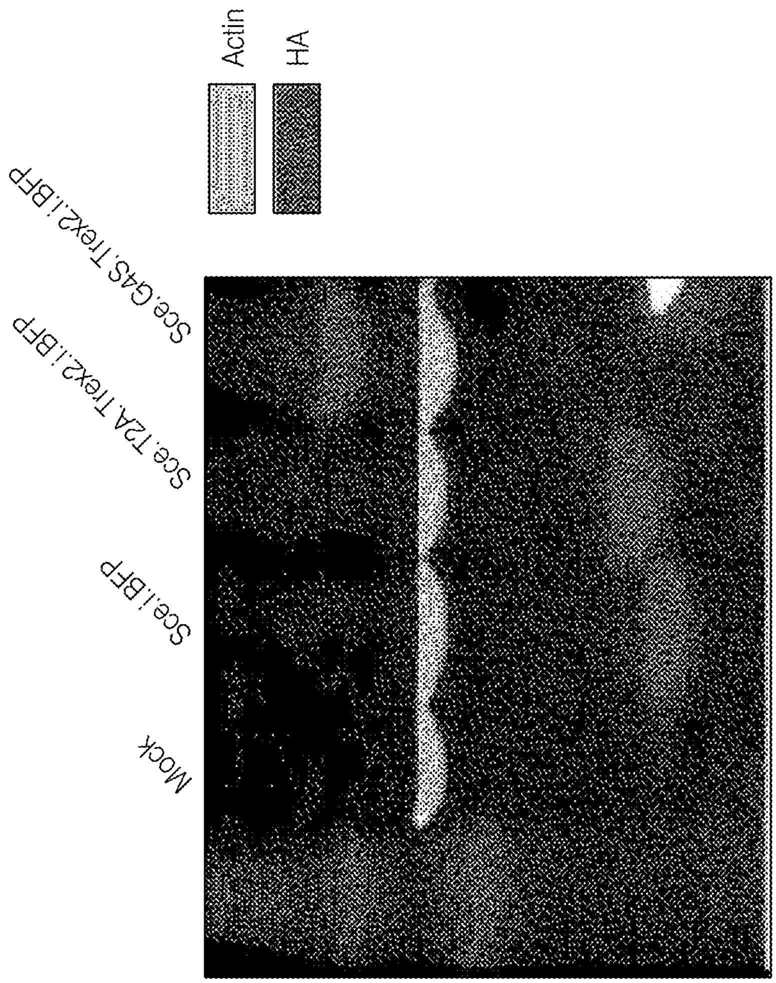
FIG. 3C is a licor western blot showing size and stability of the HA-tagged I-SceI in indicated HEK293T lysates.

An anti-HA western blot was performed to assess the stability of the HA-I-SceI, HA-I-SceI-T2A and (HA-I-SceI)-G4S-Trex2 proteins in the expressing cells. As shown in FIGS. 3B and 3C, the chimeric (HA-I-SceI)-G4S-Trex2 endo-exo fusion protein was expressed at the same levels as I-SceI alone, or I-SceI containing a residual T2A tag peptide.

Example 5

Co-Expression of I-SceI and Trex2 Exonuclease Increases the Rate of I-SceI-Induced Mutations in Primary Cells To determine if Trex2 would increase gene disruption rates in primary cells, primary murine embryonic fibroblasts (MEFs) were isolated from a mouse with an I-SceI site "knocked into" the Interleukin-2 receptor subunit gamma (IL2RG) locus ("Sce-SCID" mouse, unpublished data, G. C., D. J. R., A. M. S). MEFs were isolated from Sce-SCID embryos at 12-14 days gestation. Briefly, individual embryos were removed from the uterus and washed with PBS. The head and red tissue were removed from the embryo, and the remaining tissue was minced. The tissue was incubated with trypsin-EDTA for 10 minutes at 37° C., followed by centrifugation at 10,000×G for 5 minutes. The pellet was re-suspended in MEF media and plated at 37° C. MEF cells were cultured in glutamine-free Dulbecco's modified Eagle's medium supplemented with 2 mM L-glutamine, 10% Fetal Bovine Serum (FBS) and 1% penicillin/streptomycin.

Figure 9A:
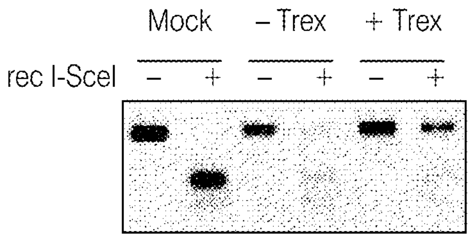
FIG. 9A shows an I-SceI restriction digest of amplicons from primary murine embryonic fibroblasts spanning an I-SceI target site 72 hours post transduction with I-SceI-IRES BFP or I-SceI-T2A-Trex2-IRES-BFP.
Figure 9B:
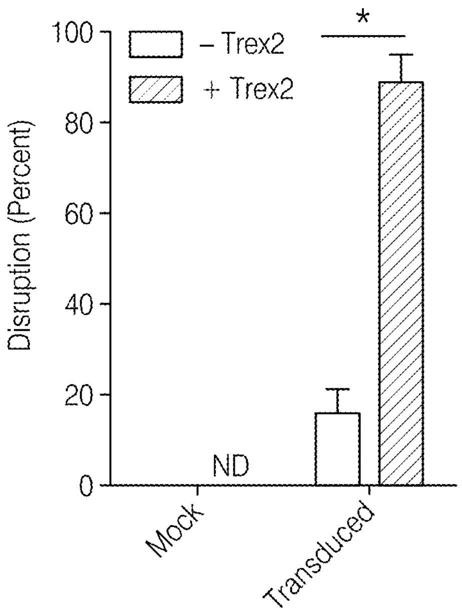
FIG. 9B shows a graph quantifying cleavage site disruption in 2 independent experiments.
Figure 9C:
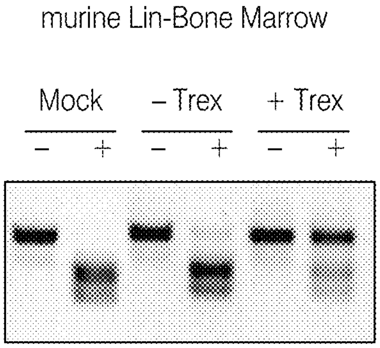
FIG. 9C shows an I-SceI restriction digest of amplicons from lineage depleted bone marrow spanning an I-SceI target site 72 hours post transduction with I-SceI-IRES BFP or I-SceI-T2A-Trex2-IRES-BFP.
Figure 9D:
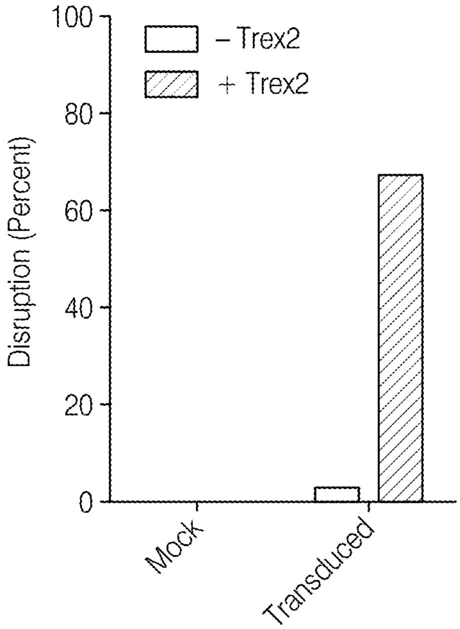
FIG. 9D shows quantification of bands from FIG. 9C.

$1.0\times10^5$ Sce-SCID MEF cells were seeded in a 24-well plate 24 hours prior to transduction with I-SceI or I-SceI.T2A.Trex2 expressing recombinant lentiviral vectors (LV). 0.5 g DNA was used for each expression vector, and transfected using Fugene6 or XtremeGene9 (Roche) according to the manufacture's protocol. Cells were passaged 24 hours later and analyzed 72 hours post transduction. Total gene disruption at the I-SceI target site was assayed using the digestion assay described in Example 1. A 6-fold increase in disruption at the common gamma chain locus was observed with I-SceI coupled to Trex2 (I-SceI=15.8, I-SceI.T2A.Trex2=88.7). See FIGS. 9A and 9B. Additionally, since IL2RG is only expressed in a subset of differentiated hematopoietic cells, these experiments demonstrate Trex2 can facilitate high frequency disruption at unexpressed loci.

Example 6

Effect of Exonuclease Over-Expression on Repair of Endogenous DNA Damage

To determine if exonuclease over-expression alters the cells ability to repair other types of endogenous DNA damage, Trex2 expressing cells are treated with model DNA damage inducing agents. 1.0x106 Sce-SCID MEFs were seeded in a 10 cm dish 24 hours before transduction. 500 μL of 10×LV (pCVL.SFFV.sceD44A.IRES.BFP or T2A.TREX2.IRES.BFP) was added to the culture with 4 g/mL polybrene. 24 hours post-transduction, cells were passaged to 15 cm plates. 72 hours post-transduction, 1.0×105 Sce-SCID MEFs were seeded in a 12-well plate with 1 mL media and treated as indicated with DNA damage inducing agents: Mitomycin C (Sigma Aldrich, St. Louis), Camptothecin (Sigma Aldrich, St. Louis), or ionizing radiation. 48 hours after exposure, cells were incubated in 0.5 g/mL PI as above and analyzed by flow cytometry. For CD34+ cells, 72 hours post-transduction with Trex2 expressing LV, 2.0×$10^5$ CD34+ HSCs were seeded in a 96-well plate in 200 L of media, DNA damaging agents were added to the media, and plates analyzed as above. Overexpression of Trex2 had no adverse effect on cell cycle or sensitivity to model DNA damaging agents, suggesting cells maintain high fidelity DNA repair at lesions occurring independently of those created by the endonuclease. See FIGS. 13, 14, 15A, 15B, 15C, 16A and 16B.

Example 7

Co-Expression of I-SceI and End-Processing Enzymes Increases the Rate of I-SceI-Induced Mutations To determine if the results of coupling homing endonucleases with Trex2 could be extended to other DNA modifying enzymes, a library of 13 candidate enzymes possessing an array of biochemical end-processing activities derived from mammalian, bacterial or viral species was generated. See Table 2. The library of DNA end-processing enzymes was cloned into the pExodus vector with genes synthesized by Genscript (Piscataway, NJ) as cDNA codon-optimized for human expression. See SEQ ID NOs. 110-145.

Figure 17B:
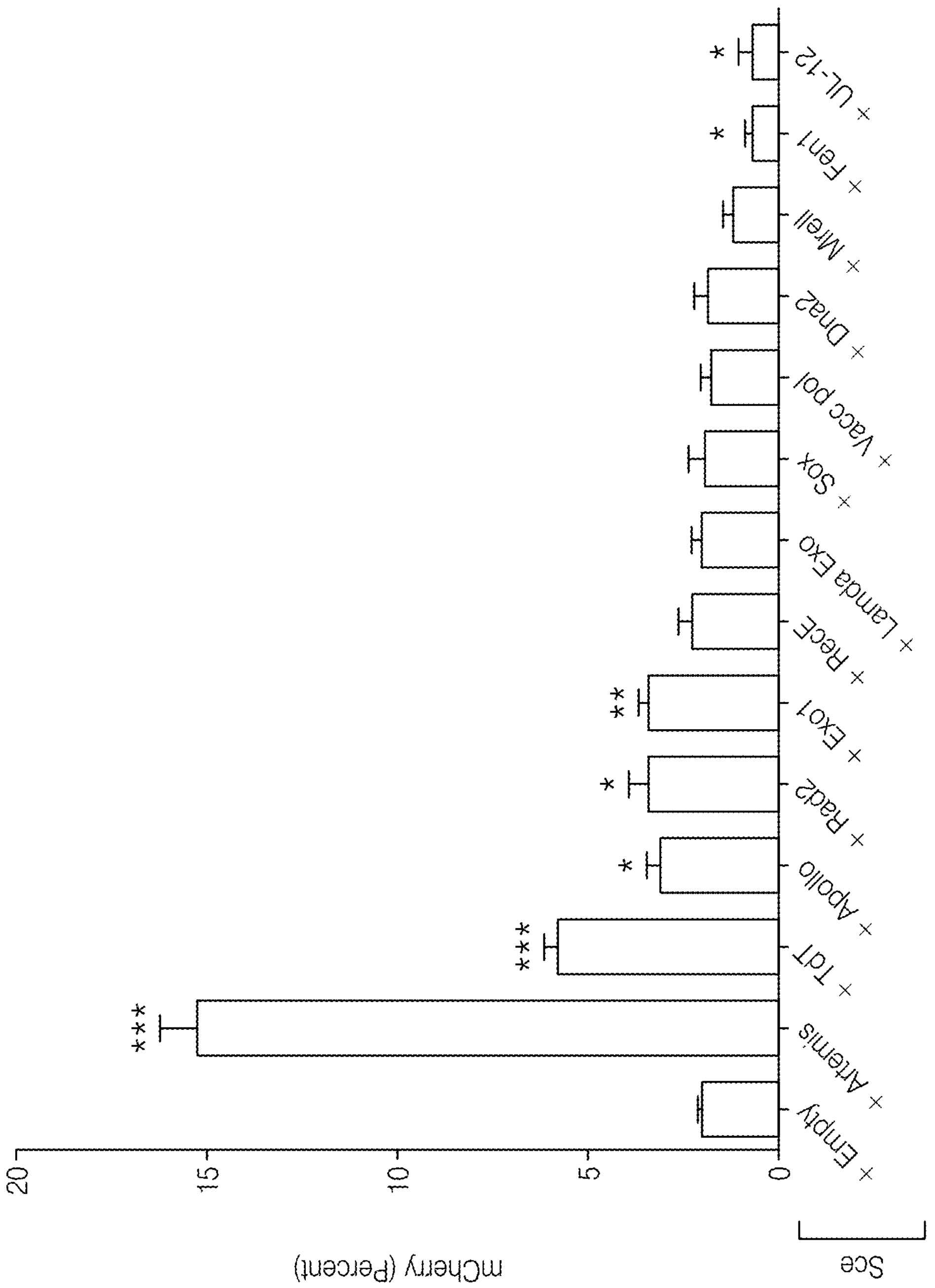
FIG. 17B shows a graph quantifying 3 independent experiments as performed in FIG. $17A_1$ and FIG. $17A_2$.
Figure 18A:
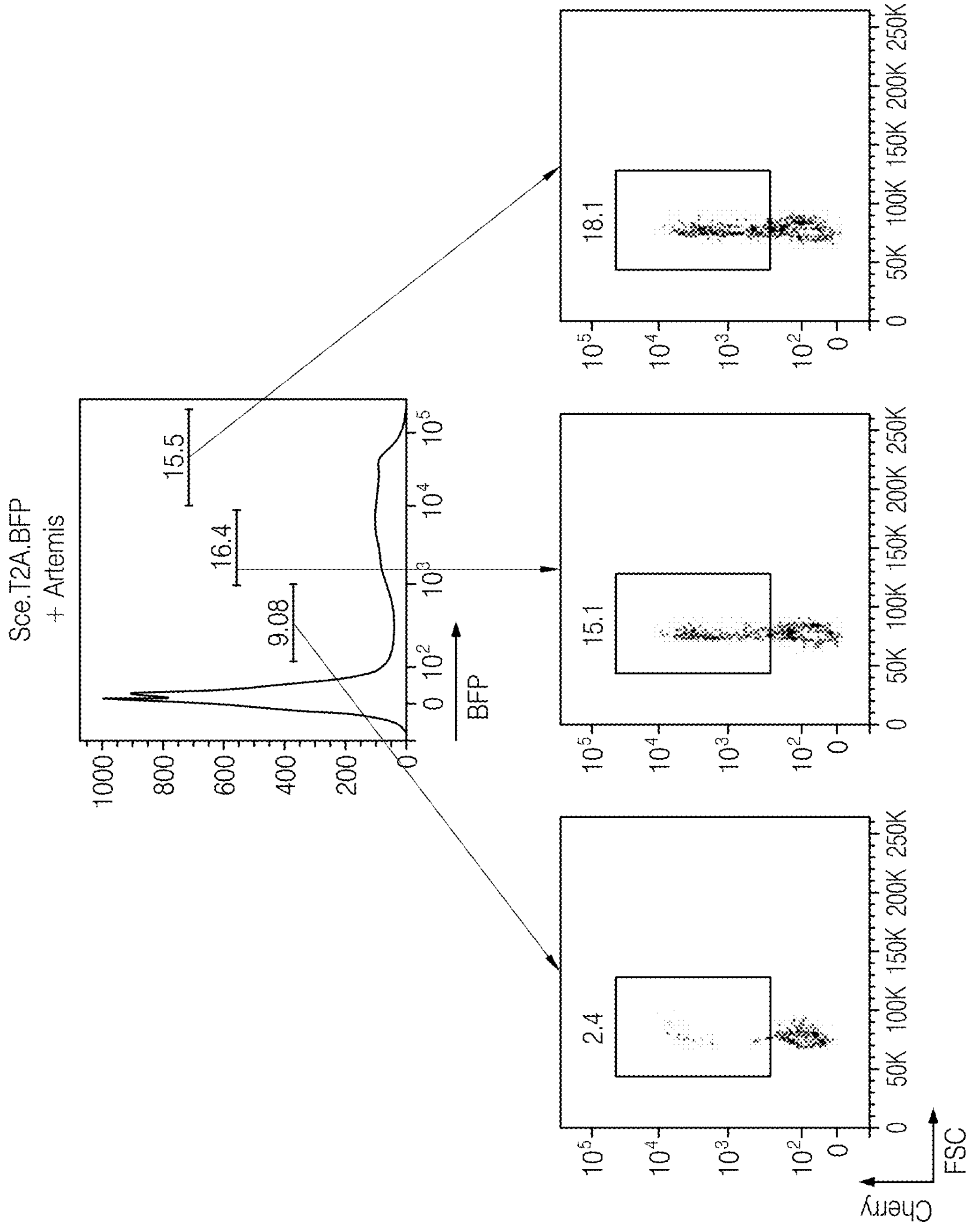
FIG. 18A shows representative flow plots of a gating analysis of I-SceI-IRES-BFP co-transfected with ARTEMIS expression plasmid as indicated in FIG. $17A_1$ and FIG. $17A_2$.
Figure 18B:
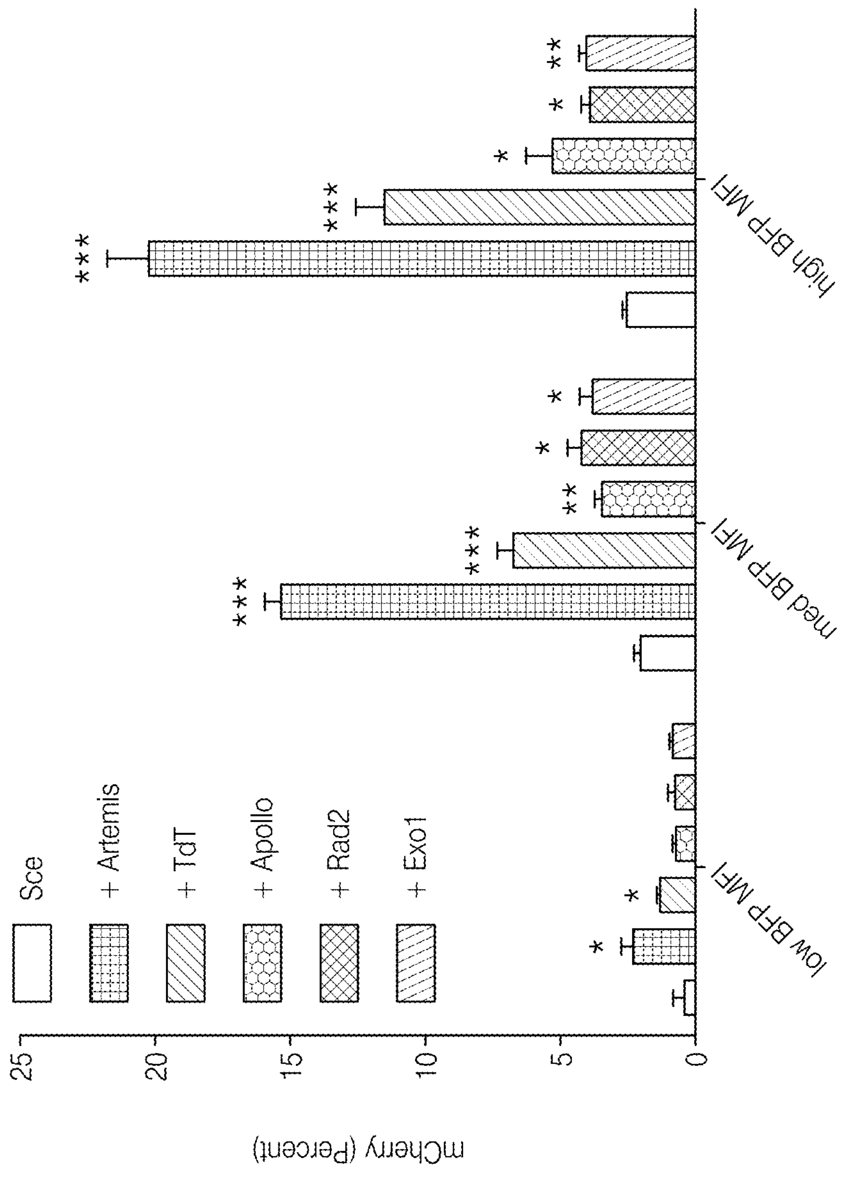
FIG. 18B shows a graph quantifying gating analysis of several end-processing enzymes from 3 independent experiments as indicated in FIG. $18A_1$ and FIG. $17A_2$.
Figure 19A:
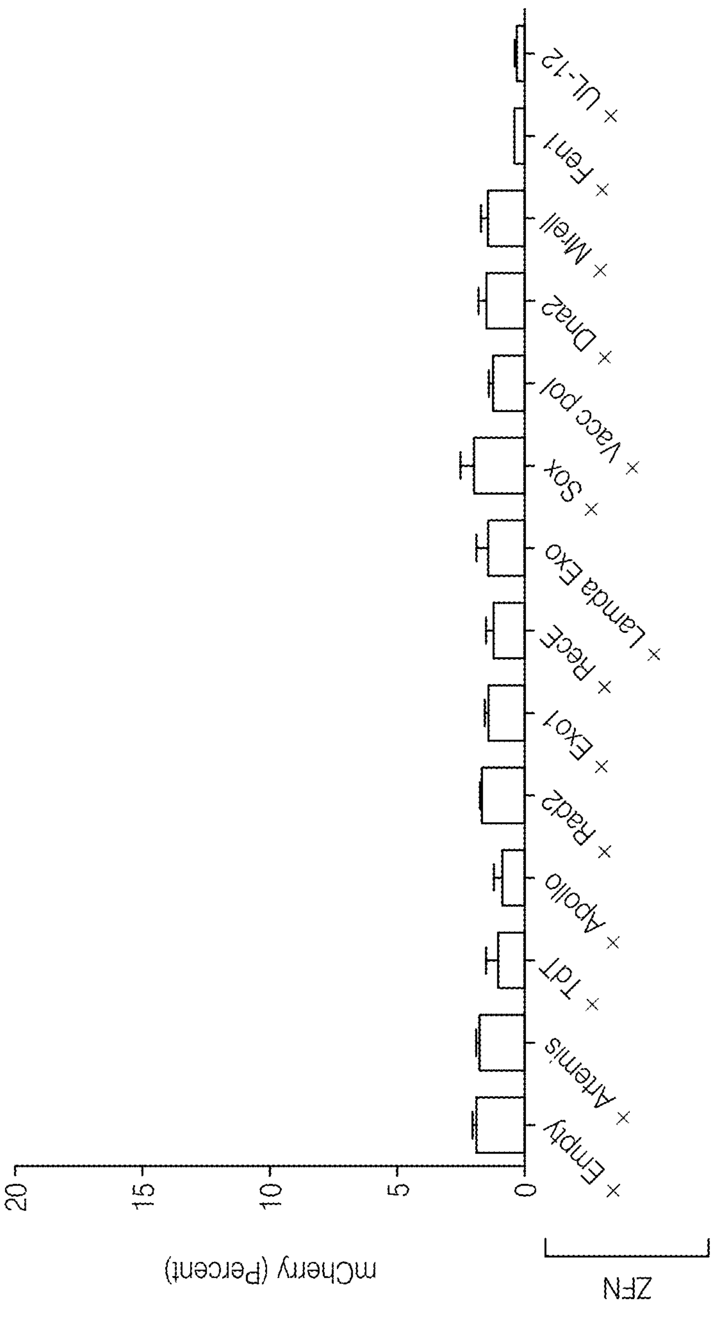
FIG. 19A shows a graph of HEK293 Traffic Light Reporter cells following co-transfection with a zinc finger nuclease and the indicated end-processing enzyme expression plasmid.

The library of DNA end-processing enzymes was screened by co-expressing each enzyme with either the homing endonuclease, I-SceI, or the Zinc Finger Nuclease, VF2468, in the respective HEK293T TLR cells. See FIGS. 17$A_1$, 17$A_2$, 17B, 18A, 19A and 19B. Five of DNA end-processing enzymes (Artemis, Tdt, Apollo, Rad2, and Exo1) robustly increased the gene disruption efficiency of I-SceI. See FIGS. 17$A_1$, 17$A_2$ and 17B. Additionally, the gene disruption activity of these five enzymes was analyzed at three levels of I-SceI expression (quantified by the mean fluorescence intensity, MFI, of the BFP fluorophore). Coexpression of these enzymes with I-SceI increased I-SceI's mutagenic efficiency, even at low levels of endonuclease expression. See FIGS. 18A and 18B. In contrast, although several of the DNA end-processing enzymes possess 5' exonuclease activity, a significant effect of any enzyme on increasing the gene disruption efficiency of the VF2468 ZFN was not observed. See FIG. 19A.

Figure 19B:
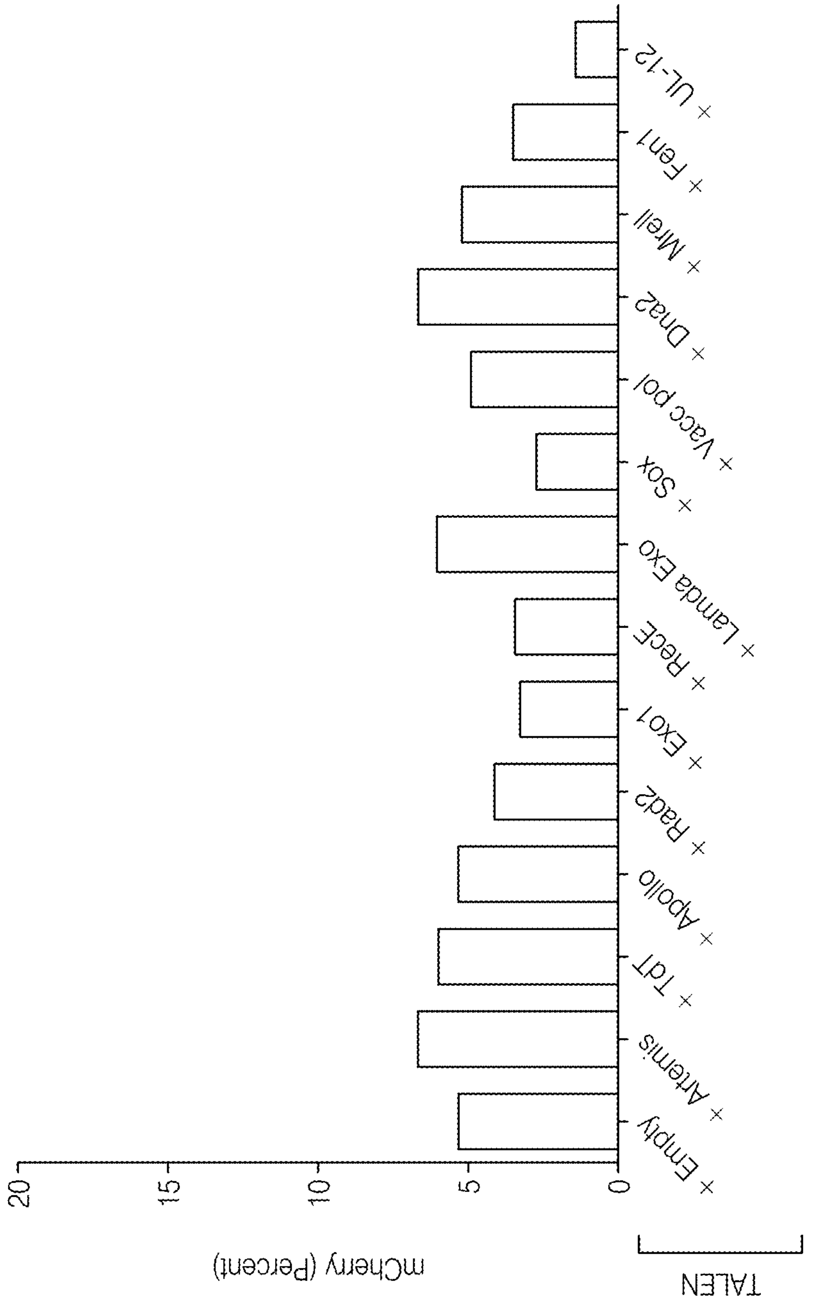
FIG. 19B shows a graph of HEK293 Traffic Light Reporter cells following co-transfection with a TALEN and the indicated end-processing enzyme expression plasmid.
Figure 20A:
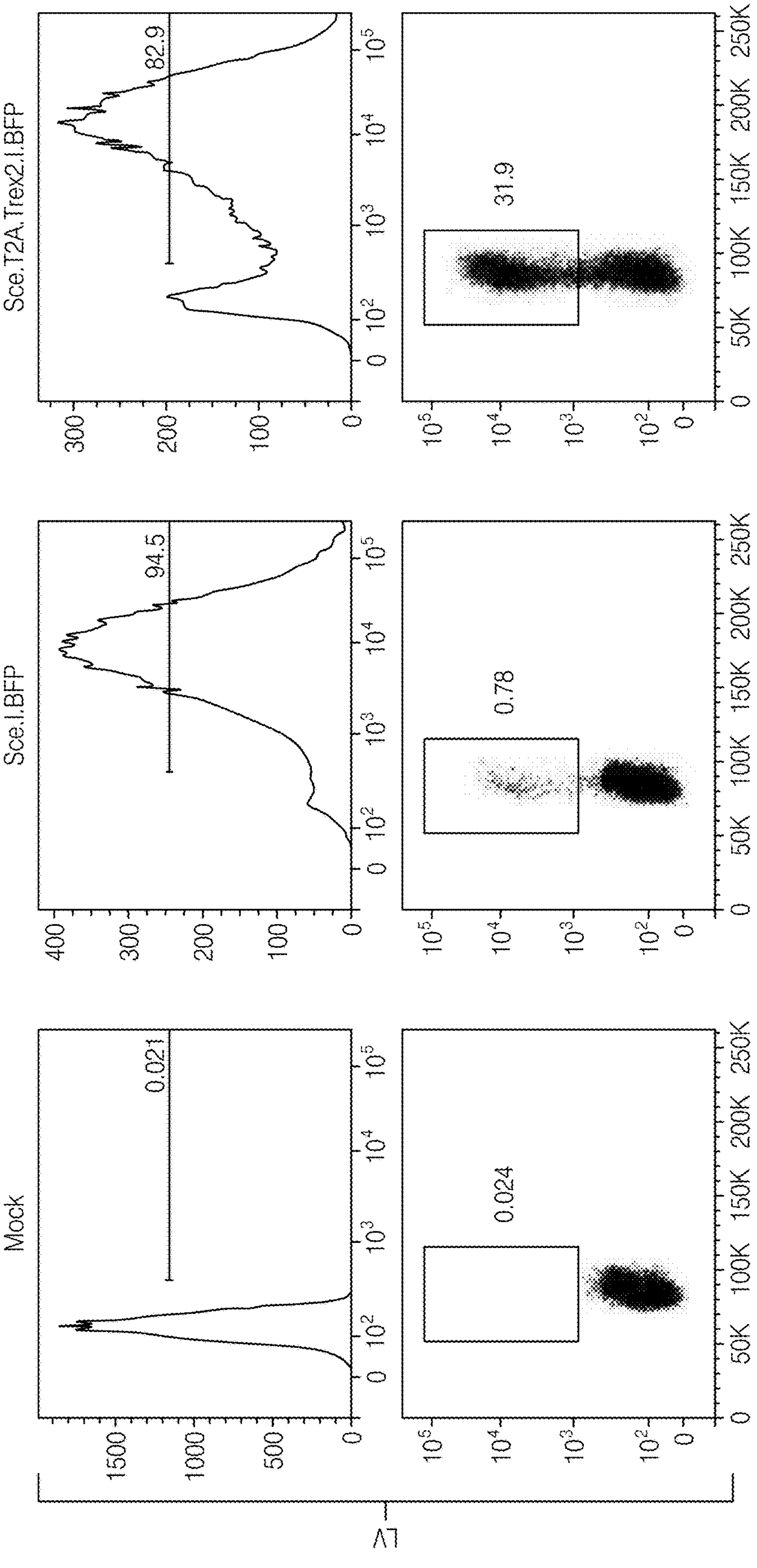
FIGS. 20A and 20B show a comparison of expression levels and gene disruption rates between integrating lentivirus and integrase deficient lentivirus from I-SceI with and without exonuclease coupling on HEK293 Traffic Light reporter cells.
Figure 20B:
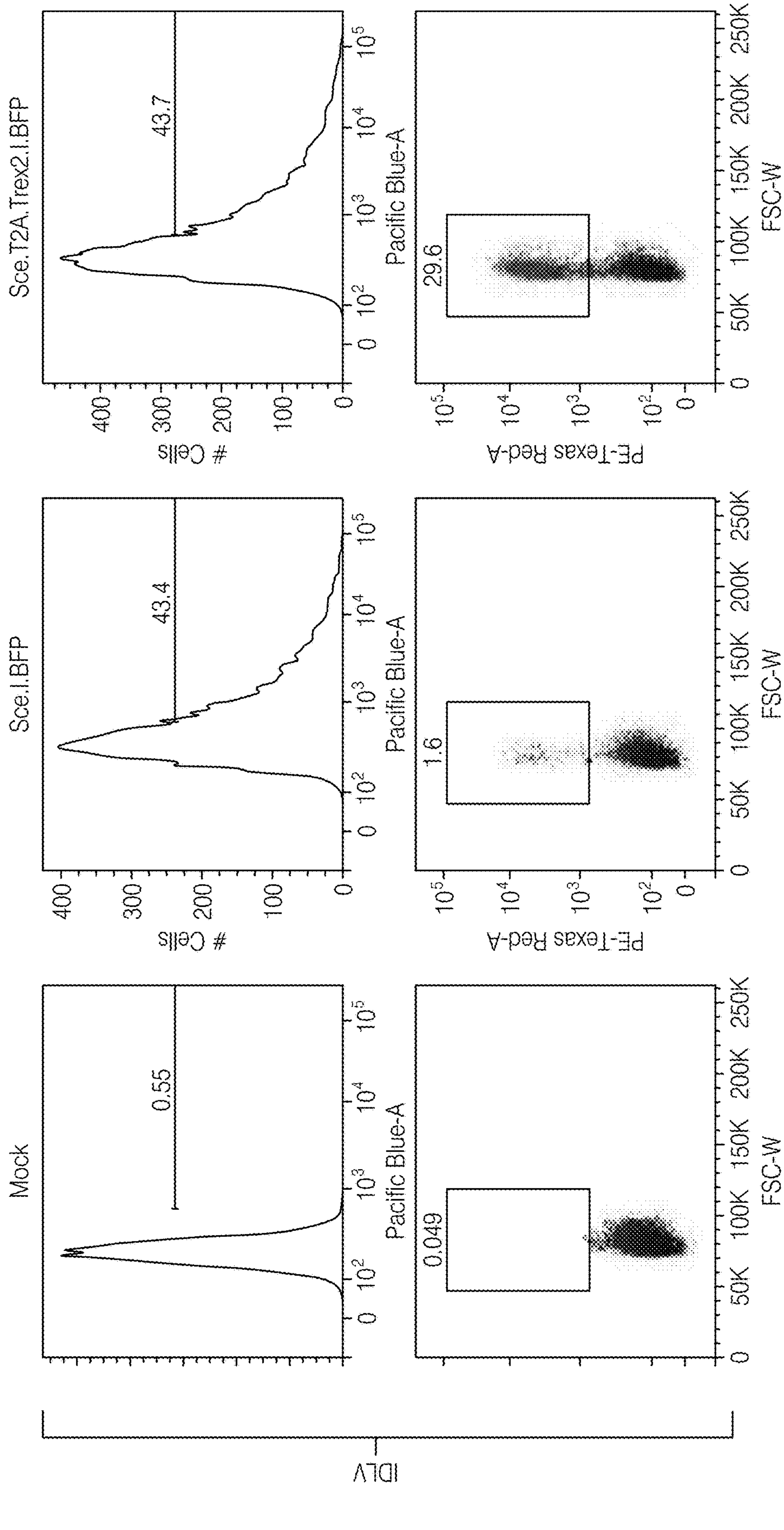

In addition, the library of DNA end-processing enzymes was screened by co-expressing each enzyme with TALEN. See FIG. 19B.

TABLE 2

Library of DNA End-Processing Enzymes.

| Enzyme | Gene name | Activity | Species of origin | NLS added | Reference |
|---|---|---|---|---|---|
| Apollo | SNM1B | 5-3' exonuclease | Human | No | Lenain, C. et al., The Apollo 5' exonuclease functions together with TRF2 to protect telomeresfrom DNA repair. *Curr. Biol.* 16, 1303-1310 (2006). |
| Artemis | Artemis | 5-3' exonuclease | Human | No | Kurosawa, A., and Adachi, N. Functions and regulation of Artemis: a goddess in the maintenance ofgenome integrity. *J Radiat. Res. (Tokyo)* 51, 503-509 (2010). |
| Dna2 | DNA2 | 5-3' exonuclease, helicase | Human | No | Nimonkar, A. V., et al. BLM-DNA2-RPA-MRN and EXO1-BLM-RPA-MRN constitute two DNA end resection machineries for human DNA break repair. *Genes Dev* 25, 350-362 (2011). |
| Exo1 | EXO1 | 5-3' exonuclease | Human | No | Nimonkar, A. V. et al. BLM-DNA2-RPA-MRN and EXO1-BLM-RPA-MRN constitute two DNA end resection machineries for human DNA break repair. *Genes Dev* 25, 350-362 (2011). |

TABLE 2-continued

Library of DNA End-Processing Enzymes.

| Enzyme | Gene name | Activity | Species of origin | NLS added | Reference |
|---|---|---|---|---|---|
| | | | | | Orans, J., et al. Structures of human exonuclease 1 DNA complexes suggest a unified mechanism for nuclease family. *Cell* 145, 212-223 (2011). |
| Fen1 | FEN1 | 5' flap endonuclease | Human | No | Jagannathan, I., Pepenella, S. Hayes, J.J. Activity of FEN1 endonuclease on nucleosome substrates is dependent upon DNA sequence but not flap orientation. *J. Biol. Chem.* 286, 17521-17529 (2011). Tsutakawa, S. E., et al., Human flap endonuclease structures, DNA double-base flipping, and a unified understanding of the FEN1 superfamily. *Cell* 145, 198-211 (2011). |
| Mre11 | MRE11 | 5-3' and 3-5' exonuclease | Human | No | Garcia, V., Phelps, S. E., Gray, S., and Neale, M.J. Bidirectional resection of DNA double-strand breaks by Mrell and Exo1. *Nature* 479, 241-244 (2011). |
| Rad2 | n/a (catalytic domain of Exo1) | 5-3' exonuclease (Exo1 catalytic domain) | Human | No | Lee, B. I., and Wilson, D.M., 3rd The RAD2 domain of human exonuclease 1 exhibits 5' to 3' exonuclease and flap structure-specific endonuclease activities. *J Bio.l Chem.* 274, 37763-37769 (1999). |
| TdT (terminal deoxynucleotidyl transferase) | TdT | Single-stranded Template independent DNA polymerase | Human | No | Mahajan, K. N., et al., Association of terminal deoxynucleotidyl transferase with Ku. *Proc. Natl.Acad. Sci. USA* 96, 13926-13931 (1999). |
| RecE | RecE | 5-3' exonuclease | *E. coli* | Yes | Zhang, J., Xing, X., Herr, A. B., and Bell, C. E. Crystal structure of *E. coli* RecE protein reveals a toroidal tetramer for processing double-stranded DNA breaks. *Structure* 17, 690-702 (2009). |
| Lambda exonuclease | λ exonuclease | 5-3' exonuclease | Bacteriophage λ | Yes | Zhang, J., McCabe, K. A., and Bell, C. E. Crystal structures of lambda exonuclease in complex withDNA suggest an |

TABLE 2-continued

| Library of DNA End-Processing Enzymes. | | | | | |
|---|---|---|---|---|---|
| Enzyme | Gene name | Activity | Species of origin | NLS added | Reference |
| | | | | | electrostatic ratchet mechanism for processivity. *Proc. Natl. Acad. Sci.* USA 108, 11872-11877 (2011). |
| Sox (T24I mutation) | SOX | 5-3' alkaline exonuclease | Kaposi's sarcoma associated herpes virus | Yes | Glaunsinger, B., Chavez, L., and Ganem, D., The exonuclease and host shutoff functions of the SOX protein of Kaposi's sarcoma-associated herpesvirus are genetically separable. *J Virol.* 79, 7396-7401 (2005). Dahlroth, S. L., et al., Crystal structure of the shutoff and exonuclease protein from the oncogenic Kaposi's sarcoma-associated herpes virus. *FEBS J* 276, 6636-6645 (2009). |
| Vaccinia DNA polymerase | E9L | 3-5' exonuclease | Vaccinia poxvirus | Yes | Gammon, D. B., and Evans, D. H., The 3'-to-5' exonuclease activity of vaccinia virus DNA polymerase is essential and plays a role in promoting virus genetic recombination. *J. Virol.* 83, 4236-4250 (2009). |
| UL-12 | UL12 | 5-3' alkaline exonuclease | Herpes simplex virus (HSV)-1 | Yes | Reuven, N. B., et al. The herpes simplex virus type 1 alkaline nuclease and single-stranded DNA binding protein mediate strand exchange in vitro. *J. Virol.* 77, 7425-7433 (2003). Balasubramanian, N., et al. Physical interaction between the herpes simplex virus type 1 exonuclease, UL12, and the DNA double-strand break-sensing MRN complex. *J. Virol.* 84, 12504-12514 (2010). |

Example 8

Exonuclease Screen

An expression library containing both 3' and 5' specific exonucleases is screened by expressing the exonucleases in cells containing a targeted disruption reporter harboring a homing endonuclease target site, for example an I-SceI target site. The exonucleases are co-expressed in the reporter cells with a homing endonuclease, for example I-Sce-I, which generates 3' overhangs upon cleaving its target site. Exonucleases which increase the rate of disruption, as visualized by mCherry+ expression, of the homing endonuclease target site over expression of the homing endonuclease alone are then identified.

An expression library containing both 3' and 5' specific exonucleases is additionally screened by expressing the exonucleases in cells containing a targeted disruption reporter harboring a zinc finger endonuclease target site. The exonucleases are co-expressed in the reporter cells with a zinc finger endonuclease, which generates 5' overhangs upon cleaving its target site with Fok1. Exonucleases which increase the rate of disruption, as visualized by mCherry+ expression, of the zinc finger endonuclease target site over expression of the zinc finger endonuclease alone are identified.

Example 9

Trex-Multiplex

Increasing disruption rates for individual nucleases by coupling endonuclease activity with exonuclease activity, enables multiple simultaneous changes to a genome (multiplexing).

Three homing endonuclease are designed to knock out three different genes (x, y, and z). In the absence of exonuclease co-expression, the efficiency of producing a disruptive mutation, knockout, for each gene individually is 10%, which means that the chance of successfully producing all three disruptive mutations in a single cell with a single round of endonuclease expression is 0.1%. An exonuclease, for example Trex2, is co-expressed with the three homing endonucleases to increase the rate of mutagenesis induced by the homing endonucleases. A 5-fold increase in the mutagenesis rate, to 50% for each individual gene, improves the chance of disrupting all three in a single cell, in a single round to 12.5%, a 125-fold difference.

Example 10

Reduction of Chromosomal Abnormalities During Endonuclease Mediated Targeted Disruption Endonucleases, such as homing endonucleases, zinc finger nucleases, and TAL effector nucleases, induce indiscriminate chromosomal abnormalities, such as translocations. To test the ability of co-expression of an exonuclease that facilitates disruption of an endonuclease target site to decrease the incidence of indiscriminate chromosomal abnormalities, an endonuclease, or a series of endonucleases are expressed in the presence and absence of Trex2. Karyotyping analysis or GCH array analysis is performed to determine if the incidence of genomic abnormalities induced by the endonucleases is reduced.

Example 11

Imparting Site-Specificity to Exonucleases

An exonuclease of interest, for example Trex2, is directly fused or coupled through a linker peptide to an endonuclease or to a DNA binding domain which specifically binds to a target site adjacent to the site where exonuclease activity is desired.

Example 12

Method of Treating, Preventing, or Inhibiting HIV Infection in a Human Patient

Hematopoetic stem cells are isolated from bone marrow obtained from a human subject. The isolated stem cells are contacted with an effective amount of a zinc finger nuclease (ZFN) having target sites in the human CCR-5 gene and contemporaneously contacted with a 5' exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results received and the judgment of the attending physician. The protocol is preferably continued for at least about 1 or 2 weeks, preferably at least about 1 or 2 months, and may be continued on a chronic basis.

Example 13

Method of Treating, Preventing, or Inhibiting HIV Infection in a Human Patient

Hematopoetic stem cells are isolated from bone marrow obtained from a human subject. The isolated stem cells are contacted with an effective amount of a homing endonuclease engineered to cleave a target site in the human CCR-5 gene and contemporaneously contacted with Trex2 exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 14

Method of Treating, Preventing, or Inhibiting HIV Infection in a Human Patient

Hematopoetic stem cells are isolated from bone marrow obtained from a human subject. The isolated stem cells are contacted with an effective amount of a fusion protein comprising an endonuclease domain linked to an exonuclease domain wherein the endonuclease domain comprises a homing endonuclease engineered to cleave a target site in the human CCR-5 gene or fragment thereof and wherein the exonuclease domain comprises Trex2 exonuclease or a fragment thereof. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 15

End-Modifying Enzyme Screen

An expression library containing end-modifying enzymes is screened by expressing the end-modifying enzymes in cells containing a targeted disruption reporter harboring a homing endonuclease target site, for example an I-SceI target site. The end-modifying enzymes are co-expressed in the reporter cells with a homing endonuclease, for example I-Sce-I, which generates 3' overhangs upon cleaving its target site. End-modifying enzymes which increase the rate of disruption, as visualized by mCherry+ expression, of the homing endonuclease target site over expression of the homing endonuclease alone are then identified.

An expression library containing end-modifying enzymes is additionally screened by expressing the exonucleases in cells containing a targeted disruption reporter harboring a zinc finger endonuclease target site. The end-modifying enzymes are co-expressed in the reporter cells with a zinc finger endonuclease, which generates 5' overhangs upon cleaving its target site with Fok1. End-modifying enzymes which increase the rate of disruption, as visualized by mCherry+ expression, of the zinc finger endonuclease target site over expression of the zinc finger endonuclease alone are identified.

Example 16

Method of Treating, Preventing, or Inhibiting Cancer in a Human Patient

A patient having cancer is identified. The isolated an effective amount of an endonuclease targeting a site within the regulatory or coding sequence of an anti-apoptotic gene is administered in combination with an end processing enzyme. The patient is monitored for increased apoptosis and or decreased malignant cell proliferation. In some embodiments, tumor growth is monitored. The protocol may be administered on a periodic or chronic basis.

What is claimed is:

1. A method of increasing mutagenesis at a double-strand DNA (dsDNA) break at a selected dsDNA target site in a eukaryotic cell comprising:

a) selecting a dsDNA target site for mutagenesis; and b) introducing into the eukaryotic cell a polynucleotide sequence encoding:

(i) an endonuclease having a >14 base pair cleavage site, wherein said endonuclease binds and cleaves the selected dsDNA target site; and (ii) an exonuclease;

wherein the exonuclease exhibits exonuclease activity at the cleaved dsDNA target site, resulting in increased mutagenesis at the selected dsDNA target site as compared to mutagenesis that occurs in the absence of exonuclease activity.

2. The method of claim 1, wherein the endonuclease is engineered to bind and cleave the selected dsDNA target site.

3. The method of claim 1, wherein the eukaryotic cell is a human cell.

4. The method of claim 1, wherein the mutagenesis is an insertion or deletion at the selected dsDNA target site.

5. The method of claim 1, wherein the exonuclease exhibits 3' to 5' exonuclease activity.

6. The method of claim 1, wherein the exonuclease is Trex2 or a biologically active fragment thereof.

7. The method of claim 1, wherein the exonuclease is Trex2.

8. The method of claim 1, wherein the endonuclease and the exonuclease are encoded by a single polynucleotide.

9. The method of claim 8, wherein the endonuclease is coupled to the exonuclease by a linker domain.

10. The method of claim 9, wherein the linker domain is a peptide linker comprising 4 to 30 amino acids.

11. The method of claim 10, wherein the linker domain is a G4S linker.

12. The method of claim 10, wherein the linker domain is a T2A linker.

13. The method of claim 1, wherein the dsDNA target site is within a non-coding sequence of a gene.

14. The method of claim 13, wherein the non-coding sequence is a regulatory sequence.

15. The method of claim 14, wherein the regulatory sequence is a promoter, enhancer, or splice site.

16. The method of claim 1, wherein the dsDNA target site is within a coding sequence of a gene.

17. The method of claim 9, wherein the linker domain is a chemical linker.

* * * * *